US011332536B2

(12) United States Patent
Van Dijk et al.

(10) Patent No.: US 11,332,536 B2
(45) Date of Patent: *May 17, 2022

(54) VECTORS COMPRISING NUCLEIC ACIDS ENCODING ANTI-OX40 ANTIBODIES

(71) Applicants: Agenus Inc., Lexington, MA (US); Memorial Sloan-Kettering Cancer Center, New York, NY (US); Ludwig Institute for Cancer Research Ltd., Zurich (CH)

(72) Inventors: Marc Van Dijk, Bosch en Duin (NL); Ekaterina V. Breous-Nystrom, Basel (CH); Gerd Ritter, New York, NY (US); David Schaer, Mamaroneck, NY (US); Daniel Hirschhorn-Cymerman, New York, NY (US); Taha Merghoub, Jersey City, NJ (US); Hao Tang, Lexington, MA (US); David A. Savitsky, Boxford, MA (US); Nicholas S. Wilson, San Carlos, CA (US)

(73) Assignees: AGENUS INC., Lexington, MA (US); Memorial Sloan-Kettering Cancer Center, New York, NY (US); Ludwig Institute for Cancer Research Ltd., Zurich (CH)

( * ) Notice: Subject to any disclaimer, the term of this patent is extended or adjusted under 35 U.S.C. 154(b) by 270 days.

This patent is subject to a terminal disclaimer.

(21) Appl. No.: 16/784,469

(22) Filed: Feb. 7, 2020

(65) Prior Publication Data

US 2020/0270356 A1 Aug. 27, 2020

Related U.S. Application Data

(60) Continuation of application No. 16/384,116, filed on Apr. 15, 2019, now Pat. No. 10,626,181, which is a division of application No. 15/148,720, filed on May 6, 2016, now Pat. No. 10,259,882.

(60) Provisional application No. 62/323,458, filed on Apr. 15, 2016, provisional application No. 62/262,373, filed on Dec. 2, 2015, provisional application No. 62/161,198, filed on May 13, 2015, provisional application No. 62/158,515, filed on May 7, 2015.

(51) Int. Cl.
| | |
|---|---|
| *C12N 15/13* | (2006.01) |
| *C07K 16/28* | (2006.01) |
| *A61K 39/395* | (2006.01) |
| *A61K 45/06* | (2006.01) |
| *G01N 33/68* | (2006.01) |
| *A61K 39/00* | (2006.01) |

(52) U.S. Cl.
CPC ...... *C07K 16/2878* (2013.01); *A61K 39/3955* (2013.01); *A61K 45/06* (2013.01); *C07K 16/2875* (2013.01); *G01N 33/6863* (2013.01); *A61K 2039/505* (2013.01); *C07K 2317/21* (2013.01); *C07K 2317/33* (2013.01); *C07K 2317/34* (2013.01); *C07K 2317/41* (2013.01); *C07K 2317/51* (2013.01); *C07K 2317/515* (2013.01); *C07K 2317/524* (2013.01); *C07K 2317/56* (2013.01); *C07K 2317/565* (2013.01); *C07K 2317/70* (2013.01); *C07K 2317/71* (2013.01); *C07K 2317/74* (2013.01); *C07K 2317/75* (2013.01); *C07K 2317/92* (2013.01); *G01N 2333/70578* (2013.01)

(58) Field of Classification Search
None
See application file for complete search history.

(56) References Cited

U.S. PATENT DOCUMENTS

| | | | |
|---|---|---|---|
| 5,759,546 | A | 6/1998 | Weinberg et al. |
| 6,277,962 | B1 | 8/2001 | Godfrey et al. |
| 6,566,082 | B1 | 5/2003 | Weinberg et al. |
| 7,364,733 | B2 | 4/2008 | Godfrey et al. |
| 7,387,271 | B2 | 6/2008 | Noelle et al. |
| 7,402,431 | B2 | 7/2008 | Har-Noy |
| 7,435,592 | B2 | 10/2008 | Har-Noy |
| 7,504,101 | B2 | 3/2009 | Weinberg |
| 7,531,170 | B1 | 5/2009 | Croft et al. |
| 7,534,808 | B2 | 5/2009 | Evenou et al. |

(Continued)

FOREIGN PATENT DOCUMENTS

| | | |
|---|---|---|
| EP | 3292152 A1 | 3/2018 |
| WO | WO-1999042585 A1 | 8/1999 |

(Continued)

OTHER PUBLICATIONS

US 10,975,156 B1, 04/2021, Wilson et al. (withdrawn)
"A comprehensive immuno-oncology Ecosystem" Cowen and Company 36th Annual Health Care Conference Mar. 2016.

(Continued)

*Primary Examiner* — Phillip Gambel
(74) *Attorney, Agent, or Firm* — Dechert LLP; Andrew T. Wilkins; Sharla F. Flohr

(57) ABSTRACT

The present disclosure provides antibodies that specifically bind to human OX40 receptor (OX40) and compositions comprising such antibodies. In a specific aspect, the antibodies specifically bind to human OX40 and modulate OX40 activity, e.g., enhance, activate, or induce OX40 activity, or reduce, deactivate, or inhibit OX40 activity. The present disclosure also provides methods for treating disorders, such as cancer, by administering an antibody that specifically binds to human OX40 and modulates OX40 activity, e.g., enhances, activates, or induces OX40 activity. Also provided are methods for treating autoimmune or inflammatory diseases or disorders, by administering an antibody that specifically binds to human OX40 and modulates OX40 activity, e.g., reduces, deactivates, or inhibits OX40 activity.

22 Claims, 45 Drawing Sheets

Specification includes a Sequence Listing.

(56) References Cited

U.S. PATENT DOCUMENTS

| | | |
|---|---|---|
| 7,550,140 B2 | 6/2009 | Bakker et al. |
| 7,563,443 B2 | 7/2009 | Grant et al. |
| 7,592,431 B2 | 9/2009 | Har-Noy |
| 7,635,472 B2 | 12/2009 | Kufer et al. |
| 7,648,989 B2 | 1/2010 | Van Eis et al. |
| 7,807,156 B1 | 10/2010 | Croft et al. |
| 7,812,133 B2 | 10/2010 | Martin |
| 7,820,672 B2 | 10/2010 | Von Matt |
| 7,829,084 B2 | 11/2010 | Ledbetter et al. |
| 7,960,515 B2 | 6/2011 | Min et al. |
| 8,101,175 B1 | 1/2012 | Croft et al. |
| 8,124,085 B2 | 2/2012 | Nielsen et al. |
| 8,133,983 B2 | 3/2012 | Bakker et al. |
| 8,147,835 B2 | 4/2012 | Ledbetter et al. |
| 8,153,765 B2 | 4/2012 | Park et al. |
| 8,197,810 B2 | 6/2012 | Ledbetter et al. |
| 8,236,930 B2 | 8/2012 | Min et al. |
| 8,283,450 B2 | 10/2012 | Kato et al. |
| 8,329,197 B2 | 12/2012 | Noelle et al. |
| 8,409,577 B2 | 4/2013 | Thompson et al. |
| 8,481,029 B2 | 7/2013 | Glennie et al. |
| 8,551,477 B1 | 10/2013 | Croft et al. |
| 8,614,295 B2 | 12/2013 | Lawson et al. |
| 8,652,836 B2 | 2/2014 | Hu |
| 8,748,585 B2 | 6/2014 | Attinger et al. |
| 8,865,873 B2 | 10/2014 | Liu et al. |
| 8,956,615 B1 | 2/2015 | Croft et al. |
| 8,993,524 B2 | 3/2015 | Bedi et al. |
| 8,993,614 B2 | 3/2015 | Bartkovitz et al. |
| 9,005,612 B2 | 4/2015 | Ledbetter et al. |
| 9,005,619 B2 | 4/2015 | Kohrt et al. |
| 9,006,399 B2 | 4/2015 | Liu et al. |
| 9,028,824 B2 | 5/2015 | Min et al. |
| 9,040,048 B2 | 5/2015 | Adams et al. |
| 9,102,733 B2 | 8/2015 | Endl et al. |
| 9,132,281 B2 | 9/2015 | Zeng et al. |
| 9,161,976 B2 | 10/2015 | Noelle et al. |
| 9,163,085 B2 | 10/2015 | Liu et al. |
| 9,228,016 B2 | 1/2016 | Wang et al. |
| 9,248,183 B2 | 2/2016 | Glennie et al. |
| 9,352,001 B2 | 5/2016 | Har-Noy |
| 9,365,496 B2 | 6/2016 | Cerundolo et al. |
| 9,409,987 B2 | 8/2016 | Toporik et al. |
| 9,428,570 B2 | 8/2016 | Lawson et al. |
| 9,441,044 B2 | 9/2016 | Bedi et al. |
| 9,475,878 B2 | 10/2016 | Kato et al. |
| 9,475,880 B2 | 10/2016 | Simons et al. |
| 9,486,520 B2 | 11/2016 | Borrebaeck et al. |
| 9,493,563 B2 | 11/2016 | Blein et al. |
| 9,511,127 B2 | 12/2016 | Har-Noy |
| 9,527,917 B2 | 12/2016 | Liu et al. |
| 9,540,442 B2 | 1/2017 | Tsurushita et al. |
| 9,695,246 B2 | 7/2017 | Liu et al. |
| 9,700,532 B2 | 7/2017 | Cerundolo et al. |
| 9,713,641 B2 | 7/2017 | Hicklin et al. |
| 9,738,723 B2 | 8/2017 | Hammond et al. |
| 9,758,589 B2 | 9/2017 | Kohrt et al. |
| 9,782,463 B2 | 10/2017 | Har-Noy |
| 9,790,281 B2 | 10/2017 | Simons et al. |
| 9,828,432 B2 | 11/2017 | Curti et al. |
| 9,834,610 B2 | 12/2017 | Tykocinski |
| 9,840,536 B2 | 12/2017 | Currie et al. |
| 9,850,306 B2 | 12/2017 | Bedi et al. |
| 9,873,735 B2 | 1/2018 | Adams et al. |
| 9,873,744 B1 | 1/2018 | Croft et al. |
| 9,926,374 B2 | 3/2018 | Glennie et al. |
| 10,259,882 B2 | 4/2019 | Van Dijk et al. |
| 10,626,181 B2 | 4/2020 | Van Dijk et al. |
| 10,836,830 B2 | 11/2020 | Wilson et al. |
| 2003/0035790 A1 | 2/2003 | Chen et al. |
| 2003/0223989 A1 | 12/2003 | Pluenneke |
| 2004/0009174 A1 | 1/2004 | Arndt et al. |
| 2004/0022760 A1 | 2/2004 | McKenna et al. |
| 2004/0197312 A1 | 10/2004 | Moskalenko et al. |
| 2005/0002916 A1 | 1/2005 | Jooss et al. |
| 2005/0123536 A1 | 6/2005 | Law et al. |
| 2006/0148064 A1 | 7/2006 | Srivastava |
| 2006/0217531 A1 | 9/2006 | Godfrey et al. |
| 2006/0280728 A1 | 12/2006 | Weinberg et al. |
| 2006/0281072 A1 | 12/2006 | Bakker |
| 2007/0036783 A1 | 2/2007 | Humeau et al. |
| 2007/0092511 A1 | 4/2007 | Godfrey et al. |
| 2008/0286286 A1 | 11/2008 | Liu et al. |
| 2008/0317751 A1 | 12/2008 | Heath |
| 2009/0069535 A1 | 3/2009 | Godfrey et al. |
| 2009/0087440 A1 | 4/2009 | Vicari et al. |
| 2009/0137003 A1 | 5/2009 | Tolstrup et al. |
| 2009/0175867 A1 | 7/2009 | Thompson et al. |
| 2009/0214560 A1 | 8/2009 | Min et al. |
| 2009/0317407 A1 | 12/2009 | LaCelle et al. |
| 2010/0008920 A1 | 1/2010 | Schneck et al. |
| 2010/0015143 A1 | 1/2010 | Hussell et al. |
| 2010/0098712 A1 | 4/2010 | Adler et al. |
| 2010/0136030 A1 | 6/2010 | Salah-Eddine et al. |
| 2010/0196359 A1 | 8/2010 | Kato et al. |
| 2010/0240873 A1 | 9/2010 | Godfrey et al. |
| 2010/0254978 A1 | 10/2010 | Lawson et al. |
| 2011/0008368 A1 | 1/2011 | Liu et al. |
| 2011/0123552 A1 | 5/2011 | Bakker et al. |
| 2011/0206681 A1 | 8/2011 | Min et al. |
| 2011/0256184 A1 | 10/2011 | Lei et al. |
| 2011/0262454 A1 | 10/2011 | Park et al. |
| 2011/0280903 A1 | 11/2011 | Noelle et al. |
| 2011/0318380 A1 | 12/2011 | Brix et al. |
| 2012/0070450 A1 | 3/2012 | Ishikawa et al. |
| 2012/0128687 A1 | 5/2012 | Adler et al. |
| 2012/0141465 A1 | 6/2012 | Croft et al. |
| 2012/0225086 A1 | 9/2012 | Min et al. |
| 2012/0251531 A1 | 10/2012 | Baehner et al. |
| 2012/0269825 A1 | 10/2012 | Liu et al. |
| 2013/0071403 A1 | 3/2013 | Rolland et al. |
| 2013/0183311 A1 | 7/2013 | Nielsen et al. |
| 2013/0183315 A1 | 7/2013 | Attinger et al. |
| 2013/0211050 A1 | 8/2013 | Stennicke et al. |
| 2013/0243772 A1 | 9/2013 | Adams et al. |
| 2013/0280265 A1 | 10/2013 | Rolland et al. |
| 2013/0280275 A1 | 10/2013 | Liu et al. |
| 2013/0295091 A1 | 11/2013 | Esslinger et al. |
| 2013/0330344 A1 | 12/2013 | Lawson et al. |
| 2013/0336977 A1 | 12/2013 | Thompson et al. |
| 2014/0044703 A1 | 2/2014 | Kato et al. |
| 2014/0079706 A1 | 3/2014 | Cannarile et al. |
| 2014/0127203 A1 | 5/2014 | Thompson et al. |
| 2014/0141022 A1 | 5/2014 | Thompson et al. |
| 2014/0154250 A1 | 6/2014 | Thompson et al. |
| 2014/0154252 A1 | 6/2014 | Thompson et al. |
| 2014/0294765 A1 | 10/2014 | Cojocaru et al. |
| 2014/0294824 A1 | 10/2014 | Attinger et al. |
| 2014/0302033 A1 | 10/2014 | Adams et al. |
| 2014/0308276 A1 | 10/2014 | Liu et al. |
| 2014/0377221 A1 | 12/2014 | Tufaro et al. |
| 2014/0377284 A1 | 12/2014 | Simons et al. |
| 2015/0017141 A1 | 1/2015 | June et al. |
| 2015/0037346 A1 | 2/2015 | Lesokhin et al. |
| 2015/0119555 A1 | 4/2015 | Jung et al. |
| 2015/0132288 A1 | 5/2015 | Simons et al. |
| 2015/0157710 A1 | 6/2015 | Redmond et al. |
| 2015/0158947 A1 | 6/2015 | Cojocaru et al. |
| 2015/0190505 A1 | 7/2015 | Yeung |
| 2015/0190506 A1 | 7/2015 | Cheung et al. |
| 2015/0202291 A1 | 7/2015 | Bosch et al. |
| 2015/0218279 A1 | 8/2015 | Min et al. |
| 2015/0273033 A1 | 10/2015 | Bosch et al. |
| 2015/0307617 A1 | 10/2015 | Du et al. |
| 2015/0307620 A1 | 10/2015 | Vella et al. |
| 2015/0315281 A1 | 11/2015 | Liu et al. |
| 2015/0329617 A1 | 11/2015 | Winther et al. |
| 2015/0353637 A1 | 12/2015 | Wang et al. |
| 2015/0374731 A1 | 12/2015 | Maio et al. |
| 2016/0031974 A1 | 2/2016 | Adams et al. |
| 2016/0068604 A1 | 3/2016 | Liu et al. |
| 2016/0101128 A1 | 4/2016 | Wang et al. |
| 2016/0129095 A1 | 5/2016 | Noelle et al. |
| 2016/0137740 A1 | 5/2016 | Hammond et al. |

(56) References Cited

U.S. PATENT DOCUMENTS

| | | |
|---|---|---|
| 2016/0152720 A1 | 6/2016 | Kim et al. |
| 2016/0159905 A1 | 6/2016 | Abdiche et al. |
| 2016/0159927 A1 | 6/2016 | Molloy et al. |
| 2016/0193239 A1 | 7/2016 | Baylin et al. |
| 2016/0235842 A1 | 8/2016 | Goldstein et al. |
| 2016/0243218 A1 | 8/2016 | Gilboa |
| 2016/0289645 A1 | 10/2016 | Tufaro et al. |
| 2016/0347847 A1 | 12/2016 | Van Dijk et al. |
| 2016/0347848 A1 | 12/2016 | Hammond et al. |
| 2016/0347849 A1 | 12/2016 | Cai et al. |
| 2016/0355589 A1 | 12/2016 | Williams et al. |
| 2016/0355598 A1 | 12/2016 | Lawson et al. |
| 2017/0014496 A1 | 1/2017 | Fotin-Mleczek et al. |
| 2017/0042997 A1 | 2/2017 | Wirth |
| 2017/0051061 A1 | 2/2017 | Snyder et al. |
| 2017/0051069 A1 | 2/2017 | Simons et al. |
| 2017/0056391 A1 | 3/2017 | Li |
| 2017/0081417 A1 | 3/2017 | Kato et al. |
| 2017/0106048 A1 | 4/2017 | Kunz et al. |
| 2017/0137530 A1 | 5/2017 | Baehner et al. |
| 2017/0158770 A1 | 6/2017 | Bedi et al. |
| 2017/0165230 A1 | 6/2017 | Rudd et al. |
| 2017/0182156 A1 | 6/2017 | Khleif |
| 2017/0202902 A1 | 7/2017 | Mclaughlin et al. |
| 2017/0209574 A1 | 7/2017 | Cao et al. |
| 2017/0216403 A1 | 8/2017 | Wittrup et al. |
| 2017/0224777 A1 | 8/2017 | Wittrup et al. |
| 2017/0239338 A1 | 8/2017 | Szalay et al. |
| 2017/0240634 A1 | 8/2017 | Eisenbach-Schwartz et al. |
| 2017/0261497 A1 | 9/2017 | Schneck et al. |
| 2017/0267759 A1 | 9/2017 | Liang et al. |
| 2017/0267773 A1 | 9/2017 | Liu et al. |
| 2017/0290914 A1 | 10/2017 | Liang et al. |
| 2017/0296659 A1 | 10/2017 | Lebwohl et al. |
| 2017/0320950 A1 | 11/2017 | Snyder et al. |
| 2017/0340733 A1 | 11/2017 | Cao |
| 2017/0362295 A1 | 12/2017 | June et al. |
| 2017/0369586 A1 | 12/2017 | Simons et al. |
| 2018/0044428 A1 | 2/2018 | Gough et al. |
| 2018/0057608 A1 | 3/2018 | Jung et al. |
| 2018/0064765 A1 | 3/2018 | Petit et al. |
| 2018/0078625 A1 | 3/2018 | Moon et al. |
| 2018/0079821 A1 | 3/2018 | Tykocinski |
| 2018/0118823 A1 | 5/2018 | Thompson et al. |
| 2018/0194825 A1 | 7/2018 | Dubinett et al. |
| 2018/0194849 A1 | 7/2018 | Sahin et al. |
| 2018/0194850 A1 | 7/2018 | Faustman |
| 2019/0284291 A1 | 9/2019 | Van Dijk et al. |
| 2020/0079861 A1 | 3/2020 | Wilson et al. |
| 2020/0317796 A1 | 10/2020 | Van Dijk et al. |

FOREIGN PATENT DOCUMENTS

| | | |
|---|---|---|
| WO | WO-2001077342 A1 | 10/2001 |
| WO | WO-2002028440 A1 | 4/2002 |
| WO | WO-2003106498 A2 | 12/2003 |
| WO | WO-2004056873 A1 | 7/2004 |
| WO | WO-2004073732 A1 | 9/2004 |
| WO | WO-2005049085 A1 | 6/2005 |
| WO | WO-2006069202 A2 | 6/2006 |
| WO | WO-2008106116 A2 | 9/2008 |
| WO | WO-2009079335 A1 | 6/2009 |
| WO | WO-2010054007 A1 | 5/2010 |
| WO | WO-2010056898 A2 | 5/2010 |
| WO | WO-2011086091 A1 | 7/2011 |
| WO | WO-2012130831 A1 | 10/2012 |
| WO | WO-2012163769 A1 | 12/2012 |
| WO | WO-2013008171 A1 | 1/2013 |
| WO | WO-2013028231 A1 | 2/2013 |
| WO | WO-2013038191 A2 | 3/2013 |
| WO | WO-2013049307 A2 | 4/2013 |
| WO | WO-2013068563 A2 | 5/2013 |
| WO | WO-2013083659 A1 | 6/2013 |
| WO | WO-2013092001 A1 | 6/2013 |
| WO | WO-2014121099 A1 | 8/2014 |
| WO | WO-2014148895 A1 | 9/2014 |
| WO | WO-2015009726 A2 | 1/2015 |
| WO | WO-2015095423 A2 | 6/2015 |
| WO | WO-2015116178 A1 | 8/2015 |
| WO | WO-2015135558 A1 | 9/2015 |
| WO | WO-2015153513 A1 | 10/2015 |
| WO | WO-2015153514 A1 | 10/2015 |
| WO | WO-2015174439 A1 | 11/2015 |
| WO | WO-2016059602 A2 | 4/2016 |
| WO | WO-2016062722 A1 | 4/2016 |
| WO | WO-2016066634 A2 | 5/2016 |
| WO | WO-2016075174 A1 | 5/2016 |
| WO | WO-2016168361 A1 | 10/2016 |
| WO | WO-2016179517 A1 | 11/2016 |
| WO | WO-2017096179 A1 | 6/2017 |
| WO | WO-2017096182 A1 | 6/2017 |
| WO | WO-2017096281 A1 | 6/2017 |
| WO | WO-2017157964 A1 | 9/2017 |
| WO | WO-2017186928 A1 | 11/2017 |
| WO | WO-2018089628 A1 | 5/2018 |

OTHER PUBLICATIONS

"Agenus Announces Commencement of Phase 1-2 Clinical Trial of anti-OX40 Checkpoint Antibody INCAGN1949 in Patients with Solid Tumors"—PRNewswire—(Nov. 30, 2016).
"Agenus Presents Posters on Checkpoint Antibody Product Candidates at the American Association for Cancer Research (AACR) 2016 Annual Meeting" (Business Wire) (Apr. 18, 2016).
"Agenus R&D Day" (May 14, 2015).
"Agenus R&D Day" New York, NY (Nov. 19, 2015).
"Agenus, Driving the immune system to fight cancer and infectious disease," Mar. 2015.
"Agenus, Driving the immune system to fight cancer and infectious disease," May 15, 2015.
"Agonist Checkpoint Modulators: Challenges and Opportunities" PEGS Boston May 8, 2015.
"Emerging Leader In Immuno-Oncology", Lexington, MA (Nov. 2015).
"Four Agenus Abstracts Accepted for Presentation at the American Association for Cancer Research(AAUI-<) 2017 Annual Meetilly" PRNewswire, Mar. 7, 2017.
"Immuno-Oncology" RBS Immunotherapy Conference Mar. 27, 2014.
"Integrated Approach to Immuno-Oncology" Blair Maidstone 1-O Conference NYC, Mar. 31, 2016.
"Integrated Solutions in Immuno-Oncology" Apr. 2016.
"Integrated Solutions in Immuno-Oncology" May 2016.
"Targeting TNFR Family Members: Therapeutic opportunities in immuno-oncology and immuno-inflammation" PEGS Boston 2016.
Aspeslagh et al., "Rationale for anti-OX40 cancer immunotherapy," Eur J Cancer. 2016;52:50-66.
Aspord et al., "Plasmacytoid dendritic cells support melanoma progression by promoting Th2 and regulatory immunity through OX40L and ICOSL," Cancer Immunol Res. 2013;1 (6):402-15.
Back, "Dampening Pathological Immune Responses via Targeting OX40 with GBR830, an Antagonist Monoclonal Antibody," PEGS, Biologies for Autoimmune Disease, May 12, 2015.
Baum et al., "Identification of OX40 ligand and preliminary characterization of its activities on OX40 receptor," Circ Shock. 1994;44(1):30-4.
Berrong et al., "Antigen-Specific Antitumor Responses Induced by OX40 Agonist Are Enhanced by the IDO Inhibitor Indoximod," Cancer Immunol Res. 2018;6(2):201-208.
Berrong et al., "Immune combinational therapy targeting OX40 and IDO synergistically enhances efficacy of a cancer vaccine," J Immunother Cancer. 2014;2(Suppl 3):P226.
Blazar et al., "Ligation of OX40 (CD134) regulates graft-versus-host disease (GVHD) and graft rejection in allogeneic bone marrow transplant recipients," Blood. 2003;101(9):3741-8.
Buchan et al., "Death receptors is essential for generating optimal protective CD4? T-cell immunity against *Salmonella*," Eur J Immunol. 2012;42(3):580-8.

(56) References Cited

OTHER PUBLICATIONS

Bulliard et al., "Activating Fc gamma receptors contribute to the antitumor activities of immunoregulatory receptor-targeting antibodies," J Exp Med. 2013;210(9):1685-93.
Bulliard et al., "OX40 engagement depletes intratumoral Tregs via activating Fc?Rs, leading to antitumor efficacy," Immunol Cell Biol. 2014;92(6):475-80.
Capello et al., "Immunoglobulin Kappa Chain Variable Region, Partial [*Homo sapiens*]," National Center for Biotechnology Information. GenBank Entry, Jul. 20, 1999 [Retrieved on Apr. 25, 2016] Retrieved from the Internet, URL: http:--www.ncbi.nlm.nih.gov-protein-5578794, pp. 1-2.
Chan and Carter, "Therapeutic antibodies for autoimmunity and inflammation," Nat Rev Immunol. 2010;10(5):301-16.
Chen and Mellman, "Oncology meets immunology: the cancer-immunity cycle," Immunity. 2013;39(1):1-10.
Collins et al., "The interaction properties of costimulatory molecules revisited," Immunity. 2002;17(2):201-10.
Compaan and Hymowitz, "The crystal structure of the costimulatory OX40-OX40L complex," Structure. 2006;14(8):1321-30.
Croft, "Control of immunity by the TNFR-related molecule OX40 (CD134)," Ann Rev Immunol. 2010;28:57-78.
Curti et al., "OX40 is a potent immune-stimulating target in late-stage cancer patients," Cancer Res. 2013;73(24):7189-7198.
Ehrenstein and Notley, "The importance of natural IgM: scavenger, protector and regulator," Nat Rev Immunol. 2010;10(11):778-86.
Finco et al., "Cytokine release assays: current practices and future directions," Cytokine 2014; 66(2):143-55.
Fromm et al., "Gp96-Ig/Costimulator (OX40L, ICOSL, or 4-1BBL) Combination Vaccine Improves T-cell Priming and Enhances Immunity, Memory, and Tumor Elimination," Cancer Immunol Res. 2016;4(9):766-78.
Furness et al., "Impact of tumour microenvironment and Fc receptors on the activity of immunomodulatory antibodies," Trends Immunol. 2014;35(7):290-8.
Genbank, "*Homo Sapiens* cDNA FLJ50815 Complete cds, Highly Similar to Tumor Necrosis Factor Ligand Superfamilymember 4", Accession No. AK297932.1, accessed at https:--www.ncbi.nlm.nih.gov-nuccore-AK297932.1.
Genbank, "*Homo Sapiens* mRNA for Glycoprotein 34, Complete CDS," Accession No. D90224.1, accessed at https://www.ncbi.nlm.nih.gov-nuccore-D90224.1.
Godfrey et al., "Identification of a human OX-40 ligand, a costimulator of CD4+ T cells with homology to tumor necrosis factor," J Exp Med. 1994;180(2):757-62.
Gong et al., "A heat shock protein 70-based vaccine with enhanced immunogenicity for clinical use," J Immunol. 2010;184(1):488-96.
Gonzalez, et al., "INCAGN1876, a Unique GITR Agonist Antibody That Facilitates GITR Oligomerization" 3643 Presented at the American Association for Cancer Research Annual Meeting 2017 Washington, DC, USA Apr. 1-5, 2017.
Gough et al., "Targeting macrophages in the tumour environment to enhance the efficacy of ?OX40 therapy," Immunology. 2012;136(4):437-47.
Gramaglia et al., "Ox-40 ligand: a potent costimulatory molecule for sustaining primary CD4 T cell responses," J Immunol. 1998;161(12):6510-7.
Gramaglia et al., "The OX40 costimulatory receptor determines the development of CD4 memory by regulating primary clonal expansion," J Immunol. 2000;165(6):3043-50.
Gravekamp and Jahangir, "Is cancer vaccination feasible at older age?" Exp Gerontol. 2014;54:138-144.
Guilliams et al., "The function of Fcgamma receptors in dendritic cells and macrophages," Nat Rev Immunol. 2014;14(2):94-108.
Guo et al., "PD-1 blockade and OX40 triggering synergistically protects against tumor growth in a murine model of ovarian cancer," PLoS One. 2014;9(2):e89350.
Hattori et al., "Blockade of the OX40 ligand prolongs corneal allograft survival," Eur J Immunol. 2007;37(12):3597-604.

Hebb et al., "Administration of low-dose combination anti-CTLA4, anti-CD137, and anti-OX40 into murine tumor or proximal to the tumor draining lymph node induces systemic tumor regression," Cancer Immunol Immunother. 2018;67(1):47-60.
Hirschhorn-Cymerman et al., "OX40 engagement and chemotherapy combination provides potent antitumor immunity with concomitant regulatory T cell apoptosis," J Exp Med. 2009;206(5):1103-16.
Hogarth and Pietersz, "Fc receptor-targeted therapies for the treatment of inflammation, cancer and beyond," Nat Rev Drug Discov. 2012;11(4):311-31.
Hornbach et al., "OX40 costimulation by a chimeric antigen receptor abrogates CD28 and IL-2 induced IL-10 secretion by redirected CD4(+) T cells," Oncoimmunology. 2012;1(4):458-466.
Imura et al., "The human OX40/gp34 system directly mediates adhesion of activated T cells to vascular endothelial cells," J Exp Med. 1996;183(5):2185-95.
International Preliminary Report on Patentability for PCT-US2016-031257 dated Nov. 7, 2017.
International Preliminary Report on Patentability for PCT/US2016/064649, dated Jan. 18, 2018.
International Search Report and Written Opinion received for PCT/US2016/031257, dated Jul. 18, 2016.
International Search Report and Written Opinion received for PCT/US2016/064649, dated Feb. 28, 2017.
Jensen et al., "Signaling through OX40 enhances antitumor immunity," Semin Oncol. 2010;37(5):524-32.
Katschke et al., "A novel inhibitor of the alternative pathway of complement reverses inflammation and bone destruction in experimental arthritis," J Exp Med. 2007;204(6):1319-1325.
Kim and Ashkenazi, "Fcgamma receptors enable anticancer action of proapoptotic and immune-modulatory antibodies," J Exp Med. 2013;210(9):1647-51.
Kjaergaard et al., "Therapeutic efficacy of OX-40 receptor antibody depends on tumor immunogenicity and anatomic site of tumor growth," Cancer Res. 2000;60(19):5514-21.
Kober et al., "The capacity of the TNF family members 4-1BBL, OX40L, CD70, GITRL, CD30L and LIGHT to costimulate human T cells," Eur J Immunol. 2008;38(10):2678-88.
Koene et al., "Fc gammaRIIIa-158V/F polymorphism influences the binding of IgG by natural killer cell Fc gammaRIIIa, independently of the Fc gammaRIIIa-48L/R/H phenotype," Blood. 1997;90(3):1109-14.
Krause et al., "Prostaglandin E2 enhances T-cell proliferation by inducing the costimulatory molecules OX40L, CD70, and 4-1BBL on dendritic cells," Blood. 2009;113(11):2451-2460.
Kunitomi et al., "Vascular endothelial cells provide T cells with costimulatory signals via the OX40/gp34 system," J Leukoc Biol. 2000;68(1):111-8.
Li and Ravetch, "Inhibitory Fc? receptor engagement drives adjuvant and anti-tumor activities of agonistic CD40 antibodies," Science. 2011;333(6045):1030-1034.
Lightle et al., "Mutations within a human IgG2 antibody form distinct and homogeneous disulfide isomers but do not affect Fc gamma receptor or C1q binding," Protein Sci. 2010;19(4):753-762.
Linch and Redmond, "ombined OX40 ligation plus CTLA-4 blockade More than the sum of its parts," Oncoimmunology. 2014;3:e28245.
Linch et al., "Combination OX40 agonism/CTLA-4 blockade with HER2 vaccination reverses T-cell anergy and promotes survival in tumor-bearing mice," Proc. Natl. Acad. Sci. USA. 2016;113(3):E319-27.
Linch et al., "OX40 Agonists and Combination Immunotherapy: Putting the Pedal to the Metal," Front Oncol. 2015;5:34.
Linton et al., "Costimulation via OX40L expressed by B cells is sufficient to determine the extent of primary CD4 cell expansion and Th2 cytokine secretion in vivo," J Exp Med. 2003;197(7):875-83.
Mahmud et al., "Costimulation via the tumor-necrosis factor receptor superfamily couples TCR signal strength to the thymic differentiation of regulatory T cells," Nat Immunol. 2014;15(5):473-81.
Mallett et al., "Characterization of the MRC OX40 antigen of activated CD4 positive T lymphocytes—a molecule related to nerve growth factor receptor," EMBO J. 1990;9(4):1063-1068.

(56) References Cited

OTHER PUBLICATIONS

Marabelle et al., "Depleting tumor-specific Tregs at a single site eradicates disseminated tumors," J Clin Invest. 2013;123(6):2447-63.

Melero et al., "Agonist antibodies to TNFR molecules that costimulate T and NK cells," Clin Cancer Res. 2013; 19(5):1044-53.

Mellman et al., "Cancer immunotherapy comes of age," Nature. 2011;480(7378):480-9.

Messenheimer et al., "Timing of PD-1 Blockade Is Critical to Effective Combination Immunotherapy with Anti-OX40," Clin Cancer Res. 2017;23(20):6165-6177.

Meylan et al., "TL1A and DR3, a TNF family ligand-receptor pair that promotes lymphocyte costimulation, mucosal hyperplasia, and autoimmune inflammation," Immunol Rev. 2011;244(1):188-96.

Miura et al., "Molecular cloning and characterization of a novel glycoprotein, gp34, that is specifically induced by the human T-cell leukemia virus type I transactivator p40tax," Mol Cell Biol. 1991;11(3):1313-25.

Montier et al., "OX40, PD-1 and CTLA-4 are selectively expressed on tumor-infiltrating T cells in head and neck cancer," Clin Transl Immunology. 2016;5(4):e70.

Moran et al., "The TNFRs OX40, 4-1BB, and CD40 as targets for cancer immunotherapy," Curr Opin Immunol. 2013;25(2):230-7.

Murphy et al., "CD8+ T cell-independent tumor regression induced by FC-OX40L and therapeutic vaccination in a mouse model of glioma," J Immunol. 2014:192(1):224-33.

Nimmerjahn and Ravetch, "Antibodies, Fc receptors and cancer," Curr Opin Immunol. 2007;19(2):239-45.

Nimmerjahn and Ravetch, "Fcgamma receptors as regulators of immune responses," Nat Rev Immunol. 2008;8(1):34-47.

Nimmerjahn and Ravetch, "Translating basic mechanisms of IgG effector activity into next generation cancer therapies," Cancer Immun. 2012;12:13.

Nuebling et al., "The Immune Checkpoint Modulator OX40 and Its Ligand OX40L in NK-Cell Immunosurveillance and Acute Myeloid Leukemia," Cancer Immunol Res. 2018;6(2):209-221.

Ohshima et al., "Expression and function of OX40 ligand on human dendritic cells," J Immunol. 1997;159(8):3838-48.

Paterson et al., "Antigens of activated rat T lymphocytes including a molecule of 50,000 Mr detected only on CD4 positive T blasts," Mol immunol. 1987;24(12):1281-90.

Piconese et al., "Human OX40 tunes the function of regulatory T cells in tumor and nontumor areas of hepatitis C virus-infected liver tissue," Hepatology. 2014;60(5):1494-507.

Piconese et al., "OX40 triggering blocks suppression by regulatory T cells and facilitates tumor rejection," J Exp Med. 2008;205(4):825-39.

Piconese et al., "'Hardcore' OX40+ immunosuppressive regulatory T cells in hepatic cirrhosis and cancer," Oncoimmunology. 2014;3:e29257.

Prell et al., "OX40-mediated memory T cell generation is TNF receptor-associated factor 2 dependent," J Immunol. 2003;171(11):5997-6005.

Ravetch and Lanier, "Immune inhibitory receptors," Science. 2000;290(5489):84-9.

Redmond and Weinberg, "Targeting OX40 and OX40L for the treatment of autoimmunity and cancer," Crit Rev Immunol. 2007;27(5):415-36.

Redmond et al., "Combined targeting of costimulatory (OX40) and coinhibitory (CTLA-4) pathways elicits potent effector T cells capable of driving robust antitumor immunity," Cancer Immunol Res. 2014;2(2):142-53.

Redmond et al., "Dual anti-OX40/IL-2 therapy augments tumor immunotherapy via IL-2R-mediated regulation of OX40 expression," PLoS One. 2012;7(4):e34467.

Richard et al., "The TNF-family ligand TL1A and its receptor DR3 promote T cell-mediated allergic immunopathology by enhancing differentiation and pathogenicity of IL-9-producing T cells," J Immunol. 2015;194(8):3567-82.

Rodman & Renshaw Annual Global Investment Conference Sep. 2015.

Rogers et al., "OX40 promotes Bcl-xL and Bcl-2 expression and is essential for long-term survival of CD4 T cells," Immunity. 2001;15(3):445-55.

Ruby et al., "Cutting Edge: OX40 agonists can drive regulatory T cell expansion if the cytokine milieu is right," J Immunol. 2009;183(8):4853-7.

Sagiv-Barfi et al., "Eradication of spontaneous malignancy by local immunotherapy," Sci Transl Med. 2018;10(426):eaan4488.

Salek-Ardakani et al., "OX40 (CD134) controls memory T helper 2 cells that drive lung inflammation," J Exp Med.2003;198(2):315-24.

Schreiber and Podack, "Immunobiology of TNFSFI5 and TNFRSF25," Immunol Res. 2013;57(1-3):3-11.

Schreiber et al., "T Cell Costimulation by TNFRSF4 and TNFRSF25 in the Context of Vaccination," J Immunol. 2012;189(7):3311-3318.

Schreiber et al., "Therapeutic Treg expansion in mice by TNFRSF25 prevents allergic lung inflammation," J Clin Invest. 2010;120(10):3629-40.

Seshasayee et al., "In vivo blockade of OX40 ligand inhibits thymic stromal lymphopoietin driven atopic inflammation," J Clin Invest. 2007;117(12):3868-78.

Sheridan, "IDO inhibitors move center stage in immuno-oncology," Nat Biotechnol. 2015;33(4):321-2.

Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem. 2001;276(9):6591-604.

Shrimali et al., "Concurrent PD-1 Blockade Negates the Effects of OX40 Agonist Antibody in Combination Immunotherapy through Inducing T-cell Apoptosis," Cancer Immunol Res. 2017;5(9):755-766.

Simpson et al., "Fc-dependent depletion of tumor-infiltrating regulatory T cells co-defines the efficacy of anti-CTLA-4 therapy against melanoma," J Exp Med. 2013:210(9):1695-710.

Smyth et al., "Targeting regulatory T cells in tumor immunotherapy," Immunology and Cell Biology. 2014;92:473-474.

So et al., "Immune Regulation and Control of Regulatory T cells by OX40 and 4-1BB," Cytokine Growth Factor Rev. 2008;19(3-4):253-262.

Soroosh et al., "OX40-OX40 ligand interaction through T cell-T cell contact contributes to CD4 T cell longevity," J Immunol. 2006;176(10):5975-87.

Stebbings et al., "'Cytokine storm' in the phase I trial of monoclonal antibody TGN1412: better understanding the causes to improve preclinical testing of immunotherapeutics," J Immunol. 2007;179(5):3325-31.

Strbo et al., "Secreted heat shock protein gp96-lg: next-generation vaccines for cancer and infectious diseases," Immunol Res. 2013;57(1-3):311-25.

Sugamura et al., "Therapeutic targeting of the effector T-cell co-stimulatory molecule OX40," Nat Rev Immunol. 2004;4(6):420-31.

Supplemental Partial European Search Report from EP 16871583 dated Jul. 3, 2019.

Taylor and Schwarz, "Identification of a soluble OX40 isoform: development of a specific and quantitative immunoassay," J Immunol Methods. 2001;255(1-2):67-72.

Tone et al., "Gene Expression in the Gitr Locus Is Regulated by NF-?B and Foxp3 through an Enhancer," J Immunol. 2014;192(8):3915-3924.

Triplett et al., "STAT3 Signaling Is Required for Optimal Regression of Large Established Tumors in Mice Treated with Anti-OX40 and TGF? Receptor Blockade," Cancer Immunol Res. 2015;3(5):526-35.

Twohig et al., "The death receptor 3/TL1A pathway is essential for efficient development of antiviral CD4+ and CD8+ T-cell immunity," FASEB J. 2012;26(8):3575-3586.

Ukyo et al., "Costimulation through OX40 is crucial for induction of an alloreactive human T-cell response," Immunology. 2003;109(2):226-231.

Vesely et al., "Natural innate and adaptive immunity to cancer," Annu Rev Immunol. 2011;29:235-71.

(56) References Cited

OTHER PUBLICATIONS

Voo et al., "Antibodies targeting human OX40 expand effector T cells and block inducible and natural regulatory T cell function," J Immunol. 2013;191(7):3641-50.

Waight et al., "Cutting edge: epigenetic regulation of Foxp3 defines a stable population of CD4+ regulatory T cells in tumors from mice and humans," J Immunol. 2015;194(3):878-82.

Watanabe et al., "Combination of adoptive cell transfer and antibody injection can eradicate established tumors in mice—an in vivo study using anti-OX40mAb, anti-CD25mAb and anti-CTLA4mAb—," Immunopharmacol Immunotoxicol. 2010;32(2):238-45.

Weinberg et al., "Anti-OX40 (CD134) administration to nonhuman primates: immunostimulatory effects and toxicokinetic study," J Immunother. 2006;29(6):575-85.

Weinberg et al., "Blocking OX-40/OX-40 ligand interaction in vitro and in vivo leads to decreased T cell function and amelioration of experimental allergic encephalomyelitis," J Immunol. 1999;162(3):1818-26.

Weinberg et al., "Engagement of the OX-40 receptor in vivo enhances antitumor immunity," J Immunol. 2000;164(4):2160-9.

Weinberg et al., "Science gone translational: the OX40 agonist story," Immunol Rev. 2011;244(1):218-31.

Weinberg et al., "Selective depletion of myelin-reactive T cells with the anti-OX-40 antibody ameliorates autoimmune encephalomyelitis," Nat Med. 1996;2(2):183-9.

Weixler et al., "OX40 expression enhances the prognostic significance of CD8 positive lymphocyte infiltration in colorectal cancer," Oncotarget. 2015;6(35):37588-37599.

Wilson et al., "An Fcgamma Receptor-Dependent mechanism Drives Antibody-Mediated Target-Receptor Signaling in Cancer Cells," Cancer Cell. 2011;19(1):101-13.

Wolf et al., "A whole blood in vitro cytokine release assay with aqueous monoclonal antibody presentation for the prediction of therapeutic protein induced cytokine release syndrome in humans," Cytokine. 2012;60(3):828-37.

Wu et al., "The effect of OX40/OX40L and CD27/CD70 pathways on allogeneic islet graft rejection," Transplant Proc. 2001;33(1-2):217-8.

Xiao et al., "The Costimulatory Receptor OX40 Inhibits Interleukin-17 Expression through Activation of Repressive Chromatin Remodeling Pathways," Immunity. 2016;44(6):1271-83.

Xie et al., "Characterization and application of two novel monoclonal antibodies against human OX40: costimulation of T cells and expression on tumor as well as normal gland tissues," Tissue Antigens. 2006;67(4):307-17.

Xie, "TRAF molecules in cell signaling and in human diseases," J mol Signal. 2013;8(1):7.

Yao et al., "Advances in targeting cell surface signalling molecules for immune modulation," Nat Rev Drug Discov. 2013;12(2):130-46.

Yu et al., "Combinational Immunotherapy with Allo-DRibble Vaccines and Anti-OX40 Co-Stimulation Leads to Generation of Cross-Reactive Effector T Cells and Tumor Regression," Sci Rep. 2016;6:37558.

Zhang et al., "Fc Engineering Approaches to Enhance the Agonism and Effector Functions of an Anti-OX40 Antibody," J Biol Chem. 2016;291(53):27134-27146.

Bruhn, "Properties of mouse and human IgG receptors and their contribution to disease models," Blood. 2012;119(24):5640-9.

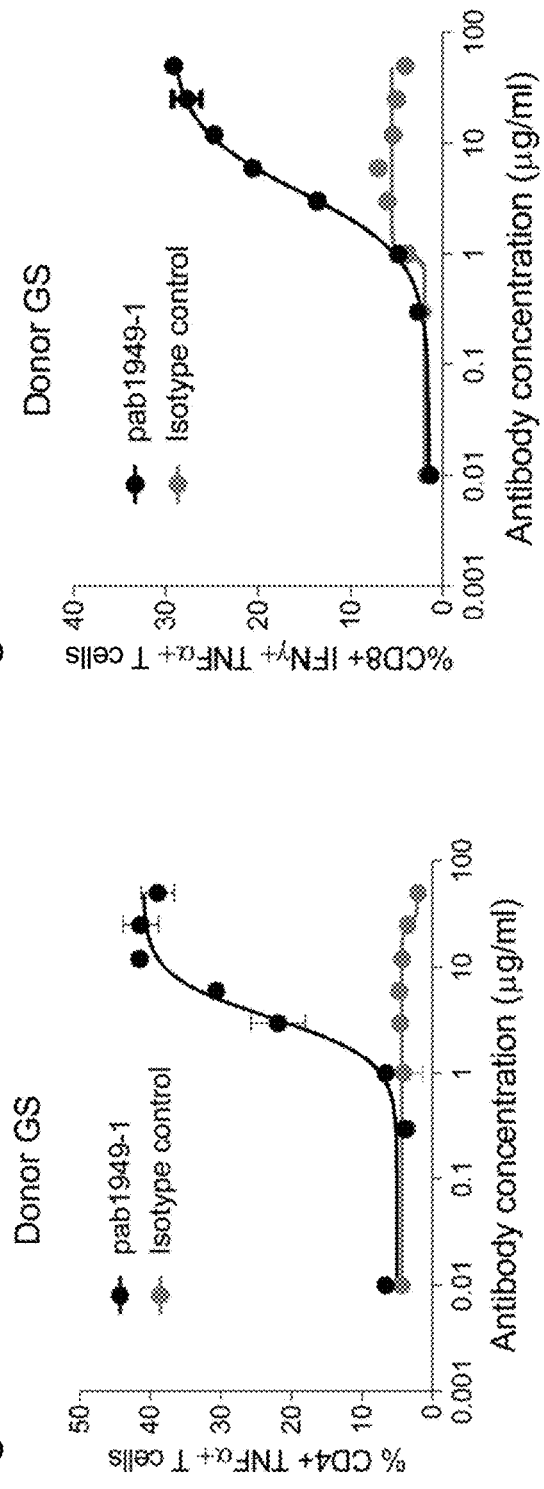
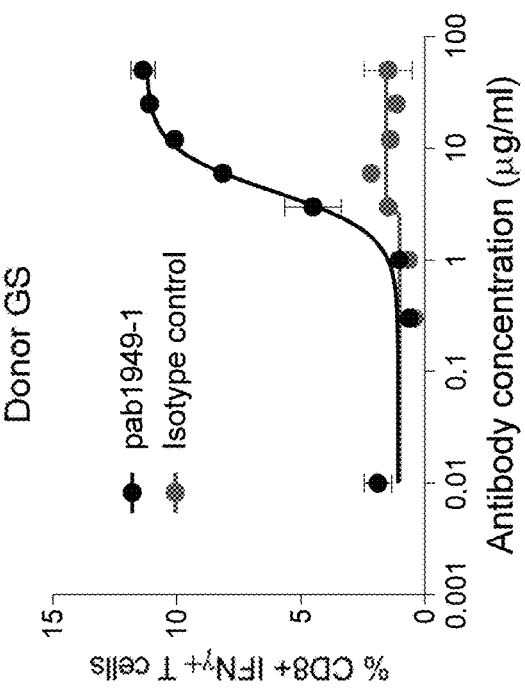
Figure 3D
Figure 3E
Figure 3F

Figure 14D

| Indication | Samples (n) | CD4+ cells | Regulatory T cells |
|---|---|---|---|
| NSCLC | 4 | +/- | +++ |
| Endometrial | 2 | +/- | +++ |
| Colorectal | 2 | - | + |
| Breast | 2 | - | + |
| Ovarian | 1 | - | ++ |
| Renal | 1 | - | + |

Figure 21

| | pab1949-1 | pab1928 |
|---|---|---|
| W58A | - | - |
| N60A | - | + |
| R62A | - | + |
| R80A | - | + |
| L88A | - | + |
| P93A | - | + |
| P99A | - | + |
| P115A | - | + |

SEQUENCE LISTING

```
<160> NUMBER OF SEQ ID NOS: 72

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide

<400> SEQUENCE: 1

Arg Ser Ser Gln Ser Leu Leu His Ser Asn Gly Tyr Asn Tyr Leu Asp
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Leu Gly Ser Asn Arg Ala Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 3

Met Gln Ala Leu Gln Thr Pro Leu Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Gly Ser Ala Met His
1               5

<210> SEQ ID NO 5
<211> LENGTH: 19
<212> TYPE: PRT
<213> ORGANISM: Artificial Sequence
<220> FEATURE:
<223> OTHER INFORMATION: Synthetic peptide

<400> SEQUENCE: 5

Arg Ile Arg Ser Lys Ala Asn Ser Tyr Ala Thr Ala Tyr Ala Ala Ser
1               5                   10                  15

Val Lys Gly

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Gly Ile Tyr Asp Ser Ser Gly Tyr Asp Tyr
1               5                   10

<210> SEQ ID NO 7
<211> LENGTH: 23
<212> TYPE: PRT
<213> ORGANISM: Artificial Sequence
<220> FEATURE:
<223> OTHER INFORMATION: Synthetic peptide

<400> SEQUENCE: 7

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide

<400> SEQUENCE: 8

Trp Tyr Leu Gln Lys Pro Gly Gln Ser Pro Gln Leu Leu Ile Tyr
1               5                   10                  15

<210> SEQ ID NO 9
<211> LENGTH: 32
<212> TYPE: PRT
```

```
<213> ORGANISM: Artificial Sequence
<220> FEATURE:
<223> OTHER INFORMATION: Synthetic peptide

<400> SEQUENCE: 9

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

Phe Gly Gly Gly Thr Lys Val Glu Ile Lys
1               5                   10

<210> SEQ ID NO 11
<211> LENGTH: 30
<212> TYPE: PRT
<213> ORGANISM: Artificial Sequence
<220> FEATURE:
<223> OTHER INFORMATION: Synthetic peptide

<400> SEQUENCE: 11

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser
            20                  25                  30

<210> SEQ ID NO 12
<211> LENGTH: 14
<212> TYPE: PRT
<213> ORGANISM: Artificial Sequence
<220> FEATURE:
<223> OTHER INFORMATION: Synthetic peptide

<400> SEQUENCE: 12

Trp Val Arg Gln Ala Ser Gly Lys Gly Leu Glu Trp Val Gly
1               5                   10

<210> SEQ ID NO 13
<211> LENGTH: 32
<212> TYPE: PRT
<213> ORGANISM: Artificial Sequence
<220> FEATURE:
<223> OTHER INFORMATION: Synthetic peptide

<400> SEQUENCE: 13

Arg Phe Thr Ile Ser Arg Asp Asp Ser Lys Asn Thr Ala Tyr Leu Gln
1               5                   10                  15

Met Asn Ser Leu Lys Thr Glu Asp Thr Ala Val Tyr Tyr Cys Thr Ser
            20                  25                  30

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide
```

<400> SEQUENCE: 14

Trp Gly Gln Gly Thr Leu Val Thr Val Ser Ser
1               5                   10

<210> SEQ ID NO 15
<211> LENGTH: 112
<212> TYPE: PRT
<213> ORGANISM: Artificial Sequence
<220> FEATURE:
<223> OTHER INFORMATION: Synthetic peptide

<400> SEQUENCE: 15

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 16
<211> LENGTH: 121
<212> TYPE: PRT
<213> ORGANISM: Artificial Sequence
<220> FEATURE:
<223> OTHER INFORMATION: Synthetic peptide

<400> SEQUENCE: 16

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser
        115                 120

<210> SEQ ID NO 17
<211> LENGTH: 277
<212> TYPE: PRT
<213> ORGANISM: Homo sapiens

<400> SEQUENCE: 17

```
Met Cys Val Gly Ala Arg Arg Leu Gly Arg Gly Pro Cys Ala Ala Leu
1               5                   10                  15
Leu Leu Leu Gly Leu Gly Leu Ser Thr Val Thr Gly Leu His Cys Val
                20                  25                  30
Gly Asp Thr Tyr Pro Ser Asn Asp Arg Cys Cys His Glu Cys Arg Pro
            35                  40                  45
Gly Asn Gly Met Val Ser Arg Cys Ser Arg Ser Gln Asn Thr Val Cys
        50                  55                  60
Arg Pro Cys Gly Pro Gly Phe Tyr Asn Asp Val Val Ser Ser Lys Pro
65                  70                  75                  80
Cys Lys Pro Cys Thr Trp Cys Asn Leu Arg Ser Gly Ser Glu Arg Lys
                85                  90                  95
Gln Leu Cys Thr Ala Thr Gln Asp Thr Val Cys Arg Cys Arg Ala Gly
                100                 105                 110
Thr Gln Pro Leu Asp Ser Tyr Lys Pro Gly Val Asp Cys Ala Pro Cys
            115                 120                 125
Pro Pro Gly His Phe Ser Pro Gly Asp Asn Gln Ala Cys Lys Pro Trp
        130                 135                 140
Thr Asn Cys Thr Leu Ala Gly Lys His Thr Leu Gln Pro Ala Ser Asn
145                 150                 155                 160
Ser Ser Asp Ala Ile Cys Glu Asp Arg Asp Pro Pro Ala Thr Gln Pro
                165                 170                 175
Gln Glu Thr Gln Gly Pro Pro Ala Arg Pro Ile Thr Val Gln Pro Thr
                180                 185                 190
Glu Ala Trp Pro Arg Thr Ser Gln Gly Pro Ser Thr Arg Pro Val Glu
            195                 200                 205
Val Pro Gly Gly Arg Ala Val Ala Ala Ile Leu Gly Leu Gly Leu Val
        210                 215                 220
Leu Gly Leu Leu Gly Pro Leu Ala Ile Leu Leu Ala Leu Tyr Leu Leu
225                 230                 235                 240
Arg Arg Asp Gln Arg Leu Pro Pro Asp Ala His Lys Pro Pro Gly Gly
                245                 250                 255
Gly Ser Phe Arg Thr Pro Ile Gln Glu Glu Gln Ala Asp Ala His Ser
                260                 265                 270
Thr Leu Ala Lys Ile
            275
```

<210> SEQ ID NO 18
<211> LENGTH: 100
<212> TYPE: PRT
<213> ORGANISM: Artificial Sequence
<220> FEATURE:
<223> OTHER INFORMATION: Synthetic peptide

<400> SEQUENCE: 18

```
Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
                20                  25                  30
Asn Gly Tyr Asn Tyr Leu Asp Trp Tyr Leu Gln Lys Pro Gly Gln Ser
            35                  40                  45
Pro Gln Leu Leu Ile Tyr Leu Gly Ser Asn Arg Ala Ser Gly Val Pro
        50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro
            100

<210> SEQ ID NO 19
<211> LENGTH: 100
<212> TYPE: PRT
<213> ORGANISM: Artificial Sequence
<220> FEATURE:
<223> OTHER INFORMATION: Synthetic peptide

<400> SEQUENCE: 19

Glu Val Gln Leu Val Glu Ser Gly Gly Gly Leu Val Gln Pro Gly Gly
  1               5                  10                  15

Ser Leu Lys Leu Ser Cys Ala Ala Ser Gly Phe Thr Phe Ser Gly Ser
                 20                  25                  30

Ala Met His Trp Val Arg Gln Ala Ser Gly Lys Gly Leu Glu Trp Val
             35                  40                  45

Gly Arg Ile Arg Ser Lys Ala Asn Ser Tyr Ala Thr Ala Tyr Ala Ala
 50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Arg
            100

<210> SEQ ID NO 20
<211> LENGTH: 219
<212> TYPE: PRT
<213> ORGANISM: Artificial Sequence
<220> FEATURE:
<223> OTHER INFORMATION: Synthetic peptide

<400> SEQUENCE: 20

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 21
<211> LENGTH: 451
<212> TYPE: PRT
<213> ORGANISM: Artificial Sequence
<220> FEATURE:
<223> OTHER INFORMATION: Synthetic peptide

<400> SEQUENCE: 21

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 22

<400> SEQUENCE: 22

000

<210> SEQ ID NO 23
<211> LENGTH: 448
<212> TYPE: PRT
<213> ORGANISM: Artificial Sequence
<220> FEATURE:
<223> OTHER INFORMATION: Synthetic peptide

<400> SEQUENCE: 23

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160
```

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 24
<211> LENGTH: 107
<212> TYPE: PRT
<213> ORGANISM: Artificial Sequence
<220> FEATURE:
<223> OTHER INFORMATION: Synthetic peptide

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105
```

<210> SEQ ID NO 25
<211> LENGTH: 107
<212> TYPE: PRT
<213> ORGANISM: Artificial Sequence
<220> FEATURE:
<223> OTHER INFORMATION: Synthetic peptide

<400> SEQUENCE: 25

```
Arg Ser Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 26
<211> LENGTH: 118
<212> TYPE: PRT
<213> ORGANISM: Artificial Sequence
<220> FEATURE:
<223> OTHER INFORMATION: Synthetic peptide

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Ser Gly Trp Tyr Leu Phe Asp Tyr Trp Gly Gln Gly Thr
            100                 105                 110

Leu Val Thr Val Ser Ser
        115
```

<210> SEQ ID NO 27

<400> SEQUENCE: 27

000

```
<210> SEQ ID NO 28
<211> LENGTH: 107
<212> TYPE: PRT
<213> ORGANISM: Artificial Sequence
<220> FEATURE:
<223> OTHER INFORMATION: Synthetic peptide

<400> SEQUENCE: 28

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 29

<400> SEQUENCE: 29

000

<210> SEQ ID NO 30
<211> LENGTH: 119
<212> TYPE: PRT
<213> ORGANISM: Artificial Sequence
<220> FEATURE:
<223> OTHER INFORMATION: Synthetic peptide

<400> SEQUENCE: 30

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Ser Val Thr Val Ser Ser
        115

<210> SEQ ID NO 31

<400> SEQUENCE: 31

000
```

```
<210> SEQ ID NO 32
<211> LENGTH: 330
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (97)..(97)
<223> OTHER INFORMATION: can be Lysine or Arginine
<220> FEATURE:
<221> NAME/KEY: MISC_FEATURE
<222> LOCATION: (239)..(239)
<223> OTHER INFORMATION: can be Aspartic Acid or Glutamic Acid
<220> FEATURE:
<221> NAME/KEY: MISC_FEATURE
<222> LOCATION: (241)..(241)
<223> OTHER INFORMATION: can be Leucine or Methionine
<220> FEATURE:
<221> NAME/KEY: MISC_FEATURE
<222> LOCATION: (314)..(314)
<223> OTHER INFORMATION: can be Glycine or Alanine

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Xaa Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Xaa Glu
225                 230                 235                 240

Xaa Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Xaa Leu His Asn His Tyr Thr
305                 310                 315                 320

Gln Lys Ser Leu Ser Leu Ser Pro Gly Lys
                325                 330

<210> SEQ ID NO 33
<211> LENGTH: 330
<212> TYPE: PRT
<213> ORGANISM: Artificial Sequence
<220> FEATURE:
<223> OTHER INFORMATION: Synthetic peptide

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

```
Gln Lys Ser Leu Ser Leu Ser Pro Gly Lys
            325                 330

<210> SEQ ID NO 34
<211> LENGTH: 330
<212> TYPE: PRT
<213> ORGANISM: Artificial Sequence
<220> FEATURE:
<223> OTHER INFORMATION: Synthetic peptide

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 35
```

<211> LENGTH: 330
<212> TYPE: PRT
<213> ORGANISM: Artificial Sequence
<220> FEATURE:
<223> OTHER INFORMATION: Synthetic peptide

<400> SEQUENCE: 35

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Gly Leu His Asn His Tyr Thr
305                 310                 315                 320

Gln Lys Ser Leu Ser Leu Ser Pro Gly Lys
                325                 330
```

<210> SEQ ID NO 36
<211> LENGTH: 327
<212> TYPE: PRT
<213> ORGANISM: Artificial Sequence
<220> FEATURE:
<223> OTHER INFORMATION: Synthetic peptide

<400> SEQUENCE: 36

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Ser Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 37
<211> LENGTH: 327
<212> TYPE: PRT
<213> ORGANISM: Artificial Sequence
<220> FEATURE:
<223> OTHER INFORMATION: Synthetic peptide

<400> SEQUENCE: 37

Ala Ser Thr Lys Gly Pro Ser Val Phe Pro Leu Ala Pro Cys Ser Arg
1               5                   10                  15

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 38
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (46)..(46)
<223> OTHER INFORMATION: can be Valine or Alanine
<220> FEATURE:
<221> NAME/KEY: MISC_FEATURE
<222> LOCATION: (84)..(84)
<223> OTHER INFORMATION: can be Leucine or Valine

<400> SEQUENCE: 38
```

```
Arg Thr Val Ala Ala Pro Ser Val Phe Ile Phe Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Xaa Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Xaa Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 39
<211> LENGTH: 107
<212> TYPE: PRT
<213> ORGANISM: Artificial Sequence
<220> FEATURE:
<223> OTHER INFORMATION: Synthetic peptide

<400> SEQUENCE: 39

```
Arg Thr Val Ala Ala Pro Ser Val Phe Ile Phe Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Val Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 40
<211> LENGTH: 107
<212> TYPE: PRT
<213> ORGANISM: Artificial Sequence
<220> FEATURE:
<223> OTHER INFORMATION: Synthetic peptide

<400> SEQUENCE: 40

```
Arg Thr Val Ala Ala Pro Ser Val Phe Ile Phe Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95
```

```
Pro Val Thr Lys Ser Phe Asn Arg Gly Glu Cys
            100                 105

<210> SEQ ID NO 41
<211> LENGTH: 107
<212> TYPE: PRT
<213> ORGANISM: Artificial Sequence
<220> FEATURE:
<223> OTHER INFORMATION: Synthetic peptide

<400> SEQUENCE: 41

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 42
<211> LENGTH: 183
<212> TYPE: PRT
<213> ORGANISM: Homo sapiens

<400> SEQUENCE: 42

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180
```

```
<210> SEQ ID NO 43
<211> LENGTH: 133
<212> TYPE: PRT
<213> ORGANISM: Homo sapiens

<400> SEQUENCE: 43

Met Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 44
<211> LENGTH: 11
<212> TYPE: PRT
<213> ORGANISM: Artificial Sequence
<220> FEATURE:
<223> OTHER INFORMATION: Synthetic peptide

<400> SEQUENCE: 44

Gln Ser Leu Leu His Ser Asn Gly Tyr Asn Tyr
1               5                   10

<210> SEQ ID NO 45
<211> LENGTH: 3
<212> TYPE: PRT
<213> ORGANISM: Artificial Sequence
<220> FEATURE:
<223> OTHER INFORMATION: Synthetic peptide

<400> SEQUENCE: 45

Leu Gly Ser
1

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide

<400> SEQUENCE: 46

Met Gln Ala Leu Gln Thr Pro Leu Thr
1               5

<210> SEQ ID NO 47
<211> LENGTH: 8
<212> TYPE: PRT
<213> ORGANISM: Artificial Sequence
```

```
<220> FEATURE:
<223> OTHER INFORMATION: Synthetic peptide

<400> SEQUENCE: 47

Gly Phe Thr Phe Ser Gly Ser Ala
1               5

<210> SEQ ID NO 48
<211> LENGTH: 10
<212> TYPE: PRT
<213> ORGANISM: Artificial Sequence
<220> FEATURE:
<223> OTHER INFORMATION: Synthetic peptide

<400> SEQUENCE: 48

Ile Arg Ser Lys Ala Asn Ser Tyr Ala Thr
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic peptide

<400> SEQUENCE: 49

Thr Ser Gly Ile Tyr Asp Ser Ser Gly Tyr Asp Tyr
1               5                   10

<210> SEQ ID NO 50
<211> LENGTH: 219
<212> TYPE: PRT
<213> ORGANISM: Artificial Sequence
<220> FEATURE:
<223> OTHER INFORMATION: Synthetic peptide

<400> SEQUENCE: 50

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Ser Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 51
<211> LENGTH: 447
<212> TYPE: PRT
<213> ORGANISM: Artificial Sequence
<220> FEATURE:
<223> OTHER INFORMATION: Synthetic peptide

<400> SEQUENCE: 51

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

```
Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 52
<211> LENGTH: 447
<212> TYPE: PRT
<213> ORGANISM: Artificial Sequence
<220> FEATURE:
<223> OTHER INFORMATION: Synthetic peptide

<400> SEQUENCE: 52

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Asp Val Ser His Glu Asp Pro Glu
        260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 53
<211> LENGTH: 326
<212> TYPE: PRT
<213> ORGANISM: Artificial Sequence
<220> FEATURE:
<223> OTHER INFORMATION: Synthetic peptide

<400> SEQUENCE: 53

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175
```

```
Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 54
<211> LENGTH: 326
<212> TYPE: PRT
<213> ORGANISM: Artificial Sequence
<220> FEATURE:
<223> OTHER INFORMATION: Synthetic peptide

<400> SEQUENCE: 54

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205
```

```
Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 55
<211> LENGTH: 249
<212> TYPE: PRT
<213> ORGANISM: Homo sapiens

<400> SEQUENCE: 55

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala Ile Leu Gly
            180                 185                 190

Leu Gly Leu Val Leu Gly Leu Leu Gly Pro Leu Ala Ile Leu Leu Ala
        195                 200                 205

Leu Tyr Leu Leu Arg Arg Asp Gln Arg Leu Pro Pro Asp Ala His Lys
    210                 215                 220

Pro Pro Gly Gly Gly Ser Phe Arg Thr Pro Ile Gln Glu Glu Gln Ala
225                 230                 235                 240
```

Asp Ala His Ser Thr Leu Ala Lys Ile
            245

<210> SEQ ID NO 56
<211> LENGTH: 122
<212> TYPE: PRT
<213> ORGANISM: Artificial Sequence
<220> FEATURE:
<223> OTHER INFORMATION: Synthetic peptide

<400> SEQUENCE: 56

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Ser Met His Trp Val Arg Gln Ala Pro Gly Gln Gly Leu Lys Trp Met
            35                  40                  45

Gly Trp Ile Asn Thr Glu Thr Gly Glu Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
                100                 105                 110

Gly Gln Gly Thr Thr Val Thr Val Ser Ser
            115                 120

<210> SEQ ID NO 57
<211> LENGTH: 107
<212> TYPE: PRT
<213> ORGANISM: Artificial Sequence
<220> FEATURE:
<223> OTHER INFORMATION: Synthetic peptide

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Leu Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Arg
                85                  90                  95

Thr Phe Gly Gln Gly Thr Lys Leu Glu Ile Lys
                100                 105

<210> SEQ ID NO 58
<211> LENGTH: 452
<212> TYPE: PRT
<213> ORGANISM: Artificial Sequence
<220> FEATURE:
<223> OTHER INFORMATION: Synthetic peptide

<400> SEQUENCE: 58

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

```
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 59
<211> LENGTH: 214
<212> TYPE: PRT
<213> ORGANISM: Artificial Sequence
<220> FEATURE:
<223> OTHER INFORMATION: Synthetic peptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Leu Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Arg
                85                  90                  95

Thr Phe Gly Gln Gly Thr Lys Leu Glu Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 60
<211> LENGTH: 450
<212> TYPE: PRT
<213> ORGANISM: Artificial Sequence
<220> FEATURE:
<223> OTHER INFORMATION: Synthetic peptide

<400> SEQUENCE: 60

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30
```

```
Ala Met His Trp Val Arg Gln Ala Ser Gly Lys Gly Leu Glu Trp Val
        35                  40                  45
Gly Arg Ile Arg Ser Lys Ala Asn Ser Tyr Ala Thr Ala Tyr Ala Ala
    50                  55                  60
Ser Val Lys Gly Arg Phe Thr Ile Ser Arg Asp Asp Ser Lys Asn Thr
65                  70                  75                  80
Ala Tyr Leu Gln Met Asn Ser Leu Lys Thr Glu Asp Thr Ala Val Tyr
                85                  90                  95
Tyr Cys Thr Ser Gly Ile Tyr Asp Ser Ser Gly Tyr Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
```

Pro Gly
    450

<210> SEQ ID NO 61
<211> LENGTH: 447
<212> TYPE: PRT
<213> ORGANISM: Artificial Sequence
<220> FEATURE:
<223> OTHER INFORMATION: Synthetic peptide

<400> SEQUENCE: 61

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

```
Pro Pro Ser Gln Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
                420                 425                 430
Leu His Asn His Tyr Thr Gln Lys Ser Leu Ser Leu Ser Leu Gly
            435                 440                 445

<210> SEQ ID NO 62
<211> LENGTH: 446
<212> TYPE: PRT
<213> ORGANISM: Artificial Sequence
<220> FEATURE:
<223> OTHER INFORMATION: Synthetic peptide

<400> SEQUENCE: 62

Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Thr Phe Ser Gly Ser
            20                  25                  30
Ala Met His Trp Val Arg Gln Ala Ser Gly Lys Gly Leu Glu Trp Val
        35                  40                  45
Gly Arg Ile Arg Ser Lys Ala Asn Ser Tyr Ala Thr Ala Tyr Ala Ala
    50                  55                  60
Ser Val Lys Gly Arg Phe Thr Ile Ser Arg Asp Asp Ser Lys Asn Thr
65                  70                  75                  80
Ala Tyr Leu Gln Met Asn Ser Leu Lys Thr Glu Asp Thr Ala Val Tyr
                85                  90                  95
Tyr Cys Thr Ser Gly Ile Tyr Asp Ser Ser Gly Tyr Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Asn Phe Gly Thr Gln Thr Tyr Thr Cys Asn Val Asp His
        195                 200                 205
Lys Pro Ser Asn Thr Lys Val Asp Lys Thr Val Glu Arg Lys Cys Cys
    210                 215                 220
Val Glu Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
```

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 63
<211> LENGTH: 446
<212> TYPE: PRT
<213> ORGANISM: Artificial Sequence
<220> FEATURE:
<223> OTHER INFORMATION: Synthetic peptide

<400> SEQUENCE: 63

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

```
Pro Ser Ser Asn Phe Gly Thr Gln Thr Tyr Thr Cys Asn Val Asp His
            195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 64
<211> LENGTH: 329
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (97)..(97)
<223> OTHER INFORMATION: X is K or R
<220> FEATURE:
<221> NAME/KEY: MISC_FEATURE
<222> LOCATION: (239)..(239)
<223> OTHER INFORMATION: X is D or E
<220> FEATURE:
<221> NAME/KEY: MISC_FEATURE
<222> LOCATION: (241)..(241)
<223> OTHER INFORMATION: X is L or M
<220> FEATURE:
<221> NAME/KEY: MISC_FEATURE
<222> LOCATION: (314)..(314)
<223> OTHER INFORMATION: X is G or A

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Xaa Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Xaa Glu
225                 230                 235                 240

Xaa Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Xaa Leu His Asn His Tyr Thr
305                 310                 315                 320

Gln Lys Ser Leu Ser Leu Ser Pro Gly
                325

<210> SEQ ID NO 65
<211> LENGTH: 329
<212> TYPE: PRT
<213> ORGANISM: Artificial Sequence
<220> FEATURE:
<223> OTHER INFORMATION: Synthetic Peptide

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 66
<211> LENGTH: 329
<212> TYPE: PRT
<213> ORGANISM: Artificial Sequence
<220> FEATURE:
<223> OTHER INFORMATION: Synthetic Peptide

<400> SEQUENCE: 66

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95
```

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 67
<211> LENGTH: 329
<212> TYPE: PRT
<213> ORGANISM: Artificial Sequence
<220> FEATURE:
<223> OTHER INFORMATION: Synthetic Peptide

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

```
Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Gly Leu His Asn His Tyr Thr
305                 310                 315                 320

Gln Lys Ser Leu Ser Leu Ser Pro Gly
                325

<210> SEQ ID NO 68
<211> LENGTH: 326
<212> TYPE: PRT
<213> ORGANISM: Artificial Sequence
<220> FEATURE:
<223> OTHER INFORMATION: Synthetic Peptide

<400> SEQUENCE: 68

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Ser Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 69
<211> LENGTH: 326
<212> TYPE: PRT
<213> ORGANISM: Artificial Sequence
<220> FEATURE:
<223> OTHER INFORMATION: Synthetic Peptide

<400> SEQUENCE: 69

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

-continued

```
Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 70
<211> LENGTH: 325
<212> TYPE: PRT
<213> ORGANISM: Artificial Sequence
<220> FEATURE:
<223> OTHER INFORMATION: Synthetic Peptide

<400> SEQUENCE: 70

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220
```

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
            325

<210> SEQ ID NO 71
<211> LENGTH: 325
<212> TYPE: PRT
<213> ORGANISM: Artificial Sequence
<220> FEATURE:
<223> OTHER INFORMATION: Synthetic Peptide

<400> SEQUENCE: 71

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255
```

```
Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 72
<211> LENGTH: 451
<212> TYPE: PRT
<213> ORGANISM: Artificial Sequence
<220> FEATURE:
<223> OTHER INFORMATION: Synthetic Peptide

<400> SEQUENCE: 72

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285
```

-continued

```
Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450
```

VECTORS COMPRISING NUCLEIC ACIDS ENCODING ANTI-OX40 ANTIBODIES

RELATED APPLICATIONS

This application is a continuation of U.S. patent application Ser. No. 16/384,116, filed Apr. 15, 2019, which is a division of U.S. patent application Ser. No. 15/148,720, filed May 6, 2016, now U.S. Pat. No. 10,259,882, which claims the benefit of U.S. Provisional Patent Application Ser. No. 62/323,458, filed Apr. 15, 2016; 62/262,373, filed Dec. 2, 2015; 62/161,198, filed May 13, 2015; and 62/158,515, filed May 7, 2015, the entire disclosures of which are hereby incorporated herein by reference in their entirety.

SEQUENCE LISTING

The instant application contains a sequence listing which has been submitted electronically in ASCII format and is hereby incorporated by reference in its entirety (said ASCII copy, created on Feb. 2, 2020, is named 701925_AGBW-132DIVCON_ST25.txt and is 121,015 bytes in size).

1. FIELD

The present disclosure relates to antibodies that specifically bind to human OX40 receptor ("OX40"), compositions comprising such antibodies, and methods of producing and using antibodies that specifically bind to OX40.

2. BACKGROUND

The contributions of the innate and adaptive immune response in the control of human tumor growth are well-characterized (Vesely M D et al., (2011) Annu Rev Immunol 29: 235-271). As a result, antibody-based strategies have emerged that aim to enhance T cell responses for the purpose of cancer therapy, such as targeting T cell expressed stimulatory receptors with agonist antibodies, or inhibitory receptors with functional antagonists (Mellman I et al., (2011) Nature 480: 480-489). Antibody-mediated agonist and antagonist approaches have shown preclinical, and more recently clinical, activity. An important stimulatory receptor that modulates T cell, Natural Killer T (NKT) cell, and NK cell function is the OX40 receptor (also known as OX40, CD134, TNRSF4, TXGP1L, ACT35, and ACT-4) (Sugamura K et al., (2004) Nat Rev Immunol 4: 420-431). OX40 is a member of the tumor necrosis factor receptor superfamily (TNFRSF) and signaling via OX40 can modulate important immune functions.

OX40 can be upregulated by antigen-specific T cells following T cell receptor (TCR) stimulation by professional antigen presenting cells (APCs) displaying MHC class I or II molecules loaded with a cognate peptide (Sugamura K et al., (2004) Nat Rev Immunol 4: 420-431). Upon maturation APCs such as dendritic cells (DCs) upregulate stimulatory B7 family members (e.g., CD80 and CD86), as well as accessory co-stimulatory molecules including OX40 ligand (OX40L), which help to sculpt the kinetics and magnitude of the T cell immune response, as well as effective memory cell differentiation. Notably, other cell types can also express constitutive and/or inducible levels of OX40L such as B cells, vascular endothelial cells, mast cells, and in some instances activated T cells (Soroosh P et al., (2006) J Immunol 176: 5975-5987). OX40:OX40L co-engagement is believed to drive the higher order clustering of receptor trimers and subsequent signal transduction (Compaan D M et al., (2006) Structure 14: 1321-1330).

OX40 expression by T cells within the tumor microenvironment has been observed in murine and human tumor tissues (Bulliard Y et al., (2014) Immunol Cell Biol 92: 475-480 and Piconese S et al., (2014) Hepatology 60: 1494-1507). OX40 is highly expressed by intratumoral populations of regulatory T cells (Tregs) relative to conventional T cell populations, a feature attributed to their proliferative status (Waight J D et al., (2015) J Immunol 194: 878-882 and Bulliard Y et al., (2014) Immunol Cell Biol 92: 475-480). Early studies demonstrated that OX40 agonist antibodies were able to elicit tumor rejection in mouse models (Weinberg A D et al., (2000) J Immunol 164: 2160-2169 and Piconese S et al., (2008) J Exp Med 205: 825-839). A mouse antibody that agonizes human OX40 signaling has also been shown to enhance immune functions in cancer patients (Curti B D et al., (2013) Cancer Res 73: 7189-7198).

OX40 and OX40L interactions also have been associated with immune responses in inflammatory and autoimmune diseases and disorders, including mouse models of asthma/atopy, encephalomyelitis, rheumatoid arthritis, colitis/inflammatory bowel disease, graft-versus-host disease (e.g., transplant rejection), diabetes in non-obese diabetic mice, and atherosclerosis (Croft M et al., (2009) Immunol Rev 229(1): 173-191, and references cited therein). Reduced symptomatology associated with the diseases and disorders has been reported in OX40- and OX40L-deficient mice, in mice receiving anti-OX40 liposomes loaded with a cytostatic drug, and in mice in which OX40 and OX40L interactions were blocked with an anti-OX40L blocking antibody or a recombinant OX40 fused to the Fc portion of human immunoglobulin (Croft M et al.; Boot E P J et al., (2005) Arthritis Res Ther 7: R604-615; Weinberg A D et al., (1999) J Immunol 162: 1818-1826). Treatment with a blocking anti-OX40L antibody was also shown to inhibit Th2 inflammation in a rhesus monkey model of asthma (Croft M et al.; Seshasayee D et al., (2007) J Clin Invest 117: 3868-3878). Additionally, polymorphisms in OX40L have been associated with lupus (Croft M et al.).

Given the role of human OX40 in modulating immune responses, provided herein are antibodies that specifically bind to OX40 and the use of these antibodies to modulate OX40 activity.

3. SUMMARY

In one aspect, provided herein are antibodies that specifically bind to OX40 (e.g., human OX40).

In one embodiment, an antibody that specifically binds to OX40 comprises a heavy chain variable region (VH) CDR1 comprising the VH CDR1 in SEQ ID NO: 16, a VH CDR2 comprising the VH CDR2 in SEQ ID NO: 16, a VH CDR3 comprising the VH CDR3 in SEQ ID NO: 16, a light chain variable region (VL) CDR1 comprising the VL CDR1 in SEQ ID NO: 15, a VL CDR2 comprising the VL CDR2 in SEQ ID NO: 15, and a VL CDR3 comprising the VL CDR3 in SEQ ID NO: 15, wherein each CDR is defined in accordance with the Kabat definition, the Chothia definition, the combination of the Kabat definition and the Chothia definition, the IMGT numbering system, the AbM definition, or the contact definition of CDR.

In one embodiment, an antibody that specifically binds to OX40 comprises (a) a heavy chain variable region comprising a heavy chain complementarity determine region 1 (CDR1) comprising the amino acid sequence of GSAMH (SEQ ID NO: 4); a heavy chain CDR2 comprising the amino acid sequence of RIRSKANSYATAYAASVKG (SEQ ID NO: 5); and a heavy chain CDR3 comprising the amino acid sequence of GIYDSSGYDY (SEQ ID NO: 6); and (b) a light chain variable region comprising a light chain CDR1 comprising the amino acid sequence of RSSQSLLHSNGYNYLD (SEQ ID NO: 1); a light chain CDR2 comprising the amino acid sequence of LGSNRAS (SEQ ID NO: 2); and a light chain CDR3 comprising the amino acid sequence of MQALQTPLT (SEQ ID NO: 3).

In one embodiment, an antibody that specifically binds to OX40 comprises (a) a heavy chain variable region comprising a heavy chain CDR1 comprising the amino acid sequence of GFTFSGSA (SEQ ID NO: 47); a heavy chain CDR2 comprising the amino acid sequence of IRSKANSYAT (SEQ ID NO: 48); and a heavy chain CDR3 comprising the amino acid sequence of TSGIYDSSGYDY (SEQ ID NO: 49); and (b) a light chain variable region comprising a light chain CDR1 comprising the amino acid sequence of QSLLHSNGYNY (SEQ ID NO: 44); a light chain CDR2 comprising the amino acid sequence of LGS (SEQ ID NO: 45); and a light chain CDR3 comprising the amino acid sequence of MQALQTPLT (SEQ ID NO: 46).

In one embodiment, the antibody comprises a heavy chain variable region having human or human derived framework regions.

In one embodiment, the antibody comprises a heavy chain variable framework region that is derived from an amino acid sequence encoded by a human gene, wherein said amino acid sequence comprises IGHV3-73*01 (SEQ ID NO: 19).

In one embodiment, the antibody comprises a light chain variable sequence having human or human derived framework regions.

In one embodiment, the antibody comprises a light chain variable framework region that is derived from an amino acid sequence encoded by a human gene, wherein said amino acid sequence comprises IGKV2-28*01 (SEQ ID NO: 18).

In one embodiment, the antibody comprises a heavy chain variable region sequence comprising the amino acid sequence of SEQ ID NO: 16.

In one embodiment, the antibody comprises a heavy chain sequence comprising an amino acid sequence selected from the group consisting of SEQ ID NOs: 21, 23, 51, and 52. In one embodiment, the antibody comprises a heavy chain sequence comprising an amino acid sequence selected from the group consisting of SEQ ID NOs 60-63.

In one embodiment, the antibody comprises a light chain variable region sequence comprising the amino acid sequence of SEQ ID NO: 15.

In one embodiment, the antibody comprises a light chain sequence comprising the amino acid sequence of SEQ ID NO: 20.

In one embodiment, an antibody that specifically binds to OX40 comprises a heavy chain variable region and a light chain variable region, wherein the heavy chain variable region comprises the amino acid sequence of SEQ ID NO: 16.

In one embodiment, an antibody that specifically binds to OX40 comprises a heavy chain variable region and a light chain variable region, wherein the light chain variable region comprises the amino acid sequence of SEQ ID NO: 15.

In one embodiment, an antibody that specifically binds to OX40 comprises a heavy chain variable region comprising the amino acid sequence of SEQ ID NO: 16; and a light chain variable region comprising the amino acid sequence of SEQ ID NO: 15.

In one embodiment, the antibody comprises a heavy chain comprising the amino acid sequence of SEQ ID NO: 21; and a light chain comprising the amino acid sequence of SEQ ID NO: 20. In one embodiment, the antibody comprises a heavy chain comprising the amino acid sequence of SEQ ID NO: 60; and a light chain comprising the amino acid sequence of SEQ ID NO: 20.

In one embodiment, the antibody comprises a heavy chain comprising the amino acid sequence of SEQ ID NO: 23; and a light chain comprising the amino acid sequence of SEQ ID NO: 20. In one embodiment, the antibody comprises a heavy chain comprising the amino acid sequence of SEQ ID NO: 61; and a light chain comprising the amino acid sequence of SEQ ID NO: 20.

In one embodiment, the antibody comprises a heavy chain comprising the amino acid sequence of SEQ ID NO: 51 or 52; and a light chain comprising the amino acid sequence of SEQ ID NO: 20. In one embodiment, the antibody comprises a heavy chain comprising the amino acid sequence of SEQ ID NO: 62 or 63; and a light chain comprising the amino acid sequence of SEQ ID NO: 20.

In one embodiment, the antibody comprises heavy and/or light chain constant regions. In one embodiment, the heavy chain constant region is selected from the group consisting of human immunoglobulins $IgG_1$, $IgG_2$, $IgG_3$, $IgG_4$, $IgA_1$, and $IgA_2$. In one embodiment, the $IgG_1$ is non-fucosylated $IgG_1$. In one embodiment, the amino acid sequence of $IgG_1$ comprises a N297A mutation. In one embodiment, the amino acid sequence of $IgG_1$ comprises a mutation selected from the group consisting of D265A, P329A, and a combination thereof. In one embodiment, the amino acid sequence of $IgG_1$ comprises a N297Q mutation. In one embodiment, the amino acid sequence of $IgG_4$ comprises a S228P mutation. In one embodiment, the amino acid sequence of $IgG_2$ comprises a C127S mutation. In one embodiment, the heavy chain constant region comprises an amino acid sequence selected from the group consisting of SEQ ID NOs: 32-37, 53-54, and 64-71. In one embodiment, the light chain constant region is selected from the group consisting of human immunoglobulins IgGκ and IgGλ.

In one embodiment, the antibody is a human antibody.

In one embodiment, an antibody that specifically binds to OX40 binds to the same epitope of human OX40 as an antibody comprising a VH CDR1 comprising the amino acid sequence of GSAMH (SEQ ID NO: 4); a VH CDR2 comprising the amino acid sequence of RIRSKANSYATAYAASVKG (SEQ ID NO: 5); a VH CDR3 comprising the amino acid sequence of GIYDSSGYDY (SEQ ID NO: 6); a VL CDR1 comprising the amino acid sequence of RSSQSLLHSNGYNYLD (SEQ ID NO: 1); a VL CDR2 comprising the amino acid sequence of LGSNRAS (SEQ ID NO: 2); and a VL CDR3 comprising the amino acid sequence of MQALQTPLT (SEQ ID NO: 3). In one embodiment, an antibody that specifically binds to OX40 binds to the same epitope of human OX40 as an antibody comprising a VH CDR1 comprising the amino acid sequence of GFTFSGSA (SEQ ID NO: 47); a VH CDR2 comprising the amino acid sequence of IRSKANSYAT (SEQ ID NO: 48); a VH CDR3 comprising the amino acid sequence of TSGIYDSSGYDY (SEQ ID NO: 49); a VL CDR1 comprising the amino acid sequence of QSLLHSNGYNY (SEQ ID NO: 44); a VL CDR2 comprising the amino acid sequence of LGS (SEQ ID NO: 45); and a VL CDR3 comprising the amino acid sequence of MQALQTPLT (SEQ ID NO: 46). In one embodiment, an antibody that specifically binds to OX40 binds to the same epitope of human OX40 as an antibody comprising a heavy chain variable region comprising the amino acid sequence of SEQ ID NO: 16; and a light chain variable region comprising the amino acid sequence of SEQ ID NO: 15.

In one embodiment, the antibody is agonistic. In one embodiment, the antibody activates, enhances, or induces an activity of human OX40. In one embodiment, the antibody induces CD4+ T cell proliferation. In one embodiment, the CD4+ T cell proliferation is a substantially increasing function of the concentration of the antibody. In one embodiment, the CD4+ T cell proliferation shows a sigmoidal dose response curve. In one embodiment, the antibody induces production of IL-2, TNFα, IFNγ, IL-4, IL-10, IL-13, or a combination thereof by anti-CD3-stimulated T cells. In one embodiment, the antibody induces production of TNFα, TNFβ, IFNγ, GM-CSF, IL-2, IL-4, IL-10, IL-13, or a combination thereof by anti-CD3-stimulated peripheral blood mononuclear cells (PBMCs). In one embodiment, the antibody induces production of TNFα, TNFβ, IFNγ, GM-CSF, IL-2, IL-10, or IL-13 by anti-CD3-stimulated PBMCs, wherein the production of TNFα, TNFβ, IFNγ, GM-CSF, IL-2, IL-10, or IL-13 is a substantially increasing function of the concentration of the antibody. In one embodiment, the antibody induces production of TNFα, TNFβ, IFNγ, GM-CSF, IL-2, IL-10, or IL-13 by anti-CD3-stimulated PBMCs, wherein the production of TNFα, TNFβ, IFNγ, GM-CSF, IL-2, IL-10, or IL-13 shows a sigmoidal dose response curve. In one embodiment, the antibody induces production of IL-2 by SEA-stimulated T cells and suppresses production of IL-10 by SEA-stimulated T cells. In one embodiment, the antibody induces IL-2 production by SEA-stimulated peripheral blood mononuclear cells (PBMCs) and suppresses IL-2 production by SEA-stimulated PBMCs. In one embodiment, the antibody induces IL-2 production by SEA-stimulated PBMCs, wherein the IL-2 production is a substantially increasing function of the concentration of the antibody. In one embodiment, the antibody the antibody induces IL-2 production by SEA-stimulated PBMCs, wherein the IL-2 production shows a sigmoidal dose response curve.

In one embodiment, the antibody relieves suppression of T effector cells by T regulatory cells.

In one embodiment, the antibody induces IL-2 production by a co-culture of T effector cells and T regulatory cells and suppresses IL-10 production by a co-culture of T effector cells and T regulatory cells.

In one embodiment, an antibody that specifically binds to OX40 comprises a VH CDR1 comprising the amino acid sequence of GSAMH (SEQ ID NO: 4); a VH CDR2 comprising the amino acid sequence of RIRSKANSYATAYAASVKG (SEQ ID NO: 5); a VH CDR3 comprising the amino acid sequence of GIYDSSGYDY (SEQ ID NO: 6); a VL CDR1 comprising the amino acid sequence of RSSQSLLHSNGYNYLD (SEQ ID NO: 1); a VL CDR2 comprising the amino acid sequence of LGSNRAS (SEQ ID NO: 2); and a VL CDR3 comprising the amino acid sequence of MQALQTPLT (SEQ ID NO: 3), wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is a substantially increasing function of antibody concentrations between, e.g., 0.032 µg/ml and 20 µg/ml, 0.16 µg/ml and 20 µg/ml, 0.8 µg/ml and 20 µg/ml, 4 µg/ml and 20 µg/ml, 0.032 µg/ml and 4 µg/ml, 0.16 µg/ml and 4 µg/ml, or 0.8 µg/ml and 4 µg/ml. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 µg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery). In one embodiment, an antibody that specifically binds to OX40 comprises a VH CDR1 comprising the amino acid sequence of GSAMH (SEQ ID NO: 4); a VH CDR2 comprising the amino acid sequence of RIRSKANSYATAYAASVKG (SEQ ID NO: 5); a VH CDR3 comprising the amino acid sequence of GIYDSSGYDY (SEQ ID NO: 6); a VL CDR1 comprising the amino acid sequence of RSSQSLLHSNGYNYLD (SEQ ID NO: 1); a VL CDR2 comprising the amino acid sequence of LGSNRAS (SEQ ID NO: 2); and a VL CDR3 comprising the amino acid sequence of MQALQTPLT (SEQ ID NO: 3), wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production shows a sigmoidal dose response curve when the anti-OX40 antibody concentration is between, e.g., 0.032 µg/ml and 20 µg/ml, 0.16 µg/ml and 20 µg/ml, 0.8 µg/ml and 20 µg/ml, 4 µg/ml and 20 µg/ml, 0.032 µg/ml and 4 µg/ml, 0.16 µg/ml and 4 µg/ml, or 0.8 µg/ml and 4 µg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 µg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In one embodiment, an antibody that specifically binds to OX40 comprises a VH CDR1 comprising the amino acid sequence of GSAMH (SEQ ID NO: 4); a VH CDR2 comprising the amino acid sequence of RIRSKANSYATAYAASVKG (SEQ ID NO: 5); a VH CDR3 comprising the amino acid sequence of GIYDSSGYDY (SEQ ID NO: 6); a VL CDR1 comprising the amino acid sequence of RSSQSLLHSNGYNYLD (SEQ ID NO: 1); a VL CDR2 comprising the amino acid sequence of LGSNRAS (SEQ ID NO: 2); and a VL CDR3 comprising the amino acid sequence of MQALQTPLT (SEQ ID NO: 3), wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is greater in the presence of 4 µg/ml of the antibody than in the presence of 0.032 µg/ml of the antibody. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 µg/ml) of the antibody and, e.g., 100 ng/ml of SEA for, e.g., 5 days at, e.g., 37° C., 5% $CO_2$, and 97% humidity; and (b)

collecting clarified supernatant and measuring the titer of IL-2 by, e.g., electrochemiluminescence, e.g., Human TH1/TH2 10-Plex tissue culture kit (Meso Scale Discovery).

In one embodiment, an antibody that specifically binds to OX40 comprises a VH CDR1 comprising the amino acid sequence of GSAMH (SEQ ID NO: 4); a VH CDR2 comprising the amino acid sequence of RIRSKANSYATAYAASVKG (SEQ ID NO: 5); a VH CDR3 comprising the amino acid sequence of GIYDSSGYDY (SEQ ID NO: 6); a VL CDR1 comprising the amino acid sequence of RSSQSLLHSNGYNYLD (SEQ ID NO: 1); a VL CDR2 comprising the amino acid sequence of LGSNRAS (SEQ ID NO: 2); and a VL CDR3 comprising the amino acid sequence of MQALQTPLT (SEQ ID NO: 3), wherein the antibody when plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, is a substantially increasing function of the concentrations of the antibody between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery). In one embodiment, an antibody that specifically binds to OX40 comprises a VH CDR1 comprising the amino acid sequence of GSAMH (SEQ ID NO: 4); a VH CDR2 comprising the amino acid sequence of RIRSKANSYATAYAASVKG (SEQ ID NO: 5); a VH CDR3 comprising the amino acid sequence of GIYDSSGYDY (SEQ ID NO: 6); a VL CDR1 comprising the amino acid sequence of RSSQSLLHSNGYNYLD (SEQ ID NO: 1); a VL CDR2 comprising the amino acid sequence of LGSNRAS (SEQ ID NO: 2); and a VL CDR3 comprising the amino acid sequence of MQALQTPLT (SEQ ID NO: 3), wherein the antibody when plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, shows a sigmoidal dose response curve when the anti-OX40 antibody concentration is between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µm/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery).

In one embodiment, an antibody that specifically binds to OX40 comprises a VH CDR1 comprising the amino acid sequence of GSAMH (SEQ ID NO: 4); a VH CDR2 comprising the amino acid sequence of RIRSKANSYATAYAASVKG (SEQ ID NO: 5); a VH CDR3 comprising the amino acid sequence of GIYDSSGYDY (SEQ ID NO: 6); a VL CDR1 comprising the amino acid sequence of RSSQSLLHSNGYNYLD (SEQ ID NO: 1); a VL CDR2 comprising the amino acid sequence of LGSNRAS (SEQ ID NO: 2); and a VL CDR3 comprising the amino acid sequence of MQALQTPLT (SEQ ID NO: 3), wherein the antibody increases CD4+ T cell proliferation, wherein the CD4+ T cell proliferation is a substantially increasing function of the concentrations of the antibody between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry. In one embodiment, an antibody that specifically binds to OX40 comprises a VH CDR1 comprising the amino acid sequence of GSAMH (SEQ ID NO: 4); a VH CDR2 comprising the amino acid sequence of RIRSKANSYATAYAASVKG (SEQ ID NO: 5); a VH CDR3 comprising the amino acid sequence of GIYDSSGYDY (SEQ ID NO: 6); a VL CDR1 comprising the amino acid sequence of RSSQSLLHSNGYNYLD (SEQ ID NO: 1); a VL CDR2 comprising the amino acid sequence of LGSNRAS (SEQ ID NO: 2); and a VL CDR3 comprising the amino acid sequence of MQALQTPLT (SEQ ID NO: 3), wherein the antibody increases CD4+ T cell proliferation, wherein the CD4+ T cell proliferation shows a sigmoidal dose response curve when the anti-OX40 antibody concentration is between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody that specifically binds to OX40 comprises a VH CDR1 comprising the amino acid sequence of GSAMH (SEQ ID NO: 4); a VH CDR2 comprising the amino acid sequence of RIRSKANSYATAYAASVKG (SEQ ID NO: 5); a VH CDR3 comprising the amino acid sequence of GIYDSSGYDY (SEQ ID NO: 6); a VL CDR1 comprising the amino acid sequence of RSSQSLLHSNGYNYLD (SEQ ID NO: 1); a VL CDR2 comprising the amino acid sequence of LGSNRAS (SEQ ID NO: 2); and a VL CDR3 comprising the amino acid sequence of MQALQTPLT (SEQ ID NO: 3), wherein the antibody results in a greater increase in CD4+ T cell proliferation when the antibody is present at a concentration of 20 µg/ml than at a concentration of 2 μg/ml, as assessed in, e.g., an assay comprising the following steps: (a) labeling, e.g., enriched CD4+ T cells with, e.g., 10 μM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 μg/ml of, e.g., plate-bound anti-CD3 antibody and varying concentrations (e.g., 0.002, 0.02, 0.2, 2, and 20 μg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody comprises a VL domain having at least 70% identity to the amino acid sequence of SEQ ID NO: 15 and a VH domain having at least 70% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is a substantially increasing function of antibody concentrations between, e.g., 0.032 μg/ml and 20 μg/ml, 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery). In one embodiment, an antibody comprises a VL domain having at least 70% identity to the amino acid sequence of SEQ ID NO: 15 and a VH domain having at least 70% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production shows a sigmoidal dose response curve when the anti-OX40 antibody concentration is between, e.g., 0.032 μg/ml and 20 μg/ml, 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In one embodiment, an antibody comprises a VL domain having at least 70% identity to the amino acid sequence of SEQ ID NO: 15 and a VH domain having at least 70% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is greater in the presence of 4 μg/ml of the antibody than in the presence of 0.032 μg/ml of the antibody. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In one embodiment, an antibody comprises a VL domain having at least 75% identity to the amino acid sequence of SEQ ID NO: 15 and a VH domain having at least 75% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is a substantially increasing function of antibody concentrations between, e.g., 0.032 μg/ml and 20 μg/ml, 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery). In one embodiment, an antibody comprises a VL domain having at least 75% identity to the amino acid sequence of SEQ ID NO: 15 and a VH domain having at least 75% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production shows a sigmoidal dose response curve when the anti-OX40 antibody concentration is between, e.g., 0.032 μg/ml and 20 μg/ml, 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In one embodiment, an antibody comprises a VL domain having at least 75% identity to the amino acid sequence of SEQ ID NO: 15 and a VH domain having at least 75% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is greater in the presence of 4 μg/ml of the antibody than in the presence of 0.032 μg/ml of the antibody. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In one embodiment, an antibody comprises a VL domain having at least 80% identity to the amino acid sequence of SEQ ID NO: 15 and a VH domain having at least 80% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is a substantially increasing function of antibody concentrations between, e.g., 0.032 μg/ml and 20 μg/ml, 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery). In one embodiment, an antibody comprises a VL domain having at least 80% identity to the amino acid sequence of SEQ ID NO: 15 and a VH domain having at least 80% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production shows a sigmoidal dose response curve when the anti-OX40 antibody concentration is between, e.g., 0.032 μg/ml and 20 μg/ml, 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In one embodiment, an antibody comprises a VL domain having at least 80% identity to the amino acid sequence of SEQ ID NO: 15 and a VH domain having at least 80% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is greater in the presence of 4 μg/ml of the antibody than in the presence of 0.032 μg/ml of the antibody. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In one embodiment, an antibody comprises a VL domain having at least 85% identity to the amino acid sequence of SEQ ID NO: 15 and a VH domain having at least 85% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is a substantially increasing function of antibody concentrations between, e.g., 0.032 μg/ml and 20 μg/ml, 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery). In one embodiment, an antibody comprises a VL domain having at least 85% identity to the amino acid sequence of SEQ ID NO: 15 and a VH domain having at least 85% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production shows a sigmoidal dose response curve when the anti-OX40 antibody concentration is between, e.g., 0.032 μg/ml and 20

μg/ml, 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In one embodiment, an antibody comprises a VL domain having at least 85% identity to the amino acid sequence of SEQ ID NO: 15 and a VH domain having at least 85% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is greater in the presence of 4 μg/ml of the antibody than in the presence of 0.032 μg/ml of the antibody. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In one embodiment, an antibody comprises a VL domain having at least 90% identity to the amino acid sequence of SEQ ID NO: 15 and a VH domain having at least 90% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is a substantially increasing function of antibody concentrations between, e.g., 0.032 μg/ml and 20 μg/ml, 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery). In one embodiment, an antibody comprises a VL domain having at least 90% identity to the amino acid sequence of SEQ ID NO: 15 and a VH domain having at least 90% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production shows a sigmoidal dose response curve when the anti-OX40 antibody concentration is between, e.g., 0.032 μg/ml and 20 μg/ml, 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In one embodiment, an antibody comprises a VL domain having at least 90% identity to the amino acid sequence of SEQ ID NO: 15 and a VH domain having at least 90% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is greater in the presence of 4 μg/ml of the antibody than in the presence of 0.032 μg/ml of the antibody. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In one embodiment, an antibody comprises a VL domain having at least 95% identity to the amino acid sequence of SEQ ID NO: 15 and a VH domain having at least 95% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is a substantially increasing function of antibody concentrations between, e.g., 0.032 μg/ml and 20 μg/ml, 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery). In one embodiment, an antibody comprises a VL domain having at least 95% identity to the amino acid sequence of SEQ ID NO: 15 and a VH domain having at least 95% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production shows a sigmoidal dose response curve when the anti-OX40 antibody concentration is between, e.g., 0.032 µg/ml and 20 µg/ml, 0.16 µg/ml and 20 µg/ml, 0.8 µg/ml and 20 µg/ml, 4 µg/ml and 20 µg/ml, 0.032 µg/ml and 4 µg/ml, 0.16 µg/ml and 4 µg/ml, or 0.8 µg/ml and 4 µg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 µg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In one embodiment, an antibody comprises a VL domain having at least 95% identity to the amino acid sequence of SEQ ID NO: 15 and a VH domain having at least 95% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is greater in the presence of 4 µg/ml of the antibody than in the presence of 0.032 µg/ml of the antibody. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 µg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In one embodiment, an antibody comprises a VL domain having at least 98% identity to the amino acid sequence of SEQ ID NO: 15 and a VH domain having at least 98% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is a substantially increasing function of antibody concentrations between, e.g., 0.032 µg/ml and 20 µg/ml, 0.16 µg/ml and 20 µg/ml, 0.8 µg/ml and 20 µg/ml, 4 µg/ml and 20 µg/ml, 0.032 µg/ml and 4 µg/ml, 0.16 µg/ml and 4 µg/ml, or 0.8 µg/ml and 4 µg/ml. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 µg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery). In one embodiment, an antibody comprises a VL domain having at least 98% identity to the amino acid sequence of SEQ ID NO: 15 and a VH domain having at least 98% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production shows a sigmoidal dose response curve when the anti-OX40 antibody concentration is between, e.g., 0.032 µg/ml and 20 µg/ml, 0.16 µg/ml and 20 µg/ml, 0.8 µg/ml and 20 µg/ml, 4 µg/ml and 20 µg/ml, 0.032 µg/ml and 4 µg/ml, 0.16 µg/ml and 4 µg/ml, or 0.8 µg/ml and 4 µg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 µg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In one embodiment, an antibody comprises a VL domain having at least 98% identity to the amino acid sequence of SEQ ID NO: 15 and a VH domain having at least 98% identity to the amino acid sequence of SEQ ID NO: 16, wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is greater in the presence of 4 µg/ml of the antibody than in the presence of 0.032 µg/ml of the antibody. The IL-2 production can be assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 µg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In one embodiment, an antibody comprises a VL domain having at least 70% identity to the amino acid sequence of SEQ ID NO: 15 and a VH domain having at least 70% identity to the amino acid sequence of SEQ ID NO: 16, wherein the antibody when plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, is a substantially increasing function of the concentrations of the antibody between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b)

collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery). In one embodiment, an antibody comprises a VL domain having at least 70% identity to the amino acid sequence of SEQ ID NO: 15 and a VH domain having at least 70% identity to the amino acid sequence of SEQ ID NO: 16, wherein the antibody hen plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, shows a sigmoidal dose response curve when the anti-OX40 antibody concentration is between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery).

In one embodiment, an antibody comprises a VL domain having at least 75% identity to the amino acid sequence of SEQ ID NO: 15 and a VH domain having at least 75% identity to the amino acid sequence of SEQ ID NO: 16, wherein the antibody when plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, is a substantially increasing function of the concentrations of the antibody between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery). In one embodiment, an antibody comprises a VL domain having at least 75% identity to the amino acid sequence of SEQ ID NO: 15 and a VH domain having at least 75% identity to the amino acid sequence of SEQ ID NO: 16, wherein the antibody hen plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, shows a sigmoidal dose response curve when the anti-OX40 antibody concentration is between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery).

In one embodiment, an antibody comprises a VL domain having at least 80% identity to the amino acid sequence of SEQ ID NO: 15 and a VH domain having at least 80% identity to the amino acid sequence of SEQ ID NO: 16, wherein the antibody when plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, is a substantially increasing function of the concentrations of the antibody between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery). In one embodiment, an antibody comprises a VL domain having at least 80% identity to the amino acid sequence of SEQ ID NO: 15 and a VH domain having at least 80% identity to the amino acid sequence of SEQ ID NO: 16, wherein the antibody hen plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, shows a sigmoidal dose response curve when the anti-OX40 antibody concentration is between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery).

In one embodiment, an antibody comprises a VL domain having at least 85% identity to the amino acid sequence of SEQ ID NO: 15 and a VH domain having at least 85% identity to the amino acid sequence of SEQ ID NO: 16, wherein the antibody when plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, is a substantially increasing function of the concentrations of the antibody between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery). In one embodiment, an antibody comprises a VL domain having at least 85% identity to the amino acid sequence of SEQ ID NO: 15 and a VH domain having at least 85% identity to the amino acid sequence of SEQ ID NO: 16, wherein the antibody hen plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, shows a sigmoidal dose response curve when the anti-OX40 antibody concentration is between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery).

In one embodiment, an antibody comprises a VL domain having at least 90% identity to the amino acid sequence of SEQ ID NO: 15 and a VH domain having at least 90% identity to the amino acid sequence of SEQ ID NO: 16, wherein the antibody when plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, is a substantially increasing function of the concentrations of the antibody between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery). In one embodiment, an antibody comprises a VL domain having at least 90% identity to the amino acid sequence of SEQ ID NO: 15 and a VH domain having at least 90% identity to the amino acid sequence of SEQ ID NO: 16, wherein the antibody hen plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, shows a sigmoidal dose response curve when the anti-OX40 antibody concentration is between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery).

In one embodiment, an antibody comprises a VL domain having at least 95% identity to the amino acid sequence of SEQ ID NO: 15 and a VH domain having at least 95% identity to the amino acid sequence of SEQ ID NO: 16, wherein the antibody when plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, is a substantially increasing function of the concentrations of the antibody between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery). In one embodiment, an antibody comprises a VL domain having at least 95% identity to the amino acid sequence of SEQ ID NO: 15 and a VH domain having at least 95% identity to the amino acid sequence of SEQ ID NO: 16, wherein the antibody hen plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, shows a sigmoidal dose response curve when the anti-OX40 antibody concentration is between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery).

In one embodiment, an antibody comprises a VL domain having at least 98% identity to the amino acid sequence of SEQ ID NO: 15 and a VH domain having at least 98% identity to the amino acid sequence of SEQ ID NO: 16, wherein the antibody when plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, is a substantially increasing function of the concentrations of the antibody between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery). In one embodiment, an antibody comprises a VL domain having at least 98% identity to the amino acid sequence of SEQ ID NO: 15 and a VH domain having at least 98% identity to the amino acid sequence of SEQ ID NO: 16, wherein the antibody hen plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, shows a sigmoidal dose response curve when the anti-OX40 antibody concentration is between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery).

In one embodiment, an antibody comprises a VL domain having at least 70% identity to the amino acid sequence SEQ ID NO: 15 and a VH domain having at least 70% identity to the amino acid sequence of SEQ ID NO: 16, wherein the antibody increases CD4+ T cell proliferation, wherein the CD4+ T cell proliferation is a substantially increasing function of the concentrations of the antibody between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry. In one embodiment, an antibody comprises a VL domain having at least 70% identity to the amino acid sequence SEQ ID NO: 15 and a VH domain having at least 70% identity to the amino acid sequence of SEQ ID NO: 16, wherein the antibody increases CD4+ T cell proliferation, wherein the CD4+ T cell proliferation shows a sigmoidal dose response curve when the anti-OX40 antibody concentration is between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody comprises a VL domain having at least 70% identity to the amino acid sequence SEQ ID NO: 15 and a VH domain having at least 70% identity to the amino acid sequence of SEQ ID NO: 16, wherein the antibody results in a greater increase in CD4+ T cell proliferation when the antibody is present at a concentration of 20 µg/ml than at a concentration of 2 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody comprises a VL domain having at least 75% identity to the amino acid sequence SEQ ID NO: 15 and a VH domain having at least 75% identity to the amino acid sequence of SEQ ID NO: 16, wherein the antibody increases CD4+ T cell proliferation, wherein the CD4+ T cell proliferation is a substantially increasing function of the concentrations of the antibody between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry. In one embodiment, an antibody comprises a VL domain having at least 75% identity to the amino acid sequence SEQ ID NO: 15 and a VH domain having at least 75% identity to the amino acid sequence of SEQ ID NO: 16, wherein the antibody increases CD4+ T cell proliferation, wherein the CD4+ T cell proliferation shows a sigmoidal dose response curve when the anti-OX40 antibody concentration is between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody comprises a VL domain having at least 75% identity to the amino acid sequence SEQ ID NO: 15 and a VH domain having at least 75% identity to the amino acid sequence of SEQ ID NO: 16, wherein the antibody results in a greater increase in CD4+ T cell proliferation when the antibody is present at a concentration of 20 µg/ml than at a concentration of 2 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody comprises a VL domain having at least 80% identity to the amino acid sequence SEQ ID NO: 15 and a VH domain having at least 80% identity to the amino acid sequence of SEQ ID NO: 16, wherein the antibody increases CD4+ T cell proliferation, wherein the CD4+ T cell proliferation is a substantially increasing function of the concentrations of the antibody between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry. In one embodiment, an antibody comprises a VL domain having at least 80% identity to the amino acid sequence SEQ ID NO: 15 and a VH domain having at least 80% identity to the amino acid sequence of SEQ ID NO: 16, wherein the antibody increases CD4+ T cell proliferation, wherein the CD4+ T cell proliferation shows a sigmoidal dose response curve when the anti-OX40 antibody concentration is between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody comprises a VL domain having at least 80% identity to the amino acid sequence SEQ ID NO: 15 and a VH domain having at least 80% identity to the amino acid sequence of SEQ ID NO: 16, wherein the antibody results in a greater increase in CD4+ T cell proliferation when the antibody is present at a concentration of 20 µg/ml than at a concentration of 2 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody comprises a VL domain having at least 85% identity to the amino acid sequence SEQ ID NO: 15 and a VH domain having at least 85% identity to the amino acid sequence of SEQ ID NO: 16, wherein the antibody increases CD4+ T cell proliferation, wherein the CD4+ T cell proliferation is a substantially increasing function of the concentrations of the antibody between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry. In one embodiment, an antibody comprises a VL domain having at least 85% identity to the amino acid sequence SEQ ID NO: 15 and a VH domain having at least 85% identity to the amino acid sequence of SEQ ID NO: 16, wherein the antibody increases CD4+ T cell proliferation, wherein the CD4+ T cell proliferation shows a sigmoidal dose response curve when the anti-OX40 antibody concentration is between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody comprises a VL domain having at least 85% identity to the amino acid sequence SEQ ID NO: 15 and a VH domain having at least 85% identity to the amino acid sequence of SEQ ID NO: 16, wherein the antibody results in a greater increase in CD4+ T cell proliferation when the antibody is present at a concentration of 20 µg/ml than at a concentration of 2 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody comprises a VL domain having at least 90% identity to the amino acid sequence SEQ ID NO: 15 and a VH domain having at least 90% identity to the amino acid sequence of SEQ ID NO: 16, wherein the antibody increases CD4+ T cell proliferation, wherein the CD4+ T cell proliferation is a substantially increasing function of the concentrations of the antibody between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry. In one embodiment, an antibody comprises a VL domain having at least 90% identity to the amino acid sequence of SEQ ID NO: 15 and a VH domain having at least 90% identity to the amino acid sequence of SEQ ID NO: 16, wherein the antibody increases CD4+ T cell proliferation, wherein the CD4+ T cell proliferation shows a sigmoidal dose response curve when the anti-OX40 antibody concentration is between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody comprises a VL domain having at least 90% identity to the amino acid sequence SEQ ID NO: 15 and a VH domain having at least 90% identity to the amino acid sequence of SEQ ID NO: 16, wherein the antibody results in a greater increase in CD4+ T cell proliferation when the antibody is present at a concentration of 20 µg/ml than at a concentration of 2 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody comprises a VL domain having at least 95% identity to the amino acid sequence SEQ ID NO: 15 and a VH domain having at least 95% identity to the amino acid sequence of SEQ ID NO: 16, wherein the antibody increases CD4+ T cell proliferation, wherein the CD4+ T cell proliferation is a substantially increasing function of the concentrations of the antibody between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry. In one embodiment, an antibody comprises a VL domain having at least 95% identity to the amino acid sequence SEQ ID NO: 15 and a VH domain having at least 95% identity to the amino acid sequence of SEQ ID NO: 16, wherein the antibody increases CD4+ T cell proliferation, wherein the CD4+ T cell proliferation shows a sigmoidal dose response curve when the anti-OX40 antibody concentration is between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody comprises a VL domain having at least 95% identity to the amino acid sequence SEQ ID NO: 15 and a VH domain having at least 95% identity to the amino acid sequence of SEQ ID NO: 16, wherein the antibody results in a greater increase in CD4+ T cell proliferation when the antibody is present at a concentration of 20 µg/ml than at a concentration of 2 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody comprises a VL domain having at least 98% identity to the amino acid sequence SEQ ID NO: 15 and a VH domain having at least 98% identity to the amino acid sequence of SEQ ID NO: 16, wherein the antibody increases CD4+ T cell proliferation, wherein the CD4+ T cell proliferation is a substantially increasing function of the concentrations of the antibody between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry. In one embodiment, an antibody comprises a VL domain having at least 98% identity to the amino acid sequence SEQ ID NO: 15 and a VH domain having at least 98% identity to the amino acid sequence of SEQ ID NO: 16, wherein the antibody increases CD4+ T cell proliferation, wherein the CD4+ T cell proliferation shows a sigmoidal dose response curve when the anti-OX40 antibody concentration is between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody comprises a VL domain having at least 98% identity to the amino acid sequence SEQ ID NO: 15 and a VH domain having at least 98% identity to the amino acid sequence of SEQ ID NO: 16, wherein the antibody results in a greater increase in CD4+ T cell proliferation when the antibody is present at a concentration of 20 µg/ml than at a concentration of 2 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$, and (c) on, e.g., day 4, staining cells with, e.g., an anti-CD4 antibody and examining CD4+ T cell proliferation by, e.g., measuring the percentage of CFSE low CD4+ cells by flow cytometry.

In one embodiment, an antibody comprises a human immunoglobulin $IgG_1$ heavy chain constant region, wherein the amino acid sequence of the $IgG_1$ heavy chain constant region comprises a mutation selected from the group consisting of N297A, N297Q, D265A, and a combination thereof. In one embodiment, the antibody comprises an $IgG_1$ heavy chain constant region, wherein the amino acid sequence of the IgG$_1$ heavy chain constant region comprises a mutation selected from the group consisting of D265A, P329A, and a combination thereof.

In one embodiment, an antibody that specifically binds to human OX40 is an antibody wherein the binding between the antibody and a variant OX40 is substantially weakened relative to the binding between the antibody and a human OX40 sequence of SEQ ID NO:55, and wherein the variant OX40 comprises the sequence of SEQ ID NO: 55 except for an amino acid mutation selected from the group consisting of: N60A, R62A, R80A, L88A, P93A, P99A, P115A, and a combination thereof.

In one embodiment, an antibody that specifically binds to human OX40 is an antibody wherein the binding between the antibody and a variant OX40 is substantially weakened relative to the binding between the antibody and a human OX40 sequence of SEQ ID NO:55, and wherein the variant OX40 comprises the sequence of SEQ ID NO: 55 except for the amino acid mutations W58A, N60A, R62A, R80A, L88A, P93A, P99A, and P115A.

In one embodiment, an antibody that specifically binds to human OX40 is an antibody that exhibits, as compared to binding to a human OX40 sequence of SEQ ID NO: 55, reduced or absent binding to a protein identical to SEQ ID NO: 55 except for the presence of an amino acid mutation selected from the group consisting of: N60A, R62A, R80A, L88A, P93A, P99A, P115A, and a combination thereof.

In one embodiment, an antibody that specifically binds to human OX40. An isolated antibody that specifically binds to human OX40, wherein the antibody exhibits, as compared to binding to a human OX40 sequence of SEQ ID NO: 55, reduced or absent binding to a protein identical to SEQ ID NO: 55 except for the presence of the amino acid mutations W58A, N60A, R62A, R80A, L88A, P93A, P99A, and P115A.

In one embodiment, an antibody that specifically binds to human OX40 is an antibody that specifically binds to an epitope of a human OX40 sequence comprising a residue of SEQ ID NO: 55 selected from the group consisting of: 60, 62, 80, 88, 93, 99, 115, and a combination thereof.

In one embodiment, an antibody that specifically binds to human OX40 is an antibody that specifically binds to an epitope of a human OX40 sequence comprising residues 58, 60, 62, 80, 88, 93, 99, and 115 of SEQ ID NO: 55.

In one embodiment, an antibody that specifically binds to human OX40 is an antibody that specifically binds to at least one residue of SEQ ID NO: 55 selected from the group consisting of: 60, 62, 80, 88, 93, 99, 115, and a combination thereof.

In one embodiment, antibody comprises a heavy chain variable region sequence and a light chain variable region sequence an antibody provided herein and is selected from the group consisting of a Fab, Fab', F(ab')2, and scFv fragment.

In one embodiment, an antibody comprises a human immunoglobulin IgG$_1$ heavy chain constant region, and wherein the amino acid sequence of the IgG$_1$ heavy chain constant region comprises a mutation selected from the group consisting of N297A, N297Q, D265A, and a combination thereof. In one embodiment, the antibody comprises an IgG$_1$ heavy chain constant region, wherein the amino acid sequence of the IgG$_1$ heavy chain constant region comprises a mutation selected from the group consisting of D265A, P329A, and a combination thereof.

In one embodiment, an antibody that specifically binds to human OX40 comprises: (a) a first antigen-binding domain that specifically binds to human OX40; and (b) a second antigen-binding domain that does not specifically bind to an antigen expressed by a human immune cell.

In one embodiment, the antigen-binding domain that specifically binds to human OX40 comprises: (a) a first heavy chain variable domain (VH) comprising a VH complementarity determining region (CDR) 1 comprising the amino acid sequence of GSAMH (SEQ ID NO:4); a VH-CDR2 comprising the amino acid sequence of RIRSKANSYATAYAASVKG (SEQ ID NO:5); and a VH-CDR3 comprising the amino acid sequence of GIYDSSGYDY (SEQ ID NO:6); and (b) a first light chain variable domain (VL) comprising a VL-CDR1 comprising the amino acid sequence of RSSQSLLHSNGYNYLD (SEQ ID NO:1); a VL-CDR2 comprising the amino acid sequence of LGSNRAS (SEQ ID NO:2); and a VL-CDR3 comprising the amino acid sequence of MQALQTPLT (SEQ ID NO:3). In one embodiment, the antigen-binding domain that specifically binds to human OX40 specifically binds to the same epitope of human OX40 as an antibody comprising a VH comprising the amino acid sequence of SEQ ID NO:16 and a VL comprising the amino acid sequence of SEQ ID NO:15. In one embodiment, the antigen-binding domain that specifically binds to human OX40 exhibits, as compared to binding to a human OX40 sequence of SEQ ID NO:55, reduced or absent binding to a protein identical to SEQ ID NO:55 except for the presence of an amino acid mutation selected from the group consisting of: N60A, R62A, R80A, L88A, P93A, P99A, P115A, and a combination thereof. In one embodiment, the antigen-binding domain that specifically binds to human OX40 comprises a VH and a VL, wherein the VH comprises the amino acid sequence of SEQ ID NO:16. In one embodiment, the antigen-binding domain that specifically binds to human OX40 comprises a VH and a VL, wherein the VL comprises the amino acid sequence of SEQ ID NO:15.

In one embodiment, the second antigen-binding domain specifically binds to a non-human antigen. In one embodiment, the second antigen-binding domain specifically binds to a viral antigen. In one embodiment, the viral antigen is a HIV antigen. In one embodiment, the second antigen-binding domain specifically binds to chicken albumin or hen egg lysozyme.

In one embodiment, an antibody that specifically binds to human OX40 comprises (a) a first heavy chain variable domain (VH) comprising a VH complementarity determining region (CDR) 1 comprising the amino acid sequence of GSAMH (SEQ ID NO:4); a VH-CDR2 comprising the amino acid sequence of RIRSKANSYATAYAASVKG (SEQ ID NO:5); and a VH-CDR3 comprising the amino acid sequence of GIYDSSGYDY (SEQ ID NO:6); and (b) a first light chain variable domain (VL) comprising a VL-CDR1 comprising the amino acid sequence of RSSQSLLHSNGYNYLD (SEQ ID NO:1); a VL-CDR2 comprising the amino acid sequence of LGSNRAS (SEQ ID NO:2); and a VL-CDR3 comprising the amino acid sequence of MQALQTPLT (SEQ ID NO:3). In one embodiment, the antigen-binding domain that specifically binds to human OX40 specifically binds to the same epitope of human OX40 as an antibody comprising a VH comprising the amino acid sequence of SEQ ID NO:16 and a VL comprising the amino acid sequence of SEQ ID NO:15. In one embodiment, the antigen-binding domain that specifically binds to human OX40 exhibits, as compared to binding to a human OX40 sequence of SEQ ID NO:55, reduced or absent binding to a protein identical to SEQ ID NO:55 except for the presence of an amino acid mutation selected from the group consisting of: N60A, R62A, R80A, L88A, P93A, P99A, P115A, and a combination thereof. In one embodiment, the antigen-binding domain that specifically binds to human OX40 comprises a VH and a VL, wherein the VH comprises the amino acid sequence of SEQ ID NO:16. In one embodiment, the antigen-binding domain that specifically binds to human OX40 comprises a VH and a VL, wherein the VL comprises the amino acid sequence of SEQ ID NO:15.

In one embodiment, the second heavy chain is a Fc fragment.

In one embodiment, the antigen-binding domain that specifically binds to human OX40 comprises a VH comprising an amino acid sequence that is at least 75%, 80%, 85%, 90%, 95%, or 99% identical to the amino acid sequence of SEQ ID NO:16. In one embodiment, the antigen-binding domain that specifically binds to human OX40 comprises a VH comprising the amino acid sequence of SEQ ID NO:16. In one embodiment, the antigen-binding domain that specifically binds to human OX40 comprises a VH comprising an amino acid sequence derived from a human IGHV3-73 germline sequence.

In one embodiment, the antigen-binding domain that specifically binds to human OX40 comprises a VL comprising an amino acid sequence that is at least 75%, 80%, 85%, 90%, 95%, or 99% identical to the amino acid sequence of SEQ ID NO:15. In one embodiment, the antigen-binding domain that specifically binds to human OX40 comprises a VL-CDR3 comprising the amino acid sequence of SEQ ID NO:3. In one embodiment, the antigen-binding domain that specifically binds to human OX40 comprises a VL comprising the amino acid sequence of SEQ ID NO:15. In one embodiment, the antigen-binding domain that specifically binds to human OX40 comprises a light chain comprising the amino acid sequence of SEQ ID NO:20. In one embodiment, the antigen-binding domain that specifically binds to human OX40 comprises a light chain comprising the amino acid sequence of SEQ ID NO:50. In one embodiment, the antigen-binding domain that specifically binds to human OX40 comprises a VL comprising an amino acid sequence derived from a human IGKV2-28 germline sequence.

In one embodiment, the antigen-binding domain that specifically binds to human OX40 comprises the VH and VL sequences set forth in SEQ ID NOs: 16 and 15, respectively. In one embodiment, the antigen-binding domain that specifically binds to human OX40 comprises a heavy chain comprising the amino acid sequence of SEQ ID NO: 21. In one embodiment, the antigen-binding domain that specifically binds to human OX40 comprises a heavy chain comprising the amino acid sequence of SEQ ID NO: 60.

In one embodiment, the first antigen-binding domain and the second antigen-binding domain comprise an identical mutation selected from the group consisting of N297A, N297Q, D265A, and a combination thereof. In one embodiment, the first antigen-binding domain and the second antigen-binding domain comprise an identical mutation selected from the group consisting of D265A, P329A, and a combination thereof. In one embodiment, the antigen-binding domain that specifically binds to human OX40 and the second heavy chain or fragment thereof comprise an identical mutation selected from the group consisting of N297A, N297Q, D265A, and a combination thereof. In one embodiment, the antigen-binding domain that specifically binds to human OX40 and the second heavy chain or fragment thereof comprise an identical mutation selected from the group consisting of D265A, P329A, and a combination thereof.

In one embodiment, the antibody is antagonistic to human OX40. In one embodiment, the antibody deactivates, reduces, or inhibits an activity of human OX40. In one embodiment, the antibody inhibits or reduces binding of human OX40 to human OX40 ligand. In one embodiment, the antibody inhibits or reduces human OX40 signaling. In one embodiment, the antibody inhibits or reduces human OX40 signaling induced by human OX40 ligand.

In one embodiment, the antibody comprises a detectable label.

In one embodiment, the present invention relates to an antibody of the present invention for use as a medicament.

In one embodiment, the present invention relates to an antibody of the present invention for use as a diagnostic.

In one embodiment, the present invention relates to the use of an antibody of the present invention for in vitro detection of OX40 in a sample. In one embodiment, OX40 is human OX40.

In one embodiment, the present invention relates to the use of an antibody of the present invention for activating, enhancing, or inducing an activity of human OX40 in vitro. In one embodiment, the antibody induces CD4+ T cell proliferation in vitro.

In one aspect, provided herein are isolated nucleic acid molecules encoding antibodies that specifically bind to OX40 (e.g., human OX40). In one embodiment, the nucleic acid molecule encodes the heavy chain variable region or heavy chain of an anti-OX40 antibody provided herein. In one embodiment, the nucleic acid molecule encodes the light chain variable region or light chain of an anti-OX40 antibody provided herein. In one embodiment, the nucleic acid molecule encodes the heavy chain variable region or heavy chain of an anti-OX40 antibody provided herein and the light chain variable region or light chain of the antibody. In one embodiment, the nucleic acid molecule encodes a heavy chain variable region comprising the amino acid sequence of SEQ ID NO: 16. In one embodiment, the nucleic acid molecule encodes a light chain variable region comprising the amino acid sequence of SEQ ID NO: 15. Isolated antibodies encoded by such nucleic acid molecules are also provided herein.

In one aspect, provided herein are vectors comprising such nucleic acid molecules.

In one aspect, provided herein are host cells comprising such nucleic acid molecules or such vectors. In one embodiment, the host cell is selected from the group consisting of *E. coli, Pseudomonas, Bacillus, Streptomyces*, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture.

In one aspect, provided herein are methods of producing antibodies that specifically bind to OX40 (e.g., human OX40) comprising culturing such host cells so that the nucleic acid molecule is expressed and the antibody is produced.

In one embodiment, the present invention relates to an antibody of the present invention, a nucleic acid molecule of the invention, a vector of the invention, and/or a host cell of the invention, for use as a medicament.

In one embodiment, the present invention relates to an antibody of the present invention, a nucleic acid molecule of the invention, a vector of the invention, and/or a host cell of the invention, for use as a diagnostic.

In one embodiment, the present invention relates to the use of to an antibody of the present invention, a nucleic acid molecule of the invention, a vector of the invention, and/or a host cell of the invention, for the in vitro detection of OX40 in a sample. In one embodiment, OX40 is human OX40.

In one embodiment, the present invention relates to the use of an antibody of the present invention for activating, enhancing, or inducing an activity of human OX40 in vitro. In one embodiment, the antibody induces CD4+ T cell proliferation in vitro.

In one aspect, provided herein are pharmaceutical compositions comprising an antibody that specifically binds to OX40 provided herein, a nucleic acid molecule encoding an antibody that specifically binds to OX40 (e.g., human OX40), a vector comprising such a nucleic acid molecule, or a host cell comprising such a nucleic acid molecule or vector.

In one aspect, provided herein are pharmaceutical compositions comprising an antibody that specifically binds to OX40 provided herein, a nucleic acid molecule encoding an antibody that specifically binds to OX40, e.g., human OX40, a vector comprising such a nucleic acid molecule, or a host cell comprising such a nucleic acid molecule or vector, for use as a medicament.

In one aspect, provided herein are pharmaceutical compositions comprising an antibody that specifically binds to OX40 provided herein, a nucleic acid molecule encoding an antibody that specifically binds to OX40, e.g., human OX40, a vector comprising such a nucleic acid molecule, or a host cell comprising such a nucleic acid molecule or vector, for use as a diagnostic.

In one aspect, provided herein are methods for modulating an immune response in a subject comprising administering to the subject an effective amount of an antibody, nucleic acid, vector, host cell, or pharmaceutical composition provided herein. In one embodiment, the method is for enhancing or inducing the immune response of the subject. In one embodiment, modulating an immune response comprises enhancing or inducing the immune response of the subject.

In one aspect, the present invention relates to an antibody, nucleic acid, vector, host cell, and/or pharmaceutical composition of the present invention, for use in a method for modulating an immune response.

In one aspect, the present invention relates to an antibody, nucleic acid, vector, host cell, and/or pharmaceutical composition of the present invention, for use in a method for enhancing or inducing an immune response. In one embodiment, the antibody is agonistic.

In one aspect, the present invention relates to an antibody, nucleic acid, vector, host cell, and/or pharmaceutical composition of the present invention, for use in a method for modulating an immune response in a subject.

In one aspect, the present invention relates to an antibody, nucleic acid, vector, host cell, and/or pharmaceutical composition of the present invention, for use in a method for enhancing or inducing an immune response in a subject. In one embodiment, the antibody is agonistic.

In one aspect, the present invention relates to an antibody, nucleic acid, vector, host cell, and/or pharmaceutical composition of the present invention, for use in a method for modulating an immune response in a subject comprising administering to the subject an effective amount of an antibody, nucleic acid, vector, host cell, or pharmaceutical composition of the invention.

In one aspect, the present invention relates to an antibody, nucleic acid, vector, host cell, and/or pharmaceutical composition of the present invention, for use in a method for enhancing or inducing an immune response in a subject comprising administering to the subject an effective amount of an antibody, nucleic acid, vector, host cell, or pharmaceutical composition of the invention. In one embodiment, the antibody is agonistic.

In one aspect, provided herein are methods for enhancing the expansion of T cells and T cell effector function in a subject comprising administering to the subject an effective amount of an antibody, nucleic acid, vector, host cell, or pharmaceutical composition provided herein.

In one aspect, the present invention relates to an antibody, nucleic acid, vector, host cell, and/or pharmaceutical composition of the present invention, for use in a method for enhancing the expansion of T cells and T cell effector function. In one embodiment, the antibody is agonistic.

In one aspect, the present invention relates to an antibody, nucleic acid, vector, host cell, and/or pharmaceutical composition of the present invention, for use in a method for enhancing the expansion of T cells and T cell effector function in a subject. In one embodiment, the antibody is agonistic.

In one aspect, the present invention relates to an antibody, nucleic acid, vector, host cell, and/or pharmaceutical composition of the present invention, for use in a method for enhancing the expansion of T cells and T cell effector function in a subject comprising administering to the subject an effective amount of an antibody, nucleic acid, vector, host cell, and/or pharmaceutical composition of the invention. In one embodiment, the antibody is agonistic.

In one aspect, provided herein are methods of treating cancer in a subject comprising administering to the subject an effective amount of an antibody, nucleic acid, vector, host cell, or pharmaceutical composition provided herein. In some embodiments, the cancer is selected from the group consisting of melanoma, renal cancer, and prostate cancer. In some embodiments, the cancer is selected from the group consisting of melanoma, renal cancer, prostate cancer, colon cancer, and lung cancer. In some embodiments, the lung cancer is non-small cell lung cancer (NSCLC). In one instance, the method further comprises administering to the subject a checkpoint targeting agent. In one instance, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-GITR antibody, an agonist anti-CD137 antibody, and an agonist anti-OX40 antibody.

In one aspect, the present invention relates to an antibody, nucleic acid, vector, host cell, and/or pharmaceutical composition of the present invention, for use in a method for the treatment of cancer. In one embodiment, the antibody is agonistic.

In one aspect, the present invention relates to an antibody, nucleic acid, vector, host cell, and/or pharmaceutical composition of the present invention, for use in a method for the treatment of cancer in a subject. In one embodiment, the antibody is agonistic.

In one aspect, the present invention relates to an antibody, nucleic acid, vector, host cell, and/or pharmaceutical composition of the present invention, for use in a method for the treatment of cancer in a subject comprising administering to the subject an effective amount of an antibody, nucleic acid, vector, host cell, and/or pharmaceutical composition of the invention. In one embodiment, the antibody is agonistic.

In one aspect, the present invention relates to (a) an antibody, nucleic acid, vector, host cell, and/or pharmaceutical composition of the present invention and (b) a checkpoint targeting agent, for use as a medicament. In one embodiment, the antibody is agonistic.

In one aspect, the present invention relates to (a) an antibody, nucleic acid, vector, host cell, and/or pharmaceutical composition of the present invention and (b) a checkpoint targeting agent, for use in a method for the treatment of cancer. In one embodiment, the antibody is agonistic.

In one aspect, the present invention relates to a pharmaceutical composition, kit or kit-of-parts comprising (a) an antibody, nucleic acid, vector, host cell, and/or pharmaceutical composition of the present invention and (b) a checkpoint targeting agent.

The antibody as described herein can be used in combination with an IDO inhibitor for treating cancer. In one embodiment, the method further comprises administering to the subject an inhibitor of indoleamine-2,3-dioxygenase (IDO). The IDO inhibitor as described herein for use in treating cancer is present in a solid dosage form of a pharmaceutical composition such as a tablet, a pill or a capsule, wherein the pharmaceutical composition includes an IDO inhibitor and a pharmaceutically acceptable excipient. As such, the antibody as described herein and the IDO inhibitor as described herein can be administered separately, sequentially or concurrently as separate dosage forms. In one embodiment, the antibody is administered parenterally, and the IDO inhibitor is administered orally. In particular embodiments, the inhibitor is selected from the group consisting of epacadostat (Incyte Corporation), F001287 (Flexus Biosciences), indoximod (NewLink Genetics), and NLG919 (NewLink Genetics). Epacadostat has been described in PCT Publication No. WO 2010/005958, which is incorporated herein by reference in its entirety for all purposes. In one embodiment, the inhibitor is epacadostat. In another embodiment, the inhibitor is F001287. In another embodiment, the inhibitor is indoximod. In another embodiment, the inhibitor is NLG919.

In one aspect, the present invention relates to (a) an antibody, nucleic acid, vector, host cell, and/or pharmaceutical composition of the present invention and (b) an IDO inhibitor, for use as a medicament.

In one aspect, the present invention relates to (a) an antibody, nucleic acid, vector, host cell, and/or pharmaceutical composition of the present invention and (b) an IDO inhibitor, for use in a method for the treatment of cancer. In one aspect, the present invention relates to a composition, kit or kit-of-parts comprising (a) an antibody, nucleic acid, vector, host cell, and/or pharmaceutical composition of the present invention and (b) an IDO inhibitor.

The antibody described herein can be used in combination with a vaccine. In a particular embodiment, the vaccine comprises a heat shock protein peptide complex (HSPPC), in which the HSPPC comprises a heat shock protein (e.g., a gp96 protein, a hsp70 protein, or a hsc70 protein) complexed with one or more antigenic peptides (e.g., tumor-associated antigenic peptides). In one embodiment, the heat shock protein is gp96 protein and is complexed with a tumor-associated antigenic peptide. In one embodiment, the heat shock protein is hsp70 or hsc70 protein and is complexed with a tumor-associated antigenic peptide. In one embodiment, the heat shock protein is gp96 protein and is complexed with a tumor-associated antigenic peptide, wherein the HSPPC is derived from a tumor obtained from a subject. In one embodiment, the heat shock protein is hsp70 or hsc70 protein and is complexed with a tumor-associated antigenic peptide, wherein the HSPPC is derived from a tumor obtained from a subject.

In one aspect, the present invention relates to (a) an antibody, nucleic acid, vector, host cell, and/or pharmaceutical composition of the present invention and (b) a vaccine, for use as a medicament. In one embodiment, the antibody is agonistic.

In one aspect, the present invention relates to (a) an antibody, nucleic acid, vector, host cell, and/or pharmaceutical composition of the present invention and (b) a vaccine, for use in a method for the treatment of cancer. In one embodiment, the antibody is agonistic.

In one aspect, the present invention relates to a composition, kit or kit-of-parts comprising (a) an antibody, nucleic acid, vector, host cell, and/or pharmaceutical composition of the present invention and (b) a vaccine. In one embodiment, the antibody is agonistic.

In some embodiments, the disclosure provides use of an antibody as described herein in the manufacture of a medicament for the treatment of cancer. In certain embodiments, the disclosure provides an antibody as described herein for use in the treatment of cancer. In certain embodiments, the disclosure provides use of a pharmaceutical composition as described herein in the manufacture of a medicament for the treatment of cancer. In certain embodiments, the disclosure provides a pharmaceutical composition as described herein for use in the treatment of cancer.

In one aspect, provided herein are methods of treating an autoimmune or inflammatory disease or disorder in a subject comprising administering to the subject an effective amount of an antibody, nucleic acid, vector, host cell, or pharmaceutical composition provided herein. In some embodiments, the disease or disorder is selected from the group consisting of: transplant rejection, vasculitis, asthma, rheumatoid arthritis, dermatitis, inflammatory bowel disease, uveitis, and lupus.

In one aspect, the present invention relates to an antibody, nucleic acid, vector, host cell, and/or pharmaceutical composition of the present invention, for use in a method for the treatment of an autoimmune or inflammatory disease or disorder. In one embodiment, the antibody is antagonistic.

In one aspect, the present invention relates to an antibody, nucleic acid, vector, host cell, and/or pharmaceutical composition of the present invention, for use in a method for the treatment of an autoimmune or inflammatory disease or disorder in a subject. In one embodiment, the antibody is antagonistic.

In one aspect, the present invention relates to an antibody, nucleic acid, vector, host cell, and/or pharmaceutical composition of the present invention, for use in a method for the treatment of an autoimmune or inflammatory disease or disorder in a subject comprising administering to the subject an effective amount of an antibody, nucleic acid, vector, host cell, and/or pharmaceutical composition of the invention. In one embodiment, the antibody is antagonistic.

In one aspect, provided herein are methods of treating an infectious disease in a subject comprising administering to the subject an effective amount of an antibody, nucleic acid, vector, host cell, or pharmaceutical composition provided herein.

In one aspect, the present invention relates to an antibody, nucleic acid, vector, host cell, and/or pharmaceutical composition of the present invention, for use in a method for the treatment of an infectious disease. In one embodiment, the antibody is agonistic. In one embodiment, the antibody is antagonistic.

In one aspect, the present invention relates to an antibody, nucleic acid, vector, host cell, and/or pharmaceutical composition of the present invention, for use in a method for the treatment of an infectious disease in a subject. In one embodiment, the antibody is agonistic. In one embodiment, the antibody is antagonistic.

In one aspect, the present invention relates to an antibody, nucleic acid, vector, host cell, and/or pharmaceutical composition of the present invention, for use in a method for the treatment of an infectious disease in a subject comprising administering to the subject an effective amount of an antibody, nucleic acid, vector, host cell, and/or pharmaceutical composition of the invention. In one embodiment, the antibody is agonistic. In one embodiment, the antibody is antagonistic.

In one embodiment of the methods provided herein, the subject is human.

In one aspect, provided herein are methods for detecting OX40 in a sample comprising contacting said sample with the antibody provided herein.

In one aspect, provided herein are methods for in vitro detecting OX40 in a sample comprising contacting said sample with the antibody provided herein. In one embodiment, OX40 is human OX40.

In one aspect, provided herein are methods for in vitro detecting OX40 in a sample comprising contacting said sample with an antibody, nucleic acid, vector, host cell, and/or pharmaceutical composition provided herein. In one embodiment, OX40 is human OX40.

In one aspect, provided herein is the use of an antibody, nucleic acid, vector, host cell, and/or pharmaceutical composition provided herein, preferably of an antibody provided herein, for in vitro detecting OX40 in a sample.

In one aspect, provided herein is an antibody, nucleic acid, vector, host cell, and/or pharmaceutical composition provided herein, preferably an antibody provided herein, for use in the detection of OX40 in a subject. In one embodiment, the subject is a human.

In one aspect, provided herein are kits comprising an antibody that specifically binds to OX40 provided herein, a nucleic acid molecule encoding an antibody that specifically binds to OX40 (e.g., human OX40), a vector comprising such a nucleic acid molecule, a host cell comprising such a nucleic acid molecule or vector, or a pharmaceutical composition comprising such an antibody, nucleic acid molecule, vector, or host cell and a) a detection reagent, b) an OX40 antigen, c) a notice that reflects approval for use or sale for human administration, or d) a combination thereof.

4. BRIEF DESCRIPTION OF THE FIGURES

FIGS. 1A, 1B, 1C, 1D, and 1E: FIG. 1A is a pair of histograms showing the binding of the anti-OX40 antibody pab1949 and an isotype control to activated human CD4+ T cells and CD8+ T cells. FIG. 1B is a pair of histograms showing the binding of pab1949-1 and an isotype control to non-stimulated and stimulated (using anti-CD3 antibody) CD4+ T cells. FIG. 1C is a graph showing the binding of a dose titration of pab1949-1 or an isotype control to activated human CD4+ T cells. FIG. 1D is a set of histograms measuring the binding of pab1949-1 and an isotype control to human non-stimulated blood-derived immune cell populations. FIG. 1E is a histogram of the binding of pab1949 and an isotype control to activated cynomolgus monkey (Macaca fascicularis) CD4+ T cells.

FIGS. 2A, 2B, and 2C are graphs of results of suboptimal CD3 stimulation assays to assess the effects of stimulation of anti-OX40 antibodies pab1949 (FIGS. 2A and 2C) and pab2044 (FIG. 2B) on enriched CD4+ T cell proliferation. The antibody pab1949 is a human IgG$_1$ antibody. The antibody pab2044 shares the same heavy chain variable region and the same light chain as pab1949 but comprises a human IgG$_4$ constant region. Cell proliferation (CFSE; x-axis) is shown for each antibody tested: IgG$_1$ isotype control, pab1949, and anti-CD28 antibody as a positive control in FIG. 2A; and IgG$_4$ isotype control, pab2044, and anti-CD28 antibody in FIG. 2B. FIG. 2C is a line graph showing the titration of the anti-OX40 antibody pab1949 (0.002, 0.02, 0.2, 2, and 20 µg/ml) and the effect of the antibody on enriched CD4+ T cell proliferation under suboptimal anti-CD3 stimulation.

FIGS. 3A, 3B, 3C, 3D, 3E, and 3F are representative results from analyses of the production of IFNγ and TNFα cytokines induced by the anti-OX40 antibody pab1949 or pab1949-1 in combination with varying suboptimal concentrations of anti-CD3 antibody and IL-2. In FIGS. 3A-3C, PBMCs from four different donors were tested: donor KM, donor TM, donor GS, and donor SB. FIGS. 3A and 3B are plots showing intracellular cytokine staining (IFNγ and TNFα) of CD4+ T cells and CD8+ T cells from donor SB (FIG. 3A) and donor GS (FIG. 3B). The percentage of IFNγ+ TNFα+ polyfunctional CD4+ T cells and CD8+ T cells or TNFα+ monofunctional CD4+ T cells and CD8+ T cells is plotted for the anti-OX40 antibody pab1949 or an isotype control (FIG. 3C). The percentages shown in FIG. 3C represent the highest response generated under three different anti-CD3 antibody concentrations. Error bars represent standard deviation (n=2). FIGS. 3D, 3E, and 3F are a set of graphs showing the percentage of TNFα+ CD4+ T cells (FIG. 3D), IFNγ+ TNFα+ polyfunctional CD8+ T cells (FIG. 3E), and IFNγ+ CD8+ T cells (FIG. 3F) induced by a dose titration of the anti-OX40 antibody pab1949-1 or an IgG$_1$ isotype control antibody in cells derived from PBMCs of donor GS in a similar suboptimal anti-CD3 stimulation assay.

FIGS. 4A, 4B, and 4C are a set of graphs showing results of a suboptimal anti-CD3 stimulation assay using cells derived from PBMCs of donors 1, 2, 4, 5, 7, 8, 9, and 10. The percentage of IFNγ+, TNFα+, or IFNγ+ TNFα+ polyfunctional CD4+ or CD8+ T cells is plotted against a range of antibody concentrations of pab1949-1 or an IgG$_1$ isotype control antibody.

FIG. 5A is a set of bar graphs showing the effect of the anti-OX40 antibody pab1949 or an isotype control on the secretion of a panel of cytokines (IL-2, TNFα, IL-10, IL-4, and IL-13) in a suboptimal anti-CD3 stimulation assay using PBMCs from donor SB and donor GS. PBMCs from healthy donors were activated using various suboptimal concentrations of anti-CD3 antibody (clone SP34), IL2 (20 U/ml), and 5 µg/ml of anti-OX40 antibody or an IgG$_1$ isotype control and cytokines were measured after either 4 days (SB #1A) or 3 days (SB #1B, SB #2, and GS) upon stimulation. The bars in FIG. 5A represent the highest cytokine secretion induced by all the anti-CD3 concentrations tested at an anti-OX40 antibody concentration of 5 µg/ml. Errors bars represent standard deviation (n=2). FIGS. 5B, 5C, and 5D are a set of graphs showing the amount of secreted cytokines (TNFα, IL-10, or IL-13) induced by various concentrations of pab1949-1 or an IgG$_1$ isotype control antibody in cells derived from PBMCs of donor GS in the presence of suboptimal concentrations of an anti-CD3 antibody.

FIGS. 6A, 6B, and 6C are a set of graphs showing the amount of secreted GM-CSF induced by a dose titration of pab1949-1 or an IgG$_1$ isotype control antibody in cells derived from PBMCs of donors 1-10 in a suboptimal anti-CD3 stimulation assay. ECL refers to electrochemiluminescence.

FIGS. 7A, 7B, and 7C are similar to FIGS. 6A, 6B, and 6C, showing the amount of secreted IL-2 induced by a dose titration of pab1949-1 or an IgG$_1$ isotype control antibody. ECL refers to electrochemiluminescence.

FIGS. 8A, 8B, and 8C are similar to FIGS. 6A, 6B, and 6C, showing the amount of secreted TNFβ induced by a dose titration of pab1949-1 or an IgG$_1$ isotype control antibody.

FIGS. 9A and 9B are bar graphs showing the production of IL-2 (FIG. 9A) and IL-10 (FIG. 9B) induced by either soluble or crosslinked (using anti-Fc F(ab')2) pab1949-1 or an IgG$_1$ isotype control antibody in T regulatory cells (Treg) and T effector cells (Teff) co-cultured at a ratio of 1:3 (Treg:Teff).

FIGS. 10A, 10B, 10C, 10D, 10E, 10F, and 10G are graphs depicting the functional activity of anti-OX40 antibodies on primary human PBMCs upon *Staphylococcus* Enterotoxin A (SEA) stimulation. Human PBMCs were stimulated with SEA in the absence or presence of a fixed concentration (10 μg/ml) or varying concentrations of anti-OX40 antibody or isotype control and assessed for IL-2 or IL-10 cytokine secretion. The anti-OX40 antibodies tested include pab1949, pab1949-1, pab2193-1, pab1949-1-N297A, and the reference antibodies pab1784 and pab2045. The fold change of IL-2 (FIG. 10A) and IL-10 (FIG. 10B) at an anti-OX40 antibody concentration of 10 μg/ml is plotted for the tested antibodies. FIGS. 10C, 10D, and 10E are dose-response curves showing the fold change of IL-2 production at different concentrations of pab1949, pab1949-1, or the reference antibodies pab1784 and pab2045. Statistical significance was determined by student's t test compared to the isotype control samples indicated by asterisk. Error bars represent standard deviation from triplicate repeats. * in FIG. 10A represents p<0.001. * in FIG. 10B represents p<0.01. FIG. 10F is a graph showing IL-2 production induced by a dose titration of pab1949-1, pab2193-1, an IgG$_1$ isotype control antibody, or an IgG$_2$ isotype control antibody. FIG. 10G is a graph showing IL-2 production in response to a dose titration of pab1949-1, pab1949-1-N297A, or an IgG$_1$ isotype control antibody.

FIGS. 11A and 11B are results from an assay in which soluble (soluble condition, FIG. 11A) or crosslinked (complexed condition, FIG. 11B) pab1949-1 or an IgG$_1$ isotype control antibody were tested using an OX40 NF-κB-luciferase reporter cell line. Relative light units (RLU) are plotted against various antibody concentrations tested.

FIGS. 12A and 12B are results from reporter assays in which anti-OX40 antibodies were tested for their ability to activate reporter cells expressing FcγRIIIA (FIG. 12A) or the FcγRIIA$^{H131}$ variant (FIG. 12B) when the antibodies were bound to OX40-expressing target cells. In FIG. 12A, Δ RLU values are plotted against various concentrations of pab1949-1 and pab2044-1. Δ RLU represents the RLU of the anti-OX40 antibody minus that of the isotype control. In FIG. 12B, the RLU values are plotted against increasing concentrations of pab1949-1, pab1949-1-S267E/L328F, pab2193-1, an IgG$_1$ isotype control antibody, or an IgG$_2$ isotype control antibody.

FIG. 13A is a bar graph showing ΔMFI of human OX40 on nTregs, CD4+ T cells or CD8+ T cells from healthy donors activated by anti-CD3/anti-CD28 beads, as measured by flow cytometry. ΔMFI represents the MFI of the anti-OX40 antibody minus the MFI of an isotype control. The anti-OX40 antibody used was a PE-conjugated mouse anti-human OX40 antibody (Biolegend: ACT35; Catalogue: 350004; Lot: B181090). FIG. 13B is a bar graph showing ΔMFI of human OX40 on activated nTregs and T effector cells from two healthy donors. The cells were stained with a commercial anti-OX40 antibody (BER-ACT35 clone) or an isotype control antibody and analyzed using flow cytometry. FIG. 13C is a graph examining the anti-OX40 antibody pab1949 using an Fc gamma receptor IIIA (FcγRIIIA) reporter cell line. Jurkat NFAT-luciferase reporter cells overexpressing FcγRIIIA (158 V/V polymorphism) were co-cultured with activated primary nTregs and T effector cells for 20 hours at 37° C. in the presence of pab1949 or an isotype control. The relative light units (RLU) were recorded after 20 hours, representing FcγRIIIA binding. Δ RLU represents the RLU of the anti-OX40 antibody minus that of the isotype control. The error bars represent standard deviation (n=2). The data shown are representative of experiments using cells from three donors. FIG. 13D is similar to FIG. 13C, showing results from a study testing pab1949-1 using a modified protocol.

FIG. 14A is a set of histograms showing the surface expression of OX40 measured by flow cytometry. Samples were collected from the blood of healthy human donors (a-c, n=3) or from tumor tissues of non-small cell lung cancer patients (NSCLC) (d-f, n=3). The cell populations were defined as: Tconv (CD3+, CD4+, CD8a−, CD25low, and FOXP3−) or Treg (CD3+, CD4+, CD8a−, CD25high, and FOXP3+). FIG. 14B is a pair of histograms from a study similar to that depicted in FIG. 14A measuring surface OX40 expression in CD8+ or CD4+ T cells, or Treg cells from endometrial cancer samples. FIG. 14C is a bar graph showing OX40 expression on Treg cells and Teff cells across various tumor types. FIG. 14D is a table summarizing OX40 expression in tumor-associated CD4+ Teff cells and Treg cells. "−" represents negative/no expression, "+" represents weak expression, "++" represents moderate expression, and "+++" represents high expression.

FIGS. 15A and 15B are a set of graphs showing the amount of secreted GM-CSF induced by a dose titration of pab1949-1 or an IgG$_1$ isotype control antibody in cells derived from cynomolgus PBMCs. Note that Cyno 2 and Cyno 9 refer to PBMCs from a same cynomolgus monkey tested in independent experiments. All the other PBMC samples were collected from different cynomolgus donors.

FIG. 21 is a table summarizing the binding of the monoclonal anti-OX40 antibodies pab1949-1 and pab1928 to 1624-5 cells expressing human OX40 alanine mutants.

5. DETAILED DESCRIPTION

Figure 1A:
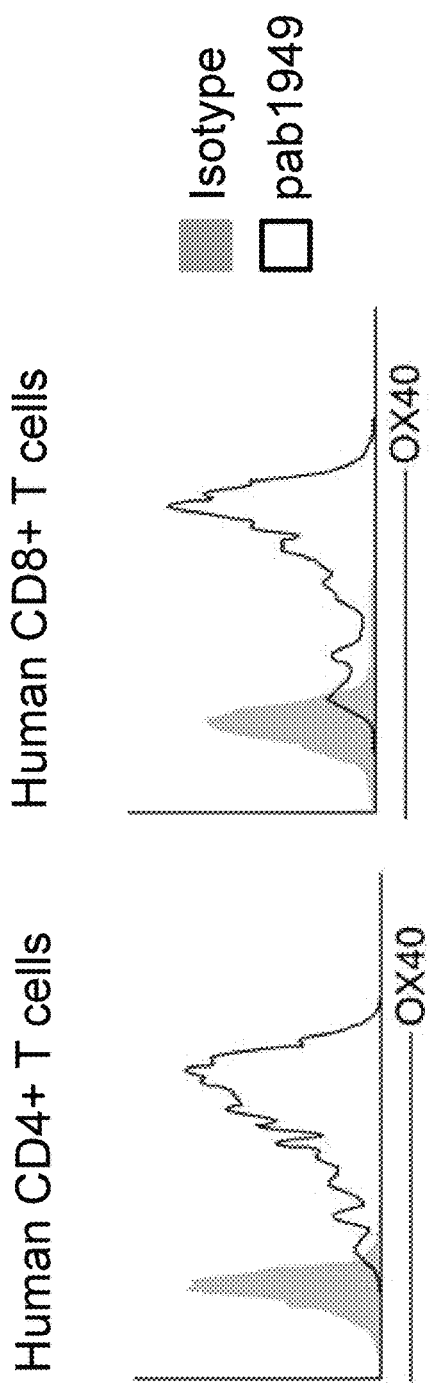

Provided herein are antibodies (e.g., monoclonal antibodies) that specifically bind to OX40 (e.g., human OX40) and modulate OX40 activity. For example, in one aspect, provided herein are antibodies that specifically bind to OX40 and enhance, induce, or increase one or more OX40 activities. For example, in another aspect, provided herein are antibodies that specifically bind to OX40 (e.g., human OX40) and deactivate, reduce, or inhibit one or more OX40 activities. In a specific embodiment, the antibodies are isolated.

Also provided are isolated nucleic acids (polynucleotides), such as complementary DNA (cDNA), encoding such antibodies. Further provided are vectors (e.g., expression vectors) and cells (e.g., host cells) comprising nucleic acids (polynucleotides) encoding such antibodies. Also provided are methods of making such antibodies. In other aspects, provided herein are methods and uses for inducing, increasing or enhancing an OX40 activity, and treating certain conditions, such as cancer. Further provided are methods and uses for deactivating, reducing, or inhibiting an OX40 (e.g., human OX40) activity, and treating certain conditions, such as inflammatory or autoimmune diseases and disorders. Related compositions (e.g., pharmaceutical compositions), kits, and detection methods are also provided.

5.1 Terminology

As used herein, the terms "about" and "approximately," when used to modify a numeric value or numeric range, indicate that deviations of 5% to 10% above and 5% to 10% below the value or range remain within the intended meaning of the recited value or range.

As used herein, B is a "substantially increasing function" of A over a specified domain of A values if B substantially increases as A increases over the specified domain, e.g., in a given experiment, or using mean values from multiple experiments. This definition allows for a value of B corresponding to a specified value of A to be up to 1%, 2%, 3%, 4%, 5%, 10%, 15%, or 20% lower relative to a value of B corresponding to any lower value of A.

As used herein, the terms "antibody" and "antibodies" are terms of art and can be used interchangeably herein and refer to a molecule with an antigen-binding site that specifically binds an antigen.

Antibodies can include, for example, monoclonal antibodies, recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), bispecific antibodies, and multi-specific antibodies. In certain embodiments, antibodies described herein refer to polyclonal antibody populations. Antibodies can be of any type (e.g., IgG, IgE, IgM, IgD, IgA, or IgY), any class (e.g., $IgG_1$, $IgG_2$, $IgG_3$, $IgG_4$, $IgA_1$, or $IgA_2$), or any subclass (e.g., $IgG_{2a}$ or $IgG_{2b}$) of immunoglobulin molecule. In certain embodiments, antibodies described herein are IgG antibodies, or a class (e.g., human $IgG_1$, $IgG_2$, or $IgG_4$) or subclass thereof. In a specific embodiment, the antibody is a humanized monoclonal antibody. In another specific embodiment, the antibody is a human monoclonal antibody, e.g., that is an immunoglobulin. In certain embodiments, an antibody described herein is an $IgG_1$, $IgG_2$, or $IgG_4$ antibody.

As used herein, the terms "antigen-binding domain," "antigen-binding region," "antigen-binding site," and similar terms refer to the portion of antibody molecules which comprises the amino acid residues that confer on the antibody molecule its specificity for the antigen (e.g., the complementarity determining regions (CDR)). The antigen-binding region can be derived from any animal species, such as rodents (e.g., mouse, rat, or hamster) and humans.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody, or an antigen-binding portion thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIAcore® or KinExA.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody can be replaced with an amino acid residue with a similar side chain.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody: antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques. In a specific embodiment, the epitope of an antibody is determined using alanine scanning mutagenesis studies.

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, Id.), or other assays known in the art. In a specific embodiment, molecules that immunospecifically bind to an antigen bind to the antigen with a $K_A$ that is at least 2 logs, 2.5 logs, 3 logs, 4 logs or greater than the $K_A$ when the molecules bind non-specifically to another antigen. In the context of antibodies with an anti-OX40 antigen-binding domain and a second antigen-binding domain that does not specifically bind to an antigen expressed by a human immune cell, the terms "immunospecifically binds," "immunospecifically recognizes," "specifically binds," and "specifically recognizes" refer to antibodies that have distinct specificities for more than one antigen (i.e., OX40 and the antigen associated with the second antigen-binding domain).

In another specific embodiment, molecules that immunospecifically bind to an antigen do not cross react with other proteins under similar binding conditions. In another specific embodiment, molecules that immunospecifically bind to an antigen do not cross react with other non-OX40 proteins. In a specific embodiment, provided herein is an antibody that binds to OX40 with higher affinity than to another unrelated antigen. In certain embodiments, provided herein is an antibody that binds to OX40 (e.g., human OX40) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-OX40 antibody described herein to an unrelated, non-OX40 protein is less than 10%, 15%, or 20% of the binding of the antibody to OX40 protein as measured by, e.g., a radioimmunoassay.

In a specific embodiment, provided herein is an antibody that binds to human OX40 with higher affinity than to another species of OX40. In certain embodiments, provided herein is an antibody that binds to human OX40 with a 5%, 10%, 15%, 20%, 25%, 30%, 35%, 40%, 45%, 50%, 55%, 60%, 65%, 70% or higher affinity than to another species of OX40 as measured by, e.g., a radioimmunoassay, surface plasmon resonance, or kinetic exclusion assay. In a specific embodiment, an antibody described herein, which binds to human OX40, will bind to another species of OX40 protein with less than 10%, 15%, or 20% of the binding of the antibody to the human OX40 protein as measured by, e.g., a radioimmunoassay, surface plasmon resonance, or kinetic exclusion assay.

As used herein, the terms "OX40 receptor" or "OX40" or "OX40 polypeptide" refer to OX40 including, but not limited to, native OX40, an isoform of OX40, or an interspecies OX40 homolog of OX40. OX40 is also known as tumor necrosis factor receptor superfamily member 4 (TNFRSF4), ACT35, CD134, IMD16, and TXGP1L. GenBank™ accession numbers BC105070 and BC105072 provide human OX40 nucleic acid sequences. Refseq number NP 003318.1 provides the amino acid sequence of human OX40. The immature amino acid sequence of human OX40 is provided as SEQ ID NO: 17. The mature amino acid sequence of human OX40 is provided as SEQ ID NO: 55. Human OX40 is designated GeneID: 7293 by Entrez Gene. RefSeq numbers XM_005545122.1 and XP_005545179.1 provide predicted cynomolgus OX40 nucleic acid sequences and amino acid sequences, respectively. A soluble isoform of human OX40 has also been reported (Taylor L et al., (2001) J Immunol Methods 255: 67-72). As used herein, the term "human OX40" refers to OX40 comprising the polypeptide sequence of SEQ ID NO:55.

As used herein, the terms "OX40 ligand" and "OX40L" refer to tumor necrosis factor ligand superfamily member 4 (TNFSF4). OX40L is otherwise known as CD252, GP34, TXGP1, and CD134L. GenBank™ accession numbers D90224.1 and AK297932.1 provide exemplary human OX40L nucleic acid sequences. RefSeq number NP_003317.1 and Swiss-Prot accession number P23510-1 provide exemplary human OX40L amino acid sequences for isoform 1. RefSeq number NP_001284491.1 and Swiss-Prot accession number P23510-2 provide exemplary human OX40L amino acid sequences for isoform 2. Human OX40L is designated GeneID: 7292 by Entrez Gene. In a particular embodiment, the OX40L is human OX40L isoform 1 of SEQ ID NO: 42 or isoform 2 of SEQ ID NO: 43.

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

As used herein, the term "effective amount" in the context of the administration of a therapy to a subject refers to the amount of a therapy that achieves a desired prophylactic or therapeutic effect. Examples of effective amounts are provided in Section 5.5.1.3, infra.

As used herein, the terms "subject" and "patient" are used interchangeably. The subject can be an animal. In some embodiments, the subject is a mammal such as a non-primate (e.g., cow, pig, horse, cat, dog, rat, etc.) or a primate (e.g., monkey or human), most preferably a human. In some embodiments, the subject is a cynomolgus monkey. In certain embodiments, such terms refer to a non-human animal (e.g., a non-human animal such as a pig, horse, cow, cat, or dog). In some embodiments, such terms refer to a pet or farm animal. In specific embodiments, such terms refer to a human.

As used herein, the binding between a test antibody and a first antigen is "substantially weakened" relative to the binding between the test antibody and a second antigen if the binding between the test antibody and the first antigen is reduced by at least 30%, 40%, 50%, 60%, 70%, or 80% relative to the binding between the test antibody and the second antigen, as measured in, e.g., a flow cytometry analysis.

The determination of "percent identity" between two sequences (e.g., amino acid sequences or nucleic acid sequences) can also be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877. Such an algorithm is incorporated into the NBLAST and XBLAST programs of Altschul S F et al., (1990) J Mol Biol 215: 403. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "antigen-binding domain that does not bind to an antigen expressed by a human immune cell" means that the antigen-binding domain does not bind to an antigen expressed by any human cell of hematopoietic origin that plays a role in the immune response. Immune cells include lymphocytes, such as B cells and T cells; natural killer cells; and myeloid cells, such as monocytes, macrophages, eosinophils, mast cells, basophils, and granulocytes. For example, such a binding domain would not bind to OX40, or any other members of the TNF receptor superfamily that are expressed by a human immune cell.

However, the antigen-binding domain can bind to an antigen such as, but not limited to, an antigen expressed in other organisms and not humans (i.e., a non-human antigen); an antigen that is not expressed by wild-type human cells; or a viral antigen, including, but not limited to, an antigen from a virus that does not infect human cells, or a viral antigen that is absent in an uninfected human immune cell.

5.2 Antibodies

In a specific aspect, provided herein are antibodies (e.g., monoclonal antibodies, such as chimeric, humanized, or human antibodies) which specifically bind to OX40 (e.g., human OX40).

In certain embodiments, an antibody described herein binds to human CD4+ T cells and human CD8+ T cells. In certain embodiments, an antibody described herein binds to human CD4+ cells and cynomolgus monkey CD4+ T cells.

In a particular embodiment, an antibody described herein, which specifically binds to OX40 (e.g., human OX40), comprises a light chain variable region (VL) comprising:

(a) a VL CDR1 comprising, consisting of, or consisting essentially of the amino acid sequence RSSQSLLHSNGY-NYLD (SEQ ID NO: 1), (b) a VL CDR2 comprising, consisting of, or consisting essentially of the amino acid sequence LGSNRAS (SEQ ID NO: 2), and (c) a VL CDR3 comprising, consisting of, or consisting essentially of the amino acid sequence MQALQTPLT (SEQ ID NO: 3), as shown in Table 1.

In some embodiments, the antibody comprises the VL framework regions described herein. In specific embodiments, the antibody comprises the VL framework regions (FRs) of an antibody set forth in Table 3.

In another embodiment, an antibody described herein, which specifically binds to OX40 (e.g., human OX40), comprises a heavy chain variable region (VH) comprising:

(a) a VH CDR1 comprising, consisting of, or consisting essentially of the amino acid sequence GSAMH (SEQ ID NO: 4), (b) a VH CDR2 comprising, consisting of, or consisting essentially of the amino acid sequence RIRSKAN-SYATAYAASVKG (SEQ ID NO: 5), and (c) a VH CDR3 comprising, consisting of, or consisting essentially of the amino acid sequence GIYDSSGYDY (SEQ ID NO: 6), as shown in Table 2.

In some embodiments, the antibody comprises the VH frameworks described herein. In specific embodiments, the antibody comprises the VH framework regions of an antibody set forth in Table 4.

TABLE 1

VL CDR Amino Acid Sequences [1]

| Antibody | VL CDR1 (SEQ ID NO:) | VL CDR2 (SEQ ID NO:) | VL CDR3 (SEQ ID NO:) |
|---|---|---|---|
| pab1949 | RSSQSLLHSNGY NYLD (1) | LGSNRAS (2) | MQALQTPLT (3) |

[1] The VL CDRs in Table 1 are determined according to Kabat.

TABLE 2

VH CDR Amino Acid Sequences [2]

| Antibody | VH CDR1 (SEQ ID NO:) | VH CDR2 (SEQ ID NO:) | VH CDR3 (SEQ ID NO:) |
|---|---|---|---|
| pab1949 | GSAMH (4) | RIRSKANSYATA YAASVKG (5) | GIYDSSGYDY (6) |

[2] The VH CDRs in Table 2 are determined according to Kabat.

TABLE 3

VL FR Amino Acid Sequences [3]

| Antibody | VL FR1 (SEQ ID NO:) | VL FR2 (SEQ ID NO:) | VL FR3 (SEQ ID NO:) | VL FR4 (SEQ ID NO:) |
|---|---|---|---|---|
| pab1949 | DIVMTQSP LSLPVTPG EPASISC (7) | WYLQKPG QSPQLLI Y (8) | GVPDRFSG SGSGTDFT LKISRVEA EDVGVYYC (9) | FGGGTKV EIK (10) |

[3] The VL framework regions described in Table 3 are determined based upon the boundaries of the Kabat numbering system for CDRs. In other words, the VL CDRs are determined by Kabat and the framework regions are the amino acid residues surrounding the CDRs in the variable region in the format FR1, CDR1, FR2, CDR2, FR3, CDR3, and FR4.

TABLE 4

VH FR Amino Acid Sequences [4]

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| pab1949 | EVQLVESGG GLVQPGGSL KLSCAASGF TFS (11) | WVRQASG KGLEWVG (12) | RFTISRDDSK NTAYLQMNSL KTEDTAVYYC TS (13) | WGQGTLVTV SS (14) |

[4] The VH framework regions described in Table 4 are determined based upon the boundaries of the Kabat numbering system for CDRs. In other words, the VH CDRs are determined by Kabat and the framework regions are the amino acid residues surrounding the CDRs in the variable region in the format FR1, CDR1, FR2, CDR2, FR3, CDR3, and FR4.

In specific embodiments, the antibody comprises the four VL framework regions (FRs) set forth in Table 3 and the four VH framework regions (FRs) set forth in Table 4.

In certain embodiments, provided herein is an antibody which specifically binds to OX40 (e.g., human OX40) and comprises light chain variable region (VL) CDRs and heavy chain variable region (VH) CDRs of pab1949 or pab2044, for example as set forth in Tables 1 and 2 (i.e., SEQ ID NOs: 1-6). In certain embodiments, provided herein is an antibody which specifically binds to OX40 (e.g., human OX40) and comprises light chain variable region (VL) CDRs and heavy chain variable region (VH) CDRs of pab1949 or pab2044, for example as set forth in Tables 1 and 2 (i.e., SEQ ID NOs: 1-6) and the VL framework regions and VH framework regions set forth in Tables 3 and 4.

In a particular embodiment, an antibody described herein, which specifically binds to OX40 (e.g., human OX40), comprises a light chain variable region (VL) comprising VL CDR1, VL CDR2, and VL CDR3 as set forth in Table 1 and the VL framework regions of set forth in Table 3.

In certain embodiments, an antibody comprises a light chain variable framework region that is derived from an amino acid sequence encoded by a human gene, wherein the amino acid sequence is that of IGKV2-28*01 (SEQ ID NO: 18).

In a particular embodiment, an antibody described herein, which specifically binds to OX40 (e.g., human OX40), comprises a heavy chain variable region (VH) comprising VH CDR1, VH CDR2, and VH CDR3 as set forth in Table 2 and the VH framework regions set forth in Table 4.

In certain embodiments, the antibody comprises a heavy chain variable framework region that is derived from an amino acid sequence encoded by a human gene, wherein the amino acid sequence is that of IGHV3-73*01 (SEQ ID NO: 19).

In a specific embodiment, an antibody that specifically binds to OX40 (e.g., human OX40) comprises a VL domain comprising the amino acid sequence of SEQ ID NO: 15. In a specific embodiment, an antibody that specifically binds to OX40 (e.g., human OX40) comprises a VL domain consisting of or consisting essentially of the amino acid sequence of SEQ ID NO: 15.

In certain embodiments, an antibody that specifically binds to OX40 (e.g., human OX40) comprises a VH domain comprising the amino acid sequence of SEQ ID NO: 16. In some embodiments, an antibody that specifically binds to OX40 (e.g., human OX40) comprises a VH domain consisting of or consisting essentially of the amino acid sequence of SEQ ID NO: 16.

In certain embodiments, an antibody that specifically binds to OX40 (e.g., human OX40) comprises a VH domain and a VL domain, wherein the VH domain and the VL domain comprise the amino acid sequences of SEQ ID NO: 16 and SEQ ID NO: 15, respectively. In certain embodiments, an antibody that specifically binds to OX40 (e.g., human OX40) comprises a VH domain and a VL domain, wherein the VH domain and the VL domain consist of or consist essentially of the amino acid sequences of SEQ ID NO: 16 and SEQ ID NO: 15, respectively.

In certain aspects, an antibody described herein may be described by its VL domain alone, or its VH domain alone, or by its 3 VL CDRs alone, or its 3 VH CDRs alone. See, for example, Rader C et al., (1998) PNAS 95: 8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also Clackson T et al., (1991) Nature 352: 624-628, which is incorporated herein by reference in its entirety, describing methods of producing antibodies that bind a specific antigen by using a specific VL domain (or VH domain) and screening a library for the complementary variable domains. The screen produced 14 new partners for a specific VH domain and 13 new partners for a specific VL domain, which were strong binders, as determined by ELISA. See also Kim S J & Hong H J, (2007) J Microbiol 45: 572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

In certain aspects, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, provided herein are antibodies that specifically bind to OX40 (e.g., human OX40) and comprise the Chothia VL CDRs of a VL of pab1949 or pab2044. In certain aspects, provided herein are antibodies that specifically bind to OX40 (e.g., human OX40) and comprise the Chothia VH CDRs of a VH of pab1949 or pab2044. In certain aspects, provided herein are antibodies that specifically bind to OX40 (e.g., human OX40) and comprise the Chothia VL CDRs of a VL of pab1949 or pab2044 and comprise the Chothia VH CDRs of a VH of pab1949 or pab2044. In certain embodiments, antibodies that specifically bind to OX40 (e.g., human OX40) comprise one or more CDRs, in which the Chothia and Kabat CDRs have the same amino acid sequence. In certain embodiments, provided herein are antibodies that specifically bind to OX40 (e.g., human OX40) and comprise combinations of Kabat CDRs and Chothia CDRs.

In certain aspects, the CDRs of an antibody can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97. In a particular embodiment, provided herein are antibodies that specifically bind to OX40 (e.g., human OX40) and comprise CDRs of pab1949 or pab2044 as determined by the IMGT numbering system, for example, as described in Lefranc M-P (1999) supra and Lefranc M-P et al., (1999) supra).

In certain aspects, the CDRs of an antibody can be determined according to MacCallum R M et al., (1996) J Mol Biol 262: 732-745. See also, e.g., Martin A. "Protein Sequence and Structure Analysis of Antibody Variable Domains," in Antibody Engineering, Kontermann and Dübel, eds., Chapter 31, pp. 422-439, Springer-Verlag, Berlin (2001). In a particular embodiment, provided herein are antibodies that specifically bind to OX40 (e.g., human OX40) and comprise CDRs of pab1949 or pab2044 as determined by the method in MacCallum R M et al.

In certain aspects, the CDRs of an antibody can be determined according to the AbM numbering scheme, which refers AbM hypervariable regions which represent a compromise between the Kabat CDRs and Chothia structural loops, and are used by Oxford Molecular's AbM antibody modeling software (Oxford Molecular Group, Inc.). In a particular embodiment, provided herein are antibodies that specifically bind to OX40 (e.g., human OX40) and comprise CDRs of pab1949 or pab2044 as determined by the AbM numbering scheme.

In a specific embodiment, the position of one or more CDRs along the VH (e.g., CDR1, CDR2, or CDR3) and/or VL (e.g., CDR1, CDR2, or CDR3) region of an antibody described herein may vary by one, two, three, four, five, or six amino acid positions so long as immunospecific binding to OX40 (e.g., human OX40) is maintained (e.g., substantially maintained, for example, at least 50%, at least 60%, at least 70%, at least 80%, at least 90%, at least 95%). For example, in one embodiment, the position defining a CDR of an antibody described herein can vary by shifting the N-terminal and/or C-terminal boundary of the CDR by one, two, three, four, five, or six amino acids, relative to the CDR position of an antibody described herein (e.g., pab1949 or pab2044), so long as immunospecific binding to OX40 (e.g., human OX40) is maintained (e.g., substantially maintained, for example, at least 50%, at least 60%, at least 70%, at least 80%, at least 90%, at least 95%). In another embodiment, the length of one or more CDRs along the VH (e.g., CDR1, CDR2, or CDR3) and/or VL (e.g., CDR1, CDR2, or CDR3) region of an antibody described herein may vary (e.g., be shorter or longer) by one, two, three, four, five, or more amino acids, so long as immunospecific binding to OX40 (e.g., human OX40) is maintained (e.g., substantially maintained, for example, at least 50%, at least 60%, at least 70%, at least 80%, at least 90%, at least 95%).

In one embodiment, a VL CDR1, VL CDR2, VL CDR3, VH CDR1, VH CDR2, and/or VH CDR3 described herein may be one, two, three, four, five or more amino acids shorter than one or more of the CDRs described herein (e.g., SEQ ID NO: 1-6) so long as immunospecific binding to OX40 (e.g., human OX40) is maintained (e.g., substantially maintained, for example, at least 50%, at least 60%, at least 70%, at least 80%, at least 90%, at least 95%). In another embodiment, a VL CDR1, VL CDR2, VL CDR3, VH CDR1, VH CDR2, and/or VH CDR3 described herein may be one, two, three, four, five or more amino acids longer than one or more of the CDRs described herein (e.g., SEQ ID NO: 1-6) so long as immunospecific binding to OX40 (e.g., human OX40) is maintained (e.g., substantially maintained, for example, at least 50%, at least 60%, at least 70%, at least 80%, at least 90%, at least 95%). In another embodiment, the amino terminus of a VL CDR1, VL CDR2, VL CDR3, VH CDR1, VH CDR2, and/or VH CDR3 described herein may be extended by one, two, three, four, five or more amino acids compared to one or more of the CDRs described herein (e.g., SEQ ID NO: 1-6) so long as immunospecific binding to OX40 (e.g., human OX40) is maintained (e.g., substantially maintained, for example, at least 50%, at least 60%, at least 70%, at least 80%, at least 90%, at least 95%). In another embodiment, the carboxy terminus of a VL CDR1, VL CDR2, VL CDR3, VH CDR1, VH CDR2, and/or VH CDR3 described herein may be extended by one, two, three, four, five or more amino acids compared to one or more of the CDRs described herein (e.g., SEQ ID NO: 1-6) so long as immunospecific binding to OX40 (e.g., human OX40) is maintained (e.g., substantially maintained, for example, at least 50%, at least 60%, at least 70%, at least 80%, at least 90%, at least 95%). In another embodiment, the amino terminus of a VL CDR1, VL CDR2, VL CDR3, VH CDR1, VH CDR2, and/or VH CDR3 described herein may be shortened by one, two, three, four, five or more amino acids compared to one or more of the CDRs described herein (e.g., SEQ ID NO: 1-6) so long as immunospecific binding to OX40 (e.g., human OX40) is maintained (e.g., substantially maintained, for example, at least 50%, at least 60%, at least 70%, at least 80%, at least 90%, at least 95%). In one embodiment, the carboxy terminus of a VL CDR1, VL CDR2, VL CDR3, VH CDR1, VH CDR2, and/or VH CDR3 described herein may be shortened by one, two, three, four, five or more amino acids compared to one or more of the CDRs described herein (e.g., SEQ ID NO: 1-6) so long as immunospecific binding to OX40 (e.g., human OX40) is maintained (e.g., substantially maintained, for example, at least 50%, at least 60%, at least 70%, at least 80%, at least 90%, at least 95%). Any method known in the art can be used to ascertain whether immunospecific binding to OX40 (e.g., human OX40) is maintained, for example, the binding assays and conditions described in the "Examples" section (Section 6) provided herein.

In specific aspects, provided herein is an antibody comprising an antibody light chain and heavy chain, e.g., a separate light chain and heavy chain. With respect to the light chain, in a specific embodiment, the light chain of an antibody described herein is a kappa light chain. In another specific embodiment, the light chain of an antibody described herein is a lambda light chain. In yet another specific embodiment, the light chain of an antibody described herein is a human kappa light chain or a human lambda light chain. In a particular embodiment, an antibody described herein, which immunospecifically binds to an OX40 polypeptide (e.g., human OX40) comprises a light chain wherein the amino acid sequence of the VL domain comprises the sequence set forth in SEQ ID NO: 15, and wherein the constant region of the light chain comprises the amino acid sequence of a human kappa light chain constant region. In another particular embodiment, an antibody described herein, which immunospecifically binds to OX40 (e.g., human OX40) comprises a light chain wherein the amino acid sequence of the VL domain comprises the sequence set forth in SEQ ID NO: 15 and wherein the constant region of the light chain comprises the amino acid sequence of a human lambda light chain constant region. In a specific embodiment, an antibody described herein, which immunospecifically binds to OX40 (e.g., human OX40) comprises a light chain wherein the amino acid sequence of the VL domain comprises the sequence set forth in SEQ ID NO: 15 and wherein the constant region of the light chain comprises the amino acid sequence of a human kappa or lambda light chain constant region. Non-limiting examples of human constant region sequences have been described in the art, e.g., see U.S. Pat. No. 5,693,780 and Kabat E A et al., (1991) supra.

In a particular embodiment, an antibody described herein, which specifically binds to OX40 (e.g., human OX40) comprises a light chain comprising the amino acid sequence set forth in SEQ ID NO: 20.

With respect to the heavy chain, in a specific embodiment, the heavy chain of an antibody described herein can be an alpha (α), delta (δ), epsilon (ε), gamma (γ) or mu (μ) heavy chain. In another specific embodiment, the heavy chain of an antibody described can comprise a human alpha (α), delta (δ), epsilon (ε), gamma (γ) or mu (0 heavy chain. In a particular embodiment, an antibody described herein, which immunospecifically binds to OX40 (e.g., human OX40), comprises a heavy chain wherein the amino acid sequence of the VH domain can comprise the sequence set forth in SEQ ID NO: 16 and wherein the constant region of the heavy chain comprises the amino acid sequence of a human gamma (γ) heavy chain constant region. In a specific embodiment, an antibody described herein, which specifically binds to OX40 (e.g., human OX40), comprises a heavy chain wherein the amino acid sequence of the VH domain comprises the sequence set forth in SEQ ID NO: 16, and wherein the constant region of the heavy chain comprises the amino acid of a human heavy chain described herein or known in the art. Non-limiting examples of human constant region sequences have been described in the art, e.g., see U.S. Pat. No. 5,693,780 and Kabat E A et al., (1991) supra.

In a particular embodiment, an antibody described herein, which specifically binds to OX40 (e.g., human OX40), comprises a heavy chain comprising the amino acid sequence set forth in SEQ ID NO: 21. In a particular embodiment, an antibody described herein, which specifically binds to OX40 (e.g., human OX40), comprises a heavy chain comprising the amino acid sequence set forth in SEQ ID NO: 60. In another embodiment, an antibody described herein, which specifically binds to OX40 (e.g., human OX40), comprises a heavy chain comprising the amino acid sequence set forth in SEQ ID NO: 23. In another embodiment, an antibody described herein, which specifically binds to OX40 (e.g., human OX40), comprises a heavy chain comprising the amino acid sequence set forth in SEQ ID NO: 61. In another embodiment, an antibody described herein, which specifically binds to OX40 (e.g., human OX40), comprises a heavy chain comprising the amino acid sequence set forth in SEQ ID NO: 51. In another embodiment, an antibody described herein, which specifically binds to OX40 (e.g., human OX40), comprises a heavy chain comprising the amino acid sequence set forth in SEQ ID NO: 62. In another embodiment, an antibody described herein, which specifically binds to OX40 (e.g., human OX40), comprises a heavy chain comprising the amino acid sequence set forth in SEQ ID NO: 52. In another embodiment, an antibody described herein, which specifically binds to OX40 (e.g., human OX40), comprises a heavy chain comprising the amino acid sequence set forth in SEQ ID NO: 63.

In a specific embodiment, an antibody described herein, which immunospecifically binds to OX40 (e.g., human OX40) comprises a VL domain and a VH domain comprising any amino acid sequences described herein, and wherein the constant regions comprise the amino acid sequences of the constant regions of an IgG, IgE, IgM, IgD, IgA, or IgY immunoglobulin molecule, or a human IgG, IgE, IgM, IgD, IgA, or IgY immunoglobulin molecule. In another specific embodiment, an antibody described herein, which immunospecifically binds to OX40 (e.g., human OX40) comprises a VL domain and a VH domain comprising any amino acid sequences described herein, and wherein the constant regions comprise the amino acid sequences of the constant regions of an IgG, IgE, IgM, IgD, IgA, or IgY immunoglobulin molecule, any class (e.g., IgG$_1$, IgG$_2$, IgG$_3$, IgG$_4$, IgA$_1$, and IgA$_2$), or any subclass (e.g., IgG$_{2a}$ and IgG$_{2b}$) of immunoglobulin molecule. In a particular embodiment, the constant regions comprise the amino acid sequences of the constant regions of a human IgG, IgE, IgM, IgD, IgA, or IgY immunoglobulin molecule, any class (e.g., IgG$_1$, IgG$_2$, IgG$_3$, IgG$_4$, IgA$_1$, and IgA$_2$), or any subclass (e.g., IgG$_2$a and IgG$_{2b}$) of immunoglobulin molecule.

In another specific embodiment, an antibody described herein, which immunospecifically binds to OX40 (e.g., human OX40), comprises a VL domain and a VH domain comprising any amino acid sequences described herein, and wherein the constant regions comprise the amino acid sequences of the constant regions of a human IgG$_1$ (e.g., allotypes G1m3, G1m17,1 or G1m17,1,2), human IgG$_2$, or human IgG$_4$. In a particular embodiment, an antibody described herein, which immunospecifically binds to OX40 (e.g., human OX40), comprises a VL domain and a VH domain comprising any amino acid sequences described herein, and wherein the constant regions comprise the amino acid sequences of the constant region of a human IgG$_1$ (allotype G1m3). Non-limiting examples of human constant regions are described in the art, e.g., see Kabat E A et al., (1991) supra.

In another embodiment, an antibody described herein, which specifically binds to OX40 (e.g., human OX40), comprises a light chain comprising the amino acid sequence set forth in SEQ ID NO: 20 and a heavy chain comprising the amino acid sequence set forth in SEQ ID NO: 21. In another embodiment, an antibody described herein, which specifically binds to OX40 (e.g., human OX40), comprises a light chain comprising the amino acid sequence set forth in SEQ ID NO: 20 and a heavy chain comprising the amino acid sequence set forth in SEQ ID NO: 60. In another embodiment, an antibody described herein, which specifically binds to OX40 (e.g., human OX40), comprises a light chain comprising the amino acid sequence set forth in SEQ ID NO: 20 and a heavy chain comprising the amino acid sequence set forth in SEQ ID NO: 23. In another embodiment, an antibody described herein, which specifically binds to OX40 (e.g., human OX40), comprises a light chain comprising the amino acid sequence set forth in SEQ ID NO: 20 and a heavy chain comprising the amino acid sequence set forth in SEQ ID NO: 61. In another embodiment, an antibody described herein, which specifically binds to OX40 (e.g., human OX40), comprises a light chain comprising the amino acid sequence set forth in SEQ ID NO: 20 and a heavy chain comprising the amino acid sequence set forth in SEQ ID NO: 51 or 52. In another embodiment, an antibody described herein, which specifically binds to OX40 (e.g., human OX40), comprises a light chain comprising the amino acid sequence set forth in SEQ ID NO: 20 and a heavy chain comprising the amino acid sequence set forth in SEQ ID NO: 62 or 63.

In certain embodiments, one, two, or more mutations (e.g., amino acid substitutions) are introduced into the Fc region of an antibody described herein (e.g., CH2 domain (residues 231-340 of human IgG$_1$) and/or CH3 domain (residues 341-447 of human IgG$_1$) and/or the hinge region, with numbering according to the Kabat numbering system (e.g., the EU index in Kabat)) to alter one or more functional properties of the antibody, such as serum half-life, complement fixation, Fc receptor binding and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain may be altered to, e.g., facilitate assembly of the light and heavy chains, or to alter (e.g., increase or decrease) the stability of the antibody.

In some embodiments, one, two, or more mutations (e.g., amino acid substitutions) are introduced into the Fc region of an antibody described herein (e.g., CH2 domain (residues 231-340 of human IgG$_1$) and/or CH3 domain (residues 341-447 of human IgG$_1$) and/or the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In a specific embodiment, one, two, or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo. In some embodiments, one, two or more amino acid mutations (i.e., substitutions, insertions, or deletions) are introduced into an IgG constant domain, or FcRn-binding fragment thereof (preferably an Fc or hinge-Fc domain fragment) to decrease the half-life of the antibody in vivo. In other embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody in vivo. In a specific embodiment, the antibodies may have one or more amino acid mutations (e.g., substitutions) in the second constant (CH2) domain (residues 231-340 of human $IgG_1$) and/or the third constant (CH3) domain (residues 341-447 of human $IgG_1$), with numbering according to the EU index in Kabat (Kabat E A et al., (1991) supra). In a specific embodiment, the constant region of the $IgG_1$ of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In certain embodiments, an antibody comprises an IgG constant domain comprising one, two, three or more amino acid substitutions of amino acid residues at positions 251-257, 285-290, 308-314, 385-389, and 428-436, numbered according to the EU index as in Kabat.

In a further embodiment, one, two, or more amino acid substitutions are introduced into an IgG constant domain Fc region to alter the effector function(s) of the antibody. For example, one or more amino acids selected from amino acid residues 234, 235, 236, 237, 297, 318, 320 and 322, numbered according to the EU index as in Kabat, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In certain embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604). In various embodiments, one or more of the following mutations in the constant region of an antibody described herein may be made: an N297A substitution; an N297Q substitution; a L235A substitution and a L237A substitution; a L234A substitution and a L235A substitution; a E233P substitution; a L234V substitution; a L235A substitution; a C236 deletion; a P238A substitution; a D265A substitution; a A327Q substitution; or a P329A substitution, numbered according to the EU index as in Kabat. In certain embodiments, a mutation selected from the group consisting of D265A, P329A, and a combination thereof may be made in the constant region of an antibody described herein.

In a specific embodiment, an antibody described herein comprises the constant domain of an $IgG_1$ with an N297Q or N297A amino acid substitution. In one embodiment, an antibody described herein comprises the constant domain of an $IgG_1$ with a mutation selected from the group consisting of D265A, P329A, and a combination thereof.

In certain embodiments, one or more amino acids selected from amino acid residues 329, 331, and 322 in the constant region of an antibody described herein, numbered according to the EU index as in Kabat, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al). In some embodiments, one or more amino acid residues within amino acid positions 231 to 238 in the N-terminal region of the CH2 domain of an antibody described herein are altered to thereby alter the ability of the antibody to fix complement. This approach is described further in International Publication No. WO 94/29351. In certain embodiments, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU index as in Kabat. This approach is described further in International Publication No. WO 00/42072.

In certain embodiments, an antibody described herein comprises the constant domain of an $IgG_1$ with a mutation (e.g., substitution) at position 267, 328, or a combination thereof, numbered according to the EU index as in Kabat. In certain embodiments, an antibody described herein comprises the constant domain of an $IgG_1$ with a mutation (e.g., substitution) selected from the group consisting of S267E, L328F, and a combination thereof. In certain embodiments, an antibody described herein comprises the constant domain of an $IgG_1$ with a S267E/L328F mutation (e.g., substitution). In certain embodiments, an antibody described herein comprising the constant domain of an $IgG_1$ with a S267E/L328F mutation (e.g., substitution) has an increased binding affinity for FcγRIIA, FcγRIIB, or FcγRIIA and FcγRIIB In certain embodiments, an antibody described herein comprises the constant region of an IgG$_4$ antibody and the serine at amino acid residue 228 of the heavy chain, numbered according to the EU index as in Kabat, is substituted for proline.

In certain embodiments, an antibody described herein comprises the constant region of an IgG$_2$ antibody and the cysteine at amino acid residue 127 of the heavy chain, numbered according to Kabat, is substituted for serine.

Antibodies with reduced fucose content have been reported to have an increased affinity for Fc receptors, such as, e.g., FcγRIIIA Accordingly, in certain embodiments, the antibodies described herein have reduced fucose content or no fucose content. Such antibodies can be produced using techniques known to one skilled in the art. For example, the antibodies can be expressed in cells deficient or lacking the ability of fucosylation. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content. Alternatively, antibodies with reduced fucose content or no fucose content can be produced by, e.g.: (i) culturing cells under conditions which prevent or reduce fucosylation; (ii) posttranslational removal of fucose (e.g., with a fucosidase enzyme); (iii) post-translational addition of the desired carbohydrate, e.g., after recombinant expression of a non-glycosylated glycoprotein; or (iv) purification of the glycoprotein so as to select for antibodies thereof which are not fucsoylated. See, e.g., Longmore G D & Schachter H (1982) Carbohydr Res 100: 365-92 and Imai-Nishiya H et al., (2007) BMC Biotechnol. 7: 84 for methods for producing antibodies thereof with no fucose content or reduced fucose content.

Engineered glycoforms may be useful for a variety of purposes, including but not limited to enhancing or reducing effector function. Methods for generating engineered glycoforms in an antibody described herein include but are not limited to those disclosed, e.g., in Umaña P et al., (1999) Nat Biotechnol 17: 176-180; Davies J et al., (2001) Biotechnol Bioeng 74: 288-294; Shields R L et al., (2002) J Biol Chem 277: 26733-26740; Shinkawa T et al., (2003) J Biol Chem 278: 3466-3473; Niwa R et al., (2004) Clin Cancer Res 1: 6248-6255; Presta L G et al., (2002) Biochem Soc Trans 30: 487-490; Kanda Y et al., (2007) Glycobiology 17: 104-118; U.S. Pat. Nos. 6,602,684; 6,946,292; and 7,214,775; U.S. Patent Publication Nos. US 2007/0248600; 2007/0178551; 2008/0060092; and 2006/0253928; International Publication Nos. WO 00/61739; WO 01/292246; WO 02/311140; and WO 02/30954; Potillegent™ technology (Biowa, Inc. Princeton, N.J.); and GlycoMAb® glycosylation engineering technology (Glycart biotechnology AG, Zurich, Switzerland). See also, e.g., Ferrara C et al., (2006) Biotechnol Bioeng 93: 851-861; International Publication Nos. WO 07/039818; WO 12/130831; WO 99/054342; WO 03/011878; and WO 04/065540.

In certain embodiments, the technology used to engineer the Fc domain of an antibody described herein is the Xmab® Technology of Xencor (Monrovia, Calif.). See, e.g., U.S. Pat. Nos. 8,367,805; 8,039,592; 8,124,731; 8,188,231; U.S. Patent Publication No. 2006/0235208; International Publication Nos. WO 05/077981; WO 11/097527; and Richards J O et al., (2008) Mol Cancer Ther 7: 2517-2527.

In certain embodiments, amino acid residues in the constant region of an antibody described herein in the positions corresponding to positions L234, L235, and D265 in a human IgG1 heavy chain, numbered according to the EU index of numbering, are not L, L, and D, respectively. This approach is described in detail in International Publication No. WO 14/108483. In a particular embodiment, the amino acids corresponding to positions L234, L235, and D265 in a human IgG1 heavy chain are F, E, and A; or A, A, and A, respectively.

In certain embodiments, any of the constant region mutations or modifications described herein can be introduced into one or both heavy chain constant regions of an antibody described herein having two heavy chain constant regions.

In another particular embodiment, an antibody described herein, which immunospecifically binds to OX40 (e.g., human OX40), comprises a light chain and a heavy chain, wherein (i) the light chain comprises a VL domain comprising the VL CDR1, VL CDR2, and VL CDR3 amino acid sequences set forth SEQ ID NOs: 1-3 (e.g., those listed in Table 1); (ii) the heavy chain comprises a VH domain comprising the VH CDR1, VH CDR2, and VH CDR3 amino acid sequences set forth in SEQ ID NOs: 4-6 (e.g., those listed in Table 2); (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG$_1$ (optionally IgG$_1$ (allotype Glm3)) heavy chain.

In another particular embodiment, an antibody described herein, which immunospecifically binds to OX40 (e.g., human OX40), comprises a light chain and a heavy chain, wherein (i) the light chain comprises a VL domain comprising the amino acid set forth in SEQ ID NO: 15; (ii) the heavy chain comprises a VH domain comprising the amino acid sequence set forth in SEQ ID NO: 16; (iii) the light chain further comprises a constant domain comprising the amino acid sequence of the constant domain of a human kappa light chain; and (iv) the heavy chain further comprises a constant domain comprising the amino acid sequence of the constant domain of a human IgG$_1$ (optionally IgG$_1$ (allotype Glm3)) heavy chain.

In another particular embodiment, an antibody described herein, which immunospecifically binds to OX40 (e.g., human OX40), comprises a light chain and a heavy chain, wherein (i) the light chain comprises a VL domain comprising the VL CDR1, VL CDR2, and VL CDR3 amino acid sequences set forth in SEQ ID NOs: 1-3 (e.g., those listed in Table 1); (ii) the heavy chain comprises a VH domain comprising the VH CDR1, VH CDR2, and VH CDR3 amino acid sequences set forth in SEQ ID NOs: 4-6 (e.g., those listed in Table 2); (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG$_4$ heavy chain.

In another particular embodiment, an antibody described herein, which immunospecifically binds to OX40 (e.g., human OX40), comprises a light chain and a heavy chain, wherein (i) the light chain comprises a VL domain comprising the amino acid sequence of SEQ ID NO: 15; (ii) the heavy chain comprises a VH domain comprising the amino acid sequence of SEQ ID NO: 16; (iii) the light chain further comprises a constant domain comprising the amino acid sequence of the constant domain of a human kappa light chain; and (iv) the heavy chain further comprises a constant domain comprising the amino acid sequence of the constant domain of a human IgG$_4$ heavy chain.

In another particular embodiment, an antibody described herein, which immunospecifically binds to OX40 (e.g., human OX40), comprises a light chain and a heavy chain, wherein (i) the light chain comprises a VL domain comprising the VL CDR1, VL CDR2, and VL CDR3 amino acid sequences set forth in SEQ ID NOs: 1-3 (e.g., those listed in Table 1); (ii) the heavy chain comprises a VH domain comprising the VH CDR1, VH CDR2, and VH CDR3 amino acid sequences set forth in SEQ ID NOs: 4-6 (e.g., those listed in Table 2); (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG$_2$ heavy chain.

In another particular embodiment, an antibody described herein, which immunospecifically binds to OX40 (e.g., human OX40), comprises a light chain and a heavy chain, wherein (i) the light chain comprises a VL domain comprising the amino acid sequence of SEQ ID NO: 15; (ii) the heavy chain comprises a VH domain comprising the amino acid sequence of SEQ ID NO: 16; (iii) the light chain further comprises a constant domain comprising the amino acid sequence of the constant domain of a human kappa light chain; and (iv) the heavy chain further comprises a constant domain comprising the amino acid sequence of the constant domain of a human IgG$_2$ heavy chain. In certain embodiments, the light chain comprises the amino acid sequence of SEQ ID NO: 50 and the heavy chain comprises the amino acid sequence of SEQ ID NO: 51. In certain embodiments, the light chain comprises the amino acid sequence of SEQ ID NO: 50 and the heavy chain comprises the amino acid sequence of SEQ ID NO: 62. In certain embodiments, the light chain comprises the amino acid sequence of SEQ ID NO: 20 and the heavy chain comprises the amino acid sequence of SEQ ID NO: 51. In certain embodiments, the light chain comprises the amino acid sequence of SEQ ID NO: 20 and the heavy chain comprises the amino acid sequence of SEQ ID NO: 62.

In another specific embodiment, an antibody provided herein, which specifically binds to OX40 (e.g., human OX40), comprises (a) a heavy chain comprising the amino acid sequence of SEQ ID NO: 21 with an amino acid substitution of N to A or Q at amino acid position 297; and (b) a light chain comprising the amino acid sequence of SEQ ID NO: 20. In another specific embodiment, an antibody provided herein, which specifically binds to OX40 (e.g., human OX40), comprises (a) a heavy chain comprising the amino acid sequence of SEQ ID NO: 60 with an amino acid substitution of N to A or Q at amino acid position 297; and (b) a light chain comprising the amino acid sequence of SEQ ID NO: 20.

In another specific embodiment, an antibody provided herein, which specifically binds to OX40 (e.g., human OX40), comprises (a) a heavy chain comprising the amino acid sequence of SEQ ID NO: 21 with an amino acid substitution selected from the group consisting of: S to E at amino acid position 267, L to F at amino acid position 328, and both S to E at amino acid position 267 and L to F at amino acid position 328; and (b) a light chain comprising the amino acid sequence of SEQ ID NO: 20. In another specific embodiment, an antibody provided herein, which specifically binds to OX40 (e.g., human OX40), comprises (a) a heavy chain comprising the amino acid sequence of SEQ ID NO: 60 with an amino acid substitution selected from the group consisting of: S to E at amino acid position 267, L to F at amino acid position 328, and both S to E at amino acid position 267 and L to F at amino acid position 328; and (b) a light chain comprising the amino acid sequence of SEQ ID NO: 20.

In specific embodiments, an antibody described herein, which immunospecifically binds to OX40 (e.g., human OX40), exhibits antibody-dependent cellular cytotoxicity (ADCC) activity. In specific embodiments, an antibody described herein, which immunospecifically binds to OX40 (e.g., human OX40), initiates natural killer cell mediated cell depletion. In specific embodiments, an antibody described herein, which immunospecifically binds to OX40 (e.g., human OX40), is used for treating tumor infiltrated with natural killer cells. In specific embodiments, an antibody described herein, which immunospecifically binds to OX40 (e.g., human OX40), exhibits antibody-dependent cellular phagocytosis (ADCP) activity. In specific embodiments, an antibody described herein, which immunospecifically binds to OX40 (e.g., human OX40), initiates macrophage mediated cell depletion. In specific embodiments, an antibody described herein, which immunospecifically binds to OX40 (e.g., human OX40), is used for treating tumor infiltrated with macrophages. In specific embodiments, an antibody described herein, which immunospecifically binds to OX40 (e.g., human OX40), selectively depletes intratumoral regulatory T cells.

In specific embodiments, an antibody described herein, which immunospecifically binds to OX40 (e.g., human OX40), comprises framework regions (e.g., framework regions of the VL domain and/or VH domain) that are human framework regions or derived from human framework regions. Non-limiting examples of human framework regions are described in the art, e.g., see Kabat E A et al., (1991) supra). In certain embodiment, an antibody described herein comprises framework regions (e.g., framework regions of the VL domain and/or VH domain) that are primate (e.g., non-human primate) framework regions or derived from primate (e.g., non-human primate) framework regions.

For example, CDRs from antigen-specific non-human antibodies, typically of rodent origin (e.g., mouse or rat), are grafted onto homologous human or non-human primate acceptor frameworks. In one embodiment, the non-human primate acceptor frameworks are from Old World apes. In a specific embodiment, the Old World ape acceptor framework is from Pan troglodytes, Pan paniscus or Gorilla gorilla. In a particular embodiment, the non-human primate acceptor frameworks are from the chimpanzee Pan troglodytes. In a particular embodiment, the non-human primate acceptor frameworks are Old World monkey acceptor frameworks. In a specific embodiment, the Old World monkey acceptor frameworks are from the genus *Macaca*. In a certain embodiment, the non-human primate acceptor frameworks are is derived from the cynomolgus monkey *Macaca cynomolgus*. Non-human primate framework sequences are described in U.S. Patent Application Publication No. US 2005/0208625.

In certain embodiments, an antibody described herein, which specifically binds to OX40 (e.g., human OX40), comprises one, two, or more VL framework regions (FRs) having the amino acid sequences described herein for the antibody set forth in Table 3, supra. In some embodiments, an antibody described herein, which specifically binds to OX40 (e.g., human OX40), comprises one, two, or more VH framework regions (FRs) having the amino acid sequences described herein for the antibody set forth in Table 4, supra. In specific embodiments, an antibody described herein, which specifically binds to OX40 (e.g., human OX40), comprises one, two, or more VL framework regions having the amino acid sequences described herein for the antibody set forth in Table 3, supra, and one, two, or more VH framework regions having the amino acid sequences described herein for the antibody set forth in Table 4, supra.

In some embodiments, an antibody described herein, which specifically binds to OX40 (e.g., human OX40), comprises one, two, three, or four framework regions of the VL domain having the amino acid sequence of pab1949 or pab2044 (e.g., SEQ ID NOs: 7-10) with 1, 2, 3, 4, 5, 6, 7, 8, 9 or more amino acid mutations (e.g., amino acid substitutions, such as conservative amino acid substitutions) and/or the framework regions of the VH domain having the amino acid sequence of pab1949 or pab2044 (e.g., SEQ ID NOs: 11-14). In certain embodiments, an antibody described herein, which specifically binds to OX40 (e.g., human OX40), comprises one, two, three, or four framework regions of the VH domain having the amino acid sequence of pab1949 or pab2044 (e.g., SEQ ID NOs: 11-14) with 1, 2, 3, 4, 5, 6, 7, 8, 9 or more amino acid mutations (e.g., amino acid substitutions, such as conservative amino acid substitutions) and/or the framework regions of the VL domain having the amino acid sequence of pab1949 or pab2044 (e.g., SEQ ID NOs: 7-10).

In certain embodiments, an antibody described herein, which specifically binds to OX40 (e.g., human OX40), comprises VL framework regions (FRs) having at least 70%, at least 75%, at least 80%, at least 85%, at least 90%, at least 95%, or at least 98% sequence identity to the VL framework regions described herein in Table 3, supra. In certain embodiments, an antibody described herein, which specifically binds to OX40 (e.g., human OX40), comprises VH framework regions (FRs) having at least 70%, at least 75%, at least 80%, at least 85%, at least 90%, at least 95%, or at least 98% sequence identity to the VH framework regions described herein Table 4, supra. In some embodiments, an antibody described herein, which specifically binds to OX40 (e.g., human OX40), comprises VH framework regions (FRs) having at least 70%, at least 75%, at least 80%, at least 85%, at least 90%, at least 95%, or at least 98% sequence identity to the VH framework regions described herein Table 4, supra, and VL framework regions (FRs) having at least 70%, at least 75%, at least 80%, at least 85%, at least 90%, at least 95%, or at least 98% sequence identity to the VL framework regions described herein Table 3, supra.

The determination of percent identity between two sequences (e.g., amino acid sequences or nucleic acid sequences) can also be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877. Such an algorithm is incorporated into the NBLAST and XBLAST programs of Altschul S F et al., (1990) J Mol Biol 215: 403. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

In certain embodiments, an antibody described herein, which immunospecifically binds to OX40 (e.g., human OX40), comprises a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15), wherein the antibody comprises VL CDRs that are identical to the VL CDRs of pab1949 or pab2044.

In certain embodiments, an antibody described herein, which immunospecifically binds to OX40 (e.g., human OX40), comprises a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody comprises VH CDRs that are identical to the VH CDRs of pab1949 or pab2044.

In certain embodiments, an antibody described herein, which immunospecifically binds to OX40 (e.g., human OX40), comprises: (i) a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15); and (ii) a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody comprises VL CDRs and VH CDRs that are identical to the VL CDRs and VH CDRs of pab1949 or pab2044.

In certain embodiments, an antibody described herein, which immunospecifically binds to OX40 (e.g., human OX40), comprises a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15), wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is a substantially increasing function of antibody concentrations between, e.g., 0.032 µg/ml and 20 µg/ml, 0.16 µg/ml and 20 µg/ml, 0.8 µg/ml and 20 µg/ml, 4 µg/ml and 20 µg/ml, 0.032 µg/ml and 4 µg/ml, 0.16 µg/ml and 4 µg/ml, or 0.8 µg/ml and 4 µg/ml. In certain embodiments, an antibody described herein, which immunospecifically binds to OX40 (e.g., human OX40), comprises a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15), wherein the antibody, in combination with *Staphylococcus* Enterotoxin A (SEA), induces IL-2 production in, e.g., PBMCs, wherein the IL-2 production is a substantially increasing function of antibody concentrations between, e.g., 0.032 µg/ml and 20 µg/ml, 0.16 µg/ml and 20 µg/ml, 0.8 µg/ml and 20 µg/ml, 4 µg/ml and 20 µg/ml, 0.032 µg/ml and 4 µg/ml, 0.16 µg/ml and 4 µg/ml, or 0.8 µg/ml and 4 µg/ml as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 µg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In certain embodiments, an antibody described herein, which immunospecifically binds to OX40 (e.g., human OX40), comprises a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15), wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production shows a sigmoidal dose response curve when the anti-OX40 antibody is between, e.g., 0.032 µg/ml and 20 µg/ml, 0.16 µg/ml and 20 µg/ml, 0.8 µg/ml and 20 µg/ml, 4 µg/ml and 20 µg/ml, 0.032 µg/ml and 4 µg/ml, 0.16 µg/ml and 4 µg/ml, or 0.8 µg/ml and 4 µg/ml. In certain embodiments, an antibody described herein, which immunospecifically binds to OX40 (e.g., human OX40), comprises a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15), wherein the antibody, in combination with *Staphylococcus* Enterotoxin A (SEA), induces IL-2 production in, e.g., PBMCs, wherein the IL-2 production shows a sigmoidal dose response curve when the anti-OX40 antibody is between, e.g., 0.032 µg/ml and 20 µg/ml, 0.16 µg/ml and 20 µg/ml, 0.8 µg/ml and 20 µg/ml, 4 µg/ml and 20 µg/ml, 0.032 µg/ml and 4 µg/ml, 0.16 µg/ml and 4 µg/ml, or 0.8 µg/ml and 4 µg/ml as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 µg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In certain embodiments, an antibody described herein, which immunospecifically binds to OX40 (e.g., human OX40), comprises a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is a substantially increasing function of antibody concentrations between, e.g., 0.032 µg/ml and 20 µg/ml, 0.16 µg/ml and 20 µg/ml, 0.8 µg/ml and 20 µg/ml, 4 µg/ml and 20 µg/ml, 0.032 µg/ml and 4 µg/ml, 0.16 µg/ml and 4 µg/ml, or 0.8 µg/ml and 4 µg/ml. In certain embodiments, an antibody described herein, which immunospecifically binds to OX40 (e.g., human OX40), comprises a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody, in combination with *Staphylococcus* Enterotoxin A (SEA), induces IL-2 production in, e.g., PBMCs, wherein the IL-2 production is a substantially increasing function of antibody concentrations between, e.g., 0.032 µg/ml and 20 µg/ml, 0.16 µg/ml and 20 µg/ml, 0.8 µg/ml and 20 µg/ml, 4 µg/ml and 20 µg/ml, 0.032 µg/ml and 4 µg/ml, 0.16 µg/ml and 4 µg/ml, or 0.8 µg/ml and 4 µg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 µg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In certain embodiments, an antibody described herein, which immunospecifically binds to OX40 (e.g., human OX40), comprises a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production shows a sigmoidal dose response curve when the anti-OX40 antibody is between, e.g., 0.032 µg/ml and 20 µg/ml, 0.16 µg/ml and 20 µg/ml, 0.8 µg/ml and 20 µg/ml, 4 µg/ml and 20 µg/ml, 0.032 µg/ml and 4 µg/ml, 0.16 µg/ml and 4 µg/ml, or 0.8 µg/ml and 4 µg/ml. In certain embodiments, an antibody described herein, which immunospecifically binds to OX40 (e.g., human OX40), comprises a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody, in combination with *Staphylococcus* Enterotoxin A (SEA), induces IL-2 production in, e.g., PBMCs, wherein the IL-2 production shows a sigmoidal dose response curve when the anti-OX40 antibody is between, e.g., 0.032 µg/ml and 20 µg/ml, 0.16 µg/ml and 20 µg/ml, 0.8 µg/ml and 20 µg/ml, 4 µg/ml and 20 µg/ml, 0.032 µg/ml and 4 µg/ml, 0.16 µg/ml and 4 µg/ml, or 0.8 µg/ml and 4 µg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 µg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In certain embodiments, an antibody described herein, which immunospecifically binds to OX40 (e.g., human OX40), comprises: (i) a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15); and (ii) a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is a substantially increasing function of antibody concentrations between, e.g., 0.032 μg/ml and 20 μg/ml, 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml. In certain embodiments, an antibody described herein, which immunospecifically binds to OX40 (e.g., human OX40), comprises: (i) a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15); and (ii) a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody, in combination with *Staphylococcus* Enterotoxin A (SEA), induces IL-2 production in, e.g., PBMCs, wherein the IL-2 production is a substantially increasing function of antibody concentrations between, e.g., 0.032 μg/ml and 20 μg/ml, 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In certain embodiments, an antibody described herein, which immunospecifically binds to OX40 (e.g., human OX40), comprises: (i) a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15); and (ii) a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody, in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production shows a sigmoidal dose response curve when the anti-OX40 antibody is between, e.g., 0.032 μg/ml and 20 μg/ml, 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml. In certain embodiments, an antibody described herein, which immunospecifically binds to OX40 (e.g., human OX40), comprises: (i) a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15); and (ii) a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody, in combination with *Staphylococcus* Enterotoxin A (SEA), induces IL-2 production in, e.g., PBMCs, wherein the IL-2 production shows a sigmoidal dose response curve when the anti-OX40 antibody is between, e.g., 0.032 μg/ml and 20 μg/ml, 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery).

In certain embodiments, an antibody described herein, which immunospecifically binds to OX40 (e.g., human OX40), comprises a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15), wherein the antibody when plate-bound, in combination with a plate-bound anti-CD3 antibody (e.g., 0.8 μg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, is a substantially increasing function of the concentrations of the antibody between, e.g., 0.7 μg/ml and 50 μg/ml, 1.6 μg/ml and 50 μg/ml, 3.1 μg/ml and 50 μg/ml, or 6.3 μg/ml and 50 μg/ml, as assessed in, e.g., an assay comprising the following steps: (a) culturing the PBMCs in the presence of a plate-bound anti-CD3 antibody (e.g., 0.8 μg/ml) and varying concentrations (e.g., 0, 0.3, 1, 3, 6, 12, 25, and 50 μg/ml; or 0, 0.7, 1.6, 3.1, 6.3, 12.5, 25, or 50 μg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery). In certain embodiments, an antibody described herein, which immunospecifically binds to OX40 (e.g., human OX40), comprises a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15), wherein the antibody when plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, shows a sigmoidal dose response curve when the anti-OX40 antibody concentration is between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery).

In certain embodiments, an antibody described herein, which immunospecifically binds to OX40 (e.g., human OX40), comprises a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody when plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, is a substantially increasing function of the concentrations of the antibody between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery). In certain embodiments, an antibody described herein, which immunospecifically binds to OX40 (e.g., human OX40), comprises a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody when plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, shows a sigmoidal dose response curve when the anti-OX40 antibody concentration is between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery).

In certain embodiments, an antibody described herein, which immunospecifically binds to OX40 (e.g., human OX40), comprises: (i) a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15); and (ii) a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody when plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, is a substantially increasing function of the concentrations of the antibody between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery). In certain embodiments, an antibody described herein, which immunospecifically binds to OX40 (e.g., human OX40), comprises: (i) a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15); and (ii) a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody when plate-bound, in combination with a plate-bound anti-CD3 antibody (e.g., 0.8 µg/ml), induces production of one or more cytokines, e.g., TNFα, TNFβ, IFNγ, GM-CSF, IL-2, IL-10, or IL-13, in, e.g., PBMCs or T cells upon stimulation for, e.g., 4 days at, e.g., 37° C. and 5% $CO_2$, as measured by, e.g., electrochemiluminescence, e.g., Human TH1/TH2 10-Plex tissue culture kit (Meso Scale Discovery) or non-human primate (NHP) V-Plex assay kit (Meso Scale Discovery), wherein the production of one or more cytokines, e.g., TNFα, TNFβ, IFNγ, GM-CSF, IL-2, IL-10, or IL-13, shows a sigmoidal dose response curve when the anti-OX40 antibody concentration is between, e.g., 0.7 µg/ml and 50 µg/ml, 1.6 µg/ml and 50 µg/ml, 3.1 µg/ml and 50 µg/ml, or 6.3 µg/ml and 50 µg/ml, as assessed in, e.g., an assay comprising the following steps: (a) culturing the PBMCs in the presence of a plate-bound anti-CD3 antibody (e.g., 0.8 µg/ml) and varying concentrations (e.g., 0, 0.3, 1, 3, 6, 12, 25, and 50 µg/ml; or 0, 0.7, 1.6, 3.1, 6.3, 12.5, 25, or 50 µg/ml) of the plate-bound antibody for, e.g., 4 days at, e.g., 37° C. and 5% $CO_2$; and (b) collecting supernatant and measuring the production of one or more cytokines, e.g., TNFα, TNFβ, IFNγ, GM-CSF, IL-2, IL-10, or IL-13, by, e.g., electrochemiluminescence, e.g., Human TH1/TH2 10-Plex tissue culture kit (Meso Scale Discovery) or non-human primate (NHP) V-Plex assay kit (Meso Scale Discovery).

In certain embodiments, an antibody described herein, which immunospecifically binds to OX40 (e.g., human OX40), comprises a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15), wherein the antibody increases CD4+ T cell proliferation, wherein the CD4+ T cell proliferation is a substantially increasing function of the concentrations of the antibody between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry. In certain embodiments, an antibody described herein, which immunospecifically binds to OX40 (e.g., human OX40), comprises a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15), wherein the antibody results in a greater increase in CD4+ T cell proliferation when the antibody is present at a concentration of 20 µg/ml than at a concentration of 2 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In certain embodiments, an antibody described herein, which immunospecifically binds to OX40 (e.g., human OX40), comprises a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15), wherein the antibody increases CD4+ T cell proliferation, wherein the CD4+ T cell proliferation shows a sigmoidal dose response curve when the anti-OX40 antibody concentration is between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In certain embodiments, an antibody described herein, which immunospecifically binds to OX40 (e.g., human OX40), comprises a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody increases CD4+ T cell proliferation, wherein the CD4+ T cell proliferation is a substantially increasing function of the concentrations of the antibody between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry. In certain embodiments, an antibody described herein, which immunospecifically binds to OX40 (e.g., human OX40), comprises a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody results in a greater increase in CD4+ T cell proliferation when the antibody is present at a concentration of 20 µg/ml than at a concentration of 2 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In certain embodiments, an antibody described herein, which immunospecifically binds to OX40 (e.g., human OX40), comprises a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody increases CD4+ T cell proliferation, wherein the CD4+ T cell proliferation shows a sigmoidal dose response curve when the anti-OX40 antibody concentration is between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In certain embodiments, an antibody described herein, which immunospecifically binds to OX40 (e.g., human OX40), comprises: (i) a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15); and (ii) a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody increases CD4+ T cell proliferation, wherein the CD4+ T cell proliferation is a substantially increasing function of the concentrations of the antibody between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry. In certain embodiments, an antibody described herein, which immunospecifically binds to OX40 (e.g., human OX40), comprises: (i) a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15); and (ii) a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody results in a greater increase in CD4+ T cell proliferation when the antibody is present at a concentration of 20 µg/ml than at a concentration of 2 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In certain embodiments, an antibody described herein, which immunospecifically binds to OX40 (e.g., human OX40), comprises: (i) a VL domain having at least 70%, at least 75%, at least 80%, at least 85%, at least 90%, at least 95%, or at least 98% sequence identity to the amino acid sequence of the VL domain of pab1949 or pab2044 (e.g., SEQ ID NO: 15); and (ii) a VH domain having at least 70%, at least 75%, at least 80%, at least 85%, at least 90%, at least 95%, or at least 98% sequence identity to the amino acid sequence of the VH domain of pab1949 or pab2044 (e.g., SEQ ID NO: 16), wherein the antibody increases CD4+ T cell proliferation, wherein the CD4+ T cell proliferation shows a sigmoidal dose response curve when the anti-OX40 antibody concentration is between, e.g., 0.2 µg/ml and 20 µg/ml, or 2 µg/ml and 20 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In another aspect, provided herein are antibodies that bind the same or an overlapping epitope of OX40 (e.g., an epitope of human OX40) as an antibody described herein (e.g., pab1949 or pab2044). In certain embodiments, the epitope of an antibody can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In a specific embodiment, the epitope of an antibody is determined using alanine scanning mutagenesis studies. In addition, antibodies that recognize and bind to the same or overlapping epitopes of OX40 (e.g., human OX40) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as OX40. Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using I-125 label (see Morel G A et al., (1988) Mol Immunol 25(1): 7-15); solid phase direct biotin-avidin EIA (Cheung R C et al., (1990) Virology 176: 546-52); and direct labeled RIA. (Moldenhauer G et al., (1990) Scand J Immunol 32: 77-82). Typically, such an assay involves the use of purified antigen (e.g., OX40 such as human OX40) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389.

In one embodiment, a competition assay is performed using surface plasmon resonance (BIAcore®), e.g., by an 'in tandem approach' such as that described by Abdiche Y N et al., (2009) Analytical Biochem 386: 172-180, whereby OX40 antigen is immobilized on the chip surface, for example, a CM5 sensor chip and the anti-OX40 antibodies are then run over the chip. To determine if an antibody competes with an anti-OX40 antibody described herein, the anti-OX40 antibody is first run over the chip surface to achieve saturation and then the potential, competing antibody is added. Binding of the competing antibody can then be determined and quantified relative to a non-competing control.

In certain aspects, competition binding assays can be used to determine whether an antibody is competitively blocked, e.g., in a dose dependent manner, by another antibody for example, an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody can be tested in competition binding assays with an antibody described herein (e.g., antibody pab1949 or pab2044), or a chimeric or Fab antibody thereof, or an antibody comprising VH CDRs and VL CDRs of an antibody described herein (e.g., pab1949 or pab2044).

In another aspect, provided herein are antibodies that compete (e.g., in a dose dependent manner) for binding to OX40 (e.g., human OX40) with an antibody described herein (e.g., pab1949 or pab2044), as determined using assays known to one of skill in the art or described herein (e.g., ELISA competitive assays or surface plasmon resonance). In another aspect, provided herein are antibodies that competitively inhibit (e.g., in a dose dependent manner) an antibody described herein (e.g., pab1949 or pab2044) from binding to OX40 (e.g., human OX40), as determined using assays known to one of skill in the art or described herein (e.g., ELISA competitive assays, or suspension array or surface plasmon resonance assay). In particular embodiments, such competitively blocking antibody activates, induces, or enhances one or more OX40 activities. In specific aspects, provided herein is an antibody which competes (e.g., in a dose dependent manner) for specific binding to OX40 (e.g., human OX40), with an antibody comprising the amino acid sequences described herein (e.g., VL and/or VH amino acid sequences of antibody pab1949 or pab2044), as determined using assays known to one of skill in the art or described herein (e.g., ELISA competitive assays, or suspension array or surface plasmon resonance assay).

In certain embodiments, provided herein is an antibody that competes with an antibody described herein for binding to OX40 (e.g., human OX40) to the same extent that the antibody described herein self-competes for binding to OX40 (e.g., human OX40). In some embodiments, provided herein is a first antibody that competes with an antibody described herein for binding to OX40 (e.g., human OX40), wherein the first antibody competes for binding in an assay comprising the following steps: (a) incubating OX40-transfected cells with the first antibody in unlabeled form in a container; and (b) adding an antibody described herein in labeled form in the container and incubating the cells in the container; and (c) detecting the binding of the antibody described herein in labeled form to the cells. In certain embodiments, provided herein is a first antibody that competes with an antibody described herein for binding to OX40 (e.g., human OX40), wherein the competition is exhibited as reduced binding of the first antibody to OX40 by more than 80% (e.g., 85%, 90%, 95%, or 98%, or between 80% to 85%, 80% to 90%, 85% to 90%, or 85% to 95%).

In specific aspects, provided herein is an antibody which competes (e.g., in a dose dependent manner) for specific binding to OX40 (e.g., human OX40), with an antibody comprising a VL domain having the amino acid sequence set forth in SEQ ID NO: 15, and a VH domain having the amino acid sequence set for the in SEQ ID NO: 16.

In specific aspects, provided herein is an antibody which competes (e.g., in a dose dependent manner) for specific binding to OX40 (e.g., human OX40), with an antibody comprising (i) a VL domain comprising a VL CDR1, VL CDR2, and VL CDR3 having the amino acid sequences of the VL CDRs listed in Table 1; and (ii) a VH domain comprising a VH CDR1, VH CDR2, and VH CDR3 having the amino acid sequences of the CDRs listed in Table 2.

In a specific embodiment, an antibody described herein is one that is competitively blocked (e.g., in a dose dependent manner) by an antibody comprising a VL domain having the amino acid sequence set forth in SEQ ID NO: 15 and a VH domain having the amino acid sequence set forth in SEQ ID NO: 16 for specific binding to OX40 (e.g., human OX40).

In another specific embodiment, an antibody described herein is one that is competitively blocked (e.g., in a dose dependent manner) by an antibody comprising (i) a VL domain comprising a VL CDR1, VL CDR2, and VL CDR3 having the amino acid sequences of the CDRs listed in Table 1; and (ii) a VH domain comprising a VH CDR1, VH CDR2, and VH CDR3 having the amino acid sequences of the CDRs listed in Table 2.

In specific aspects, provided herein is an antibody, which immunospecifically binds to the same epitope as that of pab1949 or pab2044 for specific binding to OX40 (e.g., human OX40). Assays known to one of skill in the art or described herein (e.g., X-ray crystallography, hydrogen/deuterium exchange coupled with mass spectrometry (e.g., liquid chromatography electrospray mass spectrometry), alanine scanning, ELISA assays, etc.) can be used to determine if two antibodies bind to the same epitope.

In a specific embodiment, an antibody described herein immunospecifically binds to the same epitope as that bound by pab1949 or pab2044 or an epitope that overlaps the epitope.

In another specific embodiment, an antibody described herein, immunospecifically binds to the same epitope as that of an antibody comprising (i) a VL domain comprising a VL CDR1, VL CDR2, and VL CDR3 having the amino acid sequences of the CDRs listed in Table 1 and (ii) a VH domain comprising a VH CDR1, VH CDR2, and VH CDR3 having the amino acid sequences of the CDRs listed in Table 2.

In a specific aspect, the binding between an antibody described herein and a variant OX40 is substantially weakened relative to the binding between the antibody and a human OX40 sequence of SEQ ID NO:55, and wherein the variant OX40 comprises the sequence of SEQ ID NO: 55 except for an amino acid mutation (e.g., substitution) selected from the group consisting of: N60A, R62A, R80A, L88A, P93A, P99A, P115A, and a combination thereof. In some embodiments, the variant OX40 comprises the sequence of SEQ ID NO: 55 except for any one mutation selected from the group consisting of: N60A, R62A, R80A, L88A, P93A, P99A, and P115A. In some embodiments, the variant OX40 comprises the sequence of SEQ ID NO: 55 except for any two, three, four, five, six, or seven mutations selected from the group consisting of: W58A, N60A, R62A, R80A, L88A, P93A, P99A, and P115A. In some embodiments, the variant OX40 comprises the sequence of SEQ ID NO: 55 except for the amino acid mutations W58A, N60A, R62A, R80A, L88A, P93A, P99A, and P115A.

In a specific aspect, an antibody described herein specifically binds to an epitope of a human OX40 sequence comprising, consisting essentially of, or consisting of a residue of SEQ ID NO: 55 selected from the group consisting of: 60, 62, 80, 88, 93, 99, 115, and a combination thereof. In some embodiments, the epitope comprises, consists essentially of, or consists of any one residue selected from the group consisting of: 60, 62, 80, 88, 93, 99, and 115 of SEQ ID NO: 55. In some embodiments, the epitope comprises, consists essentially of, or consists of any two, three, four, five, six, or seven residues selected from the group consisting of: 58, 60, 62, 80, 88, 93, 99, and 115 of SEQ ID NO: 55. In some embodiments, the epitope comprises, consists essentially of, or consists of residues 58, 60, 62, 80, 88, 93, 99, and 115 of SEQ ID NO: 55.

In a specific embodiment, an antibody described herein specifically binds to an epitope of SEQ ID NO: 55 comprising, consisting essentially of, or consisting of a residue selected from the group consisting of: 60, 62, 80, 88, 93, 99, 115, and a combination thereof. In some embodiments, the epitope comprises, consists essentially of, or consists of any one residue selected from the group consisting of: 60, 62, 80, 88, 93, 99, and 115 of SEQ ID NO: 55. In some embodiments, the epitope comprises, consists essentially of, or consists of any two, three, four, five, six, or seven residues selected from the group consisting of: 58, 60, 62, 80, 88, 93, 99, and 115 of SEQ ID NO: 55. In some embodiments, the epitope comprises, consists essentially of, or consists of residues 58, 60, 62, 80, 88, 93, 99, and 115 of SEQ ID NO: 55.

In a specific aspect, an antibody described herein specifically binds to at least one residue of SEQ ID NO: 55 selected from the group consisting of: 60, 62, 80, 88, 93, 99, 115, and a combination thereof. In some embodiments, an antibody described herein specifically binds to any one residue, or any two, three, four, five, six, or seven residues, selected from the group consisting of: 60, 62, 80, 88, 93, 99, and 115 of SEQ ID NO: 55. In some embodiments, an antibody described herein specifically binds to any two, three, four, five, six, or seven residues selected from the group consisting of: 58, 60, 62, 80, 88, 93, 99, and 115 of SEQ ID NO: 55. In some embodiments, an antibody described herein specifically binds to residues 58, 60, 62, 80, 88, 93, 99, 115 of SEQ ID NO: 55.

In a specific aspect, an antibody described herein exhibits, as compared to binding to a human OX40 sequence of SEQ ID NO: 55, reduced or absent binding to a protein identical to SEQ ID NO: 55 except for the presence of an amino acid mutation (e.g., substitution) selected from the group consisting of: N60A, R62A, R80A, L88A, P93A, P99A, P115A, and a combination thereof. In some embodiments, the protein is identical to SEQ ID NO: 55 except for the presence of an amino acid mutation comprising any one mutation, or any two, three, four, five, six, or seven mutations, selected from the group consisting of: N60A, R62A, R80A, L88A, P93A, P99A, and P115A. In some embodiments, the protein is identical to SEQ ID NO: 55 except for the presence of an amino acid mutation comprising any two, three, four, five, six, or seven mutations selected from the group consisting of: W58A, N60A, R62A, R80A, L88A, P93A, P99A, and P115A. In some embodiments, the protein is identical to SEQ ID NO: 55 except for the presence of an amino acid substitution comprising the mutations W58A, N60A, R62A, R80A, L88A, P93A, P99A, and P115A.

In certain embodiments, the epitope of an antibody described herein is used as an immunogen to produce antibodies. See, e.g., Section 5.3 infra for methods for producing antibodies.

In specific aspects, an antibody described herein, which immunospecifically binds to OX40 (e.g., human OX40), functions as an agonist.

In certain embodiments, an antibody described herein, which immunospecifically binds to OX40 (e.g., human OX40), increases OX40 (e.g., human OX40) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to OX40 (e.g., human OX40) activity without any antibody or with an unrelated antibody (e.g., an antibody that does not immunospecifically bind to OX40). In certain embodiments, an antibody described herein, which immunospecifically binds to OX40 (e.g., human OX40), increases OX40 (e.g., human OX40) activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to OX40 (e.g., human OX40) activity without any antibody or with an unrelated antibody (e.g., an antibody that does not immunospecifically bind to OX40). Non-limiting examples of OX40 (e.g., human OX40) activity can include OX40 (e.g., human OX40) signaling, cell proliferation, cell survival, and cytokine production (e.g., IL-2, TNF-α, IFN-γ, IL-4, IL-10, and/or IL-13). In certain embodiments, an antibody described herein, which immunospecifically binds to OX40 (e.g., human OX40), induces, enhances, or increases an OX40 (e.g., human OX40) activity. In specific embodiments, an increase in an OX40 activity is assessed as described in the Examples, infra.

In certain aspects, an antibody described herein, which immunospecifically binds to OX40 (e.g., human OX40), induces, enhances, or increases the cellular proliferation of cells that express OX40 and that respond to OX40 signaling (e.g., cells that proliferate in response to OX40 stimulation and OX40 signaling, such as T cells). Cell proliferation assays are described in the art, such as a $^3$H-thymidine incorporation assay, BrdU incorporation assay, or CFSE assay, such as described in Example 2, and can be readily carried out by one of skill in the art. In specific embodiments, T cells (e.g., CD4$^+$ or CD8$^+$ effector T cells) stimulated with a T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody), in the presence of an antibody described herein, which immunospecifically binds to OX40 (e.g., human OX40), have increased cellular proliferation relative to T cells only stimulated with the T cell mitogen or T cell receptor complex stimulating agent, such as phytohaemagglutinin (PHA) and/or phorbol myristate acetate (PMA), or a TCR complex stimulating antibody, such as an anti-CD3 antibody and anti-CD28 antibody.

In specific embodiments, an antibody described herein, which immunospecifically binds to OX40 (e.g., human OX40), increases cell proliferation (e.g., T cells, such as CD4 and CD8 effector T cells) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art (e.g., $^3$H-thymidine incorporation assay, BrdU incorporation assay or CFSE assay, such as described in Example 2, infra), relative to OX40 (e.g., human OX40) activity stimulation without any antibody or with an unrelated antibody (e.g., an antibody that does not immunospecifically bind to OX40). In specific embodiments, an antibody described herein, which immunospecifically binds to OX40 (e.g., human OX40), increases cell proliferation (e.g., T cells, such as CD4 and CD8 effector T cells) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art (e.g., $^3$H-thymidine incorporation assay, BrdU incorporation assay, or CFSE assay, such as described in Example 2, infra), relative to OX40 (e.g., human OX40) activity without any antibody or with an unrelated antibody (e.g., an antibody that does not immunospecifically bind to OX40). In specific embodiments, an antibody described herein, which immunospecifically binds to OX40 (e.g., human OX40), increases CD4+ T cell proliferation, wherein the CD4+ T cell proliferation is a substantially increasing function of the concentrations of the antibody between, e.g., 0.2 μg/ml and 20 μg/ml, as assessed in, e.g., an assay comprising the following steps: (a) labeling, e.g., enriched CD4+ T cells with, e.g., 10 μM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 μg/ml of, e.g., plate-bound anti-CD3 antibody and varying concentrations (e.g., 0.002, 0.02, 0.2, 2, and 20 μg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry. In specific embodiments, an antibody described herein, which immunospecifically binds to OX40 (e.g., human OX40), increases CD4+ T cell proliferation, wherein the CD4+ T cell proliferation is a substantially increasing function of the concentrations of the antibody between, e.g., 2 μg/ml and 20 μg/ml, as assessed in, e.g., an assay comprising the following steps: (a) labeling, e.g., enriched CD4+ T cells with, e.g., 10 μM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 μg/ml of, e.g., plate-bound anti-CD3 antibody and varying concentrations (e.g., 0.002, 0.02, 0.2, 2, and 20 μg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry. In specific embodiments, an antibody described herein, which immunospecifically binds to OX40 (e.g., human OX40), increases CD4+ T cell proliferation, wherein the CD4+ T cell proliferation shows a sigmoidal dose response curve when the anti-OX40 antibody concentration is between, e.g., 0.2 μg/ml and 20 μg/ml, as assessed in, e.g., an assay comprising the following steps: (a) labeling, e.g., enriched CD4+ T cells with, e.g., 10 μM carboxyfluorescein sucinimidyl ester (CFSE) for, e.g., 7 minutes at, e.g., 37° C.; (b) after extensive washes, stimulating the cells (e.g., $10^5$ cells in a well) with, e.g., 3 μg/ml of, e.g., plate-bound anti-CD3 antibody and varying concentrations (e.g., 0.002, 0.02, 0.2, 2, and 20 μg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry. In specific embodiments, an antibody described herein, which immunospecifically binds to OX40 (e.g., human OX40), increases CD4+ T cell proliferation, wherein the CD4+ T cell proliferation shows a sigmoidal dose response curve when the anti-OX40 antibody concentration is between, e.g., 2 μg/ml and 20 μg/ml, as assessed in, e.g., an assay comprising the following steps: (a) labeling, e.g., enriched CD4+ T cells with, e.g., 10 μM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 μg/ml of, e.g., plate-bound anti-CD3 antibody and varying concentrations (e.g., 0.002, 0.02, 0.2, 2, and 20 µg/ml) of, e.g., plate-bound antibody described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry. In specific embodiments, an antibody described herein, which immunospecifically binds to OX40 (e.g., human OX40), results in a greater increase in CD4+ T cell proliferation when the antibody is present at a concentration of 20 µg/ml than at a concentration of 2 µg/ml, as assessed in, e.g., an assay comprising the following steps: (a) labeling, e.g., enriched CD4+ T cells with, e.g., 10 µM carboxyfluorescein diacetate sucinimidyl ester (CFSE) for, e.g., 7 minutes at, e.g., 37° C.; (b) after extensive washes, stimulating the cells (e.g., $10^5$ cells in a well) with, e.g., 3 µg/ml of, e.g., plate-bound anti-CD3 antibody and varying concentrations (e.g., 0.002, 0.02, 0.2, 2, and 20 µg/ml) of, e.g., plate-bound antibody thereof described herein at, e.g., 37° C. and 5% $CO_2$; and (c) on, e.g., day 4, staining cells with, e.g., an anti-CD4 antibody and examining CD4+ T cell proliferation by, e.g., measuring the percentage of CFSE low CD4+ cells by flow cytometry.

In some embodiments, T cells (e.g., $CD4^+$ or $CD8^+$ effector T cells) stimulated with a T cell mitogen (e.g., an anti-CD3 antibody or phorbol ester) in the presence of an antibody described herein, which immunospecifically binds to OX40 (e.g., human OX40), have increased cellular proliferation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to T cells only stimulated with the T cell mitogen, as assessed by methods described herein or known to one of skill in the art (e.g., $^3$H-thymidine incorporation assay, BrdU incorporation assay, or CFSE assay, such as described in Example 2, infra). In some embodiments, T cells (e.g., $CD4^+$ or $CD8^+$ effector T cells) stimulated with a T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody) in the presence of an antibody described herein, which immunospecifically binds to OX40 (e.g., human OX40), have increased cellular proliferation by at least about 5%, 10%, 15%, 20%, 25%, 30%, 35%, 40%, 45%, 50%, 55%, 60%, 65%, 70%, 75%, 80%, 85%, 90%, 95%, 98%, or 99% relative to T cells only stimulated with the T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody), as assessed by methods described herein or known to one of skill in the art (e.g., $^3$H-thymidine incorporation assay, BrdU incorporation assay, or CFSE assay, such as described in Example 2, infra). In a specific embodiment, cell proliferation is assessed as described in Example 2, infra. In specific embodiments, 5 µg/ml of an OX40 antibody described herein increases proliferation of human CD4 T cells treated with 3 µg/ml anti-CD3 antibody by at least 20%. In specific embodiments, 5 µg/ml of an OX40 antibody described herein increases proliferation of human CD4 T cells treated with 3 µg/ml anti-CD3 antibody by at least 30%. In specific embodiments, 5 µg/ml of an OX40 antibody described herein increases proliferation of human CD4 T cells treated with 3 µg/ml anti-CD3 antibody by at least 40%. In specific embodiments, 5 µg/ml of an OX40 antibody described herein increases proliferation of human CD4 T cells treated with 3 µg/ml anti-CD3 antibody by at least 50%.

In certain aspects, an antibody described herein, which immunospecifically binds to OX40 (e.g., human OX40), increases the survival of cells (e.g., T cells, such as CD4 and CD8 effector T cells). In a specific embodiment, T cells (e.g., $CD4^+$ or $CD8^+$ effector T cells) stimulated with a T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody) in the presence of an antibody described herein, which immunospecifically binds to OX40 (e.g., human OX40), have increased survival relative to T cells only stimulated with the T cell mitogen. Cell survival assays are described in the art (e.g., a trypan blue exclusion assay) and can be readily carried out by one of skill in the art.

In specific embodiments, an antibody described herein, which immunospecifically binds to OX40 (e.g., human OX40), increases cell survival (e.g., T cells, such as CD4 and CD8 effector T cells) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art (e.g., a trypan blue exclusion assay), without any antibody or with an unrelated antibody (e.g., an antibody that does not immunospecifically bind to OX40). In specific embodiments, an antibody described herein, which immunospecifically binds to OX40 (e.g., human OX40), increases cell survival (e.g., T cells, such as CD4 and CD8 effector T cells) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art (e.g., a trypan blue exclusion assay), relative to OX40 (e.g., human OX40) activity without any antibody or with an unrelated antibody (e.g., an antibody that does not immunospecifically bind to OX40).

In some embodiments, T cells (e.g., $CD4^+$ or $CD8^+$ effector T cells) stimulated with a T cell mitogen (e.g., an anti-CD3 antibody or phorbol ester) in the presence of an antibody described herein, which immunospecifically binds to OX40 (e.g., human OX40), have increased cell survival by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to T cells only stimulated with the T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody), as assessed by methods described herein or known to one of skill in the art (e.g., a trypan blue exclusion assay). In some embodiments, T cells (e.g., $CD4^+$ or $CD8^+$ effector T cells) stimulated with a T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody) in the presence of an antibody described herein, which immunospecifically binds to OX40 (e.g., human OX40), have increased cell survival by at least about 5%, 10%, 15%, 20%, 25%, 30%, 35%, 40%, 45%, 50%, 55%, 60%, 65%, 70%, 75%, 80%, 85%, 90%, 95%, 98%, or 99% relative to T cells only stimulated with the T cell mitogen, as assessed by methods described herein or known to one of skill in the art (e.g., a trypan blue exclusion assay).

In certain embodiments, an antibody described herein, which immunospecifically binds to OX40 (e.g., human OX40), protects effector T cells (e.g., CD4⁺ and CD8⁺ effector T cells) from activation-induced cell death.

In specific embodiments, an antibody described herein, which immunospecifically binds to OX40 (e.g., human OX40), induces, enhances, or increases cytokine production (e.g., IL-2, TNF-α, IFN-γ, IL-4, IL-10, and/or IL-13) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra, such as Example 2) or known to one of skill in the art, relative to cytokine production in the presence or absence of OX40L (e.g., human OX40L) stimulation without any antibody or with an unrelated antibody (e.g., an antibody that does not immunospecifically bind to OX40). In specific embodiments, an antibody described herein, which immunospecifically binds to OX40 (e.g., human OX40), induces or enhances cytokine production (e.g., IL-2, TNF-α, IFN-γ, IL-4, IL-10, and/or IL-13) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra, such as Example 2) or known to one of skill in the art, relative to cytokine production in the presence or absence of OX40L (e.g., human OX40L) stimulation without any antibody or with an unrelated antibody (e.g., an antibody that does not immunospecifically bind to OX40).

In certain embodiments, T cells (e.g., CD4⁺ or CD8⁺ effector T cells) stimulated with a T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody) in the presence of an antibody described herein, which immunospecifically binds to OX40 (e.g., human OX40), have increased cytokine production (e.g., IL-2, TNF-α, IFN-γ, IL-4, IL-10, and/or IL-13) by at least about 5%, 10%, 15%, 20%, 25%, 30%, 35%, 40%, 45%, 50%, 55%, 60%, 65%, 70%, 75%, 80%, 85%, 90%, 95%, 98%, or 99% relative to T cells only stimulated with the T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody), as assessed by methods described herein or known to one of skill in the art (e.g., an ELISA assay or as described in the Examples, infra). In some embodiments, T cells (e.g., CD4⁺ or CD8⁺ effector T cells) stimulated with a T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody) in the presence of an antibody described herein, which immunospecifically binds to OX40 (e.g., human OX40), have increased cytokine production (e.g., IL-2, TNF-α, IFN-γ, IL-4, IL-10, and/or IL-13) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to T cells only stimulated with the T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody), as assessed by methods described herein or known to one of skill in the art (e.g., an ELISA assay or as described in the Examples, infra).

In specific embodiments, an antibody described herein, which immunospecifically binds to OX40 (e.g., human OX40), increases IL-2 production in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra, such as Example 2) or known to one of skill in the art, relative to IL-2 production without any antibody or with an unrelated antibody (e.g., an antibody that does not immunospecifically bind to OX40).

In certain embodiments, T cells (e.g., CD4⁺ or CD8⁺ T cells) stimulated with *Staphylococcus* Enterotoxin A (SEA) stimulation in the presence of an antibody described herein, which immunospecifically binds to OX40 (e.g., human OX40), have increased IL-2 production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to T cells only stimulated with SEA, as assessed by methods described herein or known to one of skill in the art (e.g., an ELISA assay or as described in the Examples, infra).

In specific embodiments, an antibody described herein, which immunospecifically binds to OX40 (e.g., human OX40), in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production is a substantially increasing function of antibody concentrations between, e.g., 0.032 μg/ml and 20 μg/ml. In certain embodiments, the IL-2 production induced by the antibody in combination with SEA is a substantially increasing function of antibody concentrations between, e.g., 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 μg/ml, or 0.8 μg/ml and 4 μg/ml. In another embodiment, an antibody described herein, which immunospecifically binds to OX40 (e.g., human OX40), in combination with *Staphylococcus* Enterotoxin A (SEA), induces IL-2 production in, e.g., PBMCs, wherein the IL-2 production is a substantially increasing function of antibody concentrations between, e.g., 0.032 μg/ml and 20 μg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 μg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery). In certain embodiments, an antibody described herein, which immunospecifically binds to OX40 (e.g., human OX40), in combination with *Staphylococcus* Enterotoxin A (SEA), induces IL-2 production in, e.g., PBMCs, wherein the IL-2 production is a substantially increasing function of antibody concentrations between, e.g., 0.16 μg/ml and 20 μg/ml, 0.8 μg/ml and 20 μg/ml, 4 μg/ml and 20 μg/ml, 0.032 μg/ml and 4 μg/ml, 0.16 μg/ml and 4 µg/ml, or 0.8 µg/ml and 4 µg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 µg/ml) of the antibody and, e.g., 100 ng/ml of SEA for, e.g., 5 days at, e.g., 37° C., 5% $CO_2$, and 97% humidity; and (b) collecting clarified supernatant and measuring the titers of IL-2 by, e.g., electrochemiluminescence, e.g., Human TH1/TH2 10-Plex tissue culture kit (Meso Scale Discovery). In specific embodiments, an antibody described herein, which immunospecifically binds to OX40 (e.g., human OX40), results in greater IL-2 production in response to *Staphylococcus* Enterotoxin A (SEA) (e.g., 100 ng/ml) upon stimulation for, e.g., 5 days at, e.g., 37° C., 5% $CO_2$, and 97% humidity, when the antibody is present at a concentration of 20 µg/ml than at a concentration of 0.032 µg/ml. In a particular embodiment, an antibody described herein, which immunospecifically binds to OX40 (e.g., human OX40), results in greater IL-2 production in response to *Staphylococcus* Enterotoxin A (SEA) (e.g., 100 ng/ml) upon stimulation for, e.g., 5 days at, e.g., 37° C., 5% $CO_2$, and 97% humidity, when the antibody is present at a concentration of 20 µg/ml than at a concentration of 0.16 µg/ml.

In specific embodiments, an antibody described herein, which immunospecifically binds to OX40 (e.g., human OX40), in combination with *Staphylococcus* Enterotoxin A (SEA) (e.g., 100 ng/ml), induces IL-2 production in, e.g., PBMCs upon stimulation for, e.g., 5 days at, e.g., 37° C., 5% $CO_2$, and 97% humidity, as measured by, e.g., electrochemiluminescence, e.g., Human TH1/TH2 10-Plex tissue culture kit (Meso Scale Discovery), wherein the IL-2 production shows a sigmoidal dose response curve when the anti-OX40 antibody concentration is between, e.g., 0.032 µg/ml and 20 µg/ml. In certain embodiments, the IL-2 production induced by the antibody in combination with SEA shows a sigmoidal dose response curve when the anti-OX40 antibody concentration is between, e.g., 0.16 µg/ml and 20 µg/ml, 0.8 µg/ml and 20 µg/ml, 4 µg/ml and 20 µg/ml, 0.032 µg/ml and 4 µg/ml, 0.16 µg/ml and 4 µg/ml, or 0.8 µg/ml and 4 µg/ml. In another embodiment, an antibody described herein, which immunospecifically binds to OX40 (e.g., human OX40), in combination with *Staphylococcus* Enterotoxin A (SEA), induces IL-2 production in, e.g., PBMCs, wherein the IL-2 production shows a sigmoidal dose response curve when the anti-OX40 antibody concentration is between, e.g., 0.032 µg/ml and 20 µg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 µg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence, e.g., Human TH1/TH2 10-Plex tissue culture kit (Meso Scale Discovery). In certain embodiments, an antibody described herein, which immunospecifically binds to OX40 (e.g., human OX40), in combination with *Staphylococcus* Enterotoxin A (SEA), induces IL-2 production in, e.g., PBMCs, wherein the IL-2 production shows a sigmoidal dose response curve when the anti-OX40 antibody concentration is between, e.g., 0.16 µg/ml and 20 µg/ml, 0.8 µg/ml and 20 µg/ml, 4 µg/ml and 20 µg/ml, 0.032 µg/ml and 4 µg/ml, 0.16 µg/ml and 4 µg/ml, or 0.8 µg/ml and 4 µg/ml, as assessed in, e.g., an assay comprising the following steps: (a) culturing the PBMCs (e.g., $10^5$ cells in a well) in the absence or presence of varying concentrations (e.g., 20, 4, 0.8, 0.16, 0.032, 0.0064, 0.00128, and 0.000256 µg/ml) of the antibody and, e.g., 100 ng/ml of SEA for, e.g., 5 days at, e.g., 37° C., 5% $CO_2$, and 97% humidity; and (b) collecting clarified supernatant and measuring the titers of IL-2 by, e.g., electrochemiluminescence, e.g., Human TH1/TH2 10-Plex tissue culture kit (Meso Scale Discovery). In specific embodiments, an antibody described herein, which immunospecifically binds to OX40 (e.g., human OX40), results in greater IL-2 production in response to *Staphylococcus* Enterotoxin A (SEA) (e.g., 100 ng/ml) upon stimulation for, e.g., 5 days at, e.g., 37° C., 5% $CO_2$, and 97% humidity, when the antibody is present at a concentration of 20 µg/ml than at a concentration of 0.032 µg/ml. In a particular embodiment, an antibody described herein, which immunospecifically binds to OX40 (e.g., human OX40), results in greater IL-2 production in response to *Staphylococcus* Enterotoxin A (SEA) (e.g., 100 ng/ml) upon stimulation for, e.g., 5 days at, e.g., 37° C., 5% $CO_2$, and 97% humidity, when the antibody is present at a concentration of 20 µg/ml than at a concentration of 0.16 µg/ml.

In specific embodiments, an antibody described herein, which immunospecifically binds to OX40 (e.g., human OX40), decreases IL-10 production in response to *Staphylococcus* Enterotoxin A (SEA) stimulation by at least about 5%, 10%, 15%, 20%, 25%, 30%, 35%, 40%, 45%, or 50%, as assessed by methods described herein (see the Examples, infra, such as Example 2) or known to one of skill in the art, relative to IL-10 production without any antibody or with an unrelated antibody (e.g., an antibody that does not immunospecifically bind to OX40).

In certain embodiments, T cells (e.g., $CD4^+$ or $CD8^+$ T cells) stimulated with *Staphylococcus* Enterotoxin A (SEA) stimulation in the presence of an antibody described herein, which immunospecifically binds to OX40 (e.g., human OX40), have decreased IL-10 production by at least about 5%, 10%, 15%, 20%, 25%, 30%, 35%, 40%, 45%, or 50% relative to T cells only stimulated with SEA, as assessed by methods described herein or known to one of skill in the art (e.g., an ELISA assay or as described in the Examples, infra).

In specific embodiments, an antibody described herein, which immunospecifically binds to OX40 (e.g., human OX40), when bound to activated regulatory T cells, binds to activating Fc gamma receptors selected from the group consisting of CD16, CD32A and CD64 to a greater extent (e.g., 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold) than the antibody, when bound to activated effector T cells, binds to the activating Fc gamma receptors selected from the group consisting of CD16, CD32A and CD64, as assessed by methods described herein or known to one of skill in the art (e.g., an Fc gamma receptor IIIA (CD16) reporter assay or as described in the Examples, infra). In specific embodiments, the activating Fc gamma receptors are expressed on a cell selected from the group consisting of myeloid-derived effector cells and lymphocyte-derived effector cells. In a particular embodiment, the activating Fc gamma receptor is CD16.

In specific embodiments, an antibody described herein, which immunospecifically binds to OX40 (e.g., human OX40), when bound to activated regulatory T cells, causes stronger activation of activating Fc gamma receptors selected from the group consisting of CD16, CD32A and CD64 than the antibody, when bound to activated effector T cells, causes activation of activating Fc gamma receptors selected from the group consisting of CD16, CD32A and CD64. In particular embodiments, the activation of the activating Fc gamma receptors, when the antibody described herein, which immunospecifically binds to OX40 (e.g., human OX40), is bound to activated regulatory T cells, is at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold stronger than the activation of the activating Fc gamma receptors, when the antibody described herein, which immunospecifically binds to OX40 (e.g., human OX40), is bound to activated effector T cells, as assessed by methods described herein or known to one of skill in the art (e.g., an Fc gamma receptor IIIA (CD16) reporter assay or as described in the Examples, infra). In specific embodiments, the activating Fc gamma receptors are expressed on a cell selected from the group consisting of myeloid-derived effector cells and lymphocyte-derived effector cells. In a particular embodiment, the activating Fc gamma receptor is CD16.

In a specific aspect, provided herein are antagonist antibodies, which immunospecifically bind to OX40 (e.g., human OX40).

The activation of OX40 signaling depends on receptor clustering to form higher order receptor complexes that efficiently recruit apical adapter proteins to drive intracellular signal transduction. Without being bound by theory, an anti-OX40 agonist antibody may mediate receptor clustering through bivalent antibody arms (i.e., two antibody arms that each bind OX40 antigen) and/or through Fc-Fc receptor (FcR) co-engagement on accessory myeloid or lymphoid cells. Consequently, one approach for developing an anti-OX40 antagonist antibody is to select an antibody that competes with OX40 ligand (OX40L) for binding to OX40, diminish or eliminate the binding of the Fc region of an antibody to Fc receptors, and/or adopt a monovalent antibody format. The monovalent antibody format can include antibodies that are structurally monovalent, such as, but not limited to, anti-OX40 antibodies comprising only one antigen-binding domain (e.g., only one Fab arm), or antibodies comprising only one antigen-binding domain that binds to OX40 (e.g., human OX40) that is paired with a heavy chain or that is paired with a fragment of a heavy chain (e.g., a Fc fragment). The monovalent antibody format can also include antibodies that are functionally monovalent, for example, antibodies comprising only one antigen-binding domain that binds to OX40 (e.g., human OX40) that is paired with a second-antigen binding domain that does not bind to an antigen expressed by a human immune cell (i.e., the antibody comprises two antigen-binding domains, but only one antigen-binding domain binds to OX40).

Examples of mutations of the IgG constant domain Fc region are discussed above that can reduce Fc receptor binding or that can remove potential glycosylation sites. In certain embodiments, the heavy chain constant region of an antibody as described herein, which immunospecifically binds to OX40 (e.g., human OX40), comprises a mutation selected from the group consisting of: N297A, N297Q, D265A, C127S, S228P, and a combination thereof. In certain embodiments, the mutation is N297A, N297Q, D265A, or a combination thereof. In certain embodiments, the mutation is C127S. In certain embodiments, the mutation is S228P. In one embodiment, the heavy chain constant region of an antibody as described herein, which immunospecifically binds to OX40 (e.g., human OX40), comprises a mutation selected from the group consisting of D265A, P329A, and a combination thereof. In certain embodiments, the heavy chain constant region is selected from the group consisting of immunoglobulins $IgG_1$, $IgG_2$, $IgG_3$, $IgG_4$, $IgA_1$, and $IgA_2$. In certain embodiments, the immunoglobulins are human immunoglobulins. Human immunoglobulins containing mutations (e.g., substitutions) are also referred to as human immunoglobulins herein. In a specific aspect, an antibody as described herein, which immunospecifically binds to OX40 (e.g., human OX40), comprises a immunoglobulin $IgG_1$ heavy chain constant region, wherein the amino acid sequence of the $IgG_1$ heavy chain constant region comprises a mutation selected from the group consisting of a N297A, N297Q, D265A, or a combination thereof. In one aspect, an antibody as described herein, which immunospecifically binds to OX40 (e.g., human OX40), comprises a immunoglobulin $IgG_1$ heavy chain constant region, wherein the amino acid sequence of the $IgG_1$ heavy chain constant region comprises a mutation selected from the group consisting of D265A, P329A, and a combination thereof. In a specific aspect, an antibody as described herein, which immunospecifically binds to OX40 (e.g., human OX40), comprises a immunoglobulin $IgG_2$ heavy chain constant region, wherein the amino acid sequence of the $IgG_2$ heavy chain constant region comprises a C127S mutation. In a specific aspect, an antibody as described herein, which immunospecifically binds to OX40 (e.g., human OX40), comprises a immunoglobulin $IgG_4$ heavy chain constant region, wherein the amino acid sequence of the $IgG_4$ heavy chain constant region comprises a S228P mutation. In certain embodiments, the antibody is antagonistic.

In a specific aspect, an antibody as described herein, which immunospecifically binds to OX40 (e.g., human OX40), is selected from the group consisting of a Fab, Fab', $F(ab')_2$, and scFv fragment, wherein the Fab, Fab', $F(ab')_2$, or scFv fragment comprises a heavy chain variable region sequence and a light chain variable region sequence of an anti-OX40 antigen-binding domain or antibody as described herein. A Fab, Fab', $F(ab')_2$, or scFv fragment can be produced by any technique known to those of skill in the art, including, but not limited to, those discussed in Section 5.3, infra. In certain embodiments, the Fab, Fab', $F(ab')_2$, or scFv fragment further comprises a moiety that extends the half-life of the antibody in vivo. The moiety is also termed a "half-life extending moiety." Any moiety known to those of skill in the art for extending the half-life of a Fab, Fab', $F(ab')_2$, or scFv fragment in vivo can be used. For example, the half-life extending moiety can include a Fc region, a polymer, an albumin, or an albumin binding protein or compound. The polymer can include a natural or synthetic, optionally substituted straight or branched chain polyalkylene, polyalkenylene, polyoxylalkylene, polysaccharide, polyethylene glycol, polypropylene glycol, polyvinyl alcohol, methoxypolyethylene glycol, lactose, amylose, dextran, glycogen, or derivative thereof. Substituents can include one or more hydroxy, methyl, or methoxy groups. In certain embodiments, the Fab, Fab', $F(ab')_2$, or scFv fragment can be modified by the addition of one or more C-terminal amino acids for attachment of the half-life extending moiety. In certain embodiments the half-life extending moiety is polyethylene glycol or human serum albumin. In certain embodiments, the Fab, Fab', $F(ab')_2$, or scFv fragment is fused to a Fc region. In certain embodiments, the antibody is antagonistic.

In a specific aspect, an antibody which immunospecifically binds to OX40 (e.g., human OX40) comprises one heavy chain and one light chain (i.e., the antibody does not comprise any additional heavy chain or light chain and comprises, consists essentially of, or consists of a single heavy chain-light chain pair), wherein the heavy chain and light chain comprise a heavy chain variable region sequence and a light chain variable region sequence, respectively, of an anti-OX40 antigen-binding domain or antibody as described herein. In certain embodiments, the heavy chain comprises a mutation selected from the group consisting of: N297A, N297Q, D265A, C127S, S228P, and a combination thereof. In certain embodiments, the mutation is N297A, N297Q, D265A, or a combination thereof. In certain embodiments, the mutation is C127S. In certain embodiments, the mutation is S228P. In certain embodiments, the heavy chain comprises a mutation selected from the group consisting of D265A, P329A, and a combination thereof. In certain embodiments, the heavy chain is selected from the group consisting of immunoglobulins $IgG_1$, $IgG_2$, $IgG_3$, $IgG_4$, $IgA_1$, and $IgA_2$. In certain embodiments, the immunoglobulins are human immunoglobulins. In certain embodiments, the heavy chain is an $IgG_1$ heavy chain comprising a mutation selected from the group consisting of N297A, N297Q, D265A, or a combination thereof. In certain embodiments, the heavy chain is an $IgG_2$ heavy chain comprising a C127S mutation. In certain embodiments, the heavy chain is an $IgG_4$ heavy chain comprising a S228P mutation. In certain embodiments, the heavy chain is an $IgG_1$ heavy chain comprising a mutation selected from the group consisting of D265A, P329A and a combination thereof. In certain embodiments, the antibody is antagonistic.

In a specific aspect, an antibody as described herein which immunospecifically binds to OX40 (e.g., human OX40), comprises a first antigen-binding domain that binds to OX40, as described herein; and a second antigen-binding domain that does not specifically bind to an antigen expressed by a human immune cell (i.e., the second antigen-binding domain does not bind to OX40 or any other antigen expressed by a human immune cell), as described herein. In certain embodiments, the first and second antigen-binding domains comprise complementary CH3 domains. For example, the complementary CH3 domains allow for heterodimerization to preferentially occur between the heavy chain of the first antigen-binding domain and the heavy chain of the second antigen-binding domain rather than homodimerization of the respective antigen-binding domains. Any technique known to those of skill in the art can be used to produce complementary CH3 domains, including, but not limited to, knob-into-hole technology as described in Ridgway J B B et al., (1996) Protein Eng 9(7): 617-621 and Merchant M et al. For example, the knob-into-hole technology replaces a small amino acid with a larger amino acid (i.e., the "knob") in a first CH3 domain and replaces a large amino acid with a smaller amino acid (i.e., the "hole") in a second CH3 domain. Polypeptides comprising the CH3 domains can then dimerize based on interaction of the knob and hole. In certain embodiments, one of the antigen-binding domains comprises a first $IgG_1$ CH3 domain comprising a substitution selected from the group consisting of T366Y and T366W, and the other antigen-binding domain comprises a second $IgG_1$ CH3 domain comprising a substitution selected from the group consisting of Y407T, T366S, L368A, and Y407V. In certain embodiments, the antigen to which the second antigen-binding domain binds is not naturally expressed by a human immune cell. In certain embodiments, the immune cell is selected from the group consisting of a T cell (e.g., a CD4+ T cell or a CD8+ T cell), a B cell, a natural killer cell, a dendritic cell, a macrophage, and an eosinophil. In certain embodiments, the antigen-binding domain that specifically binds to OX40 comprises a first VH and a first VL, and the second antigen-binding domain comprises a second VH and a second VL. In certain embodiments, the antigen-binding domain that specifically binds to OX40 comprises a first heavy chain and a first light chain, and the second antigen-binding domain comprises a second heavy chain and a second light chain. In certain embodiments, the antibody is for administration to a sample or subject in which the second antigen-binding domain is non-reactive (i.e., the antigen to which the second antigen-binding domain binds is not present in the sample or subject). In certain embodiments, the second antigen-binding domain does not specifically bind to an antigen on a cell expressing OX40 (e.g., the second antigen-binding domain does not bind to an antigen that is naturally expressed by a cell that expresses OX40). In certain embodiments, the antibody functions as a monovalent antibody (i.e., an anti-OX40-monovalent antibody) in a sample or subject, wherein the first antigen-binding domain of the antibody binds to OX40, while the second antigen-binding domain is non-reactive in the sample or subject (e.g., due to the absence of antigen to which the second antigen-binding domain binds in the sample or subject). In certain embodiments, the second antigen-binding domain specifically binds to a non-human antigen (i.e., an antigen expressed in other organisms and not humans). In certain embodiments, the second antigen-binding domain specifically binds to a viral antigen. In certain embodiments, the viral antigen is from a virus that does not infect humans (i.e., a non-human virus). In certain embodiments, the viral antigen is absent in a human immune cell (e.g., the human immune cell is uninfected with the virus associated with the viral antigen). In certain embodiments, the viral antigen is a HIV antigen. In certain embodiments, the second antigen-binding domain specifically binds to chicken albumin or hen egg lysozyme. In certain embodiments, the second antigen-binding domain specifically binds to an antigen that is not expressed by (i.e., is absent from) wild-type cells (e.g., wild-type human cells). In certain embodiments, the second antigen-binding domain specifically binds to a tumor-associated antigen that is not expressed by (i.e., is absent from) normal cells (e.g., wild-type cells, e.g., wild-type human cells). In certain embodiments, the tumor-associated antigen is not expressed by (i.e., is absent from) human cells. In certain embodiments, the heavy chain constant region of the second antigen-binding domain comprises a mutation selected from the group consisting of: N297A, N297Q, D265A, C127S, S228P, and a combination thereof. In certain embodiments, the mutation is N297A, N297Q, D265A, or a combination thereof. In certain embodiments, the mutation is C127S. In certain embodiments, the mutation is S228P. In certain embodiments, the heavy chain constant region of the second antigen-binding domain comprises a mutation selected from the group consisting of D265A, P329A, and a combination thereof. In certain embodiments, the heavy chain constant region of the first and second antigen-binding domains is selected from the group consisting of immunoglobulins $IgG_1$, $IgG_2$, $IgG_3$, $IgG_4$, $IgA_1$, and $IgA_2$. In certain embodiments, the immunoglobulins are human immunoglobulins. In certain embodiments, the heavy chain constant regions of the first and second antigen-binding domains are the same isotype. In certain embodiments, the first antigen-binding domain comprises a first $IgG_1$ heavy chain constant region and the second antigen-binding domain comprises a second $IgG_1$ heavy chain constant region, wherein the first and second heavy chain constant regions comprise an identical mutation selected from the group consisting of N297A, N297Q, D265A, or a combination thereof. In certain embodiments, the first antigen-binding domain comprises a first IgG$_1$ heavy chain constant region and the second antigen-binding domain comprises a second IgG$_1$ heavy chain constant region, wherein the first and second heavy chain constant regions comprise an identical mutation selected from the group consisting of D265A, P329A, or a combination thereof. In certain embodiments, the first antigen-binding domain comprises a first IgG$_2$ heavy chain constant region and the second antigen-binding domain comprises a second IgG$_2$ heavy chain constant region, wherein the first and second heavy chain constant regions comprise a C127S mutation. In certain embodiments, the first antigen-binding domain comprises a first IgG$_4$ heavy chain constant region and the second antigen-binding domain comprises a second IgG$_4$ heavy chain constant region, wherein the first and second heavy chain constant regions comprise a S228P mutation. In certain embodiments, the antibody is antagonistic.

In a specific aspect, an antibody as described herein which immunospecifically binds to OX40 (e.g., human OX40), comprises a first antigen-binding domain that specifically binds to OX40, comprising a first heavy chain and a first light chain; and a second heavy chain or a fragment thereof. In certain embodiments, the first and second heavy chain, or fragment of the second heavy chain, comprise complementary CH3 domains. For example, the complementary CH3 domains allow for heterodimerization to preferentially occur between the heavy chains rather than homodimerization of the respective heavy chains. In certain embodiments, one of the heavy chains comprises a first IgG$_1$ CH3 domain comprising a substitution selected from the group consisting of T366Y and T366W, and the other heavy chain comprises a second IgG$_1$ CH3 domain comprising a substitution selected from the group consisting of Y407T, T366S, L368A, Y407V. In some embodiments, the fragment of the second heavy chain is a Fc fragment. In certain embodiments, the second heavy chain or fragment thereof is from an antigen-binding domain that specifically binds to a non-human antigen (i.e., an antigen expressed in other organisms and not humans). In certain embodiments, the second heavy chain or fragment thereof is from an antigen-binding domain that specifically binds to a viral antigen. In certain embodiments, the viral antigen is absent in a human immune cell (e.g., the human immune cell is uninfected with the virus associated with the viral antigen). In certain embodiments, the viral antigen is a HIV antigen. In certain embodiments, the second heavy chain or fragment thereof is from an antigen-binding domain that specifically binds to chicken albumin or hen egg lysozyme. In certain embodiments, the second heavy chain or fragment thereof is from an antigen-binding domain that specifically binds to an antigen that is not expressed by (i.e., is absent from) wild-type cells (e.g., wild-type human cells). In certain embodiments, the second heavy chain or fragment thereof is from an antigen-binding domain that specifically binds to a tumor-associated antigen that is not expressed by (i.e., is absent from) normal cells (e.g., wild-type cells, e.g., wild-type human cells). In certain embodiments, the tumor-associated antigen is not expressed by (i.e., is absent from) human cells. In certain embodiments, the second heavy chain or fragment thereof comprises a mutation selected from the group consisting of: N297A, N297Q, D265A, C127S, S228P, and a combination thereof. In certain embodiments, the mutation is N297A, N297Q, D265A, or a combination thereof. In certain embodiments, the mutation is C127S. In certain embodiments, the mutation is S228P. In certain embodiments, the second heavy chain or fragment thereof comprises a mutation selected from the group consisting of D265A, P329A, and a combination thereof. In certain embodiments, the first and second heavy chain constant regions are selected from the group consisting of immunoglobulins IgG$_1$, IgG$_3$, IgG$_4$, IgA$_1$, and IgA$_2$. In certain embodiments, the immunoglobulins are human immunoglobulins. In certain embodiments, the first and second heavy chain constant regions are the same isotype. In certain embodiments, the first and second heavy chain constant regions are IgG$_1$ constant regions and comprise an identical mutation selected from the group consisting of N297A, N297Q, D265A, or a combination thereof. In certain embodiments, the first and second heavy chain constant regions are IgG$_1$ constant regions and comprise an identical mutation selected from the group consisting of D265A, P329A, and a combination thereof. In certain embodiments, the first and second heavy chain constant regions are IgG$_2$ heavy chain constant regions and comprise a C127S mutation. In certain embodiments, the first and second heavy chain constant regions are IgG$_4$ heavy chain constant regions and comprise a S228P mutation. In certain embodiments, the antibody is antagonistic.

In the above aspects directed to an antibody comprising an antigen-binding domain that specifically binds to OX40 (e.g., human OX40) and either a second antigen-binding domain or a second heavy chain or fragment thereof, the antigen-binding domain can comprise any of the anti-OX40 sequences described herein. In certain embodiments, the antigen-binding domain that specifically binds to OX40 (e.g., human OX40) comprises: (a) a first heavy chain variable domain (VH) comprising a VH-complementarity determining region (CDR) 1 comprising the amino acid sequence of GSAMH (SEQ ID NO:4); a VH-CDR2 comprising the amino acid sequence of RIRSKAN-SYATAYAASVKG (SEQ ID NO:5); and a VH-CDR3 comprising the amino acid sequence of GIYDSSGYDY (SEQ ID NO:6); and (b) a first light chain variable domain (VL) comprising a VL-CDR1 comprising the amino acid sequence of RSSQSLLHSNGYNYLD (SEQ ID NO:1); a VL-CDR2 comprising the amino acid sequence of LGSN-RAS (SEQ ID NO:2); and a VL-CDR3 comprising the amino acid sequence of MQALQTPLT (SEQ ID NO:3). In certain embodiments, the antigen-binding domain that specifically binds to OX40 (e.g., human OX40) specifically binds to the same epitope of OX40 (e.g., human OX40) as an antibody comprising a VH comprising the amino acid sequence of SEQ ID NO:16 and a VL comprising the amino acid sequence of SEQ ID NO:15. In certain embodiments, the antigen-binding domain that specifically binds to OX40 (e.g., human OX40) exhibits, as compared to binding to a human OX40 sequence of SEQ ID NO:55, reduced or absent binding to a protein identical to SEQ ID NO:55 except for the presence of an amino acid mutation selected from the group consisting of: N60A, R62A, R80A, L88A, P93A, P99A, P115A, and a combination thereof. In certain embodiments, the antigen-binding domain that specifically binds to OX40 (e.g., human OX40) comprises a VH and a VL, wherein the VH comprises the amino acid sequence of SEQ ID NO:16. In certain embodiments, the antigen-binding domain that specifically binds to OX40 (e.g., human OX40) comprises a VH and a VL, wherein the VL comprises the amino acid sequence of SEQ ID NO:15. In certain embodiments, the antigen-binding domain that binds to OX40 comprises a VH comprising an amino acid sequence that is at least 75%, 80%, 85%, 90%, 95%, or 99% identical to the amino acid sequence of SEQ ID NO:16. In certain embodiments, the antigen-binding domain that specifically binds to OX40 (e.g., human OX40) comprises a VH comprising the amino acid sequence of SEQ ID NO:16. In certain embodiments, the antigen-binding domain that binds to OX40 comprises a VH comprising an amino acid sequence derived from a human IGHV3-73 germline sequence (e.g., IGHV3-73*01, e.g., having the amino acid sequence of SEQ ID NO:19). In certain embodiments, the antigen-binding domain that specifically binds to OX40 (e.g., human OX40) comprises a VL comprising an amino acid sequence that is at least 75%, 80%, 85%, 90%, 95%, or 99% identical to the amino acid sequence of SEQ ID NO:15. In certain embodiments, the antigen-binding domain that specifically binds to OX40 (e.g., human OX40) comprises a VL-CDR3 comprising the amino acid sequence SEQ ID NO:3. In certain embodiments, the antigen-binding domain that specifically binds to OX40 (e.g., human OX40) comprises a VL comprising the amino acid sequence of SEQ ID NO:15. In certain embodiments, the antigen-binding domain that specifically binds to OX40 (e.g., human OX40) comprises a light chain comprising the amino acid sequence of SEQ ID NO:20. In certain embodiments, the antigen-binding domain that specifically binds to OX40 (e.g., human OX40) comprises a light chain comprising the amino acid sequence of SEQ ID NO:50. In certain embodiments, the antigen-binding domain that specifically binds to OX40 (e.g., human OX40) comprises a VL comprising an amino acid sequence derived from a human IGKV2-28 germline sequence (e.g., IGKV2-28*01, e.g., having the amino acid sequence of SEQ ID NO:18). In certain embodiments, the antigen-binding domain that specifically binds to OX40 (e.g., human OX40) comprises the VH and VL sequences set forth in SEQ ID NOs: 16 and 15, respectively. In certain embodiments, the antigen-binding domain that specifically binds to OX40 (e.g., human OX40) comprises a heavy chain comprising the amino acid sequence of SEQ ID NO: 21. In certain embodiments, the antigen-binding domain that specifically binds to OX40 (e.g., human OX40) comprises a heavy chain comprising the amino acid sequence of SEQ ID NO: 60. In certain embodiments, the antigen-binding domain that specifically binds to OX40 (e.g., human OX40) comprises a mutation selected from the group consisting of a N297A, N297Q, D265A mutation, or a combination thereof. In certain embodiments, the antigen-binding domain that specifically binds to OX40 (e.g., human OX40) comprises a mutation selected from the group consisting of D265A, P329A and a combination thereof.

In certain embodiments, an antagonistic antibody described herein is antagonistic to OX40 (e.g., human OX40). In certain embodiments, the antibody deactivates, reduces, or inhibits an activity of OX40 (e.g., human OX40). In certain embodiments, the antibody inhibits or reduces binding of OX40 (e.g., human OX40) to OX40 ligand (e.g., human OX40 ligand). In certain embodiments, the antibody inhibits or reduces OX40 (e.g., human OX40) signaling. In certain embodiments, the antibody inhibits or reduces OX40 (e.g., human OX40) activity (e.g., OX40 signaling) induced by OX40 ligand (e.g., human OX40 ligand). In certain embodiments, an antagonistic antibody described herein inhibits or reduces T cell proliferation. In certain embodiments, an antagonistic antibody described herein inhibits or reduces T cell proliferation. In certain embodiments, an antagonistic antibody described herein inhibits or reduces production of cytokines (e.g., inhibits or reduces production of IL-2, TNFα, IFNγ, IL-4, IL-10, IL-13, or a combination thereof by stimulated T cells). In certain embodiments, an antagonistic antibody described herein inhibits or reduces production of IL-2 by SEA-stimulated T cells. In certain embodiments, an antagonistic antibody described herein blocks the interaction of OX40 and OX40L (e.g., blocks the binding of OX40L and OX40 to one another, e.g., blocks the binding of human OX40 ligand and human OX40)).

In certain embodiments, an antagonistic antibody described herein, which immunospecifically binds to OX40 (e.g., human OX40), decreases OX40 (e.g., human OX40) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to OX40 (e.g., human OX40) activity without any antibody or with an unrelated antibody (e.g., an antibody that does not immunospecifically bind to OX40). In certain embodiments, an antagonistic antibody described herein, which immunospecifically binds to OX40 (e.g., human OX40), decreases OX40 (e.g., human OX40) activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to OX40 (e.g., human OX40) activity without any antibody or with an unrelated antibody (e.g., an antibody that does not immunospecifically bind to OX40). Non-limiting examples of OX40 (e.g., human OX40) activity can include OX40 (e.g., human OX40) signaling, cell proliferation, cell survival, and cytokine production (e.g., IL-2, TNF-α, IFN-γ, IL-4, IL-10, and/or IL-13). In certain embodiments, an antagonistic antibody described herein, which immunospecifically binds to OX40 (e.g., human OX40), inhibits, reduces, or inactivates an OX40 (e.g., human OX40) activity. In specific embodiments, OX40 activity is assessed as described in the Examples, infra.

In certain aspects, an antagonistic antibody described herein, which immunospecifically binds to OX40 (e.g., human OX40), inhibits, reduces, or deactivates the cellular proliferation of cells that express OX40 and that respond to OX40 signaling (e.g., cells that proliferate in response to OX40 stimulation and OX40 signaling, such as T cells). Cell proliferation assays are described in the art, such as a $^3$H-thymidine incorporation assay, BrdU incorporation assay, or CFSE assay, such as described in the Examples, infra, and can be readily carried out by one of skill in the art. In specific embodiments, T cells (e.g., CD4$^+$ or CD8$^+$ effector T cells) stimulated with a T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody), in the presence of an antagonistic antibody described herein, which immunospecifically binds to OX40 (e.g., human OX40), have decreased cellular proliferation relative to T cells only stimulated with the T cell mitogen or T cell receptor complex stimulating agent, such as phytohaemagglutinin (PHA) and/or phorbol myristate acetate (PMA), or a TCR complex stimulating antibody, such as an anti-CD3 antibody and anti-CD28 antibody.

In certain aspects, an antagonistic antibody described herein, which immunospecifically binds to OX40 (e.g., human OX40), decreases the survival of cells (e.g., T cells, such as CD4 and CD8 effector T cells). In a specific embodiment, T cells (e.g., CD4$^+$ or CD8$^+$ effector T cells) stimulated with a T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti- CD28 antibody) in the presence of an antagonistic antibody described herein, which immunospecifically binds to OX40 (e.g., human OX40), have decreased survival relative to T cells only stimulated with the T cell mitogen. Cell survival assays are described in the art (e.g., a trypan blue exclusion assay) and can be readily carried out by one of skill in the art.

In specific embodiments, an antagonistic antibody described herein, which immunospecifically binds to OX40 (e.g., human OX40), decreases cell survival (e.g., T cells, such as CD4 and CD8 effector T cells) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art (e.g., a trypan blue exclusion assay), without any antibody or with an unrelated antibody (e.g., an antibody that does not immunospecifically bind to OX40). In specific embodiments, an antagonistic antibody described herein, which immunospecifically binds to OX40 (e.g., human OX40), decreases cell survival (e.g., T cells, such as CD4 and CD8 effector T cells) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art (e.g., a trypan blue exclusion assay), relative to OX40 (e.g., human OX40) activity without any antibody or with an unrelated antibody (e.g., an antibody that does not immunospecifically bind to OX40).

In some embodiments, T cells (e.g., $CD4^+$ or $CD8^+$ effector T cells) stimulated with a T cell mitogen (e.g., an anti-CD3 antibody or phorbol ester) in the presence of an antagonistic antibody described herein, which immunospecifically binds to OX40 (e.g., human OX40), have decreased cell survival by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to T cells only stimulated with the T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody), as assessed by methods described herein or known to one of skill in the art (e.g., a trypan blue exclusion assay). In some embodiments, T cells (e.g., $CD4^+$ or $CD8^+$ effector T cells) stimulated with a T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody) in the presence of an antagonistic antibody described herein, which immunospecifically binds to OX40 (e.g., human OX40), have decreased cell survival by at least about 5%, 10%, 15%, 20%, 25%, 30%, 35%, 40%, 45%, 50%, 55%, 60%, 65%, 70%, 75%, 80%, 85%, 90%, 95%, 98%, or 99% relative to T cells only stimulated with the T cell mitogen, as assessed by methods described herein or known to one of skill in the art (e.g., a trypan blue exclusion assay).

In certain embodiments, an antagonistic antibody described herein, which immunospecifically binds to OX40 (e.g., human OX40), does not protect effector T cells (e.g., $CD4^+$ and $CD8^+$ effector T cells) from activation-induced cell death.

In specific embodiments, an antagonistic antibody described herein, which immunospecifically binds to OX40 (e.g., human OX40), inhibits, reduces, or deactivates cytokine production (e.g., IL-2, TNF-α, IFN-γ, IL-4, IL-10, and/or IL-13) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to cytokine production in the presence or absence of OX40L (e.g., human OX40L) stimulation without any antibody or with an unrelated antibody (e.g., an antibody that does not immunospecifically bind to OX40). In specific embodiments, an antagonistic antibody described herein, which immunospecifically binds to OX40 (e.g., human OX40), inhibits or reduces cytokine production (e.g., IL-2, TNF-α, IFN-γ, IL-4, IL-10, and/or IL-13) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra, such as Example 2) or known to one of skill in the art, relative to cytokine production in the presence or absence of OX40L (e.g., human OX40L) stimulation without any antibody or with an unrelated antibody (e.g., an antibody that does not immunospecifically bind to OX40).

In certain embodiments, T cells (e.g., $CD4^+$ or $CD8^+$ effector T cells) stimulated with a T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody) in the presence of an antagonistic antibody described herein, which immunospecifically binds to OX40 (e.g., human OX40), have decreased cytokine production (e.g., IL-2, TNF-α, IFN-γ, IL-4, IL-10, and/or IL-13) by at least about 5%, 10%, 15%, 20%, 25%, 30%, 35%, 40%, 45%, 50%, 55%, 60%, 65%, 70%, 75%, 80%, 85%, 90%, 95%, 98%, or 99% relative to T cells only stimulated with the T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody), as assessed by methods described herein or known to one of skill in the art (e.g., an ELISA assay or as described in the Examples, infra). In some embodiments, T cells (e.g., $CD4^+$ or $CD8^+$ effector T cells) stimulated with a T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody) in the presence of an antagonistic antibody described herein, which immunospecifically binds to OX40 (e.g., human OX40), have decreased cytokine production (e.g., IL-2, TNF-α, IFN-γ, IL-4, IL-10, and/or IL-13) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to T cells only stimulated with the T cell mitogen or T cell receptor complex stimulating agent (e.g., phytohaemagglutinin (PHA) and/or phorbol myristate acetate (PMA), or a TCR complex stimulating antibody, such as an anti-CD3 antibody and anti-CD28 antibody), as assessed by methods described herein or known to one of skill in the art (e.g., an ELISA assay or as described in the Examples, infra).

In specific embodiments, an antagonistic antibody described herein, which immunospecifically binds to OX40 (e.g., human OX40), decreases IL-2 production in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra, such as Example 2) or known to one of skill in the art, relative to IL-2 production without any antibody or with an unrelated antibody (e.g., an antibody that does not immunospecifically bind to OX40).

In certain embodiments, T cells (e.g., CD4$^+$ or CD8$^+$ T cells) stimulated with *Staphylococcus* Enterotoxin A (SEA) stimulation in the presence of an antagonistic antibody described herein, which immunospecifically binds to OX40 (e.g., human OX40), have decreased IL-2 production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to T cells only stimulated with SEA, as assessed by methods described herein or known to one of skill in the art (e.g., an ELISA assay or as described in the Examples, infra).

An anti-OX40 antibody can be fused or conjugated (e.g., covalently or noncovalently linked) to a detectable label or substance. Examples of detectable labels or substances include enzyme labels, such as, glucose oxidase; radioisotopes, such as iodine ($^{125}$I, $^{131}$I), carbon ($^{14}$C), sulfur ($^{35}$S), tritium ($^3$H), indium ($^{121}$In), and technetium ($^{99}$Tc); luminescent labels, such as luminol; and fluorescent labels, such as fluorescein and rhodamine, and biotin. Such labeled antibodies can be used to detect OX40 (e.g., human OX40) protein. See, e.g., Section 5.5.2, infra.

5.3 Antibody Production

Antibodies that immunospecifically bind to OX40 (e.g., human OX40) can be produced by any method known in the art for the synthesis of antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo.

In a certain aspect, provided herein is a method of making an antibody which immunospecifically binds to OX40 (e.g., human OX40) comprising culturing a cell or host cell described herein. In a certain aspect, provided herein is a method of making an antibody which immunospecifically binds to OX40 (e.g., human OX40) comprising expressing (e.g., recombinantly expressing) the antibody using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981). The term "monoclonal antibody" as used herein is not limited to antibodies produced through hybridoma technology. For example, monoclonal antibodies can be produced recombinantly from host cells exogenously expressing an antibody described herein.

In specific embodiments, a "monoclonal antibody," as used herein, is an antibody produced by a single cell (e.g., hybridoma or host cell producing a recombinant antibody), wherein the antibody immunospecifically binds to OX40 (e.g., human OX40) as determined, e.g., by ELISA or other antigen-binding or competitive binding assay known in the art or in the Examples provided herein. In particular embodiments, a monoclonal antibody can be a chimeric antibody or a humanized antibody. In certain embodiments, a monoclonal antibody is a monovalent antibody or multivalent (e.g., bivalent) antibody. In certain embodiments, a monoclonal antibody can be a Fab fragment or a F(ab')$_2$ fragment. Monoclonal antibodies described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., OX40 (e.g., human OX40)) used for immunization. Alternatively, lymphocytes may be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986)). Additionally, a RIMMS (repetitive immunization multiple sites) technique can be used to immunize an animal (Kilpatrick K E et al., (1997) Hybridoma 16:381-9, incorporated by reference in its entirety).

In some embodiments, mice (or other animals, such as rats, monkeys, donkeys, pigs, sheep, hamster, or dogs) can be immunized with an antigen (e.g., OX40 (e.g., human OX40)) and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the American Type Culture Collection (ATCC®) (Manassas, Va.), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as NS0 cell line or those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against OX40 (e.g., human OX40). The binding specificity of monoclonal antibodies produced by hybridoma cells is determined by methods known in the art, for example, immunoprecipitation or by an in vitro binding assay, such as radioimmunoassay (MA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of a tetrameric antibody molecule and contains the complete light chain paired with the VH and CH1 domains of the heavy chain. A F(ab')$_2$ fragment contains the two antigen-binding arms of a tetrameric antibody molecule linked by disulfide bonds in the hinge region.

Further, the antibodies described herein can also be generated using various phage display methods known in the art. In phage display methods, proteins are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antibody that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108.

As described in the above references, after phage selection, the antibody coding regions from the phage can be isolated and used to generate whole antibodies, including human antibodies, and expressed in any desired host, including mammalian cells, insect cells, plant cells, yeast, and bacteria, e.g., as described below. Techniques to recombinantly produce antibodies such as Fab, Fab' and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043.

In one aspect, to generate antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including $IgG_1$, $IgG_2$, $IgG_3$ and $IgG_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73. See also U.S. Application Publication No. US 2005/0042664 A1 (Feb. 24, 2005), which is incorporated by reference herein in its entirety.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301.

Further, antibodies that immunospecifically bind to a OX40 antigen can, in turn, be utilized to generate anti-idiotype antibodies that "mimic" an antigen using techniques well known to those skilled in the art. (See, e.g., Greenspan N S & Bona C A (1989) FASEB J 7(5): 437-444; and Nissinoff A (1991) J Immunol 147(8): 2429-2438).

In particular embodiments, an antibody described herein, which binds to the same epitope of OX40 (e.g., human OX40) as an anti-OX40 antibody described herein, is a human antibody. In particular embodiments, an antibody described herein, which competitively blocks (e.g., in a dose-dependent manner) any one of the antibodies described herein, (e.g., pab1949 or pab2044) from binding to OX40 (e.g., human OX40), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., OX40). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin).

Human antibodies which specifically bind to OX40 (e.g., human OX40) can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen (e.g., OX40 (e.g., human OX40)). Such methods are known and are described in the art, see, e.g., Shinmoto H et al., (2004) Cytotechnology 46: 19-23; Naganawa Y et al., (2005) Human Antibodies 14: 27-31.

5.3.1 Polynucleotides

In certain aspects, provided herein are polynucleotides comprising a nucleotide sequence encoding an antibody described herein or a fragment thereof (e.g., a variable light chain region and/or variable heavy chain region) that immunospecifically binds to an OX40 (e.g., human OX40) antigen, and vectors, e.g., vectors comprising such polynucleotides for recombinant expression in host cells (e.g., *E. coli* and mammalian cells). Provided herein are polynucleotides comprising nucleotide sequences encoding any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding antibodies, which immunospecifically bind to an OX40 polypeptide (e.g., human OX40) and comprises an amino acid sequence as described herein, as well as antibodies that compete with such antibodies for binding to an OX40 polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL FRs and CDRs of antibodies described herein (see, e.g., Tables 1 and 3). The polynucleotides can comprise nucleotide sequences encoding a heavy chain comprising the VH FRs and CDRs of antibodies described herein (see, e.g., Tables 2 and 4). In specific embodiments, a polynucleotide described herein encodes a VL domain comprising the amino acid sequence set forth in SEQ ID NO: 15. In specific embodiments, a polynucleotide described herein encodes a VH domain comprising the amino acid sequence set forth in SEQ ID NO: 16.

In particular embodiments, provided herein are polynucleotides comprising a nucleotide sequence encoding an anti-OX40 antibody comprising three VL chain CDRs, e.g., containing VL CDR1, VL CDR2, and VL CDR3 of any one of antibodies described herein (e.g., see Table 1). In specific embodiments, provided herein are polynucleotides comprising a nucleotide sequence encoding an anti-OX40 antibody comprising three VH chain CDRs, e.g., containing VL CDR1, VL CDR2, and VL CDR3 of any one of antibodies described herein (e.g., see Table 1) and three VH chain CDRs, e.g., containing VH CDR1, VH CDR2, and VH CDR3 of any one of antibodies described herein (e.g., see Table 2).

In particular embodiments, provided herein are polynucleotides comprising a nucleotide sequence encoding an anti-OX40 antibody or a fragment thereof comprising a VL domain, e.g., containing FR1-CDR1-FR2-CDR2-FR3-CDR3-FR4, comprising an amino acid sequence described herein (e.g., see Tables 1 and 3, e.g., the VL CDRs and VLFRs of a particular antibody identified by name in the tables). In specific embodiments, provided herein are polynucleotides comprising a nucleotide sequence encoding an anti-OX40 antibody or a fragment thereof comprising a VH domain, e.g., containing FR1-CDR1-FR2-CDR2-FR3-CDR3-FR4, comprising an amino acid sequence described herein (e.g., see Tables 2 and 4, e.g., the VH CDRs and VH FRs of a particular antibody identified by name in the Tables).

In certain embodiments, a polynucleotide described herein comprises a nucleotide sequence encoding an antibody provided herein comprising a light chain variable region comprising an amino acid sequence described herein (e.g., SEQ ID NO: 15), wherein the antibody immunospecifically binds to OX40 (e.g., human OX40). In a certain embodiment, a polynucleotide described herein comprises a nucleotide sequence encoding antibody pab1949 or pab2044 provided herein or a fragment thereof comprising a light chain variable region comprising an amino acid sequence described herein (e.g., SEQ ID NO: 15).

In certain embodiments, a polynucleotide described herein comprises a nucleotide sequence encoding an antibody provided herein comprising a heavy chain variable region comprising an amino acid sequence described herein (e.g., SEQ ID NO: 16), wherein the antibody immunospecifically binds to OX40 (e.g., human OX40). In a certain embodiment, a polynucleotide described herein comprises a nucleotide sequence encoding antibody pab1949 or pab2044 provided herein or a fragment thereof comprising a heavy chain variable region comprising an amino acid sequence described herein (e.g., SEQ ID NO: 16).

In certain aspects, a polynucleotide comprises a nucleotide sequence encoding an antibody or fragment thereof described herein comprising a VL domain comprising one or more VL FRs having the amino acid sequence described herein (e.g., see Table 3), wherein the antibody immunospecifically binds to OX40 (e.g., human OX40). In certain aspects, a polynucleotide comprises a nucleotide sequence encoding an antibody or fragment thereof described herein comprising a VH domain comprising one or more VH FRs having the amino acid sequence described herein (e.g., see Table 4), wherein the antibody immunospecifically binds to OX40 (e.g., human OX40).

In specific embodiments, a polynucleotide provided herein comprises a nucleotide sequence encoding an antibody or fragment thereof described herein comprising: framework regions (e.g., framework regions of the VL domain and VH domain) that are human framework regions, wherein the antibody immunospecifically binds OX40 (e.g., human OX40). In certain embodiments, a polynucleotide provided herein comprises a nucleotide sequence encoding an antibody or fragment thereof (e.g., CDRs or variable domain) described in Section 5.2 above.

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding an antibody described herein comprising a human kappa light chain or a human lambda light chain. In a particular embodiment, a polynucleotide provided herein comprises a nucleotide sequence encoding an antibody, which immunospecifically binds to OX40 (e.g., human OX40), wherein the antibody comprises a light chain, and wherein the amino acid sequence of the VL domain can comprise the amino acid sequence set forth in SEQ ID NO: 15 and wherein the constant region of the light chain comprises the amino acid sequence of a human kappa light chain constant region. In another particular embodiment, a polynucleotide provided herein comprises a nucleotide sequence encoding an antibody, which immunospecifically binds to OX40 (e.g., human OX40), and comprises a light chain, wherein the amino acid sequence of the VL domain can comprise the amino acid sequence set forth in SEQ ID NO: 15, and wherein the constant region of the light chain comprises the amino acid sequence of a human lambda light chain constant region. For example, human constant region sequences can be those described in U.S. Pat. No. 5,693,780.

In a particular embodiment, a polynucleotide provided herein comprises a nucleotide sequence encoding an antibody described herein, which immunospecifically binds to OX40 (e.g., human OX40), wherein the antibody comprises a heavy chain, wherein the amino acid sequence of the VH domain can comprise the amino acid sequence set forth in SEQ ID NO: 16, and wherein the constant region of the heavy chain comprises the amino acid sequence of a human gamma (γ) heavy chain constant region.

In a certain embodiment, a polynucleotide provided herein comprises a nucleotide sequence(s) encoding a VH domain and/or a VL domain of an antibody described herein (e.g., pa91949 or pab2044 such as SEQ ID NO: 16 for the VH domain or SEQ ID NO: 15 for the VL domain), which immunospecifically binds to OX40 (e.g., human OX40).

In yet another specific embodiment, a polynucleotide provided herein comprises a nucleotide sequence encoding an antibody described herein, which immunospecifically binds OX40 (e.g., human OX40), wherein the antibody comprises a VL domain and a VH domain comprising any amino acid sequences described herein, and wherein the constant regions comprise the amino acid sequences of the constant regions of a human IgG$_1$ (e.g., allotype 1, 17, or 3), human IgG$_2$, or human IgG$_4$.

In a specific embodiment, provided herein are polynucleotides comprising a nucleotide sequence encoding an anti-OX40 antibody or domain thereof, designated herein, see, e.g., Tables 1-4, for example antibody pab1949 or pab2044.

Also provided herein are polynucleotides encoding an anti-OX40 antibody or a fragment thereof that are optimized, e.g., by codon/RNA optimization, replacement with heterologous signal sequences, and elimination of mRNA instability elements. Methods to generate optimized nucleic acids encoding an anti-OX40 antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid.

In certain embodiments, an optimized polynucleotide sequence encoding an anti-OX40 antibody described herein or a fragment thereof (e.g., VL domain or VH domain) can hybridize to an antisense (e.g., complementary) polynucleotide of an unoptimized polynucleotide sequence encoding an anti-OX40 antibody described herein or a fragment thereof (e.g., VL domain or VH domain). In specific embodiments, an optimized nucleotide sequence encoding an anti-OX40 antibody described herein or a fragment hybridizes under high stringency conditions to antisense polynucleotide of an unoptimized polynucleotide sequence encoding an anti-OX40 antibody described herein or a fragment thereof. In a specific embodiment, an optimized nucleotide sequence encoding an anti-OX40 antibody described herein or a fragment thereof hybridizes under high stringency, intermediate or lower stringency hybridization conditions to an antisense polynucleotide of an unoptimized nucleotide sequence encoding an anti-OX40 antibody described herein or a fragment thereof. Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies described herein, e.g., antibodies described in Tables 1-4, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-246), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody or fragment thereof described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody or fragment thereof is not available, but the sequence of the antibody molecule or fragment thereof is known, a nucleic acid encoding the immunoglobulin or fragment can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-OX40 antibodies described herein can be readily isolated and sequenced using conventional procedures (e.g., by using oligonucleotide probes that are capable of binding specifically to genes encoding the heavy and light chains of the anti-OX40 antibodies). Hybridoma cells can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-OX40 antibodies in the recombinant host cells.

To generate antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable domain, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain (e.g., SEQ ID NO: 16) and/or VL domain (e.g., SEQ ID NO: 15) provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3.

5.3.2 Cells and Vectors

In certain aspects, provided herein are cells (e.g., host cells) expressing (e.g., recombinantly) antibodies described herein which specifically bind to OX40 (e.g., human OX40) and related polynucleotides and expression vectors. Provided herein are vectors (e.g., expression vectors) comprising polynucleotides comprising nucleotide sequences encoding anti-OX40 antibodies or a fragment for recombinant expression in host cells, preferably in mammalian cells. Also provided herein are host cells comprising such vectors for recombinantly expressing anti-OX40 antibodies described herein (e.g., human or humanized antibody). In a particular aspect, provided herein are methods for producing an antibody described herein, comprising expressing such antibody in a host cell.

Recombinant expression of an antibody or fragment thereof described herein (e.g., a heavy or light chain of an antibody described herein) that specifically binds to OX40 (e.g., human OX40) involves construction of an expression vector containing a polynucleotide that encodes the antibody or fragment. Once a polynucleotide encoding an antibody or fragment thereof (e.g., heavy or light chain variable domains) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122, 464) and variable domains of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein (e.g., an antibody comprising the CDRs of pab1949 or pab2044) or a fragment thereof. Thus, provided herein are host cells containing a polynucleotide encoding an antibody described herein (e.g., an antibody comprising the CDRs of pab1949 or pab2044) or fragments thereof (e.g., a heavy or light chain thereof, or fragment thereof), operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein (e.g., an antibody comprising the CDRs of pab1949 or pab2044), or a fragment thereof. In specific embodiments, a host cell contains two different vectors, a first vector comprising a polynucleotide encoding a heavy chain or a heavy chain variable region of an antibody described herein (e.g., an antibody comprising the CDRs of pab1949 or pab2044), or a fragment thereof, and a second vector comprising a polynucleotide encoding a light chain or a light chain variable region of an antibody described herein (e.g., an antibody comprising the CDRs of pab1949 or pab2044), or a fragment thereof. In other embodiments, a first host cell comprises a first vector comprising a polynucleotide encoding a heavy chain or a heavy chain variable region of an antibody described herein (e.g., an antibody comprising the CDRs of pab1949 or pab2044), or a fragment thereof, and a second host cell comprises a second vector comprising a polynucleotide encoding a light chain or a light chain variable region of an antibody described herein (e.g., an antibody comprising the CDRs of pab1949 or pab2044). In specific embodiments, a heavy chain/heavy chain variable region expressed by a first cell associated with a light chain/light chain variable region of a second cell to form an anti-OX40 antibody described herein (e.g., antibody comprising the CDRs pab1949 or pab2044). In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-OX40 antibody described herein (e.g., antibody comprising the CDRs of pab1949 or pab2044), and a second vector comprising a polynucleotide encoding a heavy chain/heavy chain variable region of an anti-OX40 antibody described herein (e.g., antibody comprising the CDRs of pab1949 or pab2044).

A variety of host-expression vector systems can be utilized to express antibody molecules described herein (e.g., an antibody comprising the CDRs of pab1949 or pab2044) (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein (e.g., an antibody comprising the CDRs of any one of antibodies pab1949 or pab2044) are CHO cells, for example CHO cells from the CHO GS System™ (Lonza). In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking M K & Hofstetter H (1986) Gene 45: 101-105; and Cockett M I et al., (1990) Biotechnology 8: 662-667). In certain embodiments, antibodies described herein are produced by CHO cells or NS0 cells. In a specific embodiment, the expression of nucleotide sequences encoding antibodies described herein which immunospecifically bind OX40 (e.g., human OX40) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan J & Shenk T (1984) PNAS 81: 3655-3659). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol 153: 516-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-OX40 antibodies described herein (e.g., an antibody comprising the CDRs of pab1949 or pab2044) are produced in mammalian cells, such as CHO cells.

In a specific embodiment, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express an anti-OX40 antibody described herein (e.g., an antibody comprising the CDRs of pab1949 or pab2044) can be engineered. In specific embodiments, a cell provided herein stably expresses a light chain/ light chain variable domain and a heavy chain/heavy chain variable domain which associate to form an antibody described herein (e.g., an antibody comprising the CDRs of pab1949 or pab2044).

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-OX40 antibody described herein or a fragment thereof. Such engineered cell lines can be particularly useful in screening and evaluation of compositions that interact directly or indirectly with the antibody molecule.

A number of selection systems can be used, including but not limited to, the herpes simplex virus thymidine kinase (Wigler M et al., (1977) Cell 11(1): 223-232), hypoxanthineguanine phosphoribosyltransferase (Szybalska E H & Szybalski W (1962) PNAS 48(12): 2026-2034) and adenine phosphoribosyltransferase (Lowy I et al., (1980) Cell 22(3): 817-823) genes can be employed in tk-, hgprt- or aprt-cells, respectively. Also, antimetabolite resistance can be used as the basis of selection for the following genes: dhfr, which confers resistance to methotrexate (Wigler M et al., (1980) PNAS 77(6): 3567-3570; O'Hare K et al., (1981) PNAS 78: 1527-1531); gpt, which confers resistance to mycophenolic acid (Mulligan R C & Berg P (1981) PNAS 78(4): 2072-2076); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-215); and hygro, which confers resistance to hygromycin (Santerre R F et al., (1984) Gene 30(1-3): 147-156). Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbère-Garapin F et al., (1981) J Mol Biol 150: 1-14, which are incorporated by reference herein in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N.J. (1986) Nature 322: 562-565; and Köhler G (1980) PNAS 77: 2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody. When the antibody or fragment is recombinantly produced, it is also generally substantially free of culture medium, i.e., culture medium represents less than about 20%, 10%, 2%, 1%, 0.5%, or 0.1% of the volume of the protein preparation. When the antibody or fragment is produced by chemical synthesis, it is generally substantially free of chemical precursors or other chemicals, i.e., it is separated from chemical precursors or other chemicals which are involved in the synthesis of the protein. Accordingly, such preparations of the antibody or fragment have less than about 30%, 20%, 10%, or 5% (by dry weight) of chemical precursors or compounds other than the antibody or fragment of interest. In a specific embodiment, antibodies described herein are isolated or purified.

5.4 Pharmaceutical Compositions

Provided herein are compositions comprising an antibody described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed.

Pharmaceutical compositions described herein can be useful in enhancing, inducing, or activating an OX40 activity and treating a condition, such as cancer or an infectious disease. Examples of cancer that can be treated in accordance with the methods described herein include, but are not limited to, B cell lymphomas (e.g., B cell chronic lymphocytic leukemia, B cell non-Hodgkin lymphoma, cutaneous B cell lymphoma, diffuse large B cell lymphoma), basal cell carcinoma, bladder cancer, blastoma, brain metastasis, breast cancer, Burkitt lymphoma, carcinoma (e.g., adenocarcinoma (e.g., of the gastroesophageal junction)), cervical cancer, colon cancer, colorectal cancer (colon cancer and rectal cancer), endometrial carcinoma, esophageal cancer, Ewing sarcoma, follicular lymphoma, gastric cancer, gastroesophageal junction carcinoma, gastrointestinal cancer, glioblastoma (e.g., glioblastoma multiforme, e.g., newly diagnosed or recurrent), glioma, head and neck cancer (e.g., head and neck squamous cell carcinoma), hepatic metastasis, Hodgkin's and non-Hodgkin's lymphoma, kidney cancer (e.g., renal cell carcinoma and Wilms' tumors), laryngeal cancer, leukemia (e.g., chronic myelocytic leukemia, hairy cell leukemia), liver cancer (e.g., hepatic carcinoma and hepatoma), lung cancer (e.g., non-small cell lung cancer and small-cell lung cancer), lymphblastic lymphoma, lymphoma, mantle cell lymphoma, metastatic brain tumor, metastatic cancer, myeloma (e.g., multiple myeloma), neuroblastoma, ocular melanoma, oropharyngeal cancer, osteosarcoma, ovarian cancer, pancreatic cancer (e.g., pancreatis ductal adenocarcinoma), prostate cancer (e.g., hormone refractory (e.g., castration resistant), metastatic, metastatic hormone refractory (e.g., castration resistant, androgen independent)), renal cell carcinoma (e.g., metastatic), salivary gland carcinoma, sarcoma (e.g., rhabdomyosarcoma), skin cancer (e.g., melanoma (e.g., metastatic melanoma)), soft tissue sarcoma, solid tumor, squamous cell carcinoma, synovia sarcoma, testicular cancer, thyroid cancer, transitional cell cancer (urothelial cell cancer), uveal melanoma (e.g., metastatic), verrucous carcinoma, vulval cancer, and Waldenstrom macroglobulinemia. In one embodiment, examples of cancer that can be treated in accordance with the methods described herein include, but are not limited to, advanced, recurrent, or metastatic solid tumor, lymphoma (e.g., diffuse large B-cell lymphoma or burkitt's lymphoma), breast cancer, prostate cancer, head & neck cancer, colorectal cancer, colon cancer, melanoma (e.g., metastatic melanoma), endometrial cancer, renal cell carcinoma, renal clear cell carcinoma, lung cancer (e.g., non-small cell lung cancer or lung adenocarcinoma), ovarian cancer, gastric cancer, bladder cancer, stomach cancer, uterine cancer, pheochromocytoma, metastatic cutaneous squamous cell carcinoma (e.g., in transplantation patients), merkel cell carcinoma, cutaneous T-cell lymphoma, neuro-endocrine tumor, tumor of bone origin (e.g., osteosarcoma), hemangiopericytoma, tumor related to genetic syndromes (NF1 or VHL), chordoma, ependymoma, medulloblastoma, germinoma, tumor of small intestine, appendiceal cancer, and viral related tumor (e.g., Kaposi's sarcoma). The pharmaceutical compositions described herein are in one embodiment for use as a medicament or diagnostic. The pharmaceutical compositions that comprise an agonistic antibody described herein are in one embodiment for use in a method for the treatment of cancer.

Pharmaceutical compositions described herein that comprise an antagonistic antibody described herein can be useful in reducing, inhibiting, or deactivating an OX40 activity and treating a condition, such as an inflammatory or autoimmune disease or disorder or an infectious disease. The pharmaceutical compositions that comprise an antagonistic antibody described herein are in one embodiment for use in a method for the treatment of an inflammatory or autoimmune disease or disorder or an infectious disease.

Pharmaceutical compositions described herein that comprise an antagonistic antibody described herein can be useful in reducing, deactivating, or inhibiting an OX40 activity and treating a condition selected from the group consisting of infections (viral, bacterial, fungal and parasitic), endotoxic shock associated with infection, arthritis, rheumatoid arthritis, asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, arthritis, meningoencephalitis, uveitis, autoimmune uveitis, immune mediated inflammatory disorders of the central and peripheral nervous system such as multiple sclerosis, lupus (such as systemic lupus erythematosus) and Guillain-Barr syndrome, dermatitis, atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, pancreatitis, trauma (surgery), graft-versus-host disease, transplant rejection, heart disease (i.e., cardiovascular disease) including ischaemic diseases such as myocardial infarction as well as atherosclerosis, intravascular coagulation, bone resorption, osteoporosis, osteoarthritis, periodontitis, hypochlorhydia, neuromyelitis optica, celiac disease, connective tissue disorder (e.g., lupus), post infectious inflammatory disorder (e.g., Guillain-Barre syndrome), and paraneoplastic syndromes.

The compositions to be used for in vivo administration can be sterile. This is readily accomplished by filtration through, e.g., sterile filtration membranes.

5.5 Uses and Methods 5.5.1 Therapeutic Uses and Methods

In one aspect, presented herein are methods for modulating one or more immune functions or responses in a subject, comprising to a subject in need thereof administering an anti-OX40 antibody described herein, or a composition thereof. In a specific aspect, presented herein are methods for activating, enhancing or inducing one or more immune functions or responses in a subject, comprising to a subject in need thereof administering an anti-OX40 antibody or a composition thereof. In a specific embodiment, presented herein are methods for preventing and/or treating diseases in which it is desirable to activate or enhance one or more immune functions or responses, comprising administering to a subject in need thereof an anti-OX40 antibody described herein or a composition thereof. In a certain embodiment, presented herein are methods of treating an infectious disease comprising administering to a subject in need thereof an anti-OX40 antibody or a composition thereof. In a certain embodiment, presented herein are methods of treating cancer comprising administering to a subject in need thereof an anti-OX40 antibody or a composition thereof. The cancer can be selected from a group consisting of melanoma, renal cancer, and prostate cancer. The cancer can be selected from a group consisting of melanoma, renal cancer, prostate cancer, colon cancer, and lung cancer. In a certain embodiment, presented herein are methods of treating melanoma comprising administering to a subject in need thereof an anti-OX40 antibody or a composition thereof. In a certain embodiment, presented herein are methods of treating renal cancer comprising administering to a subject in need thereof an anti-OX40 antibody or a composition thereof. In a certain embodiment, presented herein are methods of treating prostate cancer comprising administering to a subject in need thereof an anti-OX40 antibody or a composition thereof. In certain embodiments, presented herein are methods of treating colon cancer comprising administering to a subject in need thereof an anti-OX40 antibody or a composition thereof. In certain embodiments, presented herein are methods of treating lung cancer comprising administering to a subject in need thereof an anti-OX40 antibody or a composition thereof. In certain embodiments, presented herein are methods of treating non-small cell lung cancer (NSCLC) comprising administering to a subject in need thereof an anti-OX40 antibody or a composition thereof. In one instance, the method further comprises administering to the subject a checkpoint targeting agent. In one instance, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-GITR antibody, an agonist anti-CD137 antibody, and an agonist anti-OX40 antibody. In certain embodiments, the checkpoint targeting agent is an antagonist anti-PD-1 antibody. In certain embodiments, the checkpoint targeting agent is an antagonist anti-PD-L1 antibody. In certain embodiments, the checkpoint targeting agent is an agonist anti-GITR antibody. In certain embodiments, the checkpoint targeting agent is an agonist anti-CD137 antibody.

In certain embodiments, an anti-PD-1 antibody is used in methods disclosed herein. In certain embodiments, the anti-PD-1 antibody is Nivolumab, also known as BMS-936558 or MDX1106, developed by Bristol-Myers Squibb. In certain embodiments, the anti-PD-1 antibody is Pembrolizumab, also known as Lambrolizumab or MK-3475, developed by Merck & Co. In certain embodiments, the anti-PD-1 antibody is Pidilizumab, also known as CT-011, developed by CureTech. In certain embodiments, the anti-PD-1 antibody is MEDI0680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods disclosed herein are disclosed in the following patents and patent applications, which are incorporated herein by reference in their entireties for all purposes: U.S. Pat. Nos. 6,808,710; 7,332,582; 7,488, 802; 8,008,449; 8,114,845; 8,168,757; 8,354,509; 8,686, 119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, an anti-PD-L1 antibody is used in methods disclosed herein. In certain embodiments, the anti-PD-L1 antibody is atezolizumab developed by Genentech. In certain embodiments, the anti-PD-L1 antibody is durvalumab developed by AstraZeneca, Celgene and Medimmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods disclosed herein are disclosed in the following patents and patent applications, which are incorporated herein by reference in their entireties for all purposes: U.S. Pat. Nos. 7,943,743; 8,168,179; 8,217,149; 8,552,154; 8,779,108; 8,981,063; 9,175,082; U.S. Publication No. US 2010/0203056 A1; U.S. Publication No. US 2003/0232323 A1; U.S. Publication No. US 2013/0323249 A1; U.S. Publication No. US 2014/0341917 A1; U.S. Publication No. US 2014/0044738 A1; U.S. Publication No. US 2015/0203580 A1; U.S. Publication No. US 2015/0225483 A1; U.S. Publication No. US 2015/0346208 A1; U.S. Publication No. US 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In a certain embodiment, presented herein are methods of treating a cancer selected from the group consisting of: B cell lymphomas (e.g., B cell chronic lymphocytic leukemia, B cell non-Hodgkin lymphoma, cutaneous B cell lymphoma, diffuse large B cell lymphoma), basal cell carcinoma, bladder cancer, blastoma, brain metastasis, breast cancer, Burkitt lymphoma, carcinoma (e.g., adenocarcinoma (e.g., of the gastroesophageal junction)), cervical cancer, colon cancer, colorectal cancer (colon cancer and rectal cancer), endometrial carcinoma, esophageal cancer, Ewing sarcoma, follicular lymphoma, gastric cancer, gastroesophageal junction carcinoma, gastrointestinal cancer, glioblastoma (e.g., glioblastoma multiforme, e.g., newly diagnosed or recurrent), glioma, head and neck cancer (e.g., head and neck squamous cell carcinoma), hepatic metastasis, Hodgkin's and non-Hodgkin's lymphoma, kidney cancer (e.g., renal cell carcinoma and Wilms' tumors), laryngeal cancer, leukemia (e.g., chronic myelocytic leukemia, hairy cell leukemia), liver cancer (e.g., hepatic carcinoma and hepatoma), lung cancer (e.g., non-small cell lung cancer and small-cell lung cancer), lymphblastic lymphoma, lymphoma, mantle cell lymphoma, metastatic brain tumor, metastatic cancer, myeloma (e.g., multiple myeloma), neuroblastoma, ocular melanoma, oropharyngeal cancer, osteosarcoma, ovarian cancer, pancreatic cancer (e.g., pancreatis ductal adenocarcinoma), prostate cancer (e.g., hormone refractory (e.g., castration resistant), metastatic, metastatic hormone refractory (e.g., castration resistant, androgen independent)), renal cell carcinoma (e.g., metastatic), salivary gland carcinoma, sarcoma (e.g., rhabdomyosarcoma), skin cancer (e.g., melanoma (e.g., metastatic melanoma)), soft tissue sarcoma, solid tumor, squamous cell carcinoma, synovia sarcoma, testicular cancer, thyroid cancer, transitional cell cancer (urothelial cell cancer), uveal melanoma (e.g., metastatic), verrucous carcinoma, vulval cancer, and Waldenstrom macroglobulinemia. In a certain embodiment, presented herein are methods of treating a cancer selected from the group consisting of: advanced, recurrent, or metastatic solid tumor, lymphoma (e.g., diffuse large B-cell lymphoma or burkitt's lymphoma), breast cancer, prostate cancer, head & neck cancer, colorectal cancer, colon cancer, melanoma (e.g., metastatic melanoma), endometrial cancer, renal cell carcinoma, renal clear cell carcinoma, lung cancer (e.g., non-small cell lung cancer or lung adenocarcinoma), ovarian cancer, gastric cancer, bladder cancer, stomach cancer, uterine cancer, pheochromocytoma, metastatic cutaneous squamous cell carcinoma (e.g., in transplantation patients), merkel cell carcinoma, cutaneous T-cell lymphoma, neuro-endocrine tumor, tumor of bone origin (e.g., osteosarcoma), hemangiopericytoma, tumor related to genetic syndromes (NF1 or VHL), chordoma, ependymoma, medulloblastoma, germinoma, tumor of small intestine, appendiceal cancer, and viral related tumor (e.g., Kaposi's sarcoma).

In another embodiment, an anti-OX40 antibody is administered to a patient diagnosed with cancer to increase the proliferation and/or effector function of one or more immune cell populations (e.g., T cell effector cells, such as $CD4^+$ and $CD8^+$ T cells) in the patient.

In a specific embodiment, an anti-OX40 antibody described herein activates or enhances or induces one or more immune functions or responses in a subject by at least 99%, at least 98%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative to the immune function in a subject not administered the anti-OX40 antibody described herein using assays well known in the art, e.g., ELISPOT, ELISA, and cell proliferation assays. In a specific embodiment, the immune function is cytokine production (e.g., IL-2, TNF-α, IFN-γ, IL-4, IL-10, and/or IL-13 production). In another embodiment, the immune function is T cell proliferation/expansion, which can be assayed, e.g., by flow cytometry to detect the number of cells expressing markers of T cells (e.g., CD3, CD4, or CD8). In another embodiment, the immune function is antibody production, which can be assayed, e.g., by ELISA. In some embodiments, the immune function is effector function, which can be assayed, e.g., by a cytotoxicity assay or other assays well known in the art. In another embodiment, the immune function is a Th1 response. In another embodiment, the immune function is a Th2 response. In another embodiment, the immune function is a memory response.

In specific embodiments, non-limiting examples of immune functions that can be enhanced or induced by an anti-OX40 antibody are proliferation/expansion of effector lymphocytes (e.g., increase in the number of effector T lymphocytes), and inhibition of apoptosis of effector lymphocytes (e.g., effector T lymphocytes). In particular embodiments, an immune function enhanced or induced by an anti-OX40 antibody described herein is proliferation/expansion in the number of or activation of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, tumor-resident T cells, CD122$^+$ T cells, natural killer (NK) cells), macrophages, monocytes, dendritic cells, mast cells, eosinophils, basophils or polymorphonucleated leukocytes. In one embodiment, an anti-OX40 antibody described herein activates or enhances the proliferation/expansion or number of lymphocyte progenitors. In some embodiments, an anti-OX40 antibody described herein increases the number of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, tumor-resident T cells, CD122$^+$ T cells, natural killer cells (NK cells), macrophages, monocytes, dendritic cells, mast cells, eosinophils, basophils or polymorphonucleated leukocytes by approximately at least 99%, at least 98%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative a negative control (e.g., number of the respective cells not treated, cultured, or contacted with an anti-OX40 antibody described herein).

In some embodiments, an anti-OX40 antibody described herein is administered to a subject in combination with a compound that targets an immunomodulatory enzyme(s) such as IDO (indoleamine-(2,3)-dioxygenase) and TDO (tryptophan 2,3-dioxygenase). In particular embodiments, such compound is selected from the group consisting of epacadostat (Incyte Corp), F001287 (Flexus Biosciences), indoximod (NewLink Genetics), and NLG919 (NewLink Genetics). In one embodiment, the compound is epacadostat. In another embodiment, the compound is F001287. In another embodiment, the compound is indoximod. In another embodiment, the compound is NLG919.

In some embodiments, an anti-OX40 antibody described herein is administered to a subject in combination with a vaccine.

In some embodiments, an anti-OX40 antibody described herein is administered to a subject in combination with an anti-CD137 antibody, rituximab, cyclophosphamide, chemotherapy, or radiation therapy.

In some embodiments, an anti-OX40 antibody described herein is administered to a subject in combination with a heat shock protein based tumor vaccine or a heat shock protein based pathogen vaccine. In a specific embodiment, an anti-OX40 antibody is administered to a subject in combination with a heat shock protein based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind WIC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes and Th1 and Th-2-mediated immune responses. In some embodiments, HSPPCs used in methods disclosed herein comprise one or more heat shock proteins from the hsp60, hsp70, or hsp90 family of stress proteins complexed with antigenic peptides. In some embodiments, HSPPCs comprise hsc70, hsp70, hsp90, hsp110, grp170, gp96, calreticulin, or combinations of two or more thereof.

In a specific embodiment, an anti-OX40 antibody is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In some embodiments, this fingerprint contains unique antigens that are present only in that particular subject's specific cancer cells and injection of the vaccine is intended to stimulate the subject's immune system to recognize and attack any cells with the specific cancer fingerprint.

In some embodiments, the HSPPC, e.g., HSPPC-96, is produced from the tumor tissue of a subject. In a specific embodiment, the HSPPC (e.g., HSPPC-96) is produced from tumor of the type of cancer or metastatis thereof being treated. In another specific embodiment, the HSPPC (e.g., HSPPC-96) is autologous to the subject being treated. In some embodiments, the tumor tissue is non-necrotic tumor tissue. In some embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In some embodiments, after surgical resection, non-necrotic tumor tissue is frozen prior to use in vaccine preparation. In some embodiments, the HSPPC, e.g., HSPPC-96, is isolated from the tumor tissue by purification techniques, filtered and prepared for an injectable vaccine. In some embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, which are incorporated herein by reference in their entireties for all purposes, U.S. Pat. Nos. 6,391,306, 6,383,492, 6,403,095, 6,410,026, 6,436,404, 6,447,780, 6,447,781 and 6,610,659.

In some embodiment, the present invention relates to an antibody or pharmaceutical composition of the present invention for use as a medicament. In some aspects, the present invention relates to an antibody or pharmaceutical composition of the present invention, for use in a method for the treatment of cancer. In some aspects, the present invention relates to an antibody or pharmaceutical composition of the present invention, for use in a method for the treatment of cancer in a subject, comprising administering to the subject an effective amount of an antibody or pharmaceutical composition of the invention. In some aspects, the present invention relates to (a) an antibody or pharmaceutical composition of the present invention and (b) a checkpoint targeting agent, for use as a medicament. In some aspects, the present invention relates to (a) an antibody or pharmaceutical composition of the present invention and (b) a checkpoint targeting agent, for use in a method for the treatment of cancer. In some aspects, the present invention relates to a composition, kit or kit-of-parts comprising (a) an antibody or pharmaceutical composition of the present invention and (b) a checkpoint targeting agent. In one aspect, the present invention relates to (a) an antibody or pharmaceutical composition of the present invention and (b) an IDO inhibitor, for use as a medicament. In some aspects, the present invention relates to (a) an antibody or pharmaceutical composition of the present invention and (b) an IDO inhibitor, for use in a method for the treatment of cancer. In some aspects, the present invention relates to a composition, kit or kit-of-parts comprising (a) an antibody or pharmaceutical composition of the present invention and (b) an IDO inhibitor. In some aspects, the present invention relates to (a) an antibody or pharmaceutical composition of the present invention and (b) a vaccine, for use as a medicament. In some aspects, the present invention relates to (a) an antibody or pharmaceutical composition of the present invention and (b) a vaccine, for use in a method for the treatment of cancer. In some aspects, the present invention relates to a composition, kit or kit-of-parts comprising (a) an antibody or pharmaceutical composition of the present invention and (b) a vaccine. In a preferred embodiment of an antibody or pharmaceutical composition for use in a method for the treatment of cancer, the antibody is agonistic.

In one aspect, the methods for modulating one or more immune functions or responses in a subject as presented herein are methods for deactivating, reducing, or inhibiting one or more immune functions or responses in a subject, comprising to a subject in need thereof administering an anti-OX40 antagonistic antibody or a composition thereof. In a specific embodiment, presented herein are methods for preventing and/or treating diseases in which it is desirable to deactivate, reduce, or inhibit one or more immune functions or responses, comprising administering to a subject in need thereof an anti-OX40 antagonistic antibody described herein or a composition thereof. In a certain embodiment, presented herein are methods of treating an autoimmune or inflammatory disease or disorder comprising administering to a subject in need thereof an effective amount of an anti-OX40 antagonistic antibody or a composition thereof. In certain embodiments, the subject is a human. In certain embodiments, the disease or disorder is selected from the group consisting of: infections (viral, bacterial, fungal and parasitic), endotoxic shock associated with infection, arthritis, rheumatoid arthritis, asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, arthritis, meningoencephalitis, uveitis, autoimmune uveitis, immune mediated inflammatory disorders of the central and peripheral nervous system such as multiple sclerosis, lupus (such as systemic lupus erythematosus) and Guillain-Barr syndrome, dermatitis, atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, pancreatitis, trauma (surgery), graft-versus-host disease, transplant rejection, heart disease (i.e., cardiovascular disease) including ischaemic diseases such as myocardial infarction as well as atherosclerosis, intravascular coagulation, bone resorption, osteoporosis, osteoarthritis, periodontitis, hypochlorhydia, neuromyelitis optica, celiac disease, connective tissue disorders (e.g., lupus), post infectious inflammatory disorders (e.g., Guillain-Barre syndrome), and paraneoplastic syndromes. In certain embodiments, the disease or disorder is selected from the group consisting of: transplant rejection, vasculitis, asthma, rheumatoid arthritis, dermatitis, inflammatory bowel disease, uveitis, and lupus. In certain embodiments, any of the methods herein (e.g., methods of treating an infectious disease, or methods of treating an autoimmune or inflammatory disease or disorder) comprise administration to a subject of an antibody as described herein and a checkpoint targeting agent. In certain embodiments, the checkpoint targeting agent is an antibody (e.g., an anti-PD-1 antibody, an anti-PD-L1 antibody, an anti-PD-L2 antibody, an anti-CTLA-4 antibody, an anti-TIM-3 antibody, an anti-LAG-3 antibody, an anti-CEACAM1 antibody, an anti-GITR antibody, an anti-CD137 antibody, or an anti-OX40 antibody). In certain embodiments, the checkpoint targeting agent is an antagonist or agonist antibody. In certain embodiments, the checkpoint targeting agent is an anti-PD-1 antibody. In certain embodiments, the checkpoint targeting agent is an anti-GITR antibody. In certain embodiments, the checkpoint targeting agent is an anti-CD137 antibody.

In another embodiment, an anti-OX40 antagonistic antibody is administered to a patient diagnosed with an autoimmune or inflammatory disease or disorder to decrease the proliferation and/or effector function of one or more immune cell populations (e.g., T cell effector cells, such as $CD4^+$ and $CD8^+$ T cells) in the patient.

In a specific embodiment, an anti-OX40 antagonistic antibody described herein deactivates or reduces or inhibits one or more immune functions or responses in a subject by at least 99%, at least 98%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative to the immune function in a subject not administered the anti-OX40 antagonistic antibody described herein using assays well known in the art, e.g., ELISPOT, ELISA, and cell proliferation assays. In a specific embodiment, the immune function is cytokine production (e.g., IL-2, TNF-α, IFN-γ, IL-4, IL-10, and/or IL-13 production). In another embodiment, the immune function is T cell proliferation/expansion, which can be assayed, e.g., by flow cytometry to detect the number of cells expressing markers of T cells (e.g., CD3, CD4, or CD8). In another embodiment, the immune function is antibody production, which can be assayed, e.g., by ELISA. In some embodiments, the immune function is effector function, which can be assayed, e.g., by a cytotoxicity assay or other assays well known in the art. In another embodiment, the immune function is a Th1 response. In another embodiment, the immune function is a Th2 response. In another embodiment, the immune function is a memory response.

In specific embodiments, non-limiting examples of immune functions that can be reduced or inhibited by an anti-OX40 antagonistic antibody are proliferation/expansion of effector lymphocytes (e.g., decrease in the number of effector T lymphocytes), and stimulation of apoptosis of effector lymphocytes (e.g., effector T lymphocytes). In particular embodiments, an immune function reduced or inhibited by an anti-OX40 antagonistic antibody described herein is proliferation/expansion in the number of or activation of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, tumor-resident T cells, CD122$^+$ T cells, natural killer (NK) cells), macrophages, monocytes, dendritic cells, mast cells, eosinophils, basophils or polymorphonucleated leukocytes. In one embodiment, an anti-OX40 antagonistic antibody described herein deactivates or reduces or inhibits the proliferation/expansion or number of lymphocyte progenitors. In some embodiments, an anti-OX40 antagonistic antibody described herein decreases the number of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, tumor-resident T cells, CD122$^+$ T cells, natural killer cells (NK cells), macrophages, monocytes, dendritic cells, mast cells, eosinophils, basophils or polymorphonucleated leukocytes by approximately at least 99%, at least 98%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative a negative control (e.g., number of the respective cells not treated, cultured, or contacted with an anti-OX40 antagonistic antibody described herein).

In some aspects, the present invention relates to an antibody or pharmaceutical composition of the present invention, for use in a method for the treatment of an autoimmune or inflammatory disease or disorder. In one aspect, the present invention relates to an antibody or pharmaceutical composition of the present invention, for use in a method for the treatment of an infectious disease. In a preferred embodiment of an antibody or pharmaceutical composition for use in a method for the treatment of an autoimmune or inflammatory disease or disorder, or of an infectious disease, the antibody is antagonistic.

5.5.1.1 Routes of Administration & Dosage

An antibody or composition described herein can be delivered to a subject by a variety of routes, such as parenteral, subcutaneous, intravenous, intradermal, transdermal, intranasal, intratumoral, and administration to a tumor draining lymph node. In one embodiment, the antibody or composition is administered by an intravenous or intratumoral route.

The amount of an antibody or composition which will be effective in the treatment and/or prevention of a condition will depend on the nature of the disease, and can be determined by standard clinical techniques.

The precise dose to be employed in a composition will also depend on the route of administration, and the seriousness of the disease, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

Generally, human antibodies have a longer half-life within the human body than antibodies from other species due to the immune response to the foreign polypeptides. Thus, lower dosages of human antibodies and less frequent administration is often possible.

5.5.2 Detection & Diagnostic Uses

An anti-OX40 antibody described herein (see, e.g., Section 5.2) can be used to assay OX40 protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In) and technetium ($^{99}$Tc); luminescent labels, such as luminol; and fluorescent labels, such as fluorescein and rhodamine, and biotin. Such labels can be used to label an antibody described herein. Alternatively, a second antibody that recognizes an anti-OX40 antibody described herein can be labeled and used in combination with an anti-OX40 antibody to detect OX40 protein levels.

Assaying for the expression level of OX40 protein is intended to include qualitatively or quantitatively measuring or estimating the level of a OX40 protein in a first biological sample either directly (e.g., by determining or estimating absolute protein level) or relatively (e.g., by comparing to the disease associated protein level in a second biological sample). OX40 polypeptide expression level in the first biological sample can be measured or estimated and compared to a standard OX40 protein level, the standard being taken from a second biological sample obtained from an individual not having the disorder or being determined by averaging levels from a population of individuals not having the disorder. As will be appreciated in the art, once the "standard" OX40 polypeptide level is known, it can be used repeatedly as a standard for comparison.

As used herein, the term "biological sample" refers to any biological sample obtained from a subject, cell line, tissue, or other source of cells potentially expressing OX40. Methods for obtaining tissue biopsies and body fluids from animals (e.g., humans) are well known in the art. Biological samples include peripheral mononuclear blood cells.

An anti-OX40 antibody described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose and monitor to evaluate patient samples including those known to have or suspected of having an immune system-dysfunction or with regard to an anticipated or desired immune system response, antigen response or vaccine response. The assessment and evaluation of immune system status and/or immune response is also useful in determining the suitability of a patient for a clinical trial of a drug or for the administration of a particular chemotherapeutic agent or an antibody, including combinations thereof, versus a different agent or antibody. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses.

In one embodiment, an anti-OX40 antibody can be used in immunohistochemistry of biopsy samples.

In another embodiment, an anti-OX40 antibody can be used to detect levels of OX40, or levels of cells which contain OX40 on their membrane surface, which levels can then be linked to certain disease symptoms. Anti-OX40 antibodies described herein may carry a detectable or functional label. When fluorescence labels are used, currently available microscopy and fluorescence-activated cell sorter analysis (FACS) or combination of both methods procedures known in the art may be utilized to identify and to quantitate the specific binding members. Anti-OX40 antibodies described herein can carry a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-OX40 antibody can carry a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{67}Cu$, $^{90}Y$, $^{99}Tc$, $^{111}In$, $^{117}Lu$, $^{121}I$, $^{124}I$, $^{125}I$, $^{131}I$, $^{198}Au$, $^{211}At$, $^{213}Bi$, $^{225}Ac$ and $^{186}Re$. When radioactive labels are used, currently available counting procedures known in the art may be utilized to identify and quantitate the specific binding of anti-OX40 antibody to OX40 (e.g., human OX40). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-OX40 antibody under conditions that allow for the formation of a complex between the antibody and OX40. Any complexes formed between the antibody and OX40 are detected and compared in the sample and the control. In light of the specific binding of the antibodies described herein for OX40, the antibodies thereof can be used to specifically detect OX40 expression on the surface of cells. The antibodies described herein can also be used to purify OX40 via immunoaffinity purification.

Also included herein is an assay system which may be prepared in the form of a test kit for the quantitative analysis of the extent of the presence of, for instance, OX40 or OX40/OX40L complexes. The system or test kit may comprise a labeled component, e.g., a labeled antibody, and one or more additional immunochemical reagents. See, e.g., Section 5.6 below for more on kits.

In some aspects, methods for in vitro detecting OX40 in a sample, comprising contacting said sample with an antibody, are provided herein. In some aspects, provided herein is the use of an antibody provided herein, for in vitro detecting OX40 in a sample. In one aspect, provided herein is an antibody or pharmaceutical composition provided herein for use in the detection of OX40 in a subject. In one aspect, provided herein is an antibody or pharmaceutical composition provided herein for use as a diagnostic. In one preferred embodiment, the antibody comprises a detectable label. In one preferred embodiment, OX40 is human OX40. In one preferred embodiment, the subject is a human.

5.6 Kits

Provided herein are kits comprising one or more antibodies described herein or conjugates thereof. In a specific embodiment, provided herein is a pharmaceutical pack or kit comprising one or more containers filled with one or more of the ingredients of the pharmaceutical compositions described herein, such as one or more antibodies provided herein. In some embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided herein are kits that can be used in the above methods. In one embodiment, a kit comprises an antibody described herein, preferably a purified antibody, in one or more containers. In a specific embodiment, kits described herein contain a substantially isolated OX40 antigen (e.g., human OX40) that can be used as a control. In another specific embodiment, the kits described herein further comprise a control antibody which does not react with a OX40 antigen. In another specific embodiment, kits described herein contain one or more elements for detecting the binding of an antibody to a OX40 antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized OX40 antigen. The OX40 antigen provided in the kit can also be attached to a solid support. In a more specific embodiment, the detecting means of the above described kit includes a solid support to which a OX40 antigen is attached. Such a kit can also include a non-attached reporter-labeled anti-human antibody or anti-mouse/rat antibody. In this embodiment, binding of the antibody to the OX40 antigen can be detected by binding of the said reporter-labeled antibody. Also, a kit or kit-of-parts comprising (a) an antibody or pharmaceutical composition of the present invention, and (b) a checkpoint targeting agent, an IDO inhibitor and/or a vaccine, is provided.

The following examples are offered by way of illustration and not by way of limitation.

6. EXAMPLES

The examples in this Section (i.e., Section 6) are offered by way of illustration, and not by way of limitation.

6.1 Example 1: Generation of Novel Antibodies Against Human OX40

This example describes the generation and characterization of antibodies that bind to human OX40. In particular, this example describes the generation of human antibodies that specifically bind to human OX40 and exhibit a co-stimulatory effect on T cells.

6.1.1 Library Generation

The generation of the Retrocyte Display™ library is described herein. For the generation of library inserts, the total RNA was extracted via phenol/chloroform from FACS sorted CD19 positive human B lymphocytes originated from two cord blood samples. The total RNA of each cord blood sample (1 µg) was used for first-strand cDNA synthesis using RevertAid First Strand cDNA Synthesis Kit from Fermentas (Cat. No. K1621 and K1622). Antibody variable regions were amplified from the cDNA by PCR and cloned into retroviral expression vectors (pCMA). These constructs were subsequently used to transduce preB cells to express antibodies on the surface using Retrocyte Display™ technology. The retroviral expression vector contained 5' and 3' LTRs, immunoglobulin constant region (IGHG1 or IGKC) comprising membrane anchor fraction (IGHG1) and a CD4 surface maker gene.

The light chain variable regions (VLs) were amplified by semi-nested PCR using Vκ family-specific forward primers and a mixture of reverse primers. The forward primers introduced the HindIII cloning site and the reverse primers introduced the Eco47III cloning site.

The heavy chain variable regions (VHs) were amplified by PCR using VH family-specific forward primers and a mixture of reverse primers. The forward primers introduced the HindIII cloning site and the reverse primers introduced the Eco47III cloning site.

The amplified VH and Vκ regions were digested at 37° C. overnight. After digestion a band of the size of 400-450 bp was obtained and gel-purified (Macherey&Nagel, NucleoSpin Gel and PCR clean-up).

For the cloning of the heavy chain variable regions, construct 3181 (pCMA-InsX Cg(iso3) loxP2-I-tr_huCD4-loxP) was digested with HindIII/Eco47III at 37° C. for 4 hours and a band of the size of 8362 bp was gel-purified. For the cloning of the κ light chain variable regions, construct 3204 (pCMA-InsX Ck-I-CD4) was digested with HindIII/Eco47III at 37° C. for 4 hours and a band of the size of 7465 bp was gel-purified.

The digested and purified antibody variable regions were ligated in frame into the appropriate expression vectors using a 1:3 vector to insert ratio. Each VH and Vκ family was separately ligated into retroviral expression vectors and concentrated 10-fold by precipitation. The precipitated VH and Vκ ligation reactions were also separately transformed into E. coli DH10B cells for library generation. The separate ligation, precipitation and transformation of each VH and Vκ family allow the library to mirror the natural distribution of functional germline genes, ensuring that the VH or Vκ families with a high number of functional germline genes are highly represented in the final library compared with families with a lower number of functional germline genes. After the transformation, E. coli cells were harvested and combined to the final library. The quality of each library was controlled via diagnostic restriction digestion and analysis of sequencing data. The library diversity was calculated from the data of the sequence analysis.

6.1.2 Recovery of Heavy and Light Chains from Pre-Selected preB Cell Clones

The library material generated as described above was used to identify antibodies with a high binding affinity to OX40. The B cell clones were lysed and heavy and light chain variable regions were amplified from the inserted retroviral vector stably integrated in the genomic DNA using PCR methods standard in the art. The amplified heavy and light chain variable regions were subsequently cloned into mammalian expression vectors containing the human heavy chain and light chain constant regions. The DNA plasmid preparations were subsequently used to transfect CHO cells and the expressed antibodies were tested using suspension array technology. Antibody heavy and light chains were sequenced at Microsynth (Balgach, Switzerland).

6.1.3 Biophysical Characterization of Anti-OX40 Antibodies

An antibody designated pab1949 was selected and characterized in a number of assays as described below. The anti-OX40 antibody pab1949 comprises a heavy chain comprising the amino acid sequence of SEQ ID NO: 60 and a light chain comprising the amino acid sequence of SEQ ID NO: 50. The antibody pab1949 is a human IgG$_1$ antibody containing a T109S substitution in the light chain constant domain (i.e., substitution of threonine with serine at position 109 relative to the wild type light chain constant domain), numbered according to Kabat, which facilitates the cloning of the variable region in frame to the constant region. This mutation is a conservative modification that does not affect antibody binding or function. The wild type counterpart, named pab1949-1, which contains a threonine at position 109, numbered according to Kabat, was also generated. The antibody pab1949-1 is a human IgG$_1$ antibody comprising a heavy chain of SEQ ID NO: 60 and a light chain of SEQ ID NO: 20.

6.1.3.1 Affinity Measurement by Bio-Layer Interferometry

The affinity of pab1949-1 was determined by Bio-layer Interferometry (BLI). Briefly, recombinant human OX40 antigen (OX40-Fc, R&D) was diluted using 1×PBS to obtain 1,000 µl of 0.2 µM and added to a 96-well plate. pab1949-1 was diluted in 1×PBS to a concentration of 50 nM. Six-point serial dilutions of pab1949-1 were prepared from the 50 nM solution using 1×PBS to obtain antibody dilutions ranging from 50 nM to 0.78 nM and 100 µl of the respective antibody serial dilutions were added per well to a 96-well plate. Sensors were coated with the human OX40 antigen using the 16-channel mode of Octet® at 25° C. for 5 min with a threshold of 1.0 nm according to the manufacturer's instructions. For blocking, 0.5 mg/ml of a non-specific IgG$_1$ antibody was incubated for 10 minutes. The plate containing the serial antibody dilutions of pab1949-1 was placed on the Octet® instrument. The assays were conducted according to the manufacturer's instructions. Binding and dissociation of pab1949-1 to the OX40 antigen were recorded for 3 minutes and 10 minutes, respectively. Data were analyzed using the Octet® Data Analysis software and the result is shown in Table 5.

TABLE 5

| Affinity measurement of pab1949-1 | | |
|---|---|---|
| $K_a$ (1/Ms) | $K_d$ (1/s) | $K_D$ (nM) |
| $1.09 \times 10^6$ | $1.26 \times 10^{-4}$ | 0.11 |

6.1.3.2 Antibody Binding to Activated Human or Cynomolgus T Cells

The binding characteristics of the anti-OX40 antibodies pab1949 and pab1949-1 to human or cynomolgus OX40 were analyzed by flow cytometry.

Human PBMCs isolated via Ficoll gradient from healthy donor buffy coats (Research Blood Components, LLC) were enriched for untouched CD4+ and CD8+ T cells using magnetic-based separation (Miltenyi Biotec). The enriched populations of T lymphocytes were then activated with CD3-CD28 expansion beads (Miltenyi Biotec) with 500 U rIL-2 (R&D Systems) for 3 days under recommended culture conditions, and 50 U rIL-2 thereafter. The recommended culture conditions were defined as cells cultured in RPMI-1640 media, supplemented with 10% fetal bovine serum, 10 mM HEPES and 1× Pen/Strep-Glutamine at 37° C. and 5% $CO_2$. Following activation, the cells were incubated with a surface antibody cocktail containing the conjugated antibodies of CD3 (BV711, OKT3), CD4 (BV605, OKT4), CD8a (BV650, RPA-T8), and pre-conjugated anti-OX40 antibodies or isotype control (both Afluor488, 10 µg/ml) diluted in FACS buffer (PBS with 2% FBS) for 30 minutes at 4° C. Additional samples were set aside for single-stain compensation controls (CD45-BV650, CD45-Afluor488, CD45-BV605, and CD45-BV711). The cells were then washed with FACS buffer twice and analyzed using the LSRFortessa flow cytometer (BD Biosciences). The flow cytometry plots were analyzed using a combination of FACS DIVA and WEHI Weasel software. The anti-OX40 antibody pab1949 bound to activated human CD4+ T cells and CD8+ T cells (FIG. 1A).

Figure 1B:
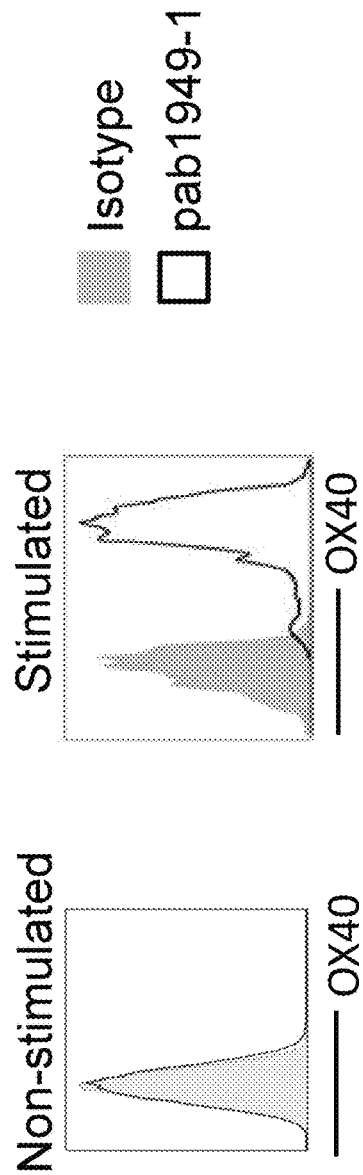
Figure 1C:
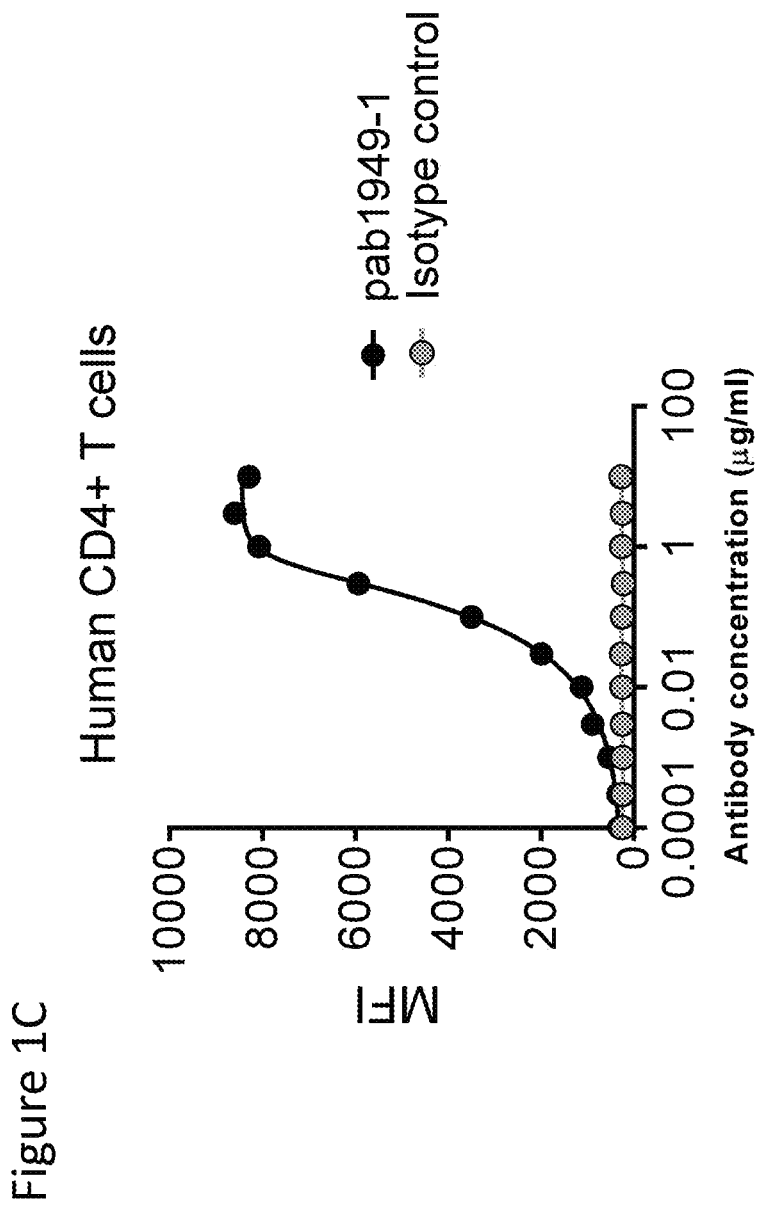

A series of concentrations of pab1949-1 was tested for binding to activated T cells to characterize a dose-response relationship. In brief, human peripheral blood mononuclear cells (PBMCs) were thawed and washed with PBS. Negative isolation of T cells was performed with magnetic beads (Miltenyi Biotec) and the purified T cells were resuspended in RPMI+10% FBS and stimulated with anti-CD3/anti-CD28 beads for 72 hours at 37° C. and 5% $CO_2$. The cells were washed and blocked with Fc blocking solution (Trustain, Biolegend) for 15 minutes at room temperature. The cells were washed again and stained with a serial dilution of pab1949-1 (10 to 0.00003 µg/ml) for 45 minutes at 4° C. in the dark. The cells were washed and then stained with lineage marker antibodies including anti-CD3 fluorescein isothiocyanate (FITC) (clone SP34) and anti-CD4 Brilliant Violet (BV) 510 (clone OKT4), together with a secondary antibody to detect pab1949-1 (anti-kappa IgG PE). Cells were washed, fixed with 1.6% paraformaldehyde, and acquired using a Becton Dickinson Fortessa flow cytometer. pab1949-1 demonstrated binding only to stimulated T cells, but not non-stimulated T cells (FIG. 1B). The binding of pab1949-1 to activated human CD4+ T cells was dose dependent (FIG. 1C).

Figure 1D:
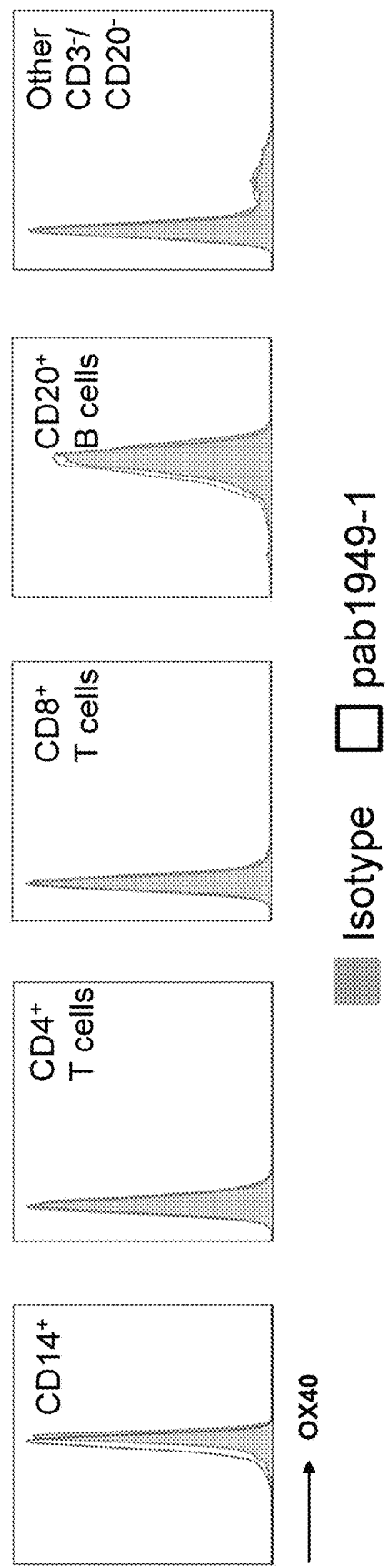

Next, a number of quiescent immune cell subtypes were tested for binding of pab1949-1. Human PBMCs were thawed and washed with PBS. To stain dead cells, infra-red (IR) viability dye was added and incubated for 15 minutes at room temperature protected from light. Cells were washed and stained with an amine dye infra red (Life Technologies) for 15 minutes at room temperature. The cells were washed and Fc-blocked (Trustain FcX, Biolegend) for 10 minutes at room temperature. After washing, the cells were incubated with 1 µg/ml of pab1949-1 or an $IgG_1$ isotype control for 30 minutes at 4° C. protected from light. Cells were washed and stained with a secondary reagent (anti-Fc F(ab') PE, Jackson Immune Research Laboratories) followed by lineage marker antibody staining that included: anti-CD3 Phycoerythrin Cyanine 7 (PECy7, clone SP34.2), anti-CD8 BV510 (clone SK1), anti-CD4 Peridinin-Chlorophyll-Protein Complex (PerCP) Cy5 (clone Ly200), and anti-CD14 FITC (clone TUK4). Cells were washed, fixed with 1.6% paraformaldehyde and acquired using a Becton Dickinson Fortessa flow cytometer. As shown in FIG. 1D, the anti-OX40 antibody pab1949-1 did not show detectable binding to CD14+ cells, CD4+ T cells, CD8+ T cells, CD20+ B cells, or CD3-CD20- cells.

Figure 1E:
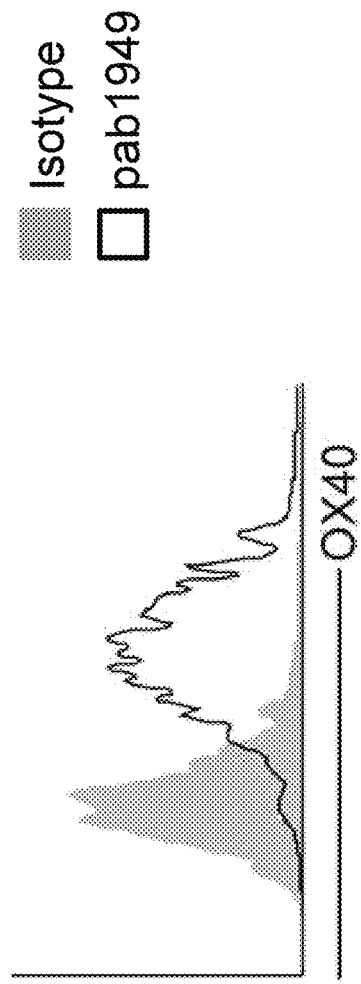

To test for species cross-reactivity, a cell binding assay was performed using activated cynomolgus monkey (*Macaca fascicularis*) PBMCs. Briefly, viable cynomolgus monkey PBMCs (Worldwide Primates Inc.) were activated with Concanavalin-A (Sigma Aldrich, 5 µg/ml) and recombinant IL-2 (Miltenyi, 20 U/ml) for 3 days in RPMI media supplemented with 10% heat-inactivated FBS at 37° C. in a 5% $CO_2$ humidified chamber. Following activation, the cells were incubated with human Fc-receptor block (Biolegend) for 15 minutes at room temperature to reduce nonspecific binding. The anti-OX40 antibody pab1949 or a human $IgG_1$ isotype control (10 µg/ml) was added to the samples and incubated for 30 minutes at 4° C. Following one wash with the FACS buffer, an antibody cocktail, containing an APC-conjugated anti-human kappa antibody as well as antibodies specific for CD4 (BV605, OKT4) and CD8a (PE, RPA-T8), all at 2.5 µg/ml, was diluted in the FACS buffer (PBS, 2 mM EDTA, 0.5% BSA and pH 7.2), added to each sample and incubated for 30 minutes at 4° C. Prior to staining, additional samples were set aside for single stain compensation controls (cyno-reactive: CD4-BV605, CD4-PE, and CD4-APC). The samples were washed twice in the FACS buffer and analyzed using the LSRFortessa flow cytometer (BD Biosciences). As shown in FIG. 1E, pab1949 bound to activated cynomolgus monkey CD4+ T cells.

6.1.3.3 OX40 Antibody Selectivity Assay

The selectivity of pab1949-1 for OX40 was assessed against other members of the TNFR superfamily using suspension array technology as a multiplex assay. A number of TNFR family members were chemically coupled to Luminex® microspheres using standard NETS-ester chemistry. Purified material of pab1949-1 was diluted in assay buffer (Roche 11112589001) to 10 ng/ml, 100 ng/ml and 1000 ng/ml. Briefly, 25 µl of each dilution was incubated in the dark (20° C., 650 rpm) with 1500 Luminex® microspheres in 5 µl assay buffer for 1 hour in 96 half-well filter plates (Millipore, MABVN1250). Luminex® microspheres (Luminex Corp, LC10001-01, LC10005-01, LC10010-01, LC10014-01, LC10015-01, LC10018-01, LC10022-01, LC10026-01, LC10052-01, LC10053-01 and LC10055-01) were coupled with recombinant human LTBR-Fc (Acros Biosystems, LTR-H5251), anti-human IgG (F(ab)$_2$-specific, JIR, 105-006-097), recombinant human OX40-Fc (R&D systems, 3388-OX), recombinant human GITR-Fc (R&D, 689-GR), recombinant human DR6-Fc (SinoBiological, 10175-H02H), recombinant human DR3-Fc (R&D, 943-D3), recombinant human GITR-His (SinoBiological, 13643-H08H), recombinant human TWEAK R-Fc (SinoBiological, 10431-H01H), recombinant human OX40-His (SinoBiological, 10481-H08H), recombinant human 4-1BB-His (SinoBiological, 10041-H08H) or recombinant human BAFFR-Fc (R&D, 1162-BR) via amine coupling with COOH bead surface. Standard curves were generated using duplicates of 25 µl of a human $IgG_1$ standard (Sigma, 15154) with 1:3 dilution series (0.08-540 ng/ml). Detection was carried out using 60 µl of goat anti-human IgG F(ab)$_2$ labeled with R-PE (2.5 µg/ml; JIR 109-116-098, AbDSerotec Rapid RPE Antibody Conjugation Kit, LNK022RPE) and another hour of incubation time (20° C., 650 rpm). Plates were analyzed using a Luminex® 200 system (Millipore). A total of 100 beads were counted per well in a 48 µl sample volume. PE MFI values were used to determine specific or nonspecific binding to the recombinant proteins mentioned above.

The antibody pab1949-1 showed specific binding to human OX40, and no significant binding to other TNFR family members was observed at tested concentrations (data not shown).

6.2 Example 2: Functional Characterization of Anti-OX40 Antibodies

This example demonstrates the ability of the anti-OX40 antibodies pab1949 and pab1949-1 generated by the methods described above to function as agonists of OX40. The antibodies pab1949 and pab1949-1 were assayed to determine their ability to costimulate primary human CD4+ or CD8+ T cells. In addition, pab1949 and pab1949-1, which are human $IgG_1$ antibodies, were converted to human $IgG_4$ antibodies, pab2044 and pab2044-1, respectively. The antibody pab2044 shares the same heavy chain variable region and the same light chain as pab1949 but comprises a human $IgG_4$ constant region. The antibody pab2044 comprises a heavy chain sequence of SEQ ID NO: 61 and a light chain sequence of SEQ ID NO: 50. Similar to pab1949, pab2044 contains the T109S single amino acid substitution, a conservative modification that does not impact antibody binding or function, in the light chain constant region to facilitate cloning. The wild type counterpart, pab2044-1, contains a threonine at position 109, numbered according to Kabat, and comprises a heavy chain sequence of SEQ ID NO: 61 and a light chain sequence of SEQ ID NO: 20. Similarly, pab1949 and pab1949-1 were also converted to human $IgG_2$ antibodies, pab2193 and pab2193-1, respectively. The antibody pab2193 comprises a heavy chain sequence of SEQ ID NO: 62 and a light chain sequence of SEQ ID NO: 50. The antibody pab2193-1 comprises a heavy chain sequence of SEQ ID NO: 62 and a light chain sequence of SEQ ID NO: 20. In some assays, the functional activities of pab1949, pab1949-1, pab2044, pab2044-1, pab2193, or pab2193-1 were examined.

In some of the assays, the agonistic activity of the anti-OX40 antibodies of this invention was compared to that of the reference antibodies pab1784 and pab2045. The antibody pab1784 was generated based on the variable regions of the antibody 11D4 provided in U.S. Pat. No. 7,960,515 (herein incorporated by reference). The heavy chain of pab1784 comprises the amino acid sequence of the heavy chain variable region of 11D4 (SEQ ID NO: 26) and a human $IgG_1$ constant region of SEQ ID NO: 65. The light chain of pab1784 comprises the amino acid sequence of the light chain variable region of 11D4 (SEQ ID NO: 24) and a constant region of SEQ ID NO: 25.

The antibody pab2045 was generated based on the variable regions of the antibody 20E5 provided in International Publication No. WO 13/038191 (herein incorporated by reference). The heavy chain of pab2045 comprises the amino acid sequence of the heavy chain variable region of 20E5 (SEQ ID NO: 30) and a human $IgG_1$ constant region of SEQ ID NO: 65. The light chain of pab2045 comprises the amino acid sequence of the light chain variable region of 20E5 (SEQ ID NO: 28) and a constant region of SEQ ID NO: 41.

6.2.1 Effect of Anti-OX40 Antibodies on Anti-CD3 Stimulated CD4+ T Cell Proliferation To examine the effect of pab1949 on T cell proliferation, human PBMCs isolated via Ficoll gradient from healthy donor buffy coats (Research Blood Components, LLC) were enriched for untouched CD4+ T cells using magnetic-based separation (Stemcell Technologies). Cellular proliferation was determined by monitoring dilution of carboxyfluorescein diacetate sucinimidyl ester (CFSE) dye within divided cells (Quah B J et al., (2007) Nat Protoc, 2(9): 2049-56). The enriched CD4+ T cells were labeled with 10 µM CellTrace™ CFSE (Life Technologies) for 7 minutes at 37° C. After extensive washes, the cells were suspended in RPMI1640 media supplemented with 10% heat-inactivated FBS at $1\times10^6$ cells/ml. A total of 100 µl ($1\times10^5$ cells) was seeded into each well of flat bottom 96 well plates pre-coated with anti-CD3 antibody (3 µg/ml, BD Biosciences) together with either 5 µg/ml of pab1949, 5 µg/ml of IgG1 isotype control, or 2 µg/ml of anti-CD28 antibody (BD Biosciences) and cultured at 37° C. and 5% $CO_2$. On day 5, the cells were stained with 0.5 µl/well of PerCP-Cy5.5 labeled anti-CD4 antibody in FACS buffer (2% FBS in PBS) at 4° C. for 30 minutes and the percentage of CFSE low CD4+ cells was determined by Flow Cytometry on a LSRFortessa (BD Biosciences). The flow cytometry data were analyzed using FlowJo.

The activity of pab2044 was assessed using a similar assay as described above where CD4+ T cells that were labeled with CFSE were seeded onto 96 well plates pre-coated with anti-CD3 antibody (3 µg/ml, BD Biosciences) together with either 5 µg/ml of pab2044, 5 µg/ml of $IgG_4$ isotype control (pab2031), or 2 µg/ml of anti-CD28 antibody (BD Biosciences). The percentage of CFSE low CD4+ cells was examined by Flow Cytometry on day 5.

Figure 2A:
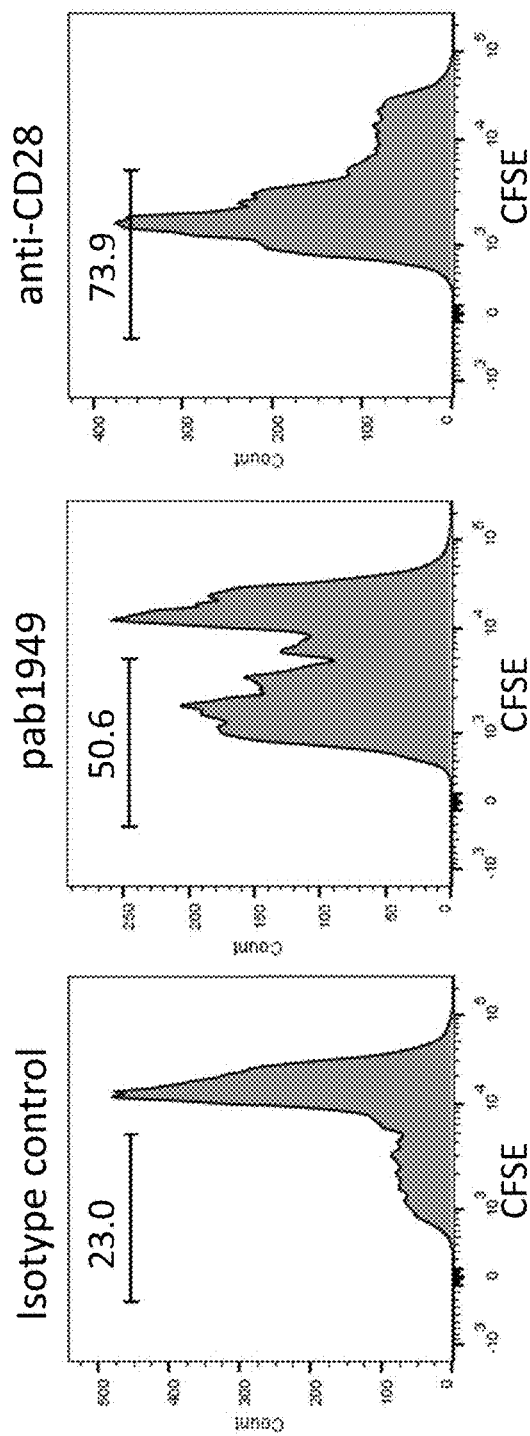
Figure 2B:
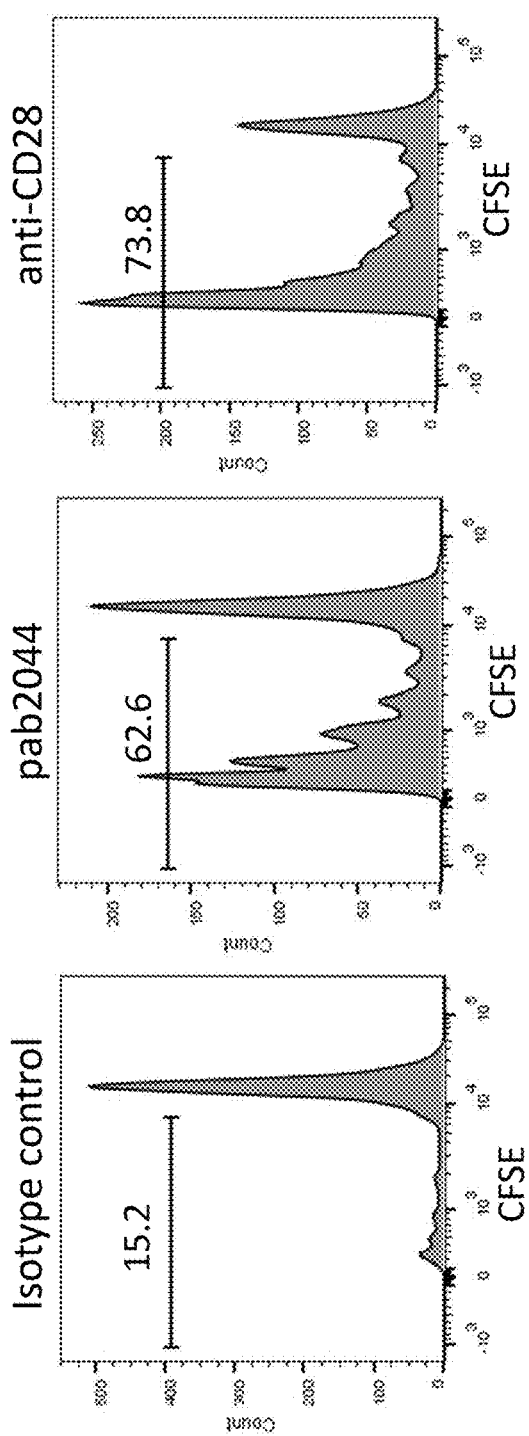

FIGS. 2A and 2B are histograms from a representative flow cytometry analysis of CD4+ T cell proliferation induced by costimulation with anti-OX40 antibodies, showing cell numbers (Y-axis) and the level of fluorescence emitted (X-axis) by the CFSE labeled CD4+ T cells. Enhanced CD4+ T cell proliferation is shown by an increased percentage of cells with a diminished level of fluorescence emitted by CFSE. The percentages of CFSE low CD4+ cells were indicated in the histograms. Both pab1949 (FIG. 2A) and pab2044 (FIG. 2B), when plate-bound, induced CD4+ T cell proliferation when added to cells activated with suboptimal concentrations of anti-CD3 antibody.

Next, the dose response of pab1949 in inducing T cell proliferation was measured. PBMCs isolated via Ficoll gradient from healthy donor buffy coats (Research Blood Components, LLC) were enriched for untouched CD4+ T cells using magnetic-based separation (Stemcell Technologies). The enriched population of CD4+ T cells was then labeled with 10 µM CellTrace™ CFSE (Life Technologies) for 7 min at 37° C. After extensive washes, the cells were suspended in RPMI1640 media supplemented with 10% heat-inactivated FBS at $1\times10^6$/ml. 100 µl ($1\times10^5$) of cells was seeded into each well of flat bottom 96 well plates pre-coated with anti-CD3 antibody (3 µg/ml, BD Biosciences) together with varying concentrations of pab1949 or an $IgG_1$ isotype control and cultured at 37° C. and 5% $CO_2$. On day 4, cells were stained with 0.5 µl/well of APC-labeled anti-CD4 antibody in FACS buffer (2% FBS in PBS) at 4° C. for 30 minutes and the percentage of CFSE low CD4+ cells was determined by Flow Cytometry on a LSRFortessa (BD Biosciences).

Figure 2C:
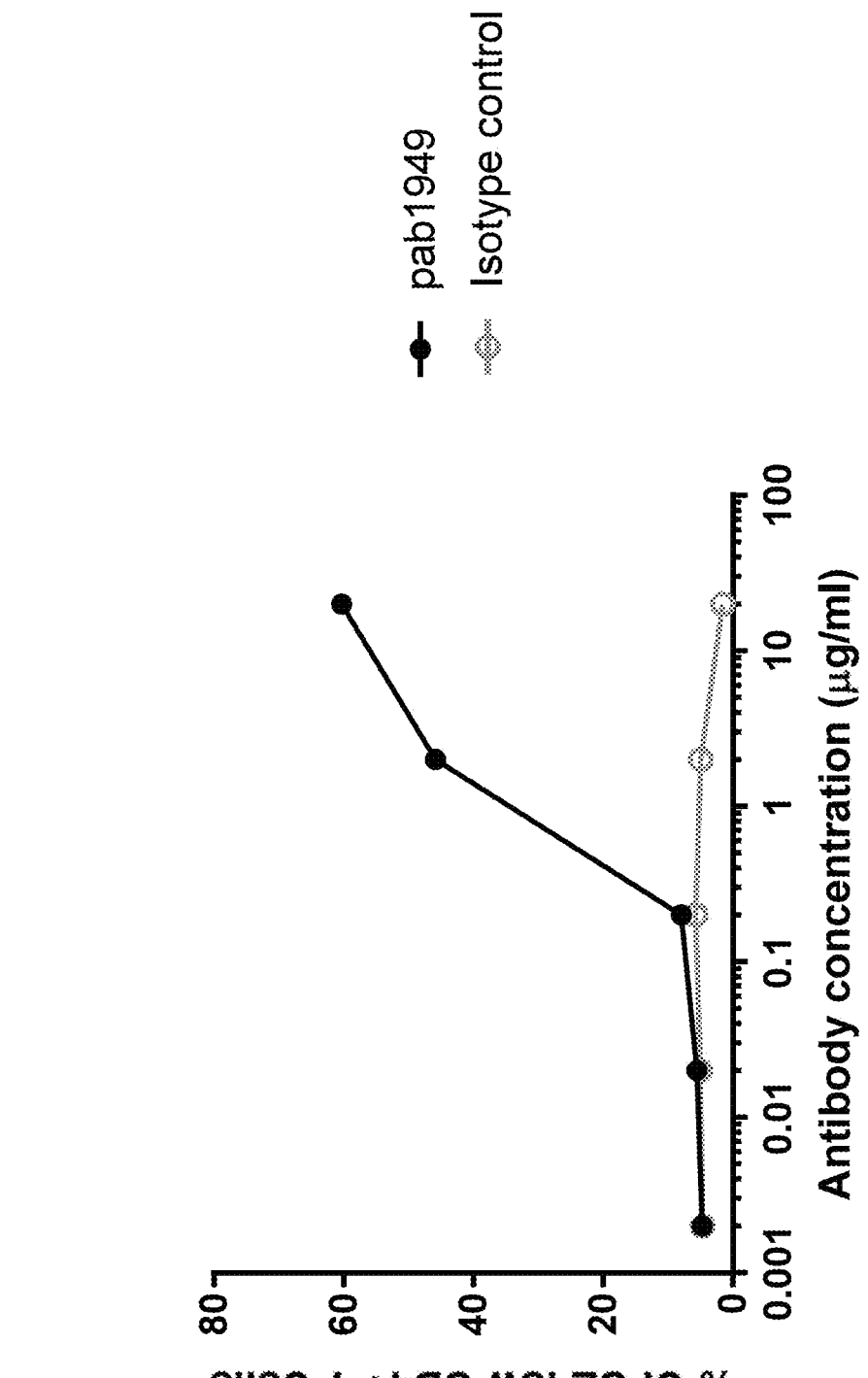

As shown in FIG. 2C, the anti-OX40 antibody pab1949 was able to maintain a high level of T cell proliferation at pharmacologically relevant antibody concentrations. CD4+ T cell proliferation was a substantially increasing function of the concentrations of pab1949 between 0.2 µg/ml and 20 µg/ml (FIG. 2C).

6.2.2 Effect of Anti-OX40 Antibodies on Anti-CD3 Stimulated Human PBMC Cytokine Production As further evidence for the agonistic activity of the anti-OX40 antibodies pab1949 and pab1949-1, cytokine production under suboptimal anti-CD3 stimulation was measured.

For an intracellular cytokine staining experiment, human PBMCs isolated via Ficoll gradient from healthy donor buffy coats (Research Blood Components, LLC) were stored in liquid nitrogen and thawed on the day of the experiment. The cells were resuspended in cell culture media (RPMI+10% FBS+20 U/mL of IL-2) and added to 96-well culture plates that contained plate-bound anti-CD3 antibody at various suboptimal concentrations plus 5 µg/ml of the anti-OX40 antibody pab1949 or the isotype control $IgG_1$ antibody. The samples were incubated for 3 days at 37° C. and 5% $CO_2$. After activation, to inhibit intracellular protein transport, the cells were treated with Brefeldin A (BD Biosciences) according to the manufacturer's instructions and the samples were incubated for 6 hours at 37° C. and 5% $CO_2$. After the incubation the cells were stained with a viability amine dye (Life technologies) for dead cells. After washing with the FACS buffer (PBS, 2% FBS, pH 7.2), an antibody cocktail containing antibodies specific for CD3 (APC Cy7, SP34.2), CD4 (PercP Cy5.5, L200), and CD8a (PE Cy7, SK1) diluted in cold FACS buffer was added to each sample and incubated for 10 minutes at 4° C. The cells were fixed and permeabilized with Cytofix-Cytoperm (BD Biosciences) for intracellular staining according to the manufacturer's instructions. The PBMCs were stained with antibodies specific for IFNγ (Alexa647, B27) and TNFα (PE, Mab 11) and incubated at room temperature for 10 minutes. Prior to staining, beads binding kappa light chains of mouse IgG antibodies were stained with the antibodies used to stain the cells using single stained compensation controls. Samples were washed using 1×Perm-wash buffer (BD Biosciences) and analyzed using the FACS Canto flow cytometer (BD Biosciences). The flow cytometry plots were analyzed using the Flojo software.

Figure 3A:
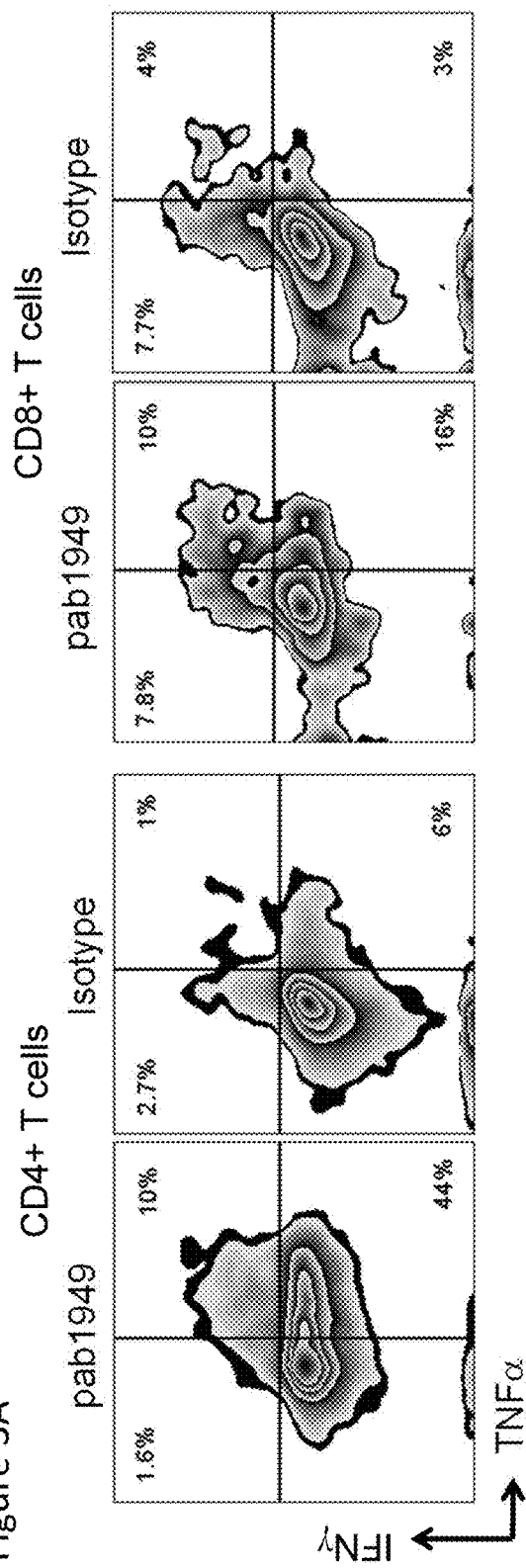
Figure 3B:
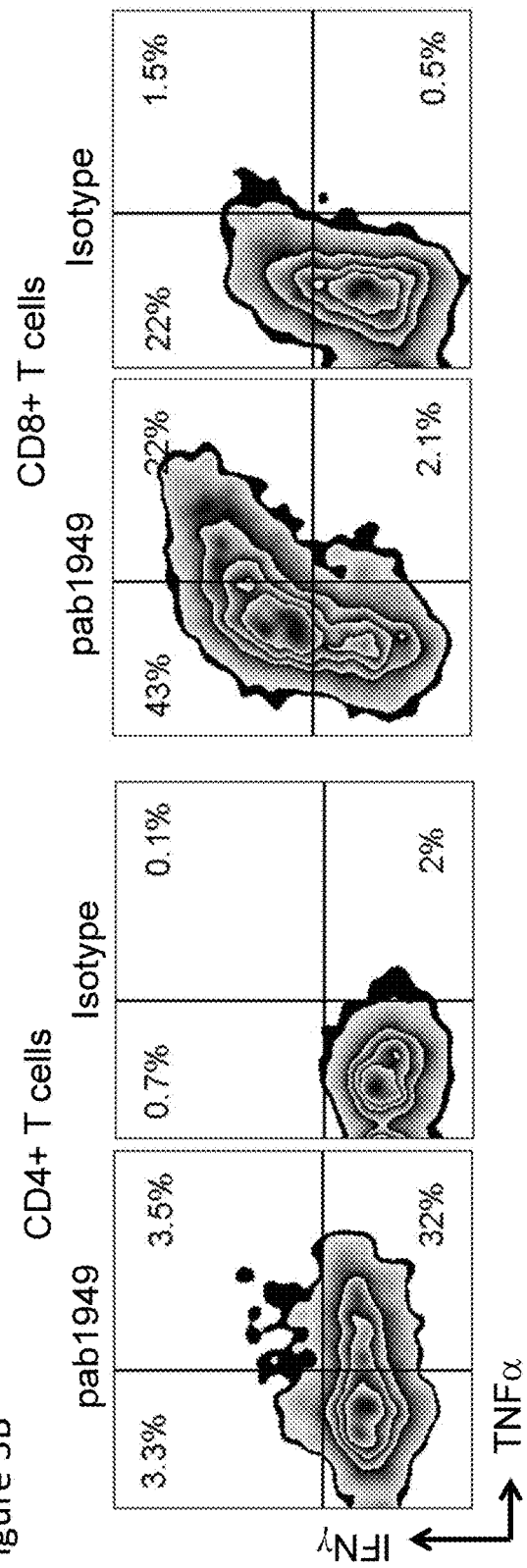
Figure 3C:
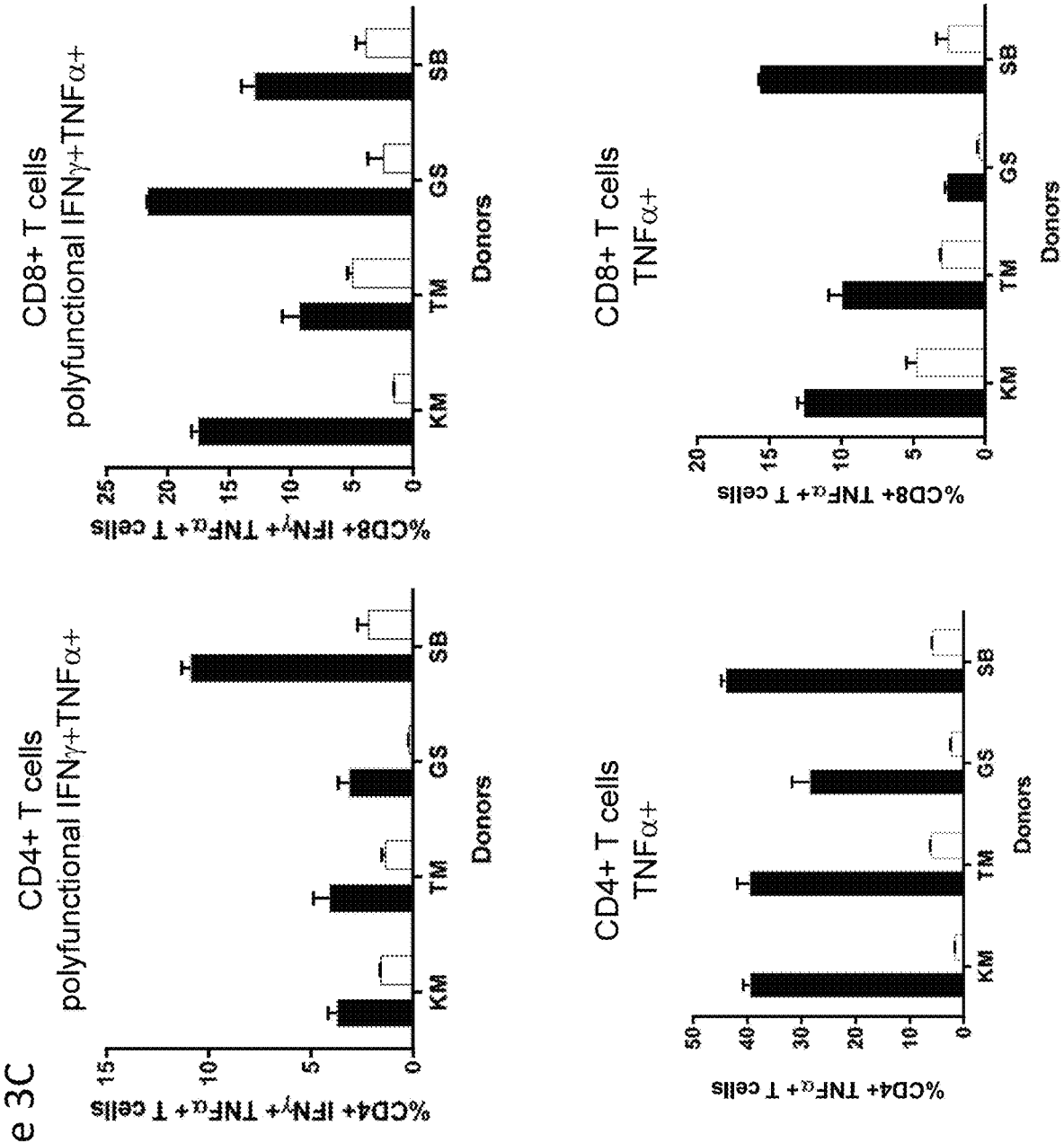

PBMCs from four different donors were tested: donor KM, donor TM, donor GS, and donor SB. For all the donors, pab1949 demonstrated costimulatory activity on human T cells, inducing IFNγ+ TNFα+ polyfunctional CD4+ T cells and CD8+ T cells and TNFα+ monofunctional CD4+ T cells and CD8+ T cells (FIGS. 3A, 3B, and 3C). In PBMCs from donor GS, pab1949 was also able to increase the percentage of IFNγ+ monofunctional T cells (FIG. 3B).

Next, a dose titration of the anti-OX40 antibody pab1949-1 was tested in a suboptimal anti-CD3 stimulation assay similar to the one described above using cells derived from PBMCs of donor GS. Briefly, PBMCs were incubated with plate-bound anti-CD3 antibody (0.8 µg/ml) and plate-bound pab1949-1 or an $IgG_1$ isotype control antibody (0, 0.3, 1, 3, 6, 12, 25, or 50 µg/ml) for 4 days at 37° C. and 5% $CO_2$. After activation, to inhibit intracellular protein transport, the cells were treated with Brefeldin A (BD Biosciences) according to the manufacturer's instructions and the samples were incubated for 6 hours at 37° C. and 5% $CO_2$. After the incubation, the cells were stained with a FITC viability amine dye (Life technologies) to differentiate live and dead cells. After washing with cold buffer (1×PBS+2% FBS, pH 7.2), an antibody cocktail containing anti-CD3 (APC Cy7, SP34.2), anti-CD4 (PercP Cy5.5, L200), and anti-CD8a (PE Cy7, SK1) was added to each sample and incubated for 10 minutes at 4° C. The cells were fixed and permeabilized with Cytofix-Cytoperm (BD Biosciences) for intracellular staining according to the manufacturer's instructions. The PBMCs were stained with anti-IFNγ (Alexa647, B27) and anti-TNFα (PE, Mab 11) antibodies and incubated at room temperature for 10 minutes. Samples were washed using 1×Perm-wash buffer (BD Biosciences) and acquired using a FACScanto flow cytometer (BD Biosciences). The flow cytometry plots were analyzed using Flojo software. As shown in FIGS. 3D-3F, the anti-OX40 antibody pab1949-1 demonstrated co-stimulatory activity and increased the percentage of TNFα+ CD4+ T cells, IFNγ+ TNFα+ polyfunctional CD8+ T cells, and IFNγ+ CD8+ T cells in a dose-dependent manner.

Figure 4A:
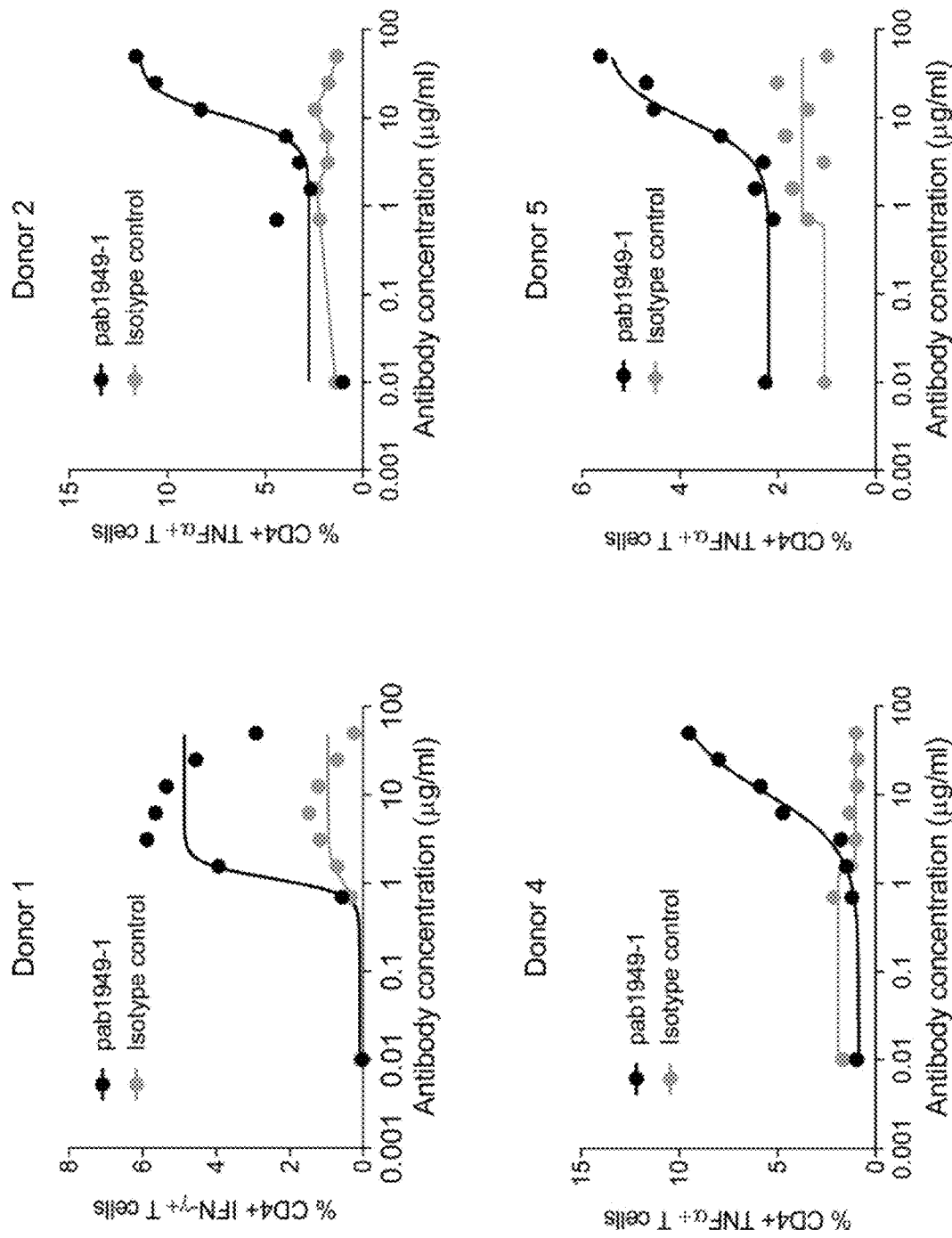
Figure 4B:
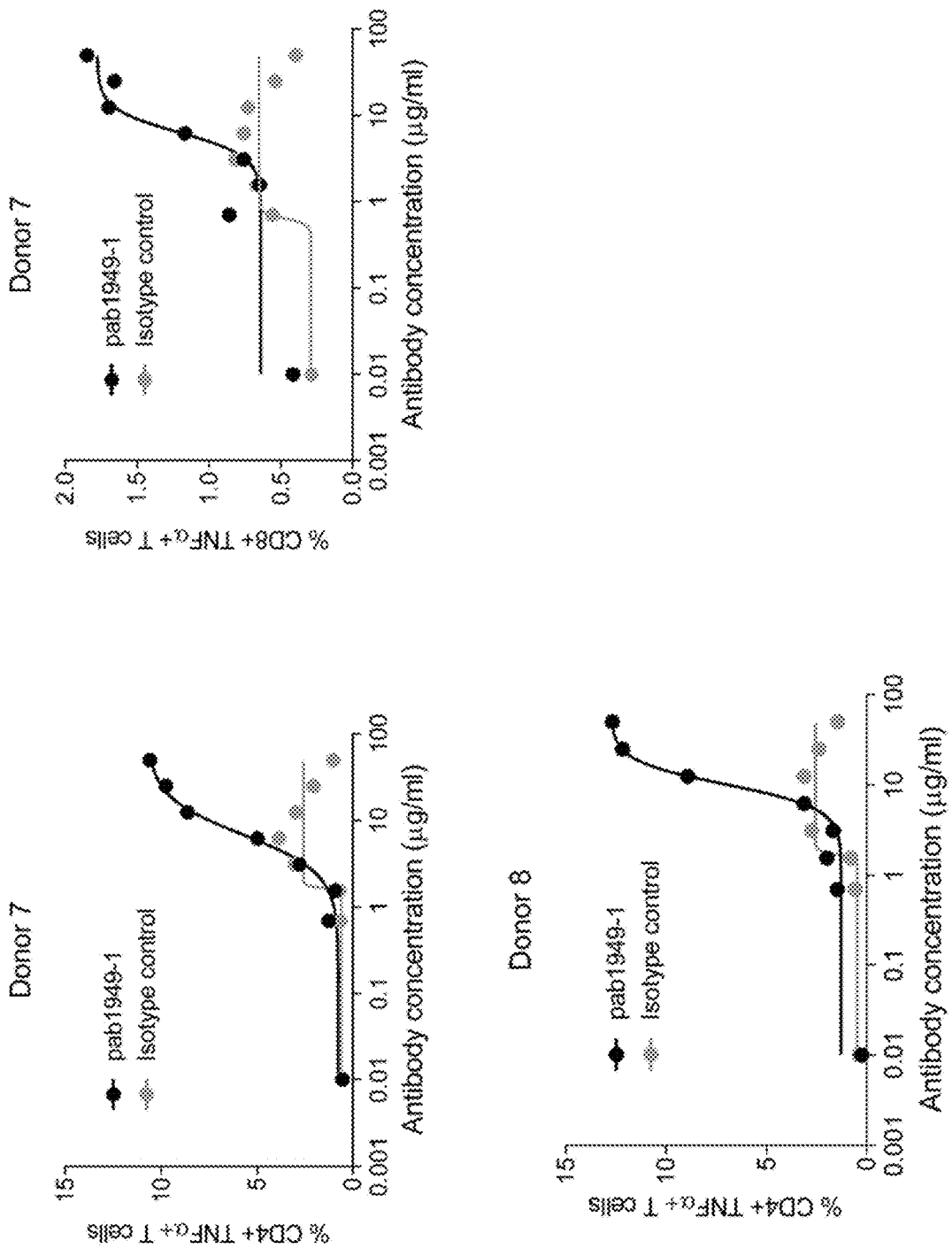
Figure 4C:
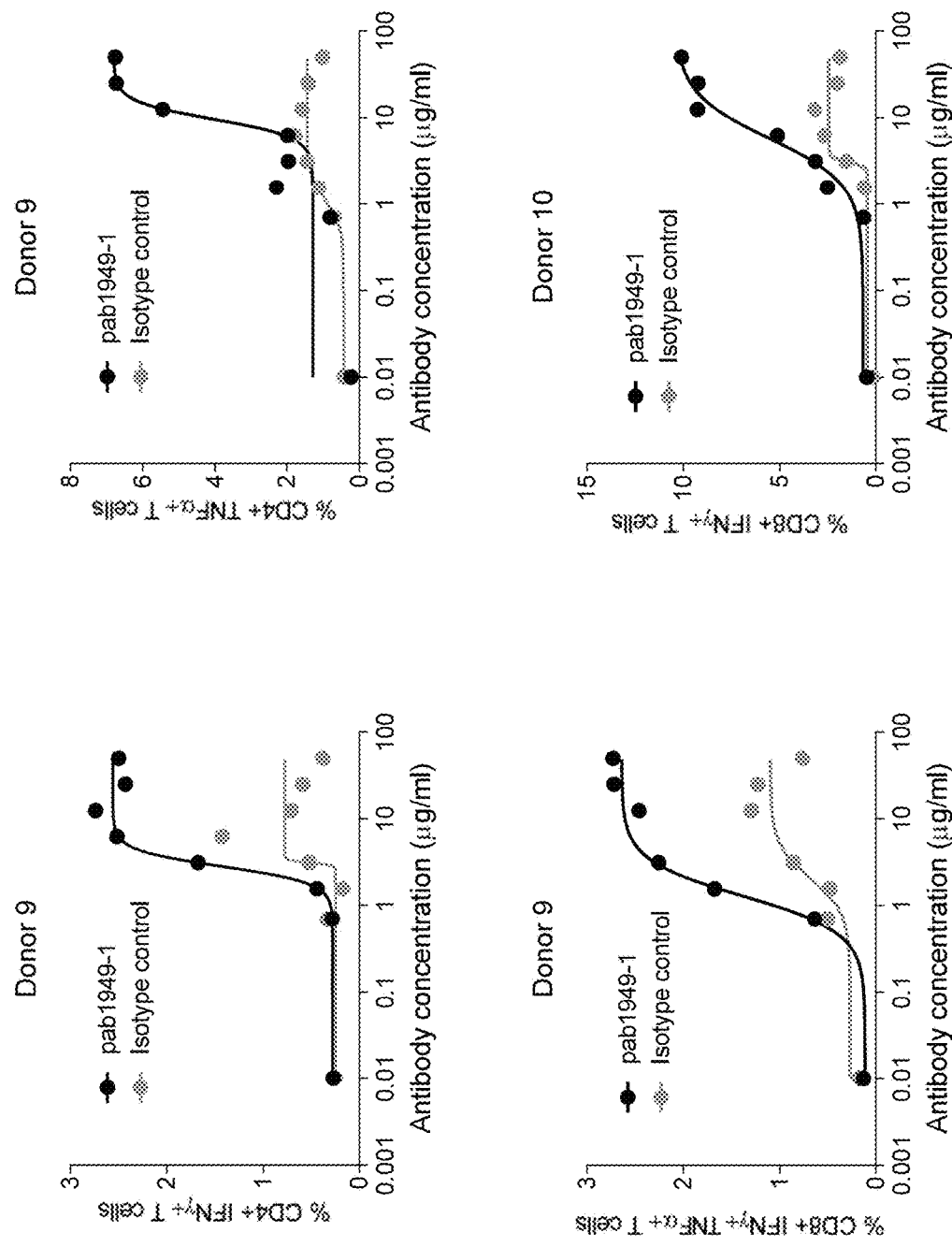

The co-stimulatory activity of a ranging dose of pab1949-1 was further tested using cells derived from PBMCs of additional donors in the suboptimal anti-CD3 stimulation assay described above. The anti-OX40 antibody pab1949-1 and an $IgG_1$ isotype control antibody were tested at 0, 0.7, 1.6, 3.1, 6.3, 12.5, 25, or 50 µg/ml. The anti-OX40 antibody pab1949-1 consistently increased the percentage of IFNγ+ and/or TNFα+ T cells in PBMCs from multiple donors (FIGS. 4A-4C).

Notably, for PBMCs from many donors, the percentage of IFNγ+ and/or TNFα+ T cells induced by the anti-OX40 antibody pab1949-1 was a substantially increasing function of antibody concentration across a wide range of antibody concentrations tested (FIGS. 3D-3F and 4A-4C).

To examine further the agonistic activity of the anti-OX40 antibody pab1949, the quantity of cytokines secreted was measured. Human PBMCs isolated via Ficoll gradient from healthy donor buffy coats (Research Blood Components, LLC) were stored in liquid nitrogen and thawed on the day of the experiment. The cells were resuspended in cell culture media (RPMI+10% FBS+20 U/mL of IL-2) and added to 96-well culture plates that contained plate-bound anti-CD3 antibody at various suboptimal concentrations plus 5 µg/ml of the anti-OX40 antibody pab1949 or the isotype control $IgG_1$ antibody. The samples were incubated at 37° C. and 5% $CO_2$ and cell culture supernatant was collected after either 4 days (SB #1A) or 3 days (SB #1B, SB #2, and GS). The samples were tested using the V-PLEX Proinflammatory Panel1 (human) Kit (Meso Scale Discovery) for the production of IL-2, TNFα, IL-10, IL-4, and IL-13 according to the manufacturer's instructions.

Figure 5A:
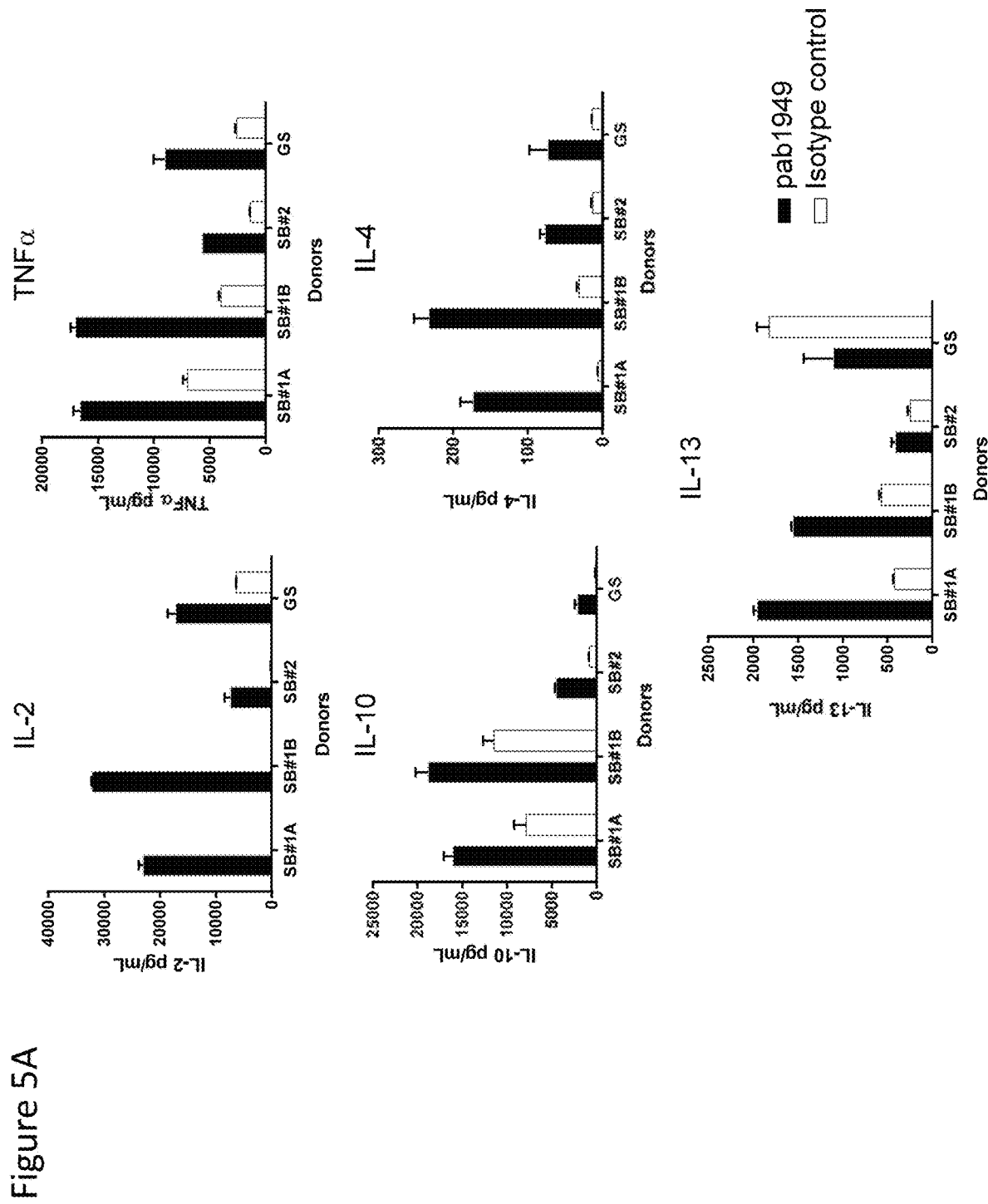

As depicted in FIG. 5A, the anti-OX40 antibody pab1949 costimulated cytokine production in human PBMCs from two different donors: donor SB and donor GS. Cytokine production of PBMCs from donor SB was tested in two separate experiments: SB #1A and SB #1B show results from a first experiment where cytokines were measured after 4 days and 3 days upon stimulation, respectively; and SB #2 shows results from a second experiment where cytokines were measured after 3 days upon stimulation.

Next, cytokine secretion induced by a dose titration of pab1949-1 was examined using cells derived from PBMCs of donor GS in a suboptimal anti-CD3 stimulation assay similar to the one described above. In brief, PBMCs were incubated with plate-bound anti-CD3 antibody (0.8 µg/ml) and plate-bound pab1949-1 or an $IgG_1$ isotype control antibody (0, 0.3, 1, 3, 6, 12, 25, or 50 µg/ml) for 4 days at 37° C. and 5% $CO_2$. After activation, cell culture supernatant was collected for detection of cytokines using the Human TH1/TH2 10-Plex tissue culture kit (Meso Scale Discovery).

Figures 5B, 5C, 5D:
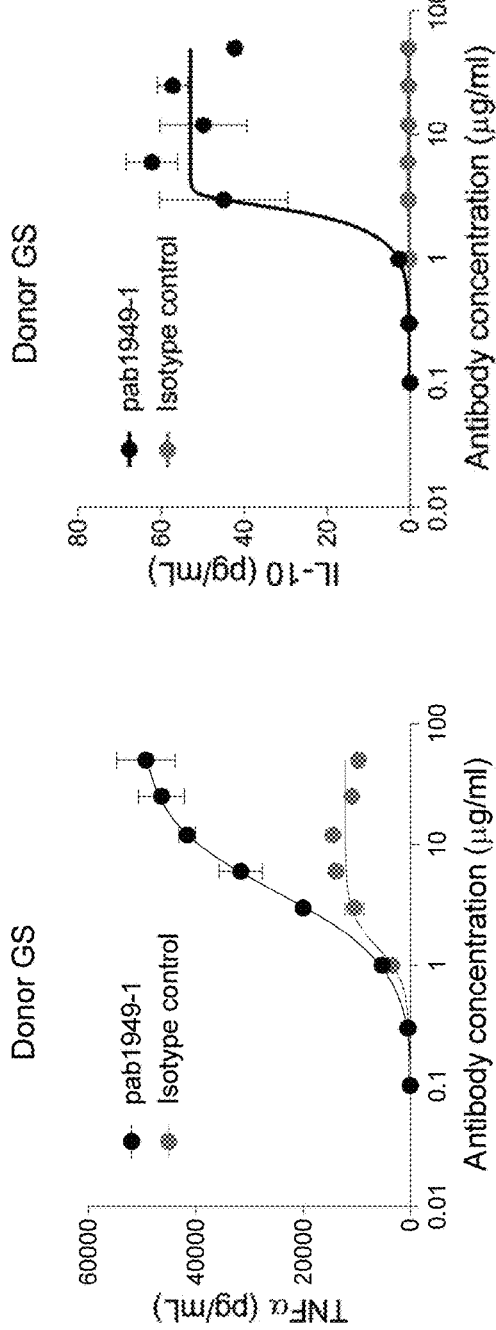

As shown in FIGS. 5B-5D, the anti-OX40 antibody pab1949-1 stimulated TNFα, IL-10, and IL-13 production in a dose-dependent manner.

The co-stimulatory activity of pab1949-1 in inducing cytokine secretion was further confirmed using cells derived from PBMCs of additional donors. Briefly, PBMCs were incubated with plate-bound anti-CD3 antibody (0.8 µg/ml) and plate-bound pab1949-1 or an IgG$_1$ isotype control antibody (0, 0.7, 1.6, 3.1, 6.3, 12.5, 25, or 50 µg/ml) for 4 days at 37° C. and 5% CO$_2$. After activation, the amount of cytokines secreted to the supernatant was measured using the non-human primate (NHP) V-Plex assay kit (Meso Scale Discovery).

Figure 6A:
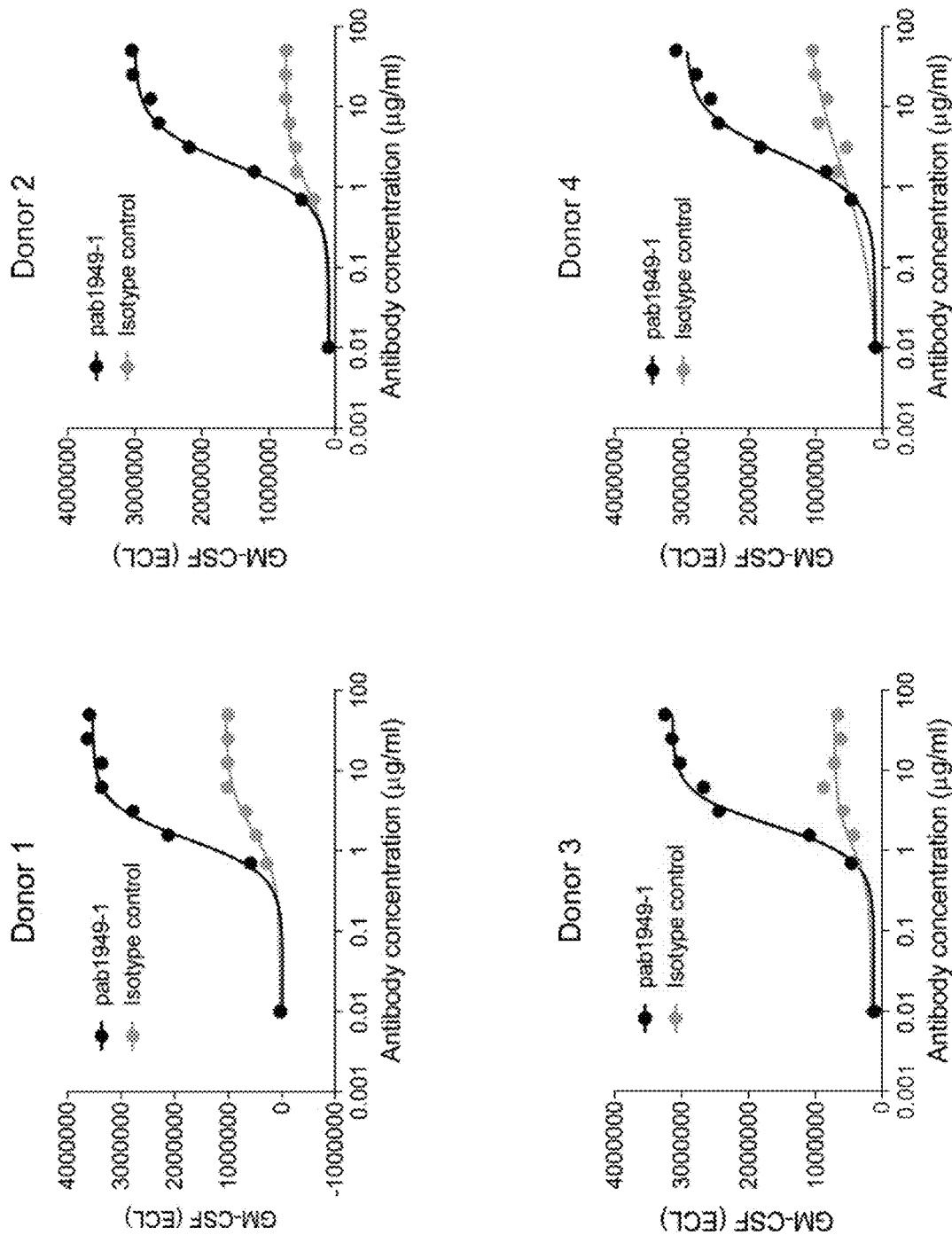
Figure 6B:
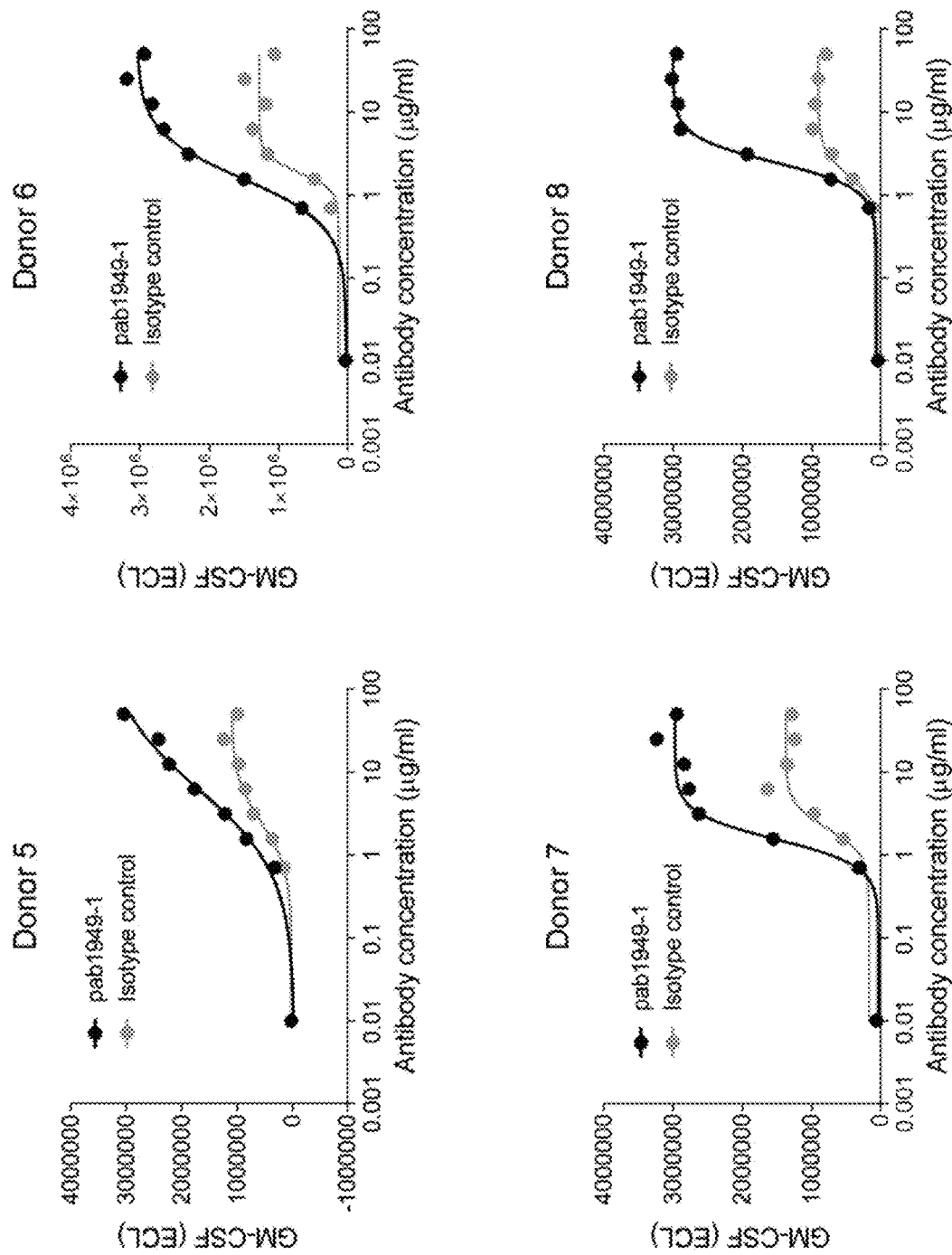
Figure 6C:
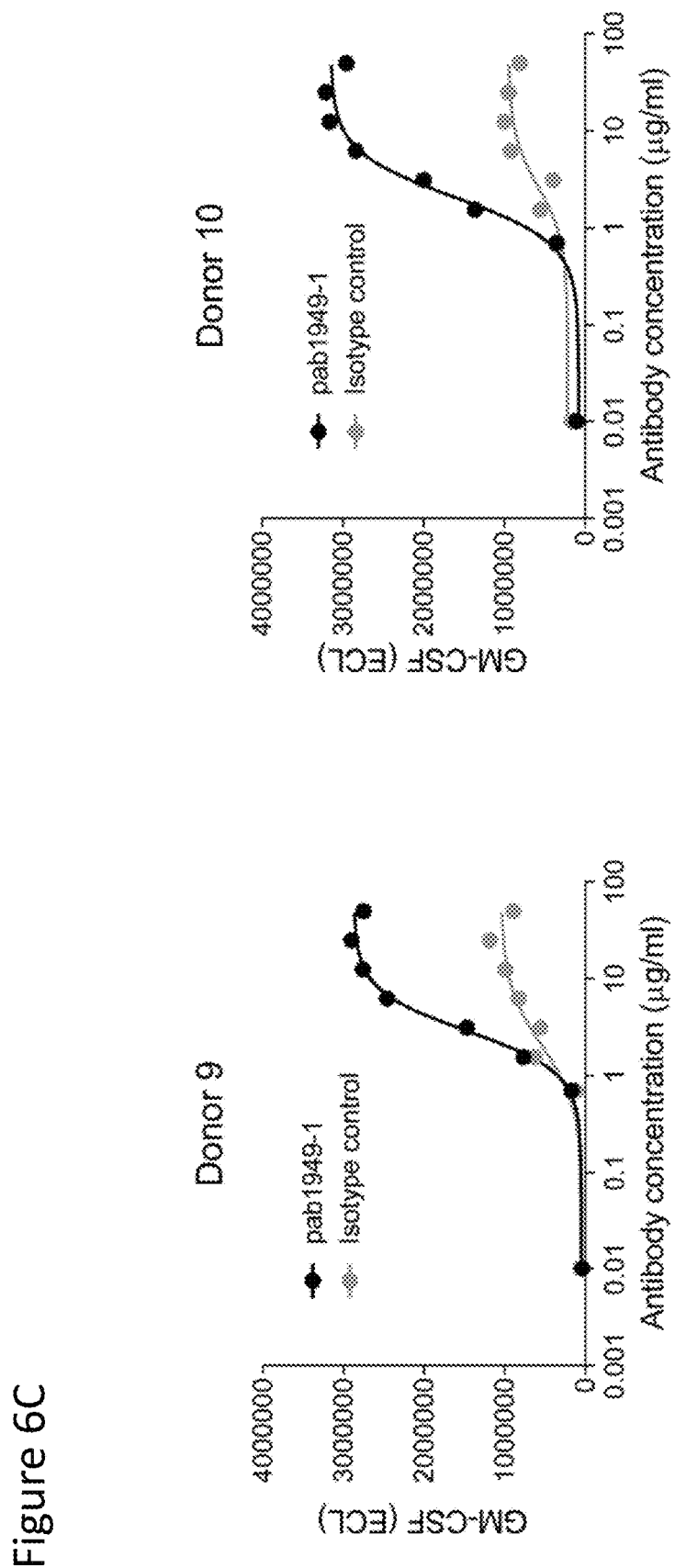
Figure 7A:
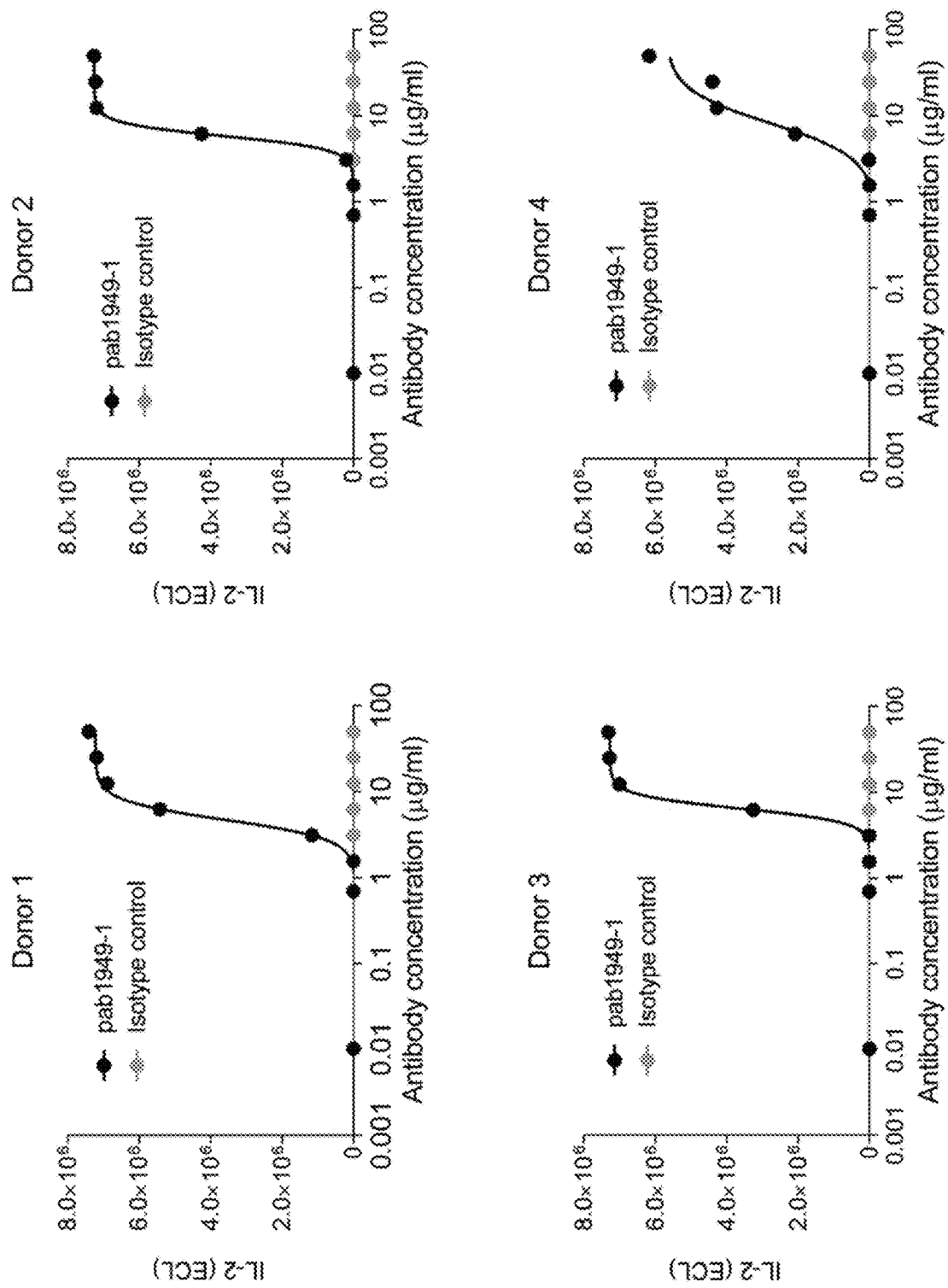
Figure 7B:
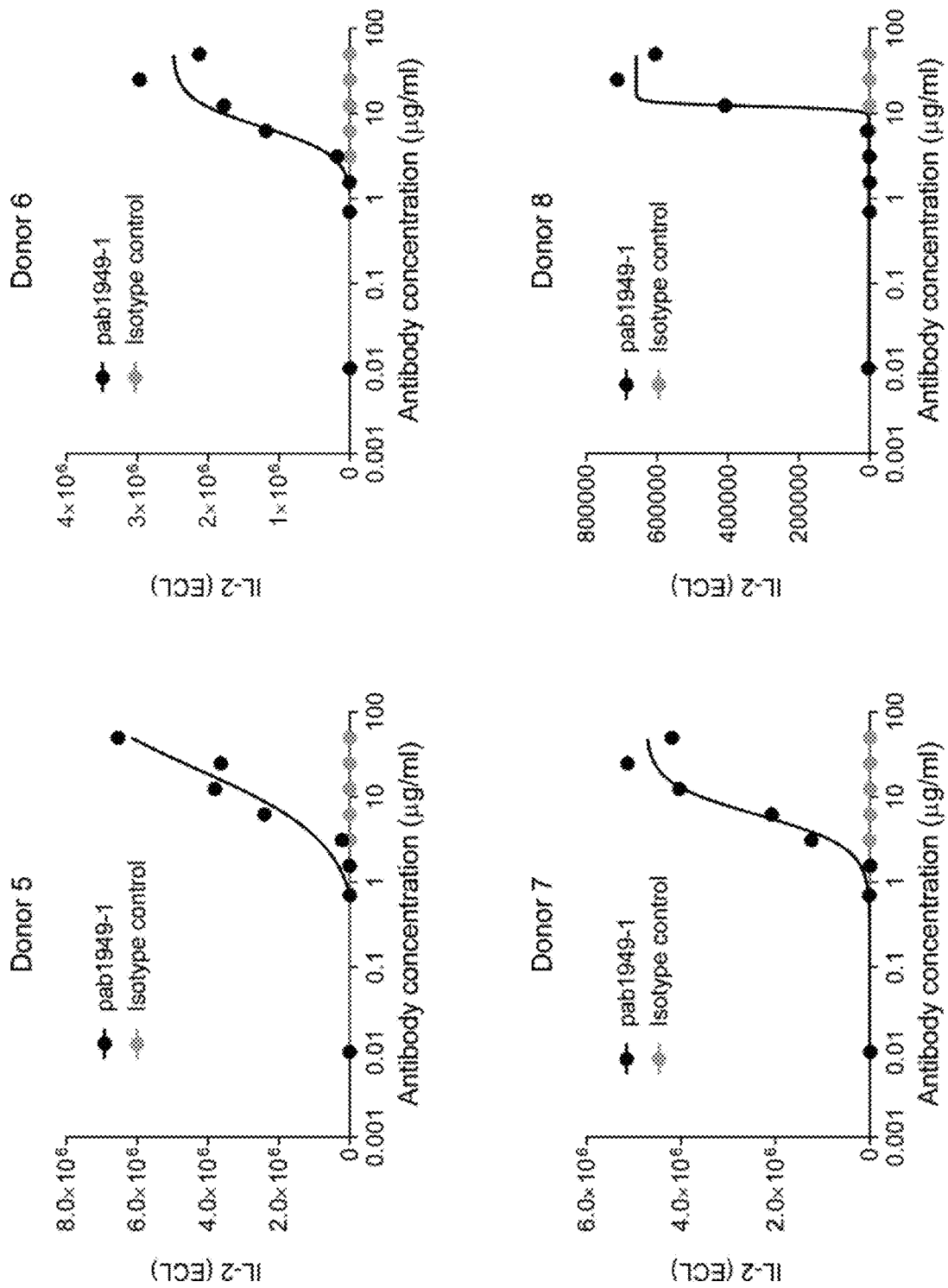
Figure 7C:
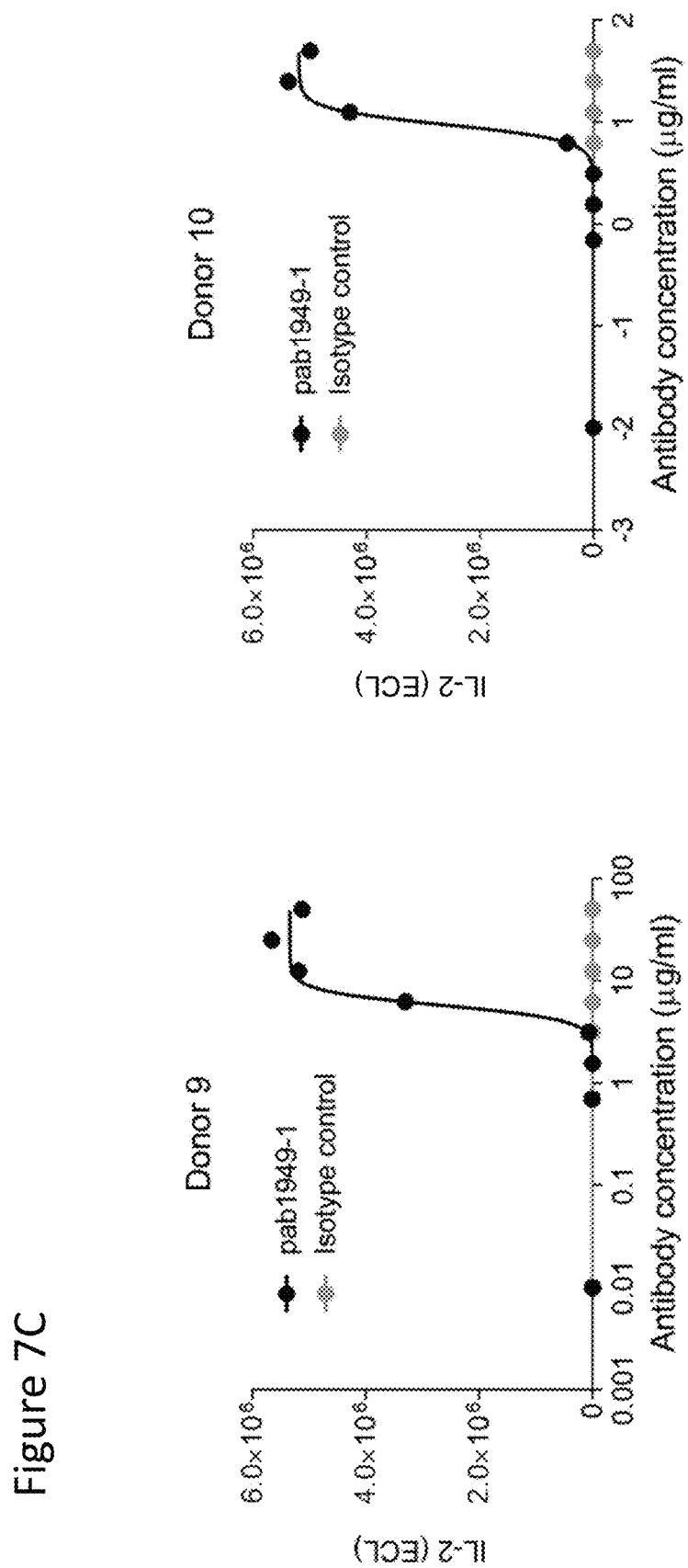
Figure 8A:
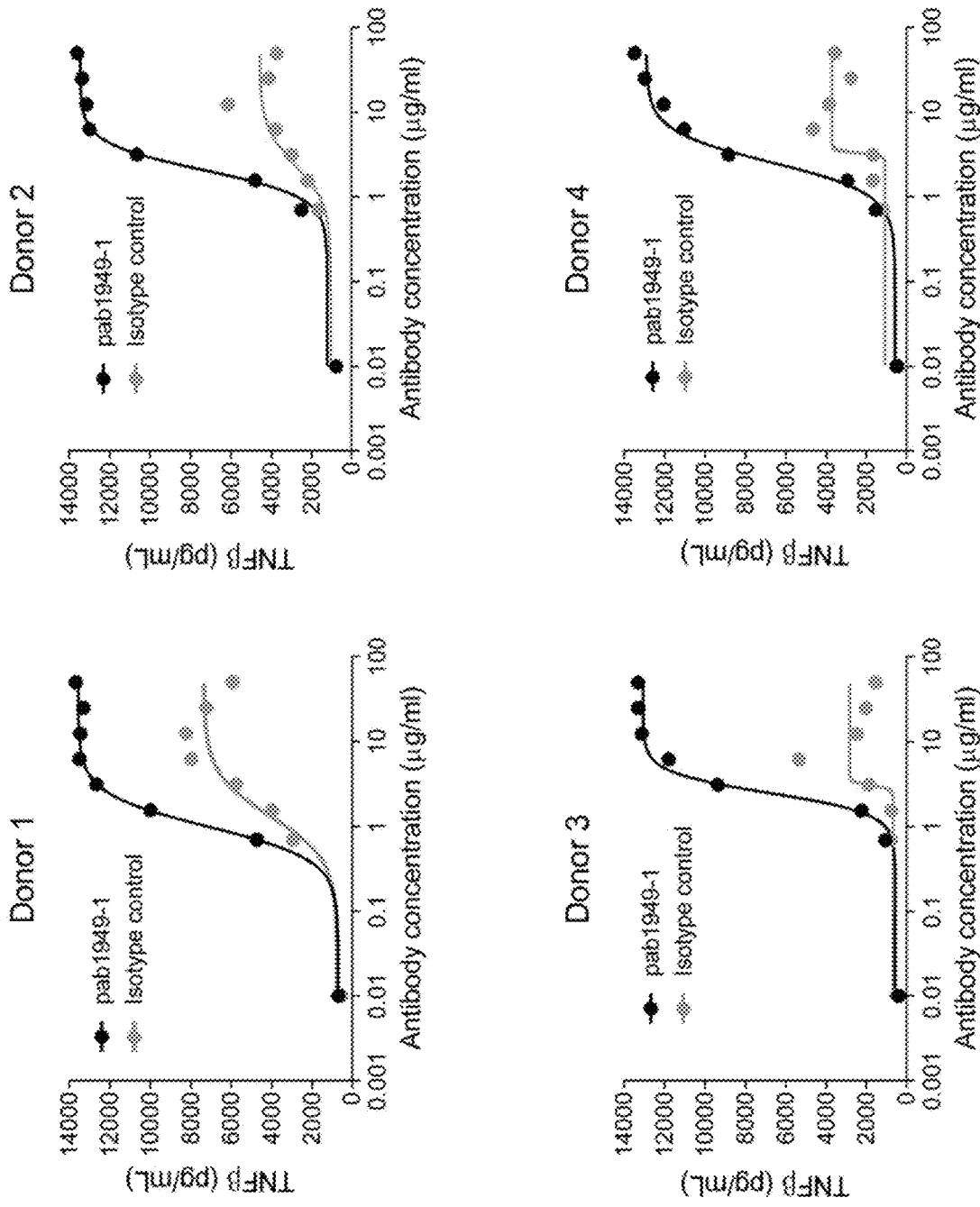
Figure 8B:
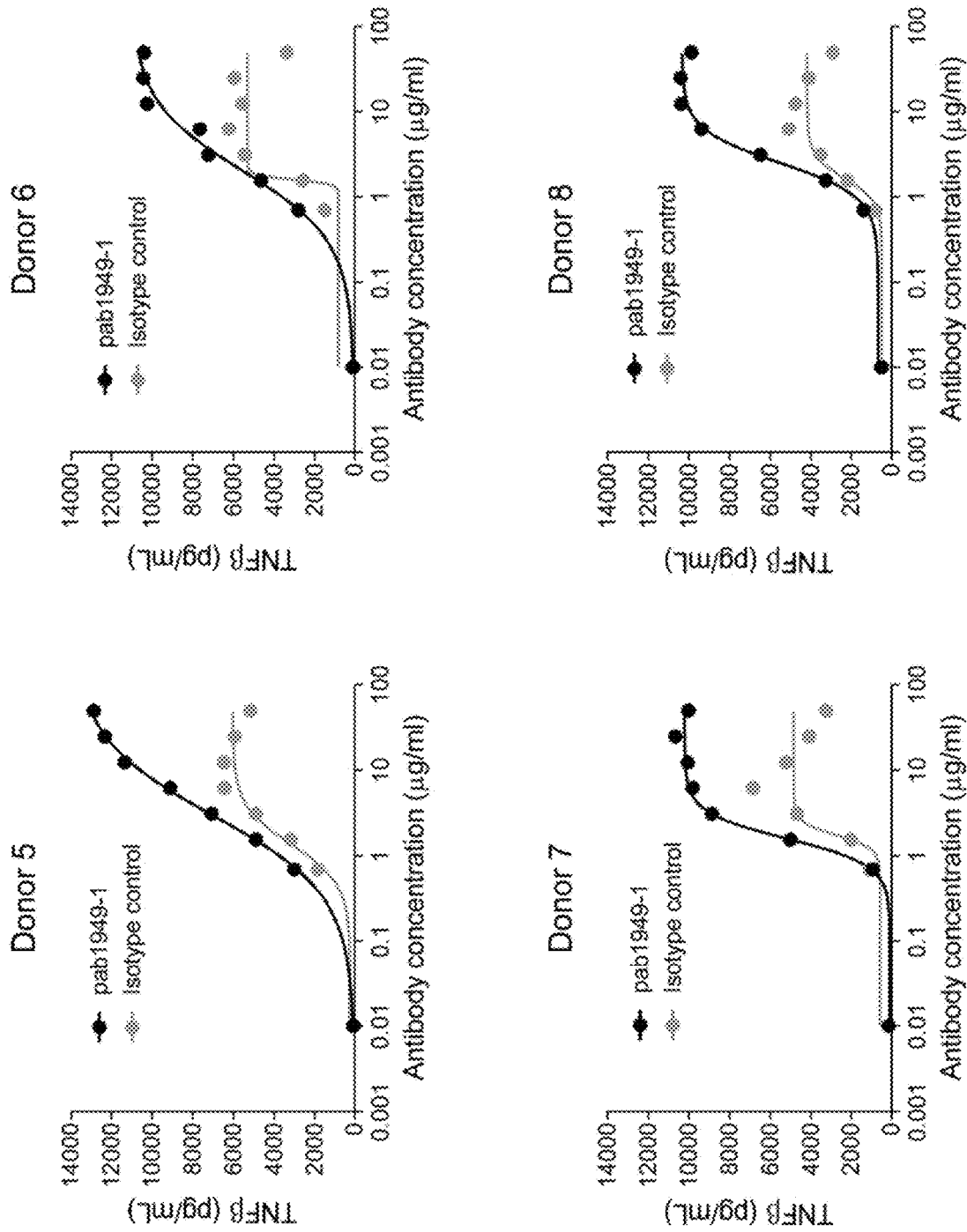
Figure 8C:
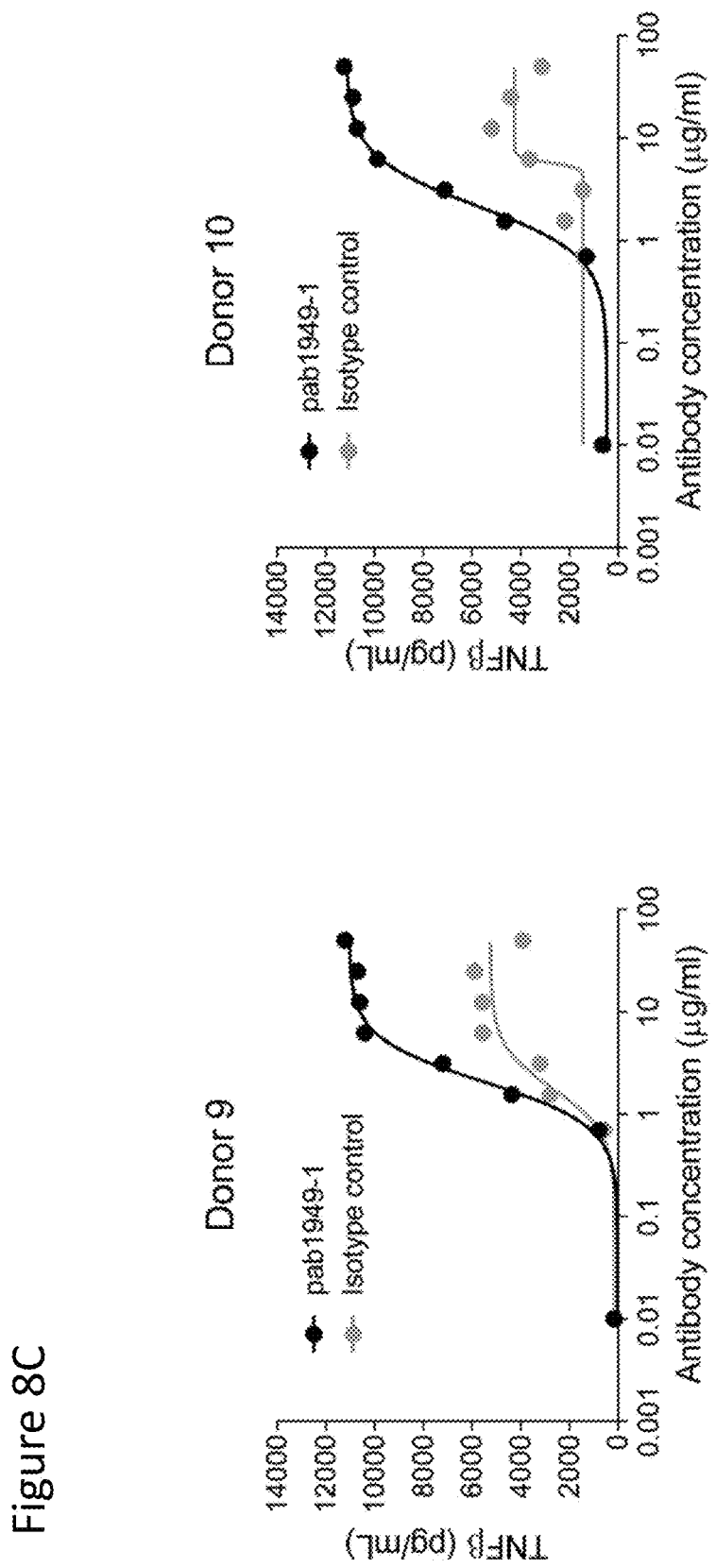

For all the donors tested, pab1949-1 dose-dependently increased the secretin of GM-CSF (FIGS. 6A-6C), IL-2 (FIGS. 7A-7C), and TNFβ (FIGS. 8A-8C).

For PBMCs from many donors, the secretion of cytokines (GM-CSF, IL-2, TNFα, TNFβ, IL-10, and IL-13) induced by the anti-OX40 antibody pab1949-1 was a substantially increasing function of antibody concentration across a wide range of antibody concentrations (FIGS. 5B-5D, 6A-6C, 7A-7C, and 8A-8C).

6.2.3 Effect of Anti-OX40 Antibody in a T Effector Cell: T Regulatory Cell Co-Culture Assay Next, the anti-OX40 antibody pab1949-1 was examined for its activity in a T effector cell (Teff): T regulatory cell (Treg) co-culture assay. In brief, human PBMCs isolated via Ficoll gradient from healthy donor buffy coats (Research Blood Components, LLC) were stored in liquid nitrogen and thawed on the day of the experiment. T regulatory cells and T effector cells were isolated by magnetic bead separation (CD4$^+$CD25$^+$CD127$^{dim/-}$ Regulatory T Cell Isolation Kit II and Pant T cell kit, respectively, Miltenyi Biotec). T regulatory cells were then activated for 2 days by incubating with anti-CD3/anti-CD28/anti-CD2 beads (Miltenyi Biotec) at a ratio of 1:2 (T cell:bead) in cell culture media (RPMI+10% FBS). After activation, T regulatory cells and T effector cells were added to 96-well culture plates at a 1:3 (Treg:Teff) ratio in the presence of anti-CD3/anti-CD28/anti-CD2 beads, soluble or crosslinked (using anti-Fc F(ab')$_2$, Jackson ImmunoResearch) pab1949-1 or an IgG$_1$ isotype control (10 µg/ml). The samples were incubated for 4 days at 37° C. and 5% CO$_2$. After activation, the supernatant was collected and IL-10 or IL-2 was measured using AlphaLISA® (Perkin Elmer).

Figure 9A:
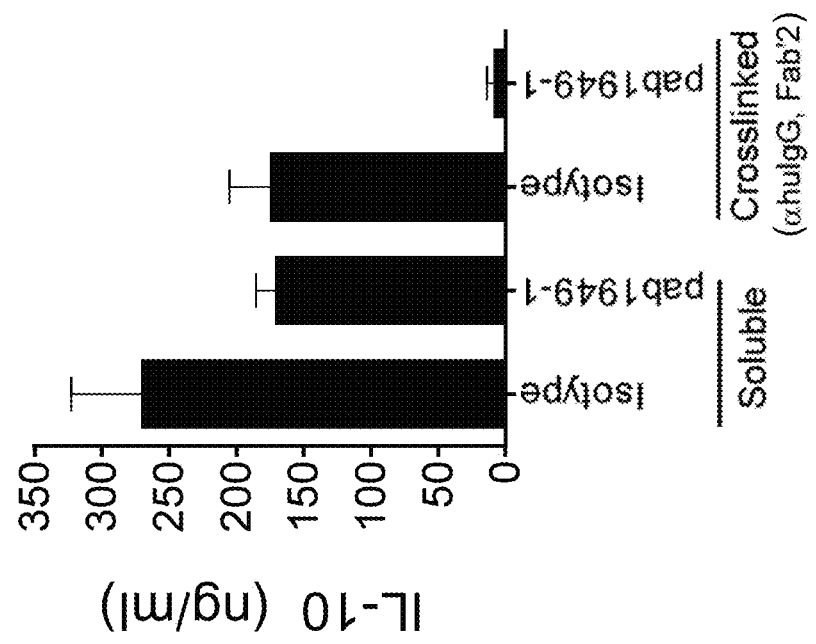
Figure 9B:
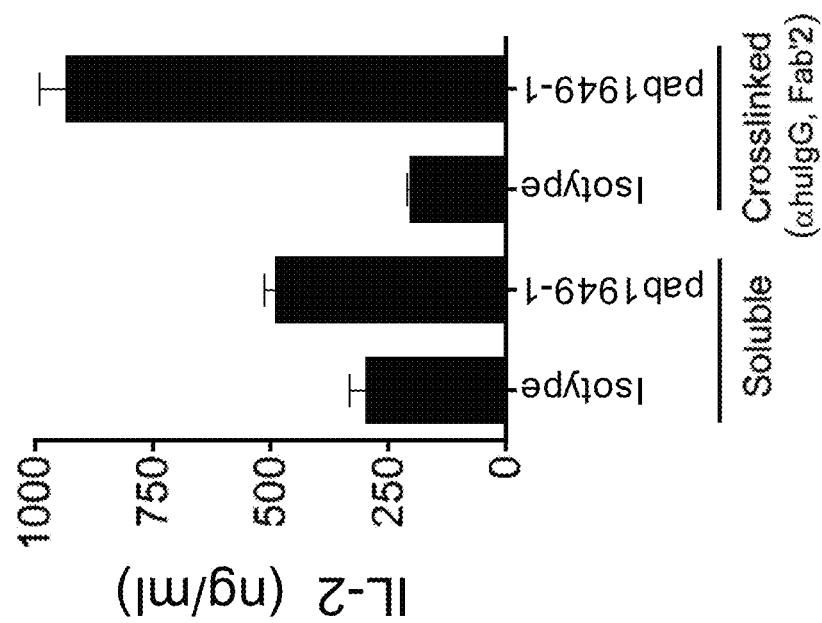

In this in vitro Teff:Treg co-culture assay, the anti-OX40 antibody pab1949-1 relieved suppression of Teff cell populations by Treg cells, as evidenced by enhanced IL-2 production (FIG. 9A) and reduced IL-10 production (FIG. 9B) from pab1949-1-treated cells as compared with isotype-treated cells.

6.2.4 Effect of Anti-OX40 Antibodies on Human PBMCs Upon *Staphylococcus* Enterotoxin A (SEA) Stimulation The functional activity of the anti-OX40 antibodies pab1949 and pab1949-1 on primary human PBMCs was further assessed following *Staphylococcus* Enterotoxin A (SEA) stimulation. Cryopreserved PBMCs (10$^5$ cells/well) in RPMI1640 supplemented with penicillin, streptomycin and 10% FBS (Hyclone) were added to 96-well NUNCLON delta surface plates (NUNC™). The cells were cultured in the absence or presence of a fixed concentration (10 µg/ml in FIGS. 10A and 10B) or varying concentrations (20, 4, 0.8, 0.16, 0.032, 0.0064, and 0.00128 µg/ml in FIGS. 10C and 10D; 50, 10, 2, 0.4, 0.08, 0.016, and 0.0032 µg/ml in FIG. 10E) of anti-OX40 antibody or isotype control and 100 ng/ml of SEA (Toxin Technologies) for 5 days at 37° C., 5% CO$_2$ and 97% humidity. Clarified supernatant was collected and stored at −80° C. until analysis. The titers of cytokines were generated using electrochemiluminescence (Meso Scale Discovery) for IL-2 and IL-10.

Figure 10A:
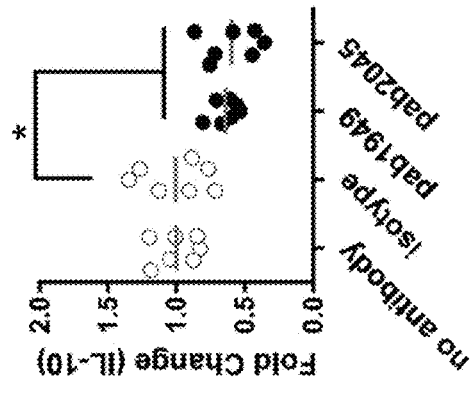
Figure 10B:
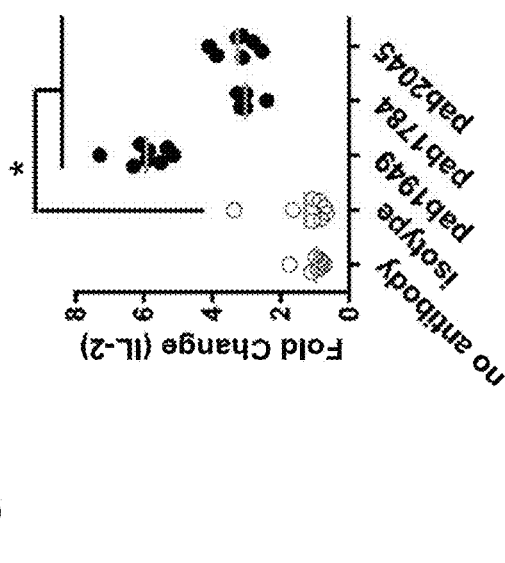
Figure 10C:
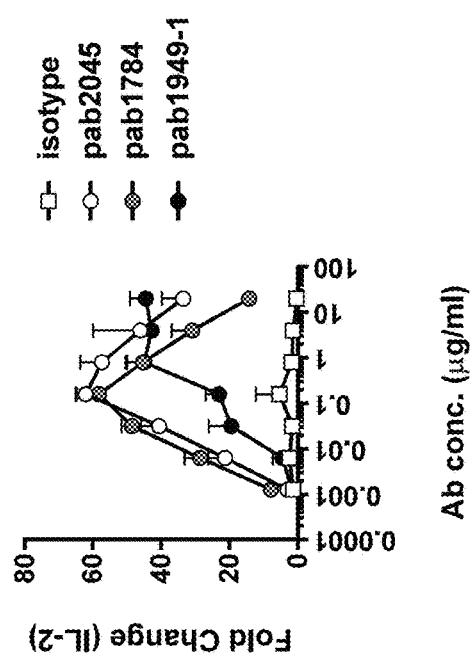
Figure 10D:
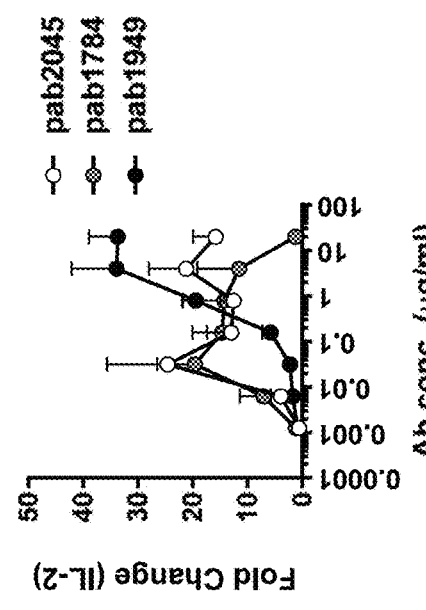

The anti-OX40 antibody pab1949 showed agonistic activity in this primary human PBMC assay, inducing IL-2 production (FIG. 10A) and suppressing IL-10 production (FIG. 10B). The enhancement of IL-2 production by pab1949 at 10 µg/ml was superior to that observed with the reference anti-OX40 antibodies pab1784 and pab2045 (FIG. 10A). FIGS. 10C, 10D, and 10E are dose-response curves from three independent experiments showing the fold change of IL-2 following costimulation with different concentrations of pab1949, pab1949-1, or the reference antibodies pab1784 and pab2045. The antibodies pab1949 and pab1949-1 exhibited a different dose-response relationship from the reference antibodies and were able to induce high levels of IL-2 production at pharmacologically relevant antibody concentrations. IL-2 production induced by pab1949 or pab1949-1 was a substantially increasing function of antibody concentration across a wide range of antibody concentrations (e.g., between 0.032 and 20 µg/ml, as shown in FIGS. 10C and 10D, or between 0.0032 and 50 µg/ml, as shown in FIG. 10E).

Next, the functional activity of the IgG$_1$ antibody pab1949-1 and the IgG$_2$ antibody pab2193-1 was compared in the primary human PBMC assay described above. Briefly, cryopreserved human PBMCs (Research Blood Components) were plated at 10$^5$ cells/well in RPMI1640 medium supplemented with Normocin™ (Invivogen, # ant-nr) and 10% heat-inactivated FBS (Gibco, Invitrogen Corporation) in 96-well NUNCLON delta surface plates. Cells were incubated with increasing concentrations (50, 10, 2, 0.4, 0.08, 0.016, and 0.0032 µg/ml) of pab1949-1, pab2193-1, an IgG$_1$ isotype control antibody, or an IgG$_2$ isotype control antibody, and 100 ng/ml SEA superantigen (Toxin Technologies) for 5 days at 37° C., 5% CO$_2$, and 97% humidity. Clarified supernatant was collected and stored at −80° C. until analysis. Concentrations of IL-2 were measured by ELISA.

Figure 10F:
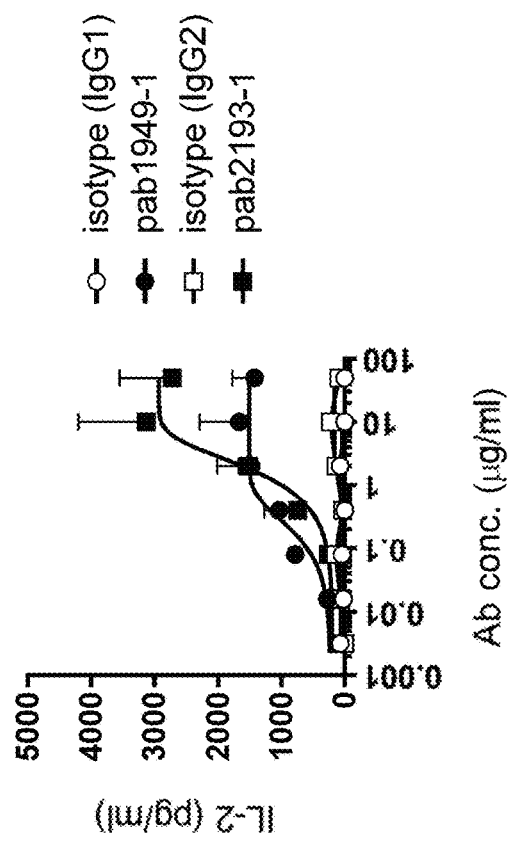
Figure 10E:
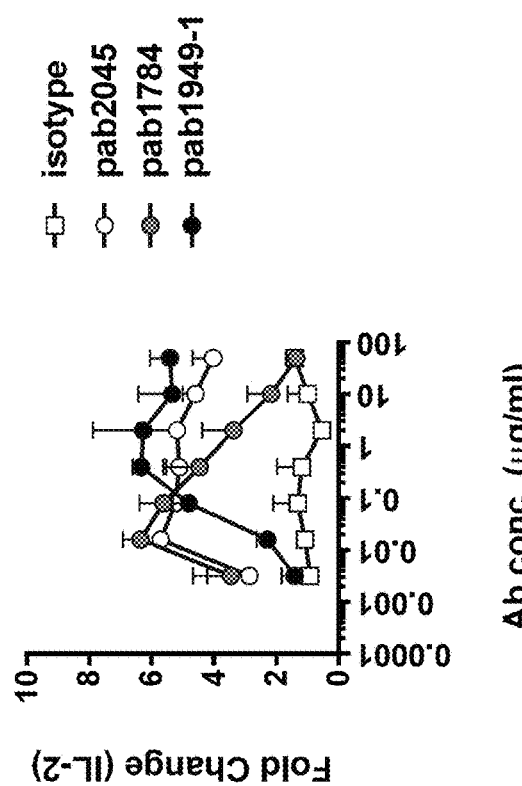

As shown in FIG. 10F, both the IgG$_1$ antibody pab1949-1 and the IgG$_2$ antibody pab2193-1 induced IL-2 production in human PBMCs. Similar to pab1949-1, pab2193-1 also exhibited a dose-response relationship in which the IL-2 production was a substantially increasing function of antibody concentration.

Further, the role of FcγR interaction in the functional activity of the anti-OX40 antibody pab1949-1 was examined by comparing the IgG$_1$ antibody pab1949-1 with an aglycosylated variant pab1949-1-N297A. pab1949-1-N297A shares the heavy chain variable region and light chain sequences with pab1949-1 but comprises an N297A substitution in the heavy chain constant region, numbered according to the EU numbering system.

Human PBMCs isolated via Ficoll gradient from healthy donor buffy coats (Research Blood Components, LLC) were stored in liquid nitrogen and thawed on the day of the experiment. The cells were resuspended in cell culture media (RPMI+10% heat-inactivated FBS) and incubated with 100 ng/ml SEA (Toxin Technologies) and a dose titration of pab1949-1, pab1949-1-N297A, or an IgG$_1$ isotype control antibody (0-50 µg/ml) for 5 days at 37° C. and 5% CO$_2$. The supernatant were collected and then tested for IL-2 using AlphaLISA® (Perkin Elmer).

Figure 10G:
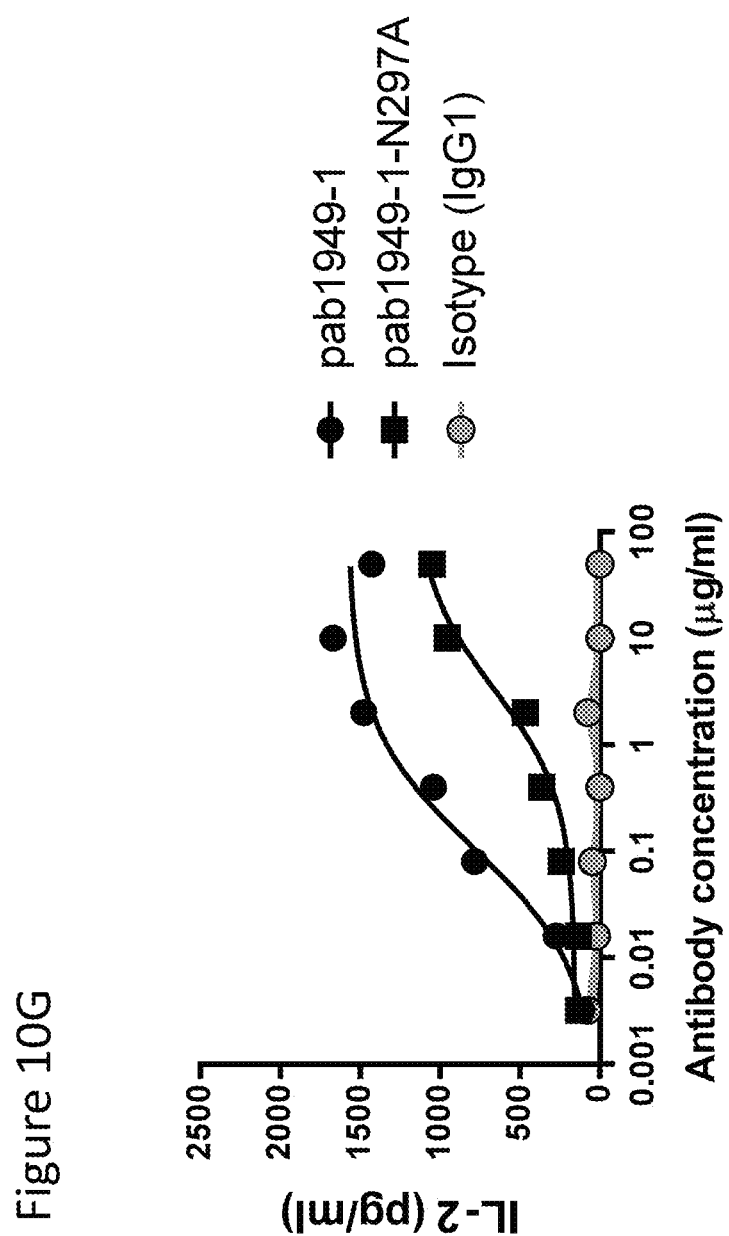

As shown in FIG. 10G, both pab1949-1 and pab1949-1-N297A induced IL-2 production in a dose-dependent manner in human PBMCs upon SEA stimulation. The presence of a key glycosylation at a single N-linked glycosylation site at asparagine 297 (N297) is lost on the pab1949-1-N297A variant antibody leading to loss of binding of its Fc fragment to FcγRs. This variant antibody exhibited reduced agonistic activity compared with the wild type counterpart.

6.2.5 Effect of Agonistic Anti-OX40 Antibody on OX40 NF-κB-Luciferase Reporter Cell Line The ability of the anti-OX40 antibody pab1949-1 to mediate signal transduction in T cells was measured using a human OX40 NF-κB-luciferase reporter cell line. The reporter cells generated using a Jurkat cell line were resuspended in assay media (RPMI+10% FBS+Penicillin/Streptomycin/Glutamate+1 µg/ml puromycin) and incubated with various concentrations of soluble pab1949-1 (0-6 µg/ml) or an $IgG_1$ isotype control antibody in the presence of an anti-Fc reagent (complexed condition) or not (soluble condition). Plates were incubated for 2 hours at 37° C. and 5% $CO_2$. After incubation, the plates were equilibrated at room temperature and then an equal volume of room temperature Nano-Glo reagent (Promega) was added. Luminescence was read using an EnVision multilabel reader 2100.

Figure 11A:
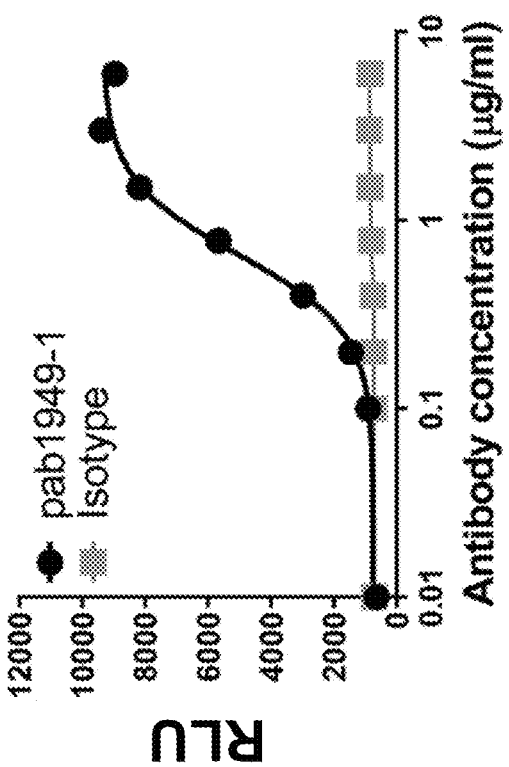
Figure 11B:
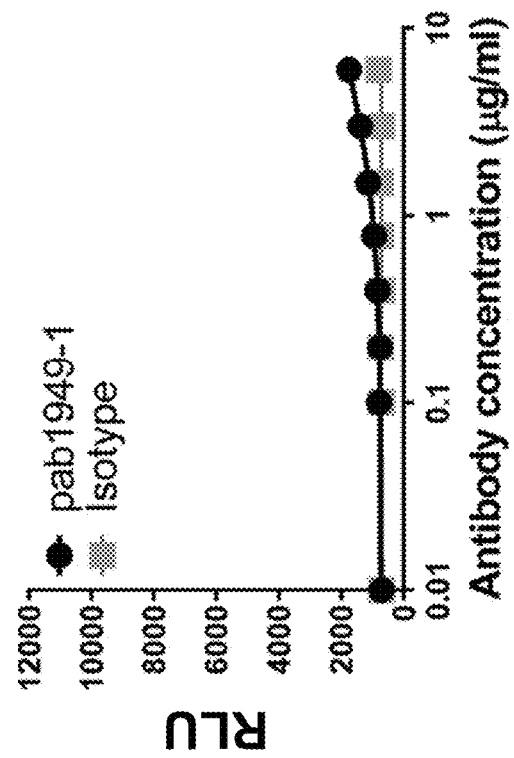

Only crosslinked pab1949-1 induced significant activation of the OX40 NF-κB-luciferase reporter cell line (FIG. 11B). Soluble pab1949-1 induced minimal activation of the reporter cell line and the $IgG_1$ isotype control antibody did not induce detectable levels of luciferase expression (FIGS. 11A and 11B).

6.2.6 Effect of Agonistic Anti-OX40 Antibody on Fc Gamma Receptor IIIA Reporter Cell Line In this example, the ability of the $IgG_1$ antibody pab1949-1 and the $IgG_4$ antibody pab2044-1 to co-engage OX40 and signal via activating Fc gamma receptors was evaluated using a reporter cell line expressing Fc gamma receptor IIIA together with target cells expressing human OX40. Jurkat NFAT-luciferase reporter cells overexpressing FcγRIIIA (158 V/V polymorphism) (Promega) were used as effector cells. Binding of antibody/antigen complex, wherein the antigen is located on the surface of target cells, to FcγRIIIA on effector cells signals to the promoter/reporter construct and results in luciferase gene expression.

OX40-overexpressing cells (PHA-activated Hut102 cells) were co-cultured with the FcγRIIIA reporter cells in the presence of a dose titration of soluble pab1949-1, pab2044-1, an $IgG_1$ isotype control, or an $IgG_2$ isotype control (0-10 µg/ml). Activation of the reporter cells was assessed according to the manufacturer's instructions and the relative light units (RLU) were recorded. Δ RLU was calculated as the RLU of the anti-OX40 antibody minus that of the isotype control. As shown in FIG. 12A, when bound to OX40-expressing cells, only the $IgG_1$ antibody pab1949-1 activated the FcγRIIIA reporter cells.

6.2.7 Effect of Agonistic Anti-OX40 Antibody on Fc Gamma Receptor IIA Reporter Cell Line Next, the ability of the $IgG_1$ antibodies pab1949-1 and pab1949-1-S267E/L328F as well as the $IgG_2$ antibody pab2193-1 to co-engage OX40 and signal via FcγRIIA was evaluated using a reporter cell line expressing FcγRIIA (Promega) together with target cells (Jurkat cells expressing human OX40). pab1949-1-S267E/L328F shares the heavy chain and light chain sequences with pab1949-1 but comprises S267E and L328F substitutions in the heavy chain constant region, numbered according to the EU numbering system.

Jurkat cells expressing FcγRIIA with the high affinity 131 H/H polymorphism and an NFAT response element driving expression of firefly luciferase were used as effector cells. Briefly, 25 µl of target cells ($6 \times 10^6$ cells/ml) were mixed with 25 µl of serially diluted antibodies in duplicate wells of 96-well white assay plates. The antibodies tested were pab1949-1, pab1949-1-S267E/L328F, pab2193-1, an $IgG_1$ isotype control antibody, and an $IgG_2$ isotype control antibody. Then, 25 µl of effector cells ($6 \times 10^6$ cells/ml) were added to each well, resulting in a 1:1 effector to target ratio. The plates were incubated for 20 hours at 37° C. and 5% $CO_2$. After this incubation, Bio-Glo Luciferase Assay Reagent (Promega) was thawed at room temperature and 75 µl was added to each well. Within 5-10 minutes, luminescence was measured using the EnVision multilabel plate reader (PerkinElmer). Background luminescence was subtracted from each sample reading and the adjusted relative light units (RLU) were recorded.

Figure 12B:
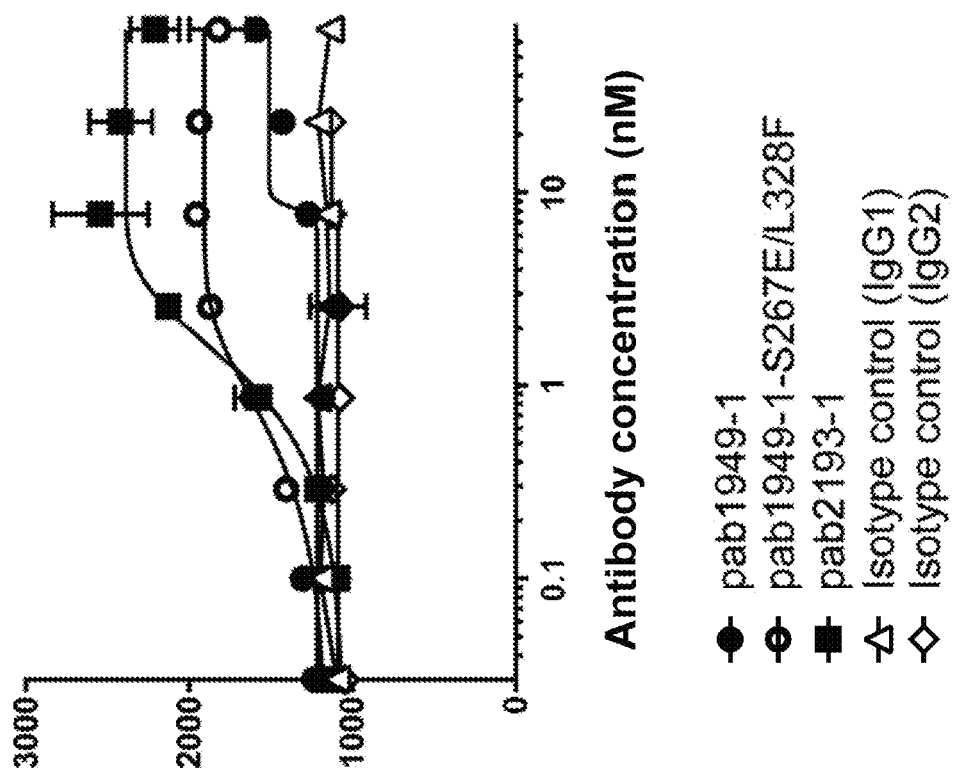
Figure 12A:
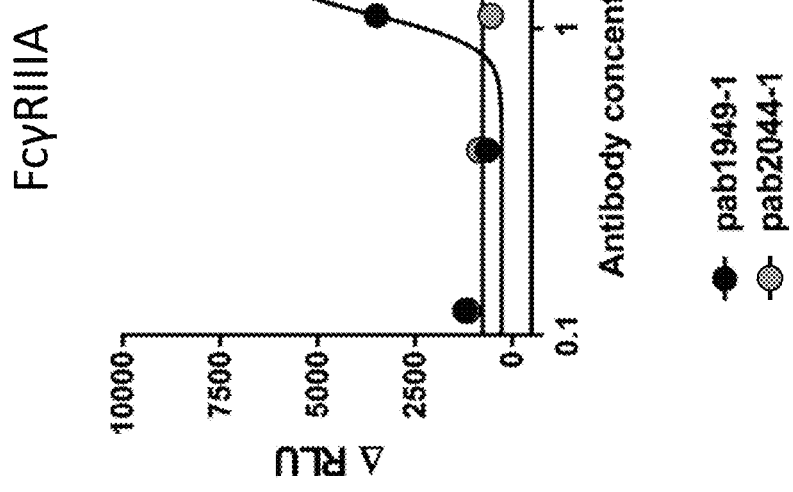

As shown in FIG. 12B, when bound to cells expressing OX40, the $IgG_2$ antibody pab2193-1 showed strongest activation of $FcγRIIA^{H131}$, followed by pab1949-1-S267E/L328F and pab1949-1.

6.2.8 Interaction of Anti-OX40 Antibody with T Regulatory Cells or T Effector Cells In this example, expression of human OX40 by activated natural T regulatory cells (nTreg) and T effector (Teff) cells was examined. PBMCs isolated from healthy donors were enriched for untouched CD3+ T cells (Teff) or CD4+ CD25+ CD45RA+ T cells (nTregs) using magnetic-based separation. T lymphocytes were activated with anti-CD3/CD28 coupled beads with 500 U rIL-2 for 4 days, and 50 U rIL-2 for an additional 4 days. Following 8 days of activation, T cells were harvested and stained with the live/dead fixable Near-IR dead cell stain in PBS for 20 minutes at 4° C. A surface antibody cocktail, containing the conjugated antibodies against CD4 (BV605, OKT4), CD8a (BV650, RPA-T8), CD127 (BV421, A01905), CD25 (APC, M-A251), and OX-40 (PE, ACT35) diluted in buffer (PBS with 2% FBS), was added to each sample and incubated for 30 minutes at 4° C. Cells were then washed with buffer and fixed and stained with an intracellular antibody cocktail, containing the conjugated antibodies against CD3 (BV711, OKT3) and Foxp3 (AF488, PCH101) diluted in buffer. One sample from each T cell population was also stained with fluorescence minus one (FMO) controls for OX40 using mouse anti-human IgG1-PE isotype control. Samples were analyzed by flow cytometry. PE-conjugated Quantibrite beads were run simultaneously and used to quantitate OX40 receptor density, as per manufacturer's instructions.

Figure 13B:
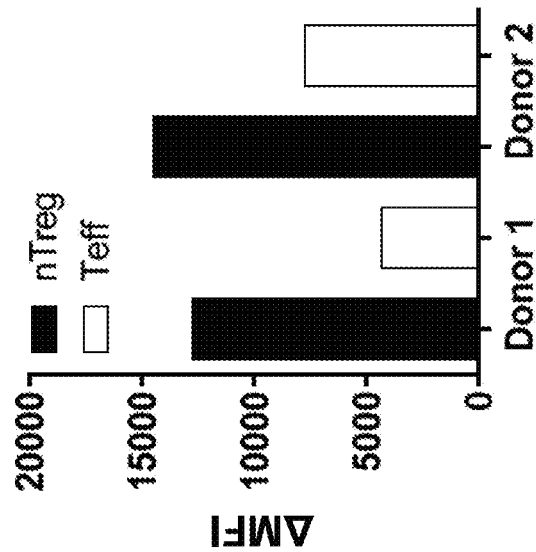
Figure 13A:
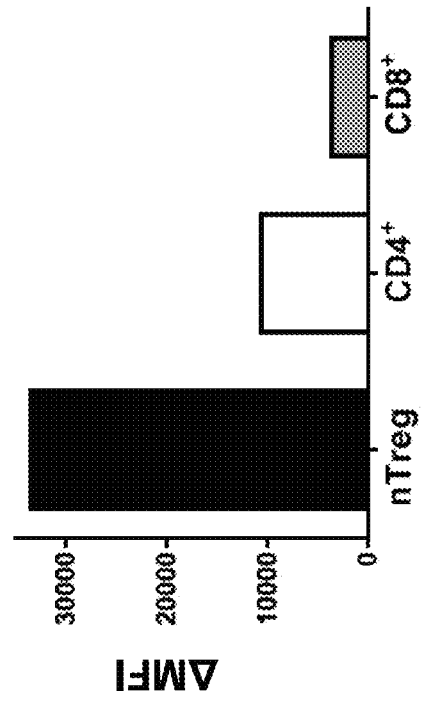

As shown in FIG. 13A, the surface expression of human OX40 on activated nTreg cells was higher than that on activated CD4+ or CD8+ T effector cells.

In a similar study, activated nTregs and Teffs from two donors were stained with a commercial anti-OX40 antibody (BER-ACT35 clone) or an isotype control antibody and analyzed by flow cytometry. Delta mean fluorescence intensity (Δ MFI) represents the MFI of the anti-OX40 antibody minus that of the isotype control. The results are shown in FIG. 13B.

Next, the ability of the anti-OX40 antibody pab1949 to co-engage OX40 and signal via activating Fc gamma receptors was evaluated using the reporter cell line expressing Fc gamma receptor IIIA (FcγRIIIA) described above together with activated T effector (Teff) or nTreg cells, generated as described. The anti-OX40 antibody pab1949 or an $IgG_1$ isotype control was serially diluted with 3-fold dilutions with a starting final concentration of 10 µg/ml. In duplicate wells, 25 µl of each antibody dilution was added to the Teff or nTreg cells. Jurkat NFAT-luciferase reporter cells overexpressing FcγRIIIA (158 V/V polymorphism) were added in a 1:1 effector to target ratio. Plates were incubated for 20 hours and then analyzed using a Bio-Glo Luciferase Assay Reagent (Promega). Background luminescence (blank outer wells) was subtracted from each sample reading and the adjusted relative light units (RLU) were recorded. Δ RLU is shown in FIG. 13C, representing the RLU of the anti-OX40 antibody minus that of the isotype control.

Figures 13C, 13D:
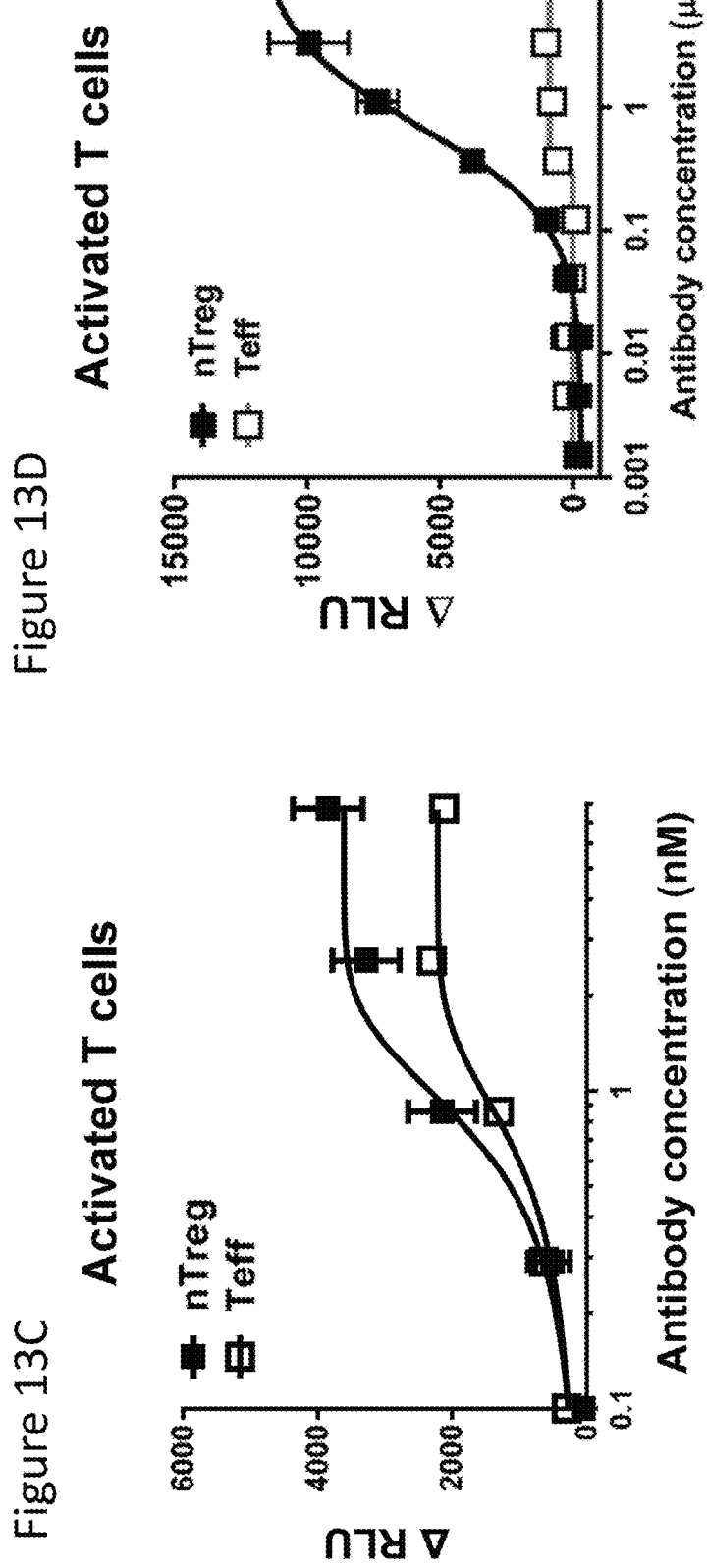

The study depicted in FIG. 13C was repeated using a slightly modified protocol. In brief, buffy coats from a healthy volunteer (Research Blood Components) were used for isolation of primary T regulatory cells and T effector cells. Both T cell subsets were purified by magnetic bead separation (CD4$^+$CD25$^+$CD127$^{dim/-}$ Regulatory T Cell Isolation Kit II and Pant T cell kit, respectively, Miltenyi Biotec) and then activated for 7 days by incubating the cells with anti-CD3/anti-CD28/anti-CD2 beads (Miltenyi Biotech) at a ratio of 1:4 (T cell:bead) in cell culture media (RPMI+10% FBS). Activated Treg cells or Teff cells were co-cultured with the FcγRIIIA-expressing Jurkat NFAT-luciferase reporter cells (Promega) described above in the presence of a dose titration of soluble pab1949-1 or an IgG$_1$ isotype control antibody (0-10 µg/ml). Activation of the reporter cells was assessed according to the manufacturer's instructions and Δ RLU is shown in FIG. 13D.

Consistent with the differential surface OX40 expression between activated nTregs and activated CD4+ or CD8+ T effector cells (FIGS. 13A and 13B), the anti-OX40 antibodies pab1949 (FIG. 13C) and pab1949-1 (FIG. 13D) preferentially labeled activated nTreg cells, inducing FcγRIIIA-dependent signaling in the reporter cell line.

Figure 14A:
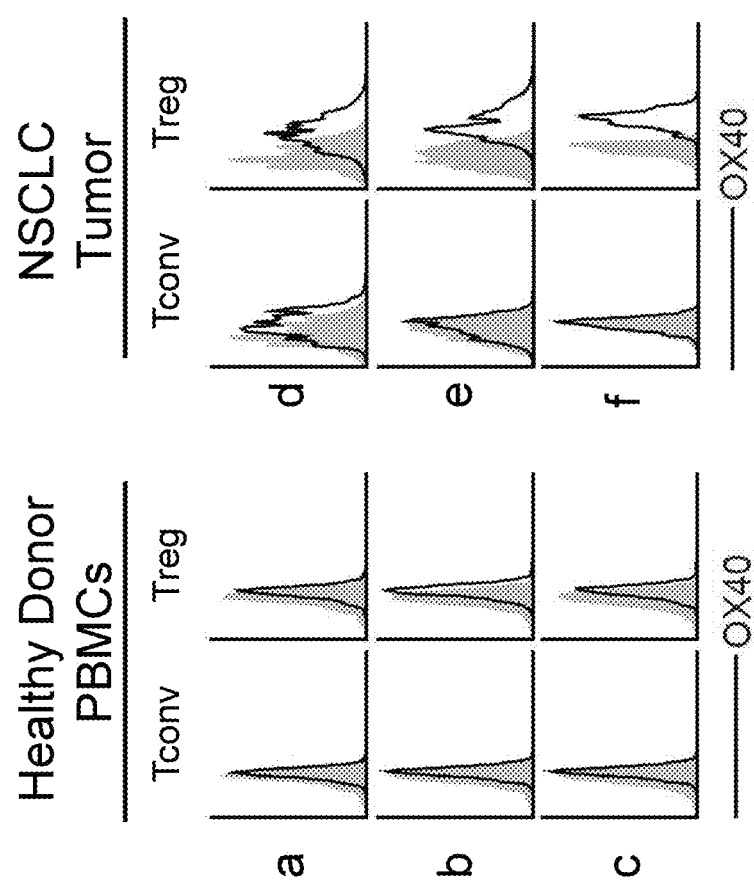

To evaluate if OX40 overexpression was a feature of regulatory T cells located within tumor microenvironment, OX40 expression was compared on T cells isolated from the blood of healthy human donors (FIG. 14A, a-c, n=3) or from tumor tissues of non-small cell lung cancer (NSCLC) patients (FIG. 14A, d-f, n=3). To eliminate background binding of antibodies to immune populations, all the cells were incubated with purified CD16/32 antibody (10 µg/ml, 20 minutes at room temperature) prior to the addition of cell-surface and intracellular antibodies. Following FcR-blockade, all the samples were incubated with APC-conjugated anti-OX40 antibody (clone Ber-ACT35) or isotype control and a cell-surface antibody lineage-cocktail (CD3-FITC, CD25-PECy7, CD4-BV650 and CD8a-PE) for 45 minutes on ice (1 µg/ml each), washed three times with FACS buffer (PBS, EDTA and 0.5% BSA), followed by fixation/permeabilization and incubation with Pacific Blue-conjugated FOXP3 (fix/perm and incubation each 45 minutes on ice, 1 µg/ml). The stained samples were then analyzed using an LSRFortessa flow cytometer (BD Biosciences). The cell populations in FIG. 14A were defined as: Tconv (CD3+, CD4+, CD8a−, CD25low, FOXP3−) or Treg (CD3+, CD4+, CD8a−, CD25high, FOXP3+).

As shown in FIG. 14A, OX40 surface expression was highest on regulatory T cells isolated from the tumor tissues of NSCLC patients, with little or no detectable level on Treg or conventional T cells from healthy donors.

Similar analyses were carried out for other tumor types. In brief, frozen dissociated tumor samples (Conversant) or PBMCs were thawed in AutoMACS Rinsing Solution (washing buffer, Miltenyi Biotec) and cells were Fc-blocked (Trustain FcX, Biolegend) before cell surface staining. Cells were washed with washing buffer and stained for 45 minutes at 4° C. with lineage marker antibodies that included: anti-CD3 (clone SP34), anti-CD4 (clone OKT4), anti-CD8 (clone SK1), anti-CD25 (clone MA-251), and anti-OX40 (clone BER-ACT35). Cells were washed and permeabilized with forkhead box P3 (FOXP3)/Transcription Factor Staining Buffer Set (eBioscience) according to the manufacturer's instructions. After permeabilization, the cells were stained with anti-FOXP3 eFluor450 (clone PCH101, eBioscience).

Stained samples were acquired using a BD Biosciences Fortessa flow cytometer and data were analyzed using Flojo software.

Figure 14B:
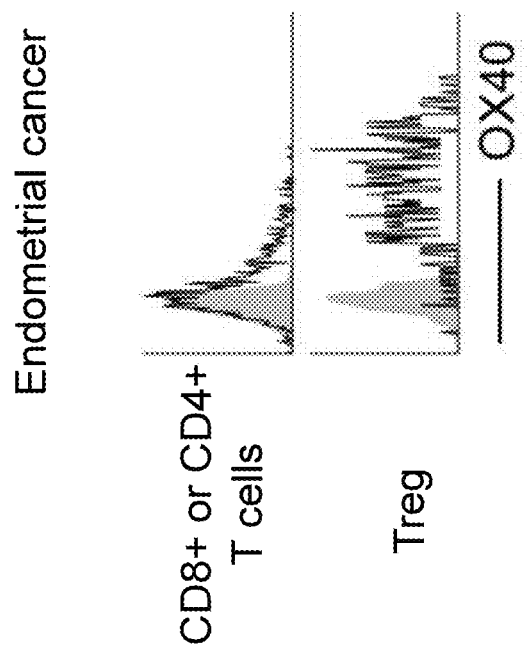
Figure 14C:
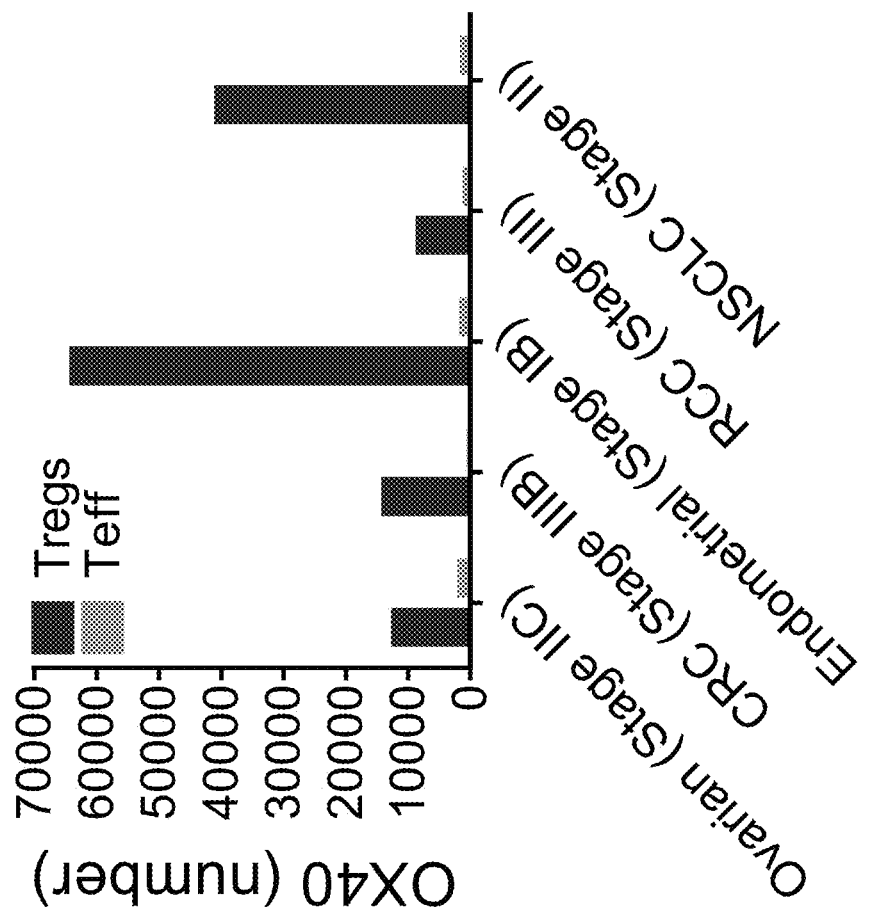

Samples from multiple tumor types, including ovarian cancer, colorectal carcinoma (CRC), endometrial carcinoma, renal cell carcinoma (RCC), non-small cell carcinoma (NSCLC), and breast cancer, demonstrated higher OX40 expression in tumor-associated T regulatory cells than in tumor-associated T effector cells (FIGS. 14B, 14C, and 14D).

6.2.9 Effect of Anti-OX40 Antibody on Anti-CD3 Stimulated Cynomolgus PBMC Cytokine Production Next, the agonistic activity of the anti-OX40 antibody pab1949-1 on cynomolgus PBMCs was examined using a suboptimal anti-CD3 stimulation assay. Briefly, frozen cynomolgus PBMCs (World Wide Primates) were stored in liquid nitrogen and thawed on the day of the experiment. The cells were resuspended in cell culture media (RPMI+10% FBS+20 U/ml of IL-2) and incubated with plate-bound anti-CD3 antibody (0.8 µg/ml) and plate-bound pab1949-1 or an IgG$_1$ isotype control antibody (0, 0.8, 1.6, 3.1, 6.3, 12.5, 25, or 50 µg/ml) for 4 days at 37° C. and 5% CO$_2$. Cell culture supernatant was collected and secreted cytokines were examined using the non-human primate (NHP) V-Plex assay kit (Meso Scale Discovery).

Figure 15A:
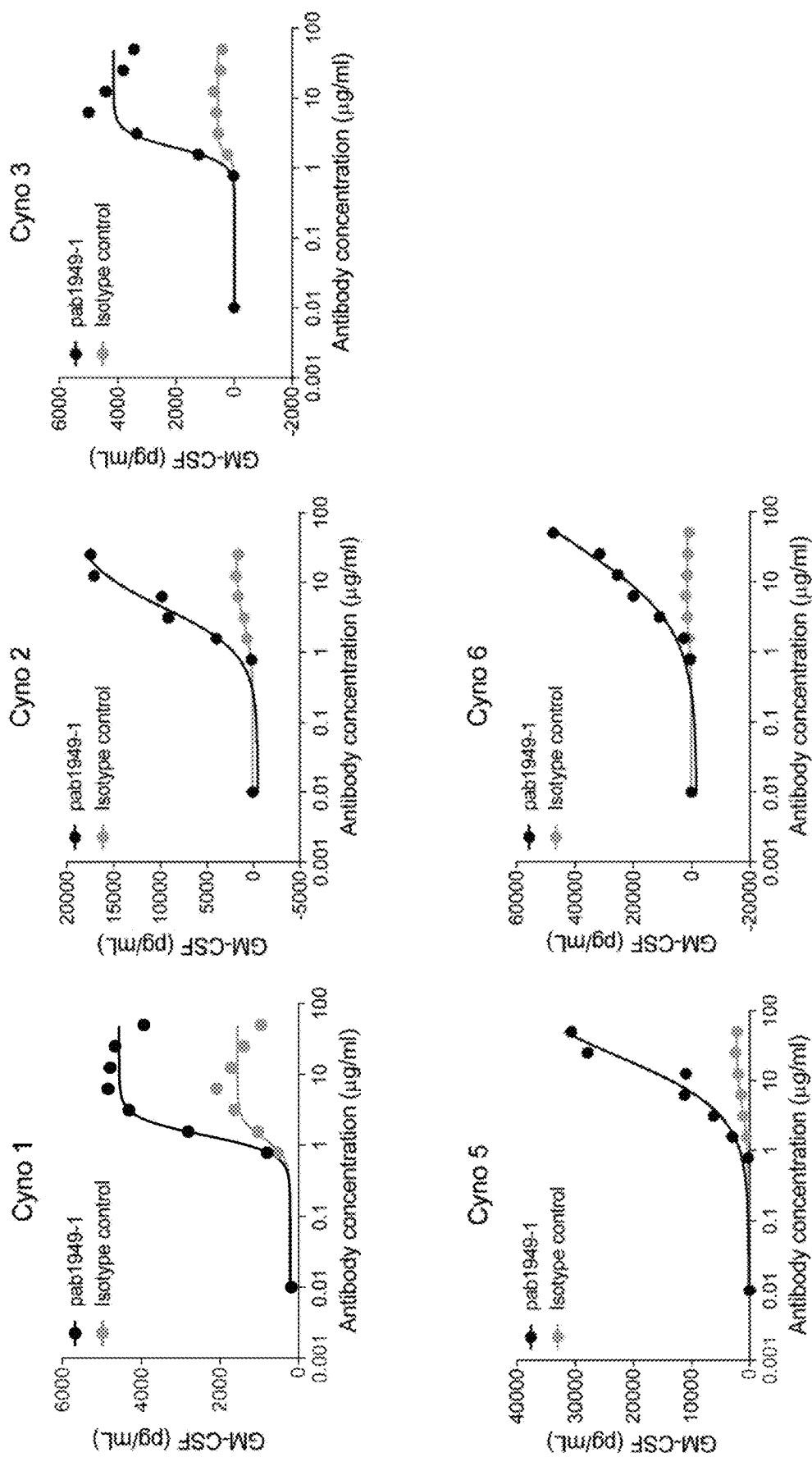
Figure 15B:
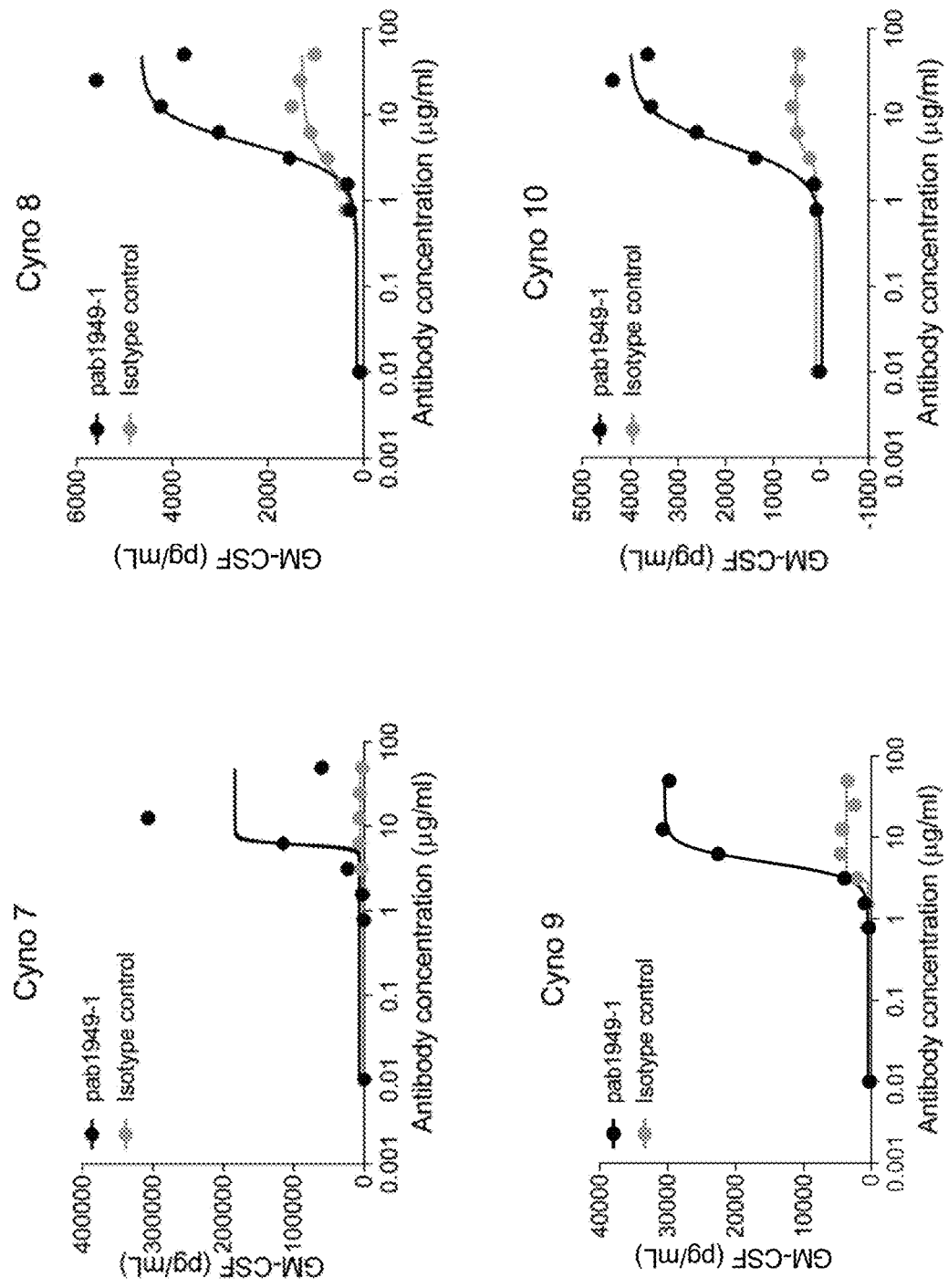
Figure 16A:
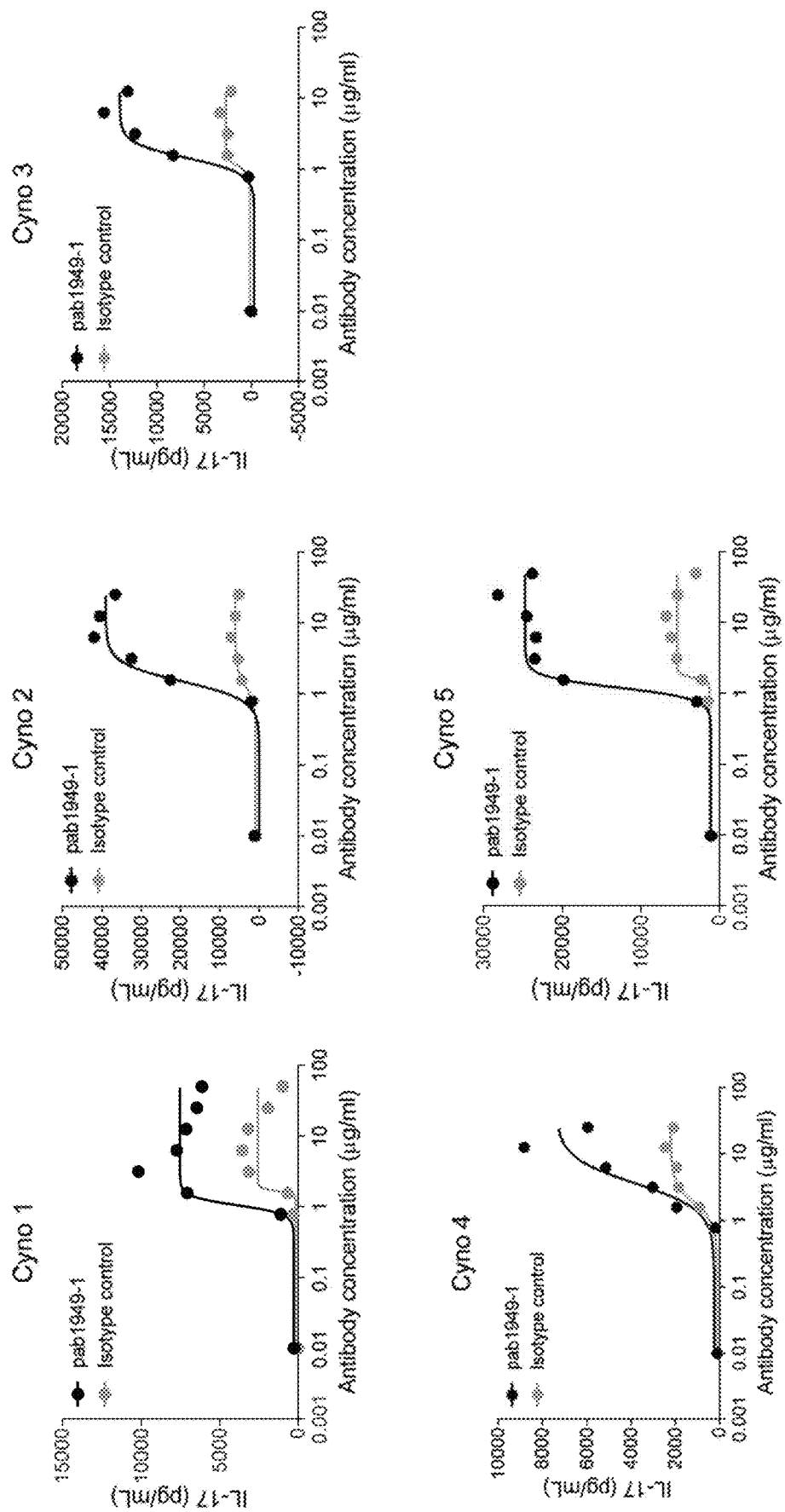
FIGS. 16A and 16B are similar to FIGS. 15A and 15B, showing the amount of secreted IL-17 induced by a dose titration of pab1949-1 or an IgG$_1$ isotype control antibody.
Figure 16B:
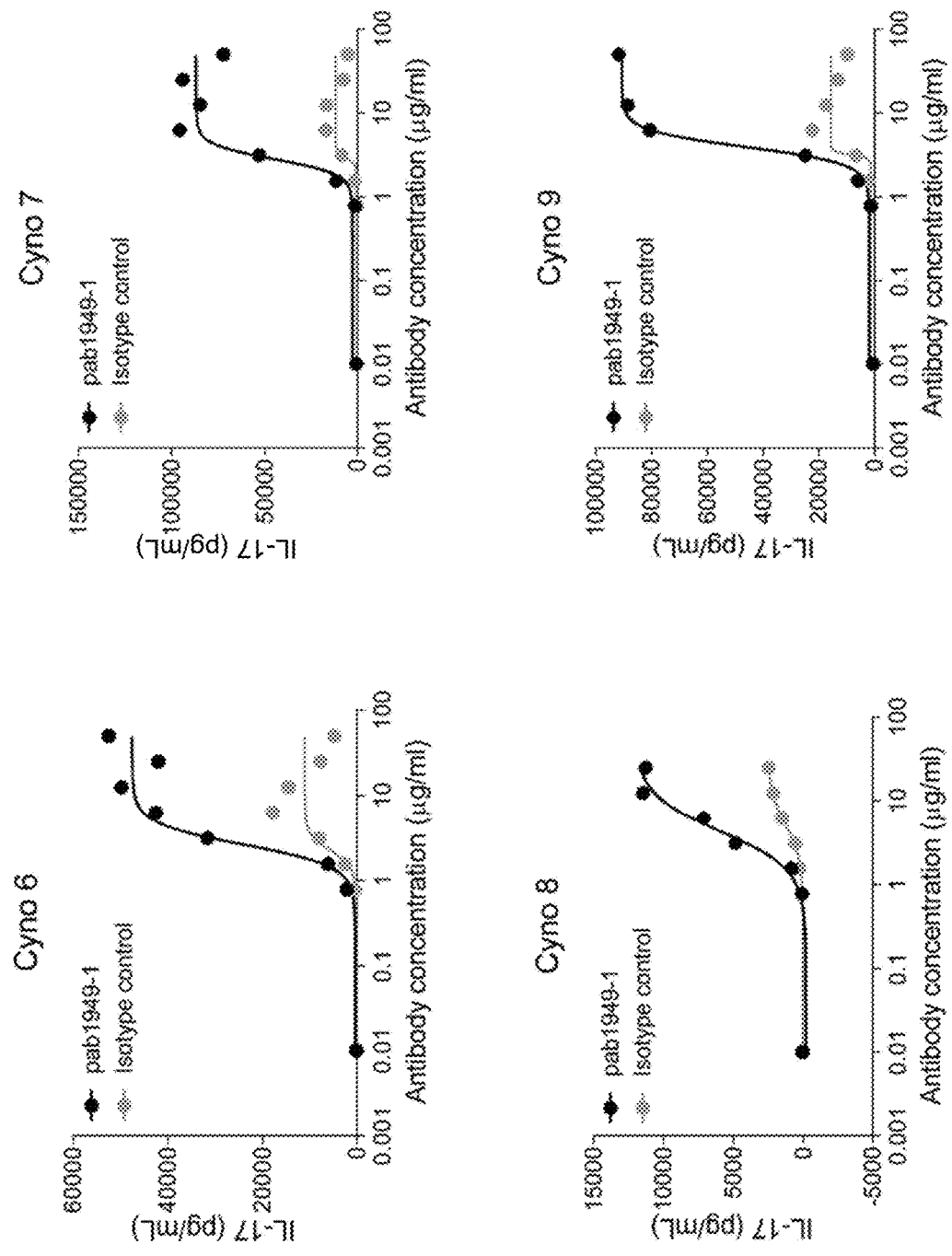
Figure 17A:
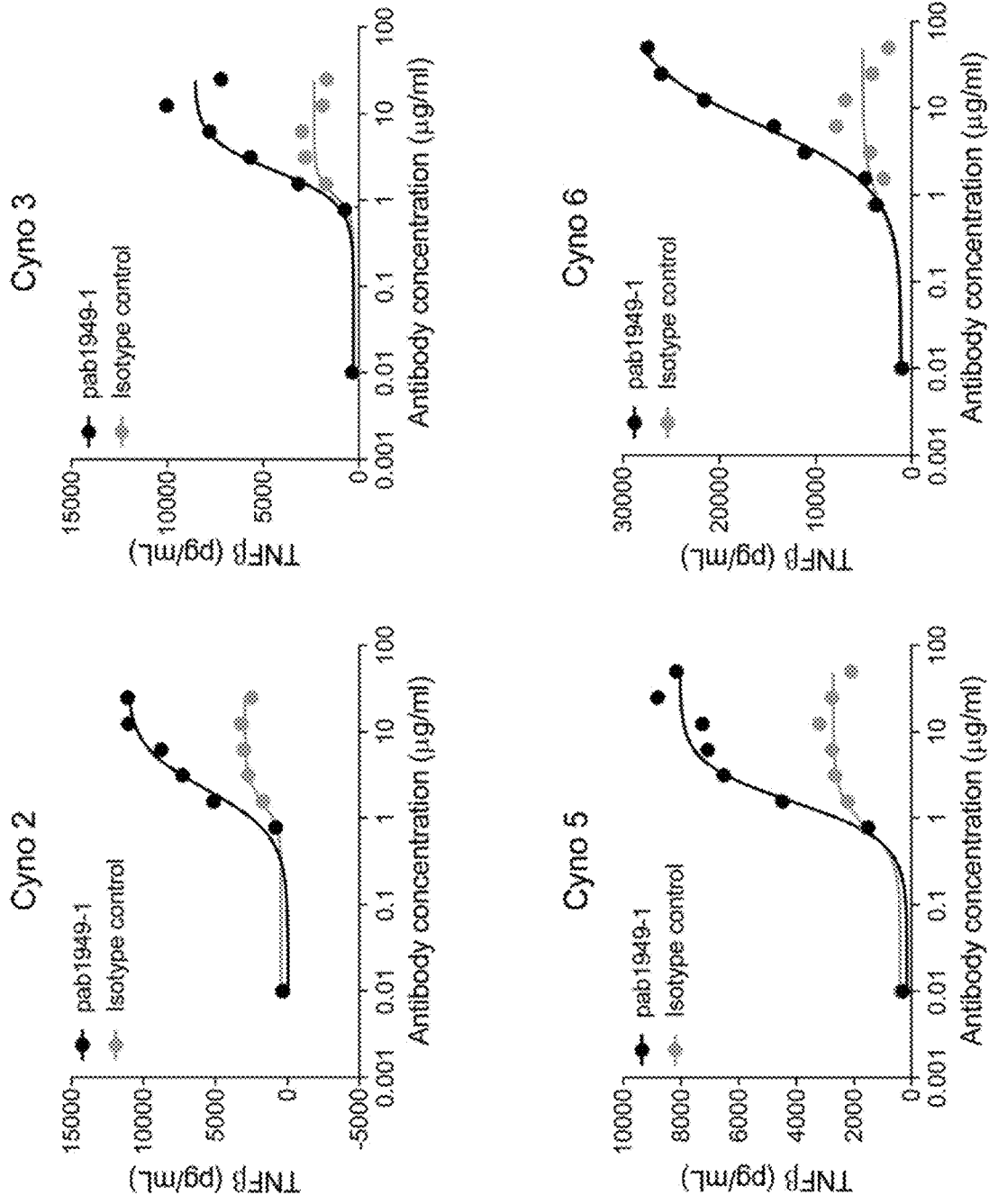
FIGS. 17A and 17B are similar to FIGS. 15A and 15B, showing the amount of secreted TNFβ induced by a dose titration of pab1949-1 or an IgG$_1$ isotype control antibody.
Figure 17B:
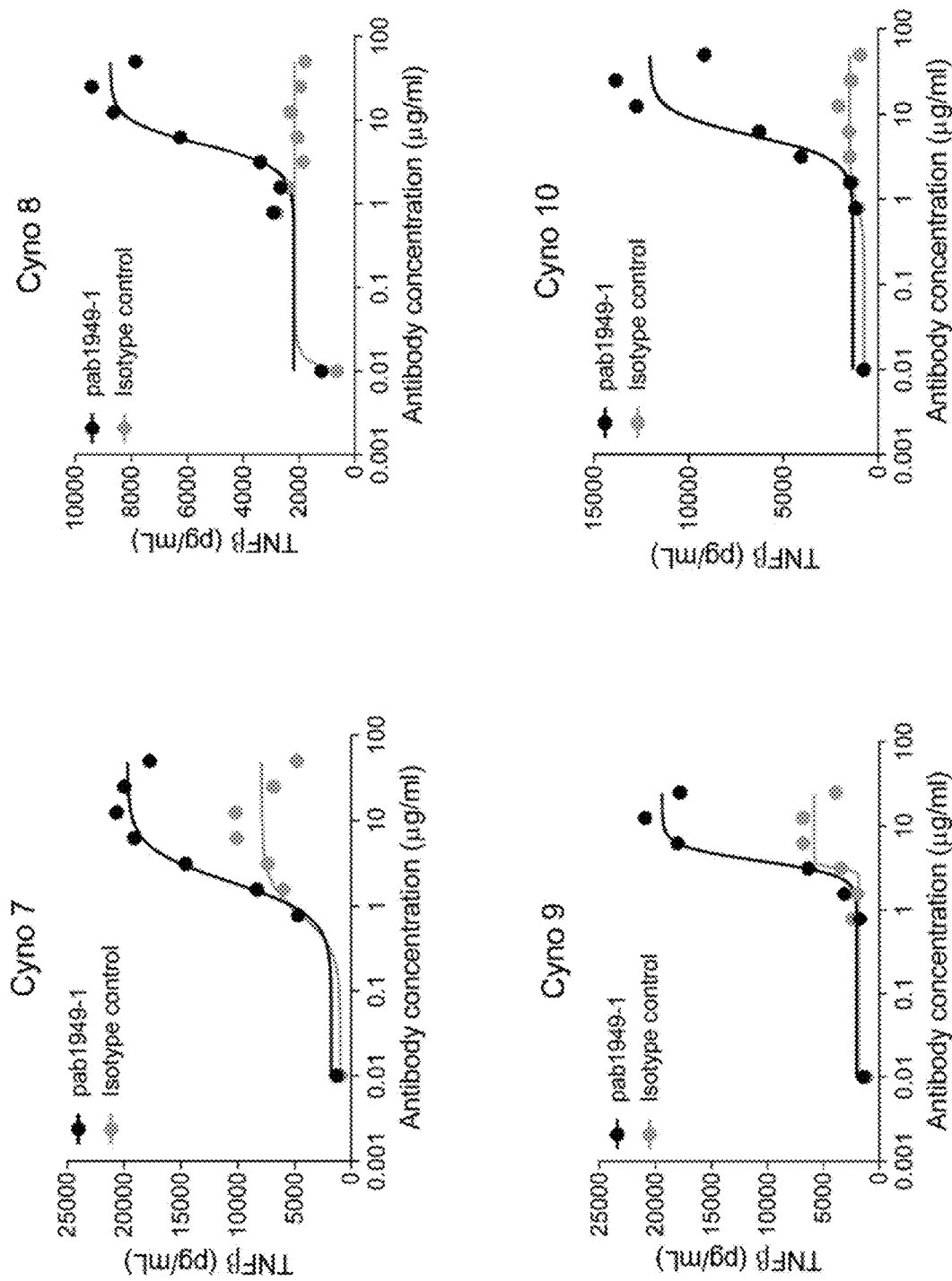
Figure 18A:
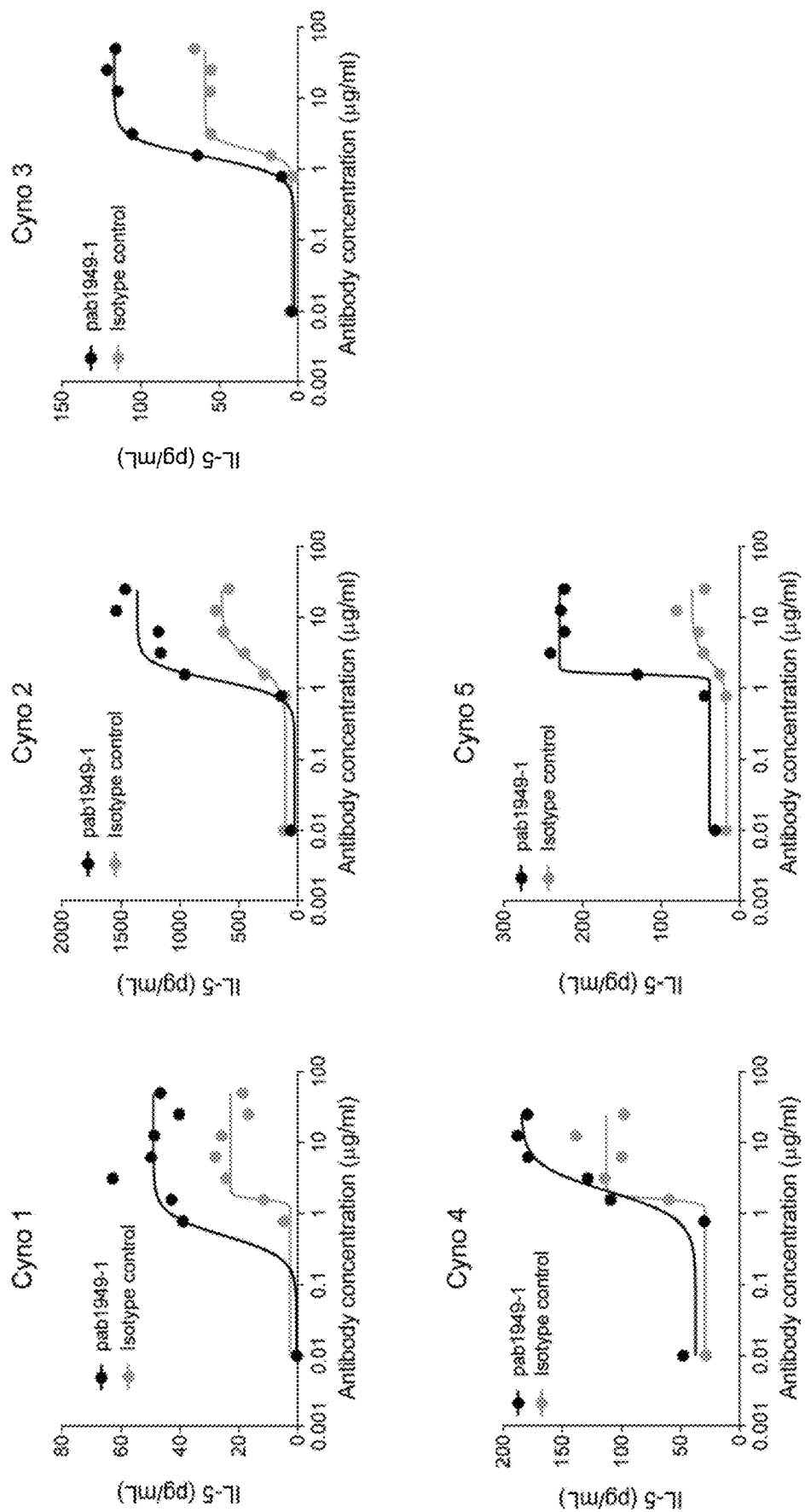
FIGS. 18A and 18B are similar to FIGS. 15A and 15B, showing the amount of secreted IL-5 induced by a dose titration of pab1949-1 or an IgG$_1$ isotype control antibody.
Figure 18B:
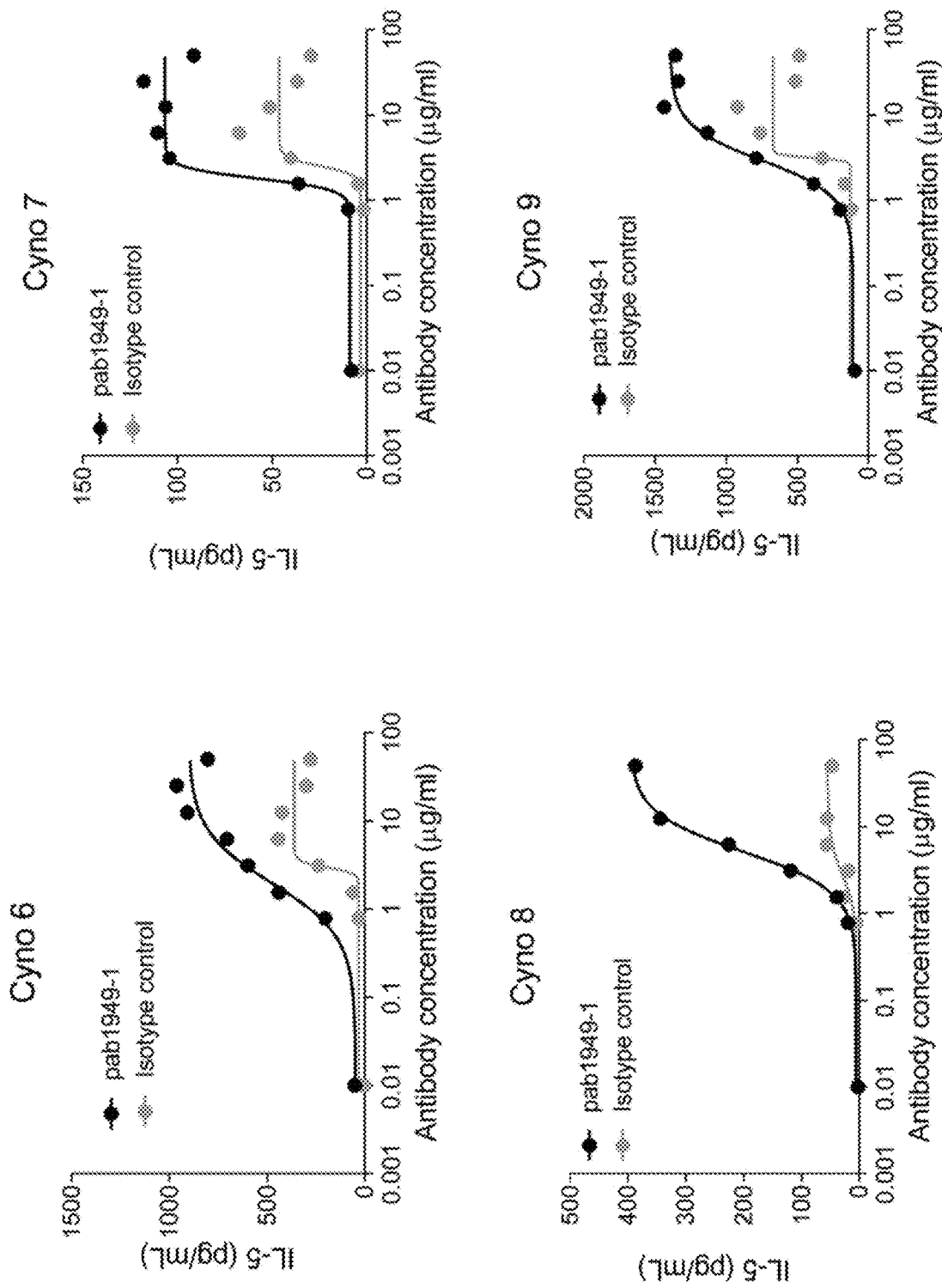
Figure 19A:
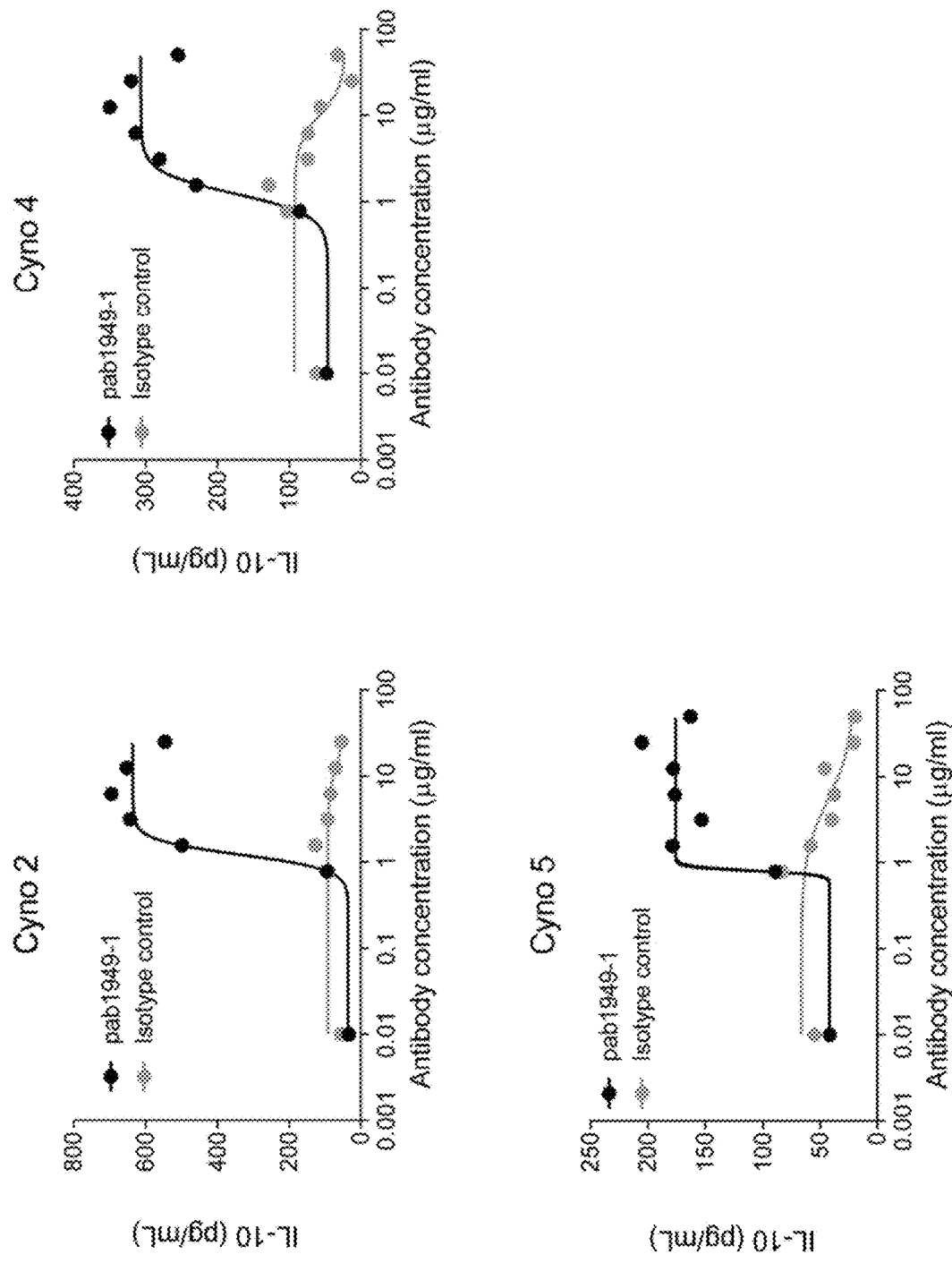
FIGS. 19A and 19B are similar to FIGS. 15A and 15B, showing the amount of secreted IL-10 induced by a dose titration of pab1949-1 or an IgG$_1$ isotype control antibody.
Figure 19B:
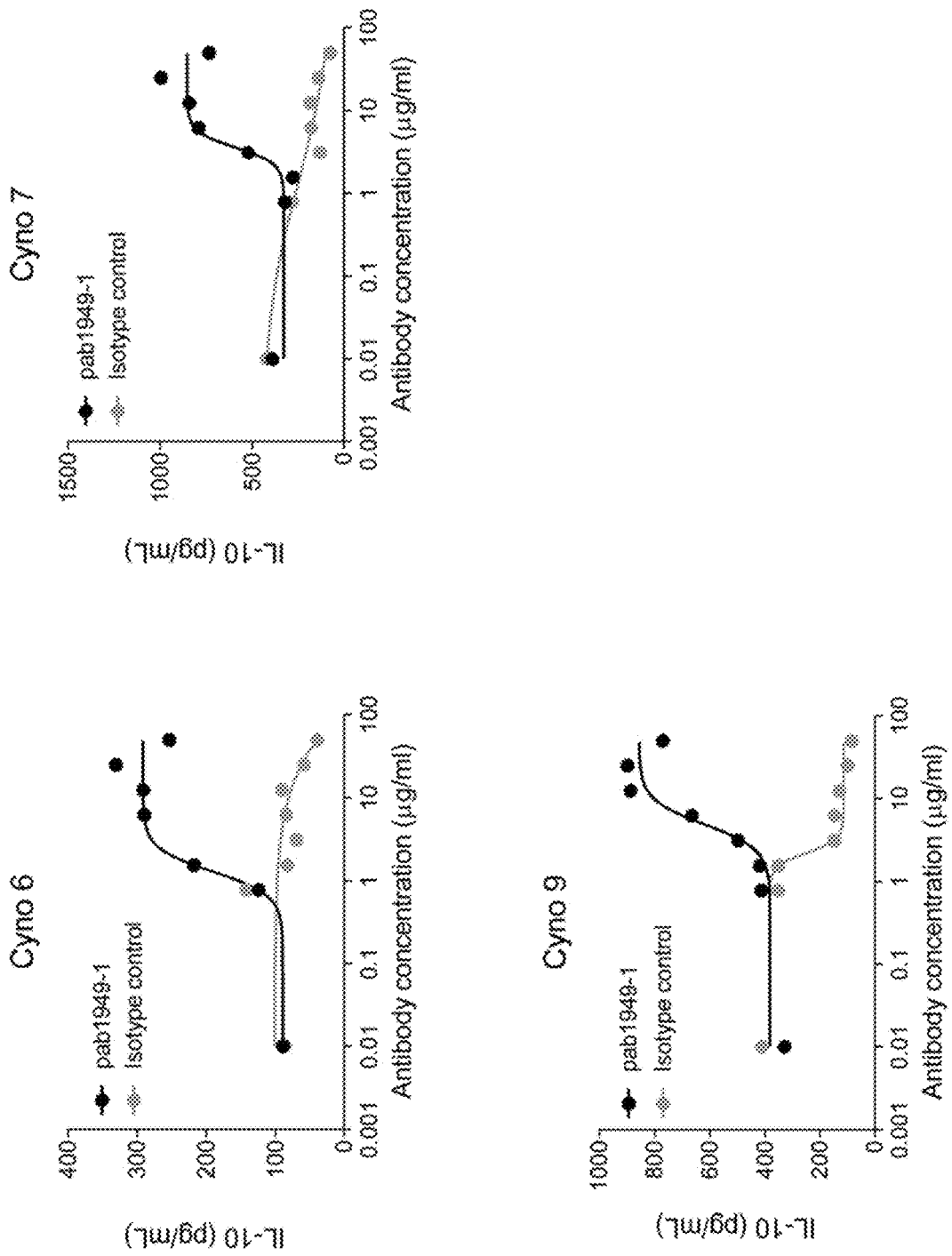

The anti-OX40 antibody pab1949-1 dose-dependently enhanced the production of GM-CSF (FIGS. 15A and 15B), IL-17 (FIGS. 16A and 16B), TNFβ (FIGS. 17A and 17B), IL-5 (FIGS. 18A and 18B), and IL-10 (FIGS. 19A and 19B) in PBMCs of multiple cynomolguses.

6.2.10 Effect of Anti-OX40 Antibody on Cynomolgus PBMCs Upon *Staphylococcus* Enterotoxin A (SEA) Stimulation The ability of pab1949-1 to co-stimulate cynomolgus PBMCs was further analyzed following *Staphylococcus* Enterotoxin A (SEA) stimulation. Frozen cynomolgus PBMCs (World Wide Primates) were stored in liquid nitrogen and thawed on the day of the experiment. The cells were resuspended in cell culture media (RPMI+10% heat-inactivated FBS) and incubated with the SEA antigen (100 ng/ml) as well as a dose titration of pab1949-1 or an IgG$_1$ isotype control antibody 0, 0.8, 1.6, 3.1, 6.3, 12.5, 25, or 50 µg/ml) for 5 days at 37° C. and 5% CO$_2$. After activation, the cell culture supernatant was collected and secreted cytokines were examined using the non-human primate (NHP) V-Plex assay kit (Meso Scale Discovery).

Figure 20A:
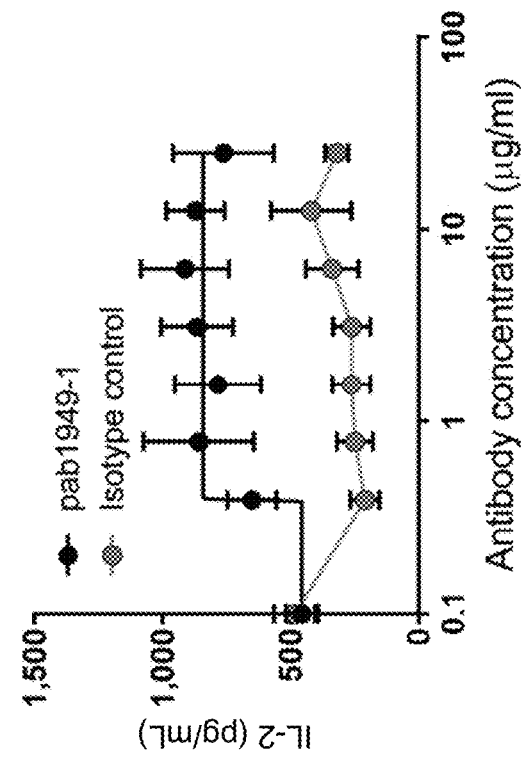
FIGS. 20A and 20B are a pair of graphs showing results from an assay examining the functional activity of the anti-OX40 antibody pab1949-1 on primary cynomolgus PBMCs upon *Staphylococcus* Enterotoxin A (SEA) stimulation. The amount of IL-2 secreted by PBMCs from two cynomolgus donors is plotted against a dose titration of pab1949-1 or an IgG$_1$ isotype control antibody.
Figure 20B:
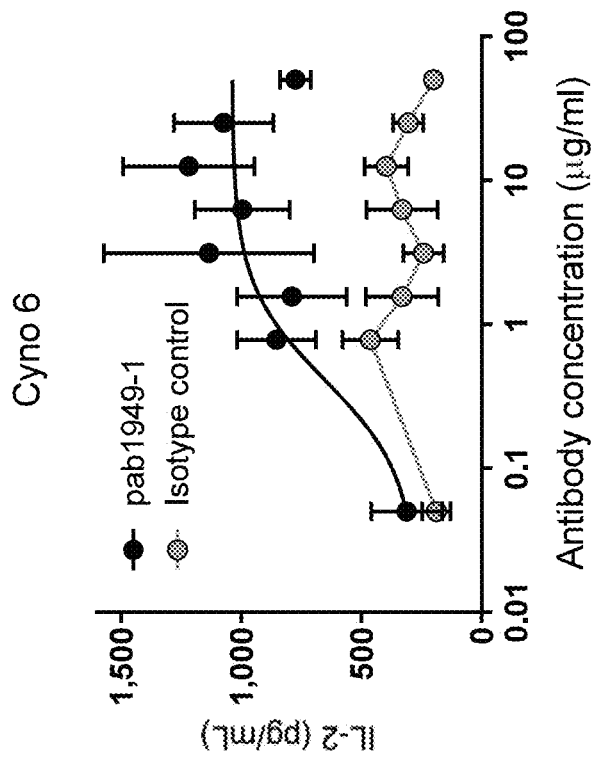

As shown in FIGS. 20A and 20B, the anti-OX40 antibody pab1949-1 increased IL-2 production in cynomolgus PBMCs from two donors.

6.3 Example 3: Epitope Mapping of Anti-OX40 Antibodies

In this example, the epitopes of pab1949 and a reference anti-OX40 antibody pab1928 were analyzed by alanine scanning. The antibody pab1928 was generated based on the variable regions of the antibody Hu106-122 provided in U.S. Patent Publication No. US 2013/0280275 (herein incorporated by reference). The heavy chain of pab1928 comprises the amino acid sequence of the heavy chain variable region of Hu106-122 (SEQ ID NO: 56) and a human IgG1 constant region of SEQ ID NO: 65. The light chain of pab1928 comprises the amino acid sequence of the light chain variable region of Hu106-122 (SEQ ID NO: 57) and a constant region of SEQ ID NO: 25. Thus the heavy chain comprises the amino acid sequence of SEQ ID NO:72, and the light chain comprises the amino acid sequence of SEQ ID NO:59.

6.3.1 Epitope Mapping—Alanine Scanning

The binding characteristics of pab1949-1 and the reference antibody pab1928 were assessed by alanine scanning. Briefly, the QuikChange HT Protein Engineering System from Agilent Technologies (G5901A) was used to generate human OX40 mutants with alanine substitutions in the extracellular domain. The human OX40 mutants were expressed on the surface of 1624-5 cells using standard techniques of transfection followed by transduction as described above.

Cells expressing correctly folded human OX40 mutants, as evidenced by binding to a polyclonal anti-OX40 antibody in flow cytometry, were further selected for a sub-population that expressed human OX40 mutants that did not bind the monoclonal anti-OX40 antibody pab1949-1 or pab1928. Cells that exhibited specific antibody binding were separated from the non-binding cell population by preparative, high-speed FACS (FACSAriaII, BD Biosciences). Antibody reactive or non-reactive cell pools were expanded again in tissue culture and, due to the stable expression phenotype of retrovirally transduced cells, cycles of antibody-directed cell sorting and tissue culture expansion were repeated, up to the point that a clearly detectable anti-OX40 antibody (pab1949-1 or pab1928) non-reactive cell population was obtained. This anti-OX40 antibody non-reactive cell population was subjected to a final, single-cell sorting step. After several days of cell expansion, single cell sorted cells were again tested for binding to a polyclonal anti-OX40 antibody and non-binding to monoclonal antibody pab1949-1 or pab1928 using flow cytometry. Briefly, 1624-5 cells expressing individual human OX40 alanine mutants were incubated with the monoclonal anti-OX40 antibody pab1949-1 or pab1928. For each antibody, two antibody concentrations were tested (pab1949-1: 2 µg/ml and 0.5 µg/ml; pab1928: 1.1 µg/ml and 0.4 µg/ml). The polyclonal anti-OX40 antibody (AF3388, R&D systems) conjugated with APC was diluted at 1:2000. Fc receptor block (1:200; BD Cat no. 553142) was added, and the samples were incubated for 20 minutes at 4° C. After washing, the cells were incubated with a secondary anti-IgG antibody if necessary for detection (PE conjugated; BD Cat no. 109-116-097) for 20 min at 4° C. The cells were then washed and acquired using a flow cytometer (BD Biosciences).

To connect phenotype (polyclonal anti-OX40 antibody+, monoclonal anti-OX40 antibody −) with genotype, sequencing of single cell sorted human OX40 mutants was performed. FIG. 21 is a table showing the human OX40 alanine mutants that still bind the polyclonal anti-OX40 antibody but do not bind the monoclonal anti-OX40 antibody pab1949-1 or pab1928. All the residues are numbered according to the mature amino acid sequence of human OX40 (SEQ ID NO: 55). "+" indicates binding and "−" indicates loss of binding based on flow cytometry analysis.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

---

What is claimed:

1. An isolated vector comprising a nucleic acid molecule encoding a heavy chain variable region (VH), wherein the VH comprises the amino acid sequence of SEQ ID NO: 16.

2. The isolated vector of claim 1, wherein the nucleic acid molecule encodes the amino acid sequence of SEQ ID NO: 21, 23, 51, 52, 60, 61, 62, or 63.

3. The isolated vector of claim 1, wherein the nucleic acid molecule encodes the amino acid sequence of SEQ ID NO: 21.

4. The isolated vector of claim 1, wherein the nucleic acid molecule encodes the amino acid sequence of SEQ ID NO: 60.

5. An isolated vector comprising a nucleic acid molecule encoding a light chain variable region (VL), wherein the VL comprises the amino acid sequence of SEQ ID NO: 15.

6. The isolated vector of claim 5, wherein the nucleic acid molecule encodes the amino acid sequence of SEQ ID NO: 20.

7. An isolated vector comprising a first and a second nucleic acid molecule, wherein the first nucleic acid molecule encodes a VH comprising the amino acid sequence of SEQ ID NO: 16, and the second nucleic acid molecule encodes a VL comprising the amino acid sequence of SEQ ID NO: 15.

8. The isolated vector of claim 7, wherein the first nucleic acid molecule encodes the amino acid sequence of SEQ ID NO: 21.

9. The isolated vector of claim 7, wherein the first nucleic acid molecule encodes the amino acid sequence of SEQ ID NO: 60.

10. The isolated vector of claim 7, wherein the second nucleic acid molecule encodes the amino acid sequence of SEQ ID NO: 20.

11. The isolated vector of claim 7, wherein the first nucleic acid molecule encodes the amino acid sequence of SEQ ID NO: 21, 23, 51, 52, 60, 61, 62, or 63, and/or the second nucleic acid molecule encodes the amino acid sequence of SEQ ID NO: 20.

12. The isolated vector of claim 7, wherein the first and second nucleic acid molecules encode, respectively, the amino acid sequences of SEQ ID NOs: 21 and 20; 60 and 20; 61 and 20; 62 and 20; or 63 and 20.

13. A host cell comprising a nucleic acid molecule encoding a VH, wherein the VH comprises the amino acid sequence of SEQ ID NO: 16.

14. The host cell of claim 13, wherein the nucleic acid molecule encodes the amino acid sequence of SEQ ID NO: 21.

15. The host cell of claim 13, wherein the nucleic acid molecule encodes the amino acid sequence of SEQ ID NO: 60.

16. A host cell comprising a nucleic acid molecule encoding a VL, wherein the VL comprises the amino acid sequence of SEQ ID NO: 15.

17. The host cell of claim 16, wherein the nucleic acid molecule encodes the amino acid sequence of SEQ ID NO: 20.

18. A method of producing an antibody that binds to human OX40 comprising culturing the host cell of claim 13 so that the nucleic acid molecule is expressed and the antibody is produced.

19. A method of producing an antibody that binds to human OX40 comprising culturing the host cell of claim 14 so that the nucleic acid molecule is expressed and the antibody is produced.

20. A method of producing an antibody that binds to human OX40 comprising culturing the host cell of claim 15 so that the nucleic acid molecule is expressed and the antibody is produced.

21. A method of producing an antibody that binds to human OX40 comprising culturing the host cell of claim 16 so that the nucleic acid molecule is expressed and the antibody is produced.

22. A method of producing an antibody that binds to human OX40 comprising culturing the host cell of claim 17 so that the nucleic acid molecule is expressed and the antibody is produced.

* * * * *